(12) United States Patent
Sun et al.

(10) Patent No.: US 7,705,126 B2
(45) Date of Patent: Apr. 27, 2010

(54) COMPOSITIONS FOR CONTROLLING HAIR GROWTH

(75) Inventors: Tung-Tien Sun, Dobbs Ferry, NY (US); Qiong Cao, Boston, MA (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 12/187,771

(22) Filed: Aug. 7, 2008

(65) Prior Publication Data

US 2009/0104623 A1 Apr. 23, 2009

Related U.S. Application Data

(60) Continuation of application No. 11/709,074, filed on Feb. 21, 2007, now Pat. No. 7,420,038, which is a division of application No. 11/096,070, filed on Mar. 31, 2005, now Pat. No. 7,223,562.

(60) Provisional application No. 60/558,341, filed on Mar. 31, 2004.

(51) Int. Cl.
*C07K 14/435* (2006.01)

(52) U.S. Cl. ................................... 530/350

(58) Field of Classification Search .................. None
See application file for complete search history.

(56) References Cited

U.S. PATENT DOCUMENTS

| | | | |
|---|---|---|---|
| 4,139,619 | A | 2/1979 | Chidsey, III |
| 5,643,898 | A | 7/1997 | Grollier et al. |
| 5,656,300 | A | 8/1997 | Levin |
| 5,663,160 | A | 9/1997 | Meybeck et al. |
| 5,674,497 | A | 10/1997 | Kuwana et al. |
| 5,679,378 | A | 10/1997 | Fischer |
| 5,723,149 | A | 3/1998 | Bonte et al. |
| 5,739,111 | A | 4/1998 | Mahe |
| 5,741,816 | A | 4/1998 | Tsujihara et al. |
| 5,750,107 | A | 5/1998 | Nomura |
| 5,753,713 | A | 5/1998 | Bass |
| 5,767,152 | A | 6/1998 | Nielsen et al. |
| 5,798,341 | A | 8/1998 | Klingelholler |
| 5,800,477 | A | 9/1998 | Groux |
| 6,093,748 | A | 7/2000 | Ahluwalia et al. |
| 6,291,740 | B1 | 9/2001 | Bremel et al. |
| 7,223,562 | B2 | 5/2007 | Sun et al. |
| 7,420,038 | B2 | 9/2008 | Sun et al. |
| 2005/0074762 | A1* | 4/2005 | Nakamura et al. ........... 435/6 |

FOREIGN PATENT DOCUMENTS

WO WO-9513796 5/1995

WO WO-0261076 8/2002

OTHER PUBLICATIONS

Bal et al., "Formation of the Extracellular Mucous Matrix of Olfactory Neuroepithelium: Identification of Partially Glycosylated and Nonglycosylated Precursors of Olfactomedin", Biochemistry, 32(4):1047-53, 1993.

Bertolino et al. Disorders of epidermal appendages and related disorders. Dermatology in General Medicine, 1993, 4th ed., pp. 671-695, Fitzpatrick et al. eds., McGraw-Hill.

Bertolino et al., "Differentiation of the hair shaft" in Differentiation of the Hair Shaft, pp. 21-37, Olsen EA (ed.), McGraw Hill, Inc. New York, 1994.

Botchkarev et al., "Molecular Biology of Hair Morphogenesis: Development and Cycling", J. Exp. Zool. Mol. Dev. Evol., 298(1):164-180, 2003.

Cao et al. Expression of an Olfactomedin-related Gene in Rat Hair Follicular Papilla Cells, J. Invest. Dermatol., 2005, pp. 24-33, vol. 125, No. 1.

Cotsarelis et al., Existence of Slow-Cycling Limbal Epithelial Basal Cells That Can be Preferentially Stimulated to Proliferate: Implications on Epithelial Stem Cells, Cell, 1989, pp. 201-209, vol. 57.

Cotsarelis et al., "Towards a Molecular Understanding of Hair Loss and Its Treatment", Trends Mol. Med., 7(7):293-301, 2001.

Elliott et al., "Differences in Hair Follicle Dermal Papilla Volume are Due to Extracellular Matrix Volume and Cell Number: Implications for the Control of Hair Follicle Size and Androgen Responses", J. Invest. Dermatol., 113:873-877, 1999.

Fields et al., "The Two-Hybrid System: An Assay for Protein-Protein Interactions", Trends Genet., 10(8):286-92, 1994.

Garces et al., "Using an Inverse PCR Strategy to Clone Large, Contiguous Genomic DNA Fragments", Methods Mol. Biol., 161:3-8, 2001.

GenBank Accession No. BX538105. *Homo sapiens* mRNA, cDNA DKFZp686J18145. (2003). cited by examiner.

Green et al., "Multidomain TIGR/Olfactomedin Protein Family with Conserved Strustural Similarity in the N-terminal Region and Conserved Motifs in the C-terminal Region," Molecular & Cellular Proteomics 1:394-403 (2002). cited by examiner.

Hardy, "The Secret Life of the Hair Follicle", Trends Genet., 8:55-61, 1992.

Hutchinson et al., "Mutagenesis at a Specific Position in a DNA Sequence", J. Biol. Chem., 253:6551, 1978.

(Continued)

*Primary Examiner*—Nashaat T Nashed
(74) *Attorney, Agent, or Firm*—Wilmer Cutler Pickering Hale and Dorr LLP

(57) ABSTRACT

FP-1 is a protein that is specifically expressed in the follicular papilla of the hair follicle. The nucleic acid and amino acid sequences of FP-1, as well as antibodies that specifically bind FP-1 are provided. In addition, methods of isolating follicular papilla cells and methods of modulating hair growth are also disclosed.

1 Claim, 49 Drawing Sheets

OTHER PUBLICATIONS

Jahoda et al., "Trans-Species Hair Growth Induction by Human Hair Follicle Dermal Papillae", Exp. Dermatol., 10(4):229-37, 2001.

Jahoda et al., "Induction of Hair Growth by Implantation of Cultured Dermal Papilla Cells", Nature, 311:560-562, 1984.

Jahoda, C. A., "Induction of Follicle Formation and Hair Growth by Vibrissa Dermal Papillae Implanted into Rat EAr Wounds: Vibrissa-Type Fibres are Specified", Development, 115:1103-1109, 1992.

Kamimura et al., "Primary Mouse Keratinocyte Cultures Contain Hair Follicle Progenitor Cells with ultiple Differentiation Potential", J. Invest. Dermatol., 109(4):534-40, 1997.

Kim et al., "Regrowth of Grafted Human Scalp Hair after Removal of the Bulb", Dermatol. Surg., 21(4):312-313, 1995.

Lachgar et al., "Minoxidil Upregulates the Expression of Vascular Endothelial Growth Factor in Human Hair Dermal Papilla Cells," Br. J. Dermatol., 138:407-411, 1998.

Lehrer et al. "Strategies of Epithelial Repair: Modulation of Stem Cell ad Transit Amplifying Cell Proliferation." *Journal of Cell Science*. 1998. pp. 2867-2975. vol. 11.

Muller-Rover et al., "A Comprehensive Guide for the Accurate Classification of Murine Hair Follicles in Distinct Hair Cycle Stages," J. Invest. Dermatol., 117:3-15, 2001.

Oliver, "Whisker Growth After Removal of the Dermal Papilla and Lengths of Follicle in the Hooded Rat," J. Embryol. Exp. Morphol., 15:331-347, 1966.

Oshima et al., "Morphogenesis and Renewal of Hair Follicles From Adult Multipotent Stem Cells," *Cell*, 104:233-245, 2001.

Philpott et al. Whole Hair Follicle Culture, Dermatologic Clinics, 1996, pp. 595-607, vol. 14, No. 4.

Philpott et al., Human Hair Growth in Vitro: A Model for the Study of Hair Follicle Biology, J. Dermatol. Sci. 7 Suppl, S55-72.

Porter, "Mouse Models for Human Hair Loss Disorders," J. Anat., 202:125-131, 2003.

Reynolds, A. J. et al., "Trans-Gender Induction of Hair Follicles," Nature, 402:33-34, 1999.

siRNA Selection Program, Whitehead Institute for Biomedical Research, 2003.

Snyder et al., "Olfactomedin: Purification, Characterization, and Localization of a Novel Olfactory Glycoprotein," Biochem., 30(38):9143-153, 1991.

Stenn et al., "Controls of Hair Follicle Cycling," Physiol. Rev., 81:449-494, 2001.

Trimble and Maley, "Optimizing Hydrolysis of N—Linked High-Mannose Oligosaccharides by Endo-β-N-acetylglucosaminidase H," Anal. Biochem., 141(2):515-22, 1984.

Yuan et al. "siRNA Selection Server: An Automated siRNA Oligonucleotide Prediction Server." *Nucleic Acids Research*. 2004. vol. 32, Web Server Issue.

Yokoe et al. "Molecular Cloning of Olfactomedin, an Extracellular Matrix Protein Specific to Olfactory Neuroepithelium," *Proc. Natl. Acad. Sci. USA*. 90:655-4659. 1993.

\* cited by examiner

FIG. 2A

```
       1  M  T  R  A  A  E  R  G  Q  G  A  T  G  W  G
       1  ACGCGGGGAGTGCTGCCCTGAGTCGTTCGGCCTGAGCACAGAGACATGACCCGAGCAGCCGAGAGGCCAGGGGCTGGGA

16  L  R  G  A  L  M  A  V  A  L  L  S  V  L  N  A  V  G  T  V  F  V  L  Y  Q  W  R  E  L  S
      91  CTGCGAGGCGCCCTGATGGCCGTGGCCCTGCTGTCAGTGCTGAACGCCGTGGGCACCGTGTTCGTGCTGTACCAGTGGCGGGAGCTGAGC

46  A  A  L  R  A  L  E  A  Q  H  G  Q  E  Q  R  E  D  S  A  L  R  A  F  L  A  E  L  S  R  A
     181  GCGGCGCTGCGGGCACTGGAGGCGCAACACGGCCAGGAGCAGCGCGAGGACAGCGCCCTACGCGCCTTTCTAGCTGAATTAAGTCGTGCG

76  P  A  R  V  P  E  P  P  Q  D  P  M  S  A  A  R  N  K  R  S  H  G  G  E  P  A  S  H  I  R
     271  CCAGCCCGAGTCCCCGAACCACCCCAGGACCCCATGAGTGCAGCGCGCAATAAGCGCAGCCACGGGGCGGAGCCTGCGTCACACATCCGC

106  A  E  S  Q  D  M  M  M  M  T  Y  S  M  V  P  I  R  V  M  I  D  L  C  N  S  T  Q  G  I
     361  GCGGAGAGCCAGGACATGATGATGATGACCTACAGCATGGTGCCGATCCGGGTGATGATAGACCTGTGCAACAGCACCCAGGGCATC

136  C  L  T  G  P  P  P  G  P  P  P  G  A  G  G  L  P  G  H  N  G  S  D  G  Q  P  G  L  Q
     451  TGCCTTACAGGACCACCGGGCCCACCAGGACCTCCAGGAGCTGGTGGGTTACCAGGGCCACAATGGATCAGATGGACCTGGTCTCCAG

166  G  P  K  G  E  K  G  A  V  G  K  R  G  K  M  G  L  P  G  A  T  G  N  P  G  E  K  G  E  K
     541  GGCCCAAAAGGAGAAAAAGGAGCAGTTGGAAAGAGAGGGAAAATGGGGTTACCCGGAGCCACAGGAAATCCAGGGGAAAAGGGAGAGAAG

196  G  D  A  G  E  L  G  L  P  G  N  E  G  P  P  G  Q  K  G  D  K  G  D  V  S  N  D
     631  GGAGATGCTGGTGAACTGGGCCTACCTGGAAATGAGGGACCACCAGGACAAAAGGAGACAAAGGAGATGTGTCCAATGAC
```

```
226   V  L  T  G  A  K  G  D  Q  G  P  P  P  G  P  P  P  P  G  P  P  P  G  P  P  S  G  S  R  R  A
721   GTGCTTTTGACAGGTGCCAAAGGTGACCAAGGGCCCCCCAGGCCCCCTGGCCCTTCCAGGCCCTTCTGGAAGCAGAGAGCC

256   K  G  P  R  Q  P  N  S  F  T  N  Q  C  P  G  E  T  C  V  I  P  N  D  D  T  L  V  G  R  A
811   AAAGGCCCTCGGCAGCCAAATTCGTTCACCAACCAGTGTCCAGGGGAGACGTGTGTCATACCCAATGATGATACCTTGTGGGGAGAGCT

286   D  E  K  V  N  E  R  H  S  P  Q  T  E  P  M  I  T  S  I  G  N  P  A  Q  V  L  K  V  K  E
901   GATGAGAAAGTCAATGAGCGCCATTCCCACAAACAGAACCATGATCACGTCCATTGGTAACCCGGCCCAAGTCCTCAAAGTGAAAGAG

316   T  F  G  T  W  L  R  E  S  A  N  R  S  D  D  R  I  W  V  T  E  H  F  S  G  I  M  V  K  E
991   ACTTTTGGGACCTGGCTAAGAGAGTCTGCTAACAGGAGTGATGACCGCATTTGGGTGACTGAACATTTTTCAGGCATCATGGTGAAGGAG

346   F  E  D  L  P  A  L  L  N  S  S  F  T  L  H  L  P  H  Y  F  H  G  C  G  H  A  V  Y  N
1081  TTTGAAGACCTGCCCGCCCTCCTGAATAGCAGCTTCACCCTCCACCTCCCACATTACTTCCATGGCTGCGGGCACGCTGTTTACAAC

376   N  S  L  Y  Y  H  K  G  G  S  N  T  I  V  R  F  E  F  G  K  E  T  P  Q  T  L  K  L  E  D
1171  AACTCTCTACTACCACAAAGGAGGCTCCAACACCATAGTGAGATTTGAATTTGGAAAGAGACACCTCAAACTCTGAGCTTGAAGAT

406   A  L  Y  F  D  R  K  Y  L  F  A  N  S  K  T  Y  F  N  I  A  V  D  E  K  G  L  W  I  I  Y
1261  GCTTTGTATTTTGATCGAAAATACCTCTTTGCGAATTCCAAGACTTACTTCAACATAGCAGTGGATGAGAAGGGCCTCTGGATTATCTAC

436   A  S  V  D  G  S  S  I  L  V  A  Q  L  D  E  R  T  F  S  V  L  Q  H  I  N  T  T  Y  P
1351  GCCTCGAGTGTGGATGGCTCAAGCATCCTTGTGGCACAGCTGGACGAGAGAGACATTCTCTGTGCTGCAGCACATCAATACCACATACCCC
```

FIG. 2B

```
466   K  S  K  A  G  N  A  F  I  A  Q  G  I  L  Y  V  T  D  T  K  D  T  R  V  T  F  A  F  D  L
1441  AAGTCCAAGGCTGGCAATGCCTTCATAGCTCAAGGGATCCTCTATGTCACGGACACAAAAGATACAAGGGTCACGTTTGCCTTTGATTTG

496   L  R  G  K  Q  I  N  A  N  F  G  L  R  M  S  Q  S  V  L  A  M  L  S  Y  N  M  R  D  Q  H
1531  TTACGAGGGAAGCAGATCAATGCAAACTTCGGTCTCAGAATGTCACAGTCTGTTCTTGCCATGTTGTCGTACAATATGAGAGACCAGCAT

526   L  Y  S  W  E  D  G  H  L  M  L  Y  P  V  H  F  S  S  T  A  P  S  Q  R  (SEQ ID NO:2)
1621  TTGTACTCGTGGGAAGACGGCCACCTGATGCTCTATCCTGTGCACTTTTCGTCAACAGCCCCAGCAGGCTGTAAAGGATATCCAGAGCATACGC

1711  CCTCATTATGCACCACACATTTCTGGGGTTTGACCAAGCCCAACGGAAAGAAGGCCTGTAAAGGATATCCAGAGCATACGC

1801  CCGTGTTACGGGCTTTTGTGCATGTGGCAAGTCCCCCTGTAAGCCAGGTAACTAAAGGCTGAAAGTTGAAATGGATAACATTTGGTGA

1891  CCCTTGGTCCCCTCTTCAAACTTAGCAAGTTAGTGCTCCCATCAGTGTCCCCTGACCTTAGTGTTATATATTAGATGCTTTCAGTTTCTTTTTTTTTCTCCACATGTAAG

1981  CATTTCCTATACCTATATGAAGTTCTGTGATTCTTGCCTGGTTATATATTAGATGCTTTCAGTTTCTTTTTTTTTCTCCACATGTAA

2071  ATGAGTTACCTGCAGCTTGAGGGTGTGCCTATCAGTGATGACGGACATTGTTGTTGGTGTTAGGAAAAAGCATTGTTTCTTATGGCT

2161  TTTAAAGTATTATATTATTCCATAATTGATATTTTTTTGAATACGCCCCTGCCACTACAGAATGATTATTGTTTCAGCTCCTAAGTA

2251  CAAATCCAAGATTAATAAAAAAACATGAATAGAAAAAAAAAAAAAACTGAGAGTATTAGTCGATGTAGGAAAAC (SEQ ID NO:1)
```

FIG. 2C

```
  1         M  T  R  A  A  E  R  G  Q  G  A  T  G  W  G
  1   ACGCGGGGAGTGCTGCCCTGAGTCGTTCGGCCCTGAGCACAGAGACATGACCCGAGCCGCAGAGCGAGGCCAAGGGGCTACAGGCTGGGGA

16    L  R  G  A  L  M  A  V  A  L  L  S  V  L  N  A  V  G  T  V  F  V  L  Y  Q  Q  R  E  D  S
 91   CTGCGAGGCGCCCTGATGGCCGTGGCGCTGCTGTCAGTGCTGAACGCCGTGGGCACCGTGTTCGTGCTGTACCAGCAGCGGGAGGACAGC

46    A  L  R  A  F  L  A  E  L  S  R  A  P  A  R  V  P  E  P  P  Q  D  P  M  S  A  A  R  N  K
181   GCCCTACGCGCCTTTCTAGCTGAATTAAGTCGTGCCCCAGCCCGAGTCCCCGAACCACCCCAGGACCCCATGAGTGCAGCGCGCAATAAG

76    R  S  H  G  G  E  P  A  S  H  I  R  A  E  S  Q  D  M  M  M  M  T  Y  S  M  V  P  I  R
271   CGCAGCCACGGGGCGGAGCCTGCGTCACACATCCGCGGGGAGAGCCAGGACATGATGATGATGACCTACAGCATGGTGCCGATCCGG

106    V  M  I  D  L  C  N  S  T  Q  G  I  C  L  T  G  P  P  P  G  P  P  P  G  A  G  G  L  P
361   GTGATGATAGACCTGTGCAACAGCACCCAGGGCATCTGCCTTACAGGACCTCCAGGAGCTCCAGGAGCTGGTGGGTTACCA

136    G  H  N  G  S  D  G  Q  P  G  L  Q  G  P  K  G  E  K  G  A  V  G  K  R  G  K  M  G  L  P
451   GGCCACAATGGATCAGATGGACAGCCTGGTCTCCAGGGCCCAAAAGGAGAAAAAGGAGCAGTTGGGAAGAGAAAAATGGGGTTACCC

166    G  A  T  G  N  P  G  E  K  G  E  K  G  D  A  G  E  L  G  L  P  G  N  E  G  P  P  G  Q  K
541   GGAGCCACAGGAGAAATCCAGGAGAAAGGGAAAAAGGGAGAAGGGAGAGATGCTGGAACTGGGCCTACCTGAAATGAGGACCAGGAGACAGAAA
```

FIG. 3A

```
196    G  D  K  G  D  K  G  D  V  S  N  D  V  L  L  T  G  A  K  G  D  Q  G  P  P  P  G  P  P  G  P
631    GGAGACAAAGGAGACAAAGGAGATGTGTCCAATGACGTGCTTTTGACAGTGGCCAAAGGTGACCAAGGGCCCCCTGGCCCACCTGACCC

226    P  G  P  P  G  P  S  G  S  R  R  A  K  G  P  R  Q  P  N  S  F  T  N  Q  C  P  G  E  T  C
721    CCAGGGCCTCCAGGCCCTTCTGGAAGCAGAAGAGCCAAAGGCCCTCGGCAGCCAAATTCGTTCACCAACCAGTGTCCAGGGGAGACGTGT

256    V  I  P  N  D  D  T  L  V  G  R  A  D  E  K  V  N  E  R  H  S  P  Q  T  E  P  M  I  T  S
811    GTCATACCCAATGATGATACCTTGGTGGGGAGAGCTGATGAGAAAGTCAATGAGCGCCATTCTCCACAAACAGAACCCATGATCACGTCC

286    I  G  N  P  A  Q  V  L  K  V  K  E  T  F  G  T  W  L  R  E  S  A  N  R  S  D  D  R  I  W
901    ATTGGTAACCCGGCCCAAGTCCTCAAAGTGAAAGAGACTTTTGGGACCTGGCTAAGAGAGTCTGCTAACAGGAGTGATGACCGCATTTGG

316    V  T  E  H  F  S  G  I  M  V  K  E  F  F  E  D  L  P  A  L  L  N  S  F  T  L  L  H  L  P
991    GTGACTGAACATTTTTCAGGCATCATGGTGAAGGAGTTTGAAGACCTGCCCGCTCCTCTGAATAGCAGTTTCACCCTCCTCCACCTCCCA

346    H  Y  F  H  G  C  G  H  A  V  Y  N  N  S  L  Y  Y  H  K  G  G  S  N  T  I  V  R  F  E  F
1081   CATTACTTCCATGGCTGCGGGCACGCTGTTTACAACAACTCTCTACTACCACAAAGGAGGCTCCAACACCATAGTGAGATTTGAATTT

376    G  K  E  T  P  Q  T  L  K  L  E  D  A  L  Y  F  D  R  K  Y  L  F  A  N  S  K  T  Y  F  N
1171   GGGAAAGAGACACCTCAAACTCTGAAGCTTGAAGATGCTTTGTATTTTGATCGAAAATACCTCTTTGCGAATTCCAAGACTTACTTCAAC

406    I  A  V  D  E  K  G  L  W  I  I  Y  A  S  S  V  D  G  S  S  I  L  V  A  Q  L  D  E  R  T
1261   ATAGCAGTGGATGAGAAGGGCCTCTGGATTATCTACGCCTCAAGTGTGGATGGCTCAAGCATCCTTGTGGCACAGCTGGACGAGAGGACA
```

FIG. 3B

```
436   F S V L Q H I N T T Y P K S K A G N A F I A Q G I L Y V T D
1351  TTCTCTGTGCTGCAGCACATCAATACCCAAGTCCCAAGTCCAAGGCTGGCAATGCCTTCATAGCTCAAGGGATCCTCTATGTCACGGAC

466   T K D T R V T F A F D L L R G K Q I N A N F G L R M S Q S V
1441  ACAAAAGATACAAGGGTCACGTTTGCCTTTGATTTGTTACGAGGAAGCAGATCAAATGCAAACTTCGGTCTCAGAATGTCACAGTCTGTT

496   L A M L S Y N M R D Q H L Y S W E D G H L M L Y P V H F S S
1531  CTTGCCATGTTGTCGTACAATATGAGAGACCAGCATTTGTACTCGTGGGAAGACGGCCACCTGATGCTCTATCCTGTGCACTTTTCGTCA

526   T A P S Q R   (SEQ ID NO:4)
1621  ACAGCACCCCAGCGCAGCGATAGGCCTGCAGTCGGCTCCCTCATTATGCACCACACATTTCTGGGGTTGACCAAGCCCAAGCGGAAAGAAG

1711  GCCTGTAAAGGATATCCAGAGTACTCAGAGCATACGCCCGTGTTACGGCTTTTGTGCATGTGGCAAGTCCCCCTGTAAGCCAGGTTAACT

1801  AAAGGCTGGAAAGTTGAAATGGATAACATTTGGTGACCCTTGGTCTCCCTCTTCAAACTTAGCAAGTTAGTGCTCCCCCCTGACCTTAGTGT

1891  CCCCATCAGTAATATGAAACATCTGTGATTGCAGCATTCCTATACCTATATGAAGTTCTGTGATTCTTGCCTGTTATATATTAGAT

1981  TGCTTTCAGTTTCTCTTTTTTTCTCCACATGTAAATGAGTTTACCTGCAGCTTGAGGGGTGTGCCTATCAGTGATGACGGACATTGT

2071  TTGGTGTTTAGGGAAAAAGCATTGTTCTTATGGCTTTTAAAGTATTATATTATCCATAATTGATATTTTTTTTGAATACGCCCCTGC

2161  CACTACAGAATGATTATTGTTTCAGCTCCTAAGTACAAATCCAAGATTAATAAAAAAAAAAAAAATGAATAGAAAAAAAAAAAAAAAC

2251  TCGAGAGTATTAGTCGATGTAGGAAAAC   (SEQ ID NO:3)
```

FIG. 3C

```
  1 GAATTCGGCACGAGGGGGGCTTCTGGGGGCCCACGATTACTGTCCCCAACCCGCCTCGCCAGACGGGTCTAAAGGCAGCTTGACTCACGACT
 93 CTGCCACCAGCCCACCACTCGCGCGGAGGGTATAAAACCTGCCACTGCGGAGGAGGCCCAGTGCTGCCCTGAGTCGTTCGGCCTGAGCAC

1           M  T  R  A  A  E  R  G  Q  G  A  T  G  W  G  L  R  G  A  L  M  A  V  A  L  L  S  V
183 AGAGACATGACCCGAGCCGCAGAGCCCGGCAAGGGCTACAGGGCTGGGACTGCGAGGCCCTGATGGCCGTGGCGCTGCTGTCAGTG

29  L  N  A  V  G  T  V  F  V  L  Y  Q  W  R  E  L  S  A  A  L  R  A  L  E  A  Q  H  G  Q  E
273 CTGAACGCCGTGGGCACCGTGTTCGTGCTGTACCAGTGGCGCGAGCTGAGCGCGGCGCTGCGGGCACTGGAGGCACAACGGCCAGGAG

59  Q  R  E  D  S  A  L  R  A  F  L  A  E  L  S  R  A  P  A  R  V  P  E  P  P  Q  D  P  M  S
363 CAGCGCGAGGACAGCGCCCTACGCGCCTTTCTAGCTGAATTAAGTCGTGCGCCAGCCCCGAGTCCCCGAACCACCCCAGGACCCCATGAGT

89  A  A  R  N  K  R  S  H  G  G  E  P  A  S  H  I  R  A  E  S  Q  D  M  M  M  M  T  Y  S
453 GCAGCGCGCAATAAGCGCAGCCACGGCGGGGAGCCTGCGTCACACATCCGCGAGAGCCAGGACATGATGATGATGACCTACAGC

119  M  V  P  I  R  V  M  I  D  L  C  N  S  T  Q  G  I  C  L  T  G  P  P  P  G  P  P  G
543 ATGGTGCCGATCCGGGTGATGATAGACCTGTGCAACAGCACCCAGGGCATCTGCCTTACAGGACCACCGGCCCACCAGGACCTCCAGGA

149  A  G  G  L  P  G  H  N  G  S  D  G  Q  P  G  L  Q  G  P  K  G  E  K  G  A  V  G  K  R  G
633 GCTGGTGGGTTACCAGGCCACAATGGATCAGATGGACAGCCTGTCTCCAGGGCCCAAAAGGAGAAAAAGGAGCAGTTGGGAAGAGAGGA

179  K  M  G  L  P  G  A  T  G  N  P  G  E  K  G  E  K  G  D  A  G  E  L  G  L  P  G  N  E  G
723 AAAATGGGGTTACCCGGAGCCACAGGAAATCCAGGGGAAAAGGGAGAAAAGGGAGAAAGGGAGATGCTGTGAACTGGCCTACCTGGAAATGAGGGA
```

FIG. 4A

| 209 | P P G Q K G D K G D V S N D V L L T G A K G D Q G P P |
| --- | --- |
| 813 | CCACCAGGACAGAAGGAGACAAAGGAGATGTGTCCAATGACGTGCTTTTGACAGGTGCCAAGGTGACCAAGGGCCCCCT |

| 239 | G P P G P P P G P P P G S R R A K G P R Q P N S F T N Q C |
| --- | --- |
| 903 | GGCCCACCTGGACCCCCAGGCCCCAGGCCCTCCTGGAAGCAGAGAGCCCAAAGGCCCAAATTCGTTCACCAACCAGTGT |

| 269 | P G E T C V I P N D D T L V G R A D E K V N E R H S P Q T E |
| --- | --- |
| 993 | CCAGGGGAGACGTGTGTCATACCCAATGATGATACCTTGGTGGGGAGAGCTGATGAGAAAGTCAATGAGCGCCATTCTCCACAAACAGAA |

| 299 | P M I T S I G N P A Q V L K V K E T F G T W L R E S A N R S |
| --- | --- |
| 1083 | CCCATGATCACGTCCATTGGTAACCCGGCCCAAGTCCTCAAGGTGAAAGAGACTTTTGGGACCTGGCTAAGAGAGTCTGCTAACAGGAGT |

| 329 | D D R I W V T E H F S G I M V K E F E D L P A L L N S S F T |
| --- | --- |
| 1173 | GACGACCGCATTTGGGTGACTGAACATTTTTCAGGCATCATGGTGAAGGAGTTTGAAGACCTGCCCGCCCTCCTGAATAGCAGCTTCACC |

| 359 | L L H P H Y F H G C G H A V Y N N S L Y Y H K G G S N T I |
| --- | --- |
| 1263 | CTCCTCCACCTCCCACATTACTTCCATGGCTGCGGCCACGCTGTTTACAACAACTCTCTCTACTACCACAAAGGAGGCTCCAACACCATA |

| 389 | V R F F G K E T P Q T L K L E D A L Y F D R K Y L F A N S |
| --- | --- |
| 1353 | GTGAGATTTGAATTTGGGAAGGAAACACCTCAAACTCTGAAGCTTGAAGATGCTTTGTATTTTGATCGAAAATACCTCTTTGCGAATTCC |

| 419 | K T Y F N I A V D E K G L W I I Y A S S V D G S S I L V A Q |
| --- | --- |
| 1443 | AAGACTTACTTCAACATAGCAGTGGATGAGAAGGGCCTCTGGATTATCTACGCCTCGAGTGTGGATGGCTCAAGCATCCTTGTGGCACAG |

FIG. 4B

```
449  L  D  E  R  T  F  S  V  L  R  H  I  N  T  T  Y  P  K  S  K  A  G  N  A  F  I  A  Q  G  I
1533 CTGGACGAGAGGACATTCTCTGTGCTGCGCACATCAATACCACACATACCCAAGTCCAAGGCTGGCAATGCCTTCATAGCTCAAGGGATC

479  L  Y  V  T  D  T  K  D  T  R  V  T  F  A  F  D  L  L  R  G  K  Q  I  N  A  N  F  G  L  R
1623 CTCTATGTCACGGACACCAAAGATACAAGGGTCACGTTTGCCTTTGATTGTTACGAGGAAGCAGATCAATGCAAACTTCGGTCTCAGA

509  M  S  Q  S  V  L  A  M  L  S  Y  N  M  R  D  Q  H  L  Y  S  W  E  D  G  H  L  M  L  Y  P
1713 ATGTCACAGTCTGTTCTTGCCATGTTGTCGTACAATATGAGAGACCAGCATTTGTACTCGTGGGAAGACGGCCACCTGATGCTCTATCCT

539  V  H  F  S  S  T  A  P  S  Q  R  (SEQ ID NO:6)
1803 GTGCACTTTTCGTCAACAGCACCCCCTCCCATTATGCACCACACATTTCTGGGGTTTGACCAAG

1893 CCCAACGGAAAGAAGCCTGTAAAGGATATCCAGAGACTCTGGGCTCTTGTGCATGTGCAAGTCCCCCTG

1983 TAAGCCCAGGTTAGCTAGAGGCTGGAAGTTGAAATGGATAACATCTGGTGACCCTTGGTCCCCTCTTCAAACTTAGCAAGTTAGTGCTCCCC

2073 CCTGACCCTTAGTGTCCCCATCAGTAATAATGAAACATCTGTGATTGACAGCATTCCTCCTACCTATATGAAGTTCTGTGATTCTTGCCT

2163 GGTTATATATTAGATTGCTTTCTGGTTTCTTTTTTTTTTTCCACACATGTAAATGAGTTTACCTGCAGCTTGAGGGGTGTGCCTATCAGTG

2253 ATGACGGACATTTGTTTGGTGTTTTAGGAAGATGCATTGTCTCTTATGGCTTCTAAAGTATTATATATTATCCATAATTGATATTTTCTC

2343 TGAATACGCACCTGCCACTACAGAATGATTATTGTTTCAGCTCCTAAGTACAAATCCAAAAAAAAAAAAAAAA (SEQ ID NO: 5)
```

FIG. 4C

```
                    M  T  R  A  A  E  R  G  Q  G  A  T  G  W  G  L  R
  1   TCAGTGCTGCCCTGAGCCGCCCGGCCTGAGCACGCAGACATGACCCGAGCCGCCGAGAGAGGCCAAGGGCTACAGGGCTGGGGCTGCGC
  1

18     G  A  L  V  A  I  A  L  L  S  A  L  N  A  A  G  T  V  F  V  L  C  Q  W  R  G  L  S  A  A
 91   GGGCGCCCTGGTGGCCATAGCGCTGCTGTCCGCACTGAACGCCGCGGGCACCGTGTTCGTGCTCTGCCAGTGGCGGGGTTAAGCGGCGCG

48     L  R  A  L  E  A  Q  R  G  R  E  Q  R  E  D  S  A  L  R  A  F  L  A  E  L  S  R  A  P  G
181   CTACGGGGCGCTGGAGGCTCAACAGCGGCCGAGAGAGCAGCGGGAGGACAGCGCCCTTCTGGCCGAATTGAGTCGTGCGCCGGGC

78     R  V  P  E  P  S  Q  D  P  M  S  A  A  R  N  K  R  S  H  N  G  E  P  A  S  H  I  R  A  E
271   CGGGTCCCCGAACCATCCCAGGACCCCATGAGCGCCGCAGCGCAACAAGCGCAGCCTGCCTCACACATCCGTGCCGAG

108     S  Q  D  M  M  M  M  T  Y  S  M  V  P  I  R  V  M  I  D  L  C  N  S  T  Q  G  I  C  L
361   AGCCAGGACATGATGATGATGACCTACTCCATGGTGCCGATTCGAGTGATGATAGACCTGTGCAACAGTACCCAGGGCATCTGCCTC

138     T  G  P  P  G  P  P  P  G  A  G  G  L  P  G  H  N  G  S  D  G  Q  P  G  L  Q  G  P
451   ACAGGACCACCCGGGCCACCACCAGGAGCCGGGGGTTACCAGGCCACAATGACAGATCAGATGAACCTGGTCTCCAGGCCCA

168     K  G  E  K  G  A  I  G  K  R  G  K  M  G  L  P  G  A  T  G  N  P  G  E  K  G  E  K  G  D
541   AAAGGAGAAAAAGGAGCAATTGGCAAGAGAGGAAAAATGGGGTTACCTGAGCACCGGAAATCCAGGGGAAAAGGGAGAAAAGGGAGAT
```

FIG. 5A

```
198  A  E  L  G  L  P  G  N  E  G  P  P  G  Q  K  G  D  K  G  D  V  S  N  D  V  L
631  GCTGGTGAACTGGGTCTACCTGGGAATGAGGGCCCACCAGGACAAAGGTGACAAAGGAGACGTGTCCAATGACGTGCTT

228  L  T  G  A  K  G  D  Q  G  P  P  G  P  P  G  P  P  G  S  R  R  S  K  G
721  TTGACAGGTGCCAAAGGTGACCAAGGTCCCCCTGGCCCTCCAGGCCCTCCTGGAAGCAGAGATCCAAAGGC

258  P  R  P  P  N  V  F  N  S  Q  C  P  G  E  T  C  V  I  P  N  D  D  T  L  V  G  R  A  D  E
811  CCTCGGCCACCAAACGTGTTCAACAGCCAGTGTCCAGGGGAGACGTGTGTCATACCCAATGATGATACCTTGGTGGGAAGAGCTGATGAG

288  K  A  N  E  R  H  S  P  Q  T  E  S  M  I  T  S  I  G  N  P  A  Q  V  L  K  V  R  E  T  F
901  AAAGCAAATGAACGCCATTCACCACAAACAGAATCTATGATCACTTCCATTGGCAACCCAGCTCAAGTCCTAAAAGTGAGAGAGACTTTT

318  G  T  W  M  R  E  S  A  N  K  S  D  D  R  I  W  V  T  E  H  F  S  G  I  M  V  K  E  F  K
991  GGGACTTGGATGAGAGAGTCTGCTAACAAAAGTGACGACCGCATTTGGGTGACTGAACATTTTTCAGGTCATCATGGTGAAGGAGTTCAAA

348  D  L  P  A  L  L  N  S  S  F  T  L  L  H  P  Y  F  H  G  C  G  H  A  V  Y  N  N  S
1081 GACCTGCCGGCTCTCCTCAATAGCAGCTTCACACTCCTACTCCACCCTTATTTCCACGGCTGTGGCCACGCTGTTTACAACAACTCT

378  L  Y  Y  H  K  G  G  S  N  T  I  V  R  F  F  E  F  G  K  E  T  P  Q  T  L  K  L  E  N  A  L
1171 CTCTACTACCACAAAGGAGGCTCCAACACCATAGTGAGATTTGAATTTGGAAAGAGACACCTCAGACTCTGAAGCTTGAAAATGCTTTG

408  Y  F  D  R  K  Y  L  F  A  N  S  K  T  Y  F  N  I  A  V  D  E  K  G  I  W  I  I  Y  A  S
1261 TATTTTGATCGAAAATACCTCTTTGCAAATTCCAAGACTTACTTCAACATAGCAGTGGATGAGAAGGGCATCTGGATTATCTACGCTTCA
```

FIG. 5B

```
438   S  V  D  G  S  S  I  L  V  A  Q  L  D  E  R  T  F  S  V  T  Q  H  I  N  T  T  Y  P  K  S
1351  AGTGTGGATGGCTCAAGCATCCTTGTAGCACAGCTGGATGAGAGGACATTCTCCGTGACACAGCACATCAACACCACATACCCAAATCC

468   K  A  G  N  A  F  I  A  R  G  I  L  Y  V  T  D  T  K  D  T  R  V  T  F  A  P  D  L  L  G
1441  AAGGCTGGCAATGCCTTCATAGCCCGAGGGATCCTCTATGTCACAGACACCAAAGATACAGAGGGTCACGTTTGCCTTTGATTTGTTAGGA

498   G  K  Q  I  N  A  N  F  D  F  R  M  S  Q  S  V  L  A  M  L  S  Y  N  M  R  D  Q  H  L  Y
1531  GGAAAGCAAATCAATGCAAACTTTGATTTCAGAATGTCCCAGTCTGTTCTTGCCATGCTGTCATACAACATGAGAGATCAGCATTTATAC

528   S  W  E  D  G  H  L  M  L  Y  P  V  Q  F  L  S  A  A  S  S  Q  R    (SEQ ID NO:8)
1621  TCGTGGGAAGATGGCCATCTGATGCTCTATCCTGTGCAGTTTCTGTCAGCGGCATCAAGTCAGGTAGGGTTCCCTGGCTGTCTGCTC

1711  CCTCTCTATACTCCACATTGTCTAGGGTTTGGTCAAGCCCAACAGAAAGCTAGCCGGTAAAGGATACCCCAGGCACTCGGAGCGTAAGCCC

1801  ATGCCACGGGCTCTTGCACAAGCGGCGAGTCCGCTCTAAGCCAGTTGTTGAAATAGCTACAGATTAGAAATGATGTGAAGAGATCTG

1891  GTGACCCAGTATCCCTCCTCAAACTCAGCAAGTTAGCTCTCCCCGACCGTAGCGTCCCATAGTAATACGAAACATCTGGGTATGACT

1981  GACATTTCCTCTTCCTAGATGAAATTCTGTGATTCTTGCCTGATTATATATTAGAATGCTTTCTGGATTCTTTTTTTTTTTTCTCCACAT

2071  GTAAGTGAGCTTACTTGCAGTTGAGGGTGGCCTTTCAGTGATGACTTATTTGTATTTAGGGAAGGTGCACTGGCTCTTATGGCTTC

2161  TAAGGTTTTATTTATTCATAATTGTTATTTCTGAATATTCACCTACCACTACAGAATGATCATTGTTTCAGCTCCTAAACACAA

2251  ATCCAAGATTAATAAACAAACAAACAAACCATGAATAGACAGGCTCAGAACTCTAAATGGAGCTGCATCAGGCCCATAGGCCATCTAG
```

```
2341  ATGCTGTCAATTTCTGATCATATTGTTTGCTGCTGGGAAAGTAAACAGGATATCTTCAGTTCGTGTGTCCCTTTGCCAAGGCCATGGGAT
2431  TGTTATCAGAGTGTCAAACACTAAGTGGCCAATAATCTGTTAGAAGCATGAAACATGATGGTTTTTCAGAAAACAGGCACCATTTAT
2521  ACTTACTGTTTAGAATGAGGGAAGGCAATTGGCTCAAAGGCCAAAGTCAGCTTAGCTCTTTTTCCTGTACCATGCATCCCTGCACCTAA
2611  GAATCTCGCCTCAGAGTGTGTCAGCAGTGAAGCAGAGCCGCTCTGTAAATCCTGAACCATTACTGCCTGGCCTTTACAGAAAGAAAGAAA
2701  AAAAAATGTTGACCTTTCATCTAAGGACAGGGAACGAGCCAGTTCTCAGAAGGGCTCACTCCCTGAGTCTGGTTAGGCTTTTTACGGAC
2791  TGACAGGCAGCATTTTATGTGGCTTGGGCTTTGCAGAGGGAACAGGTAAGGACAGCATCAGATGGAGTAAGAGAACCTCCAGCCGTGGA
2881  GATGTTCACTCCCACGTGGTCTCCTCAAAGTTGGGTCTGTCCTCTTGGATAGCAAGGATCTAGTTTAATTGTTCCTACACAAGACCTTAAATA
2971  ACCACGTTCTCTGTCAACTCATTGAGTTCCAGGCAGGCCTGTGGAGCTTCAAAGAGGAAGCTGTGGATTTCATGCCCCCCCCCCCGG
3061  AATATAGAAAAGACACTACAGAAACTGTCCAGGAAAGACTGGCCAGCTGTTCCAAACCCACTCTCAGTGGGCCTGTGACCTGGTTTAGT
3151  TTTTTTAATAGAAGCATCTGAGGCTTGGGGTATGCATTTAACTATTTAACTTCCCTGCCCTCTGAAAGCACCCAGGCAGCTGTTACT
3241  GGTGAACCTGTTGAGTTCTCAAGGTCATGGGTCCCAAAGCTTCCCACTTCTTGATTAGATGGTTTTGCAGTTGGTCATCACAGCTTTTA
3331  AAGATATTCTCAGATTCATTTGTTGCAATGTAGAGTTCTAATGTTCATCAGTGTATCTAATGAATGGTATTGTTCTTTAAAGTATT
3421  CAAATATGAGATACTGTTCTGAGTGCGGTAGACCTGGATATACATATAATTCCATTTTTTATTACTTAGTAGCATTGCTGAGAATAGA
```

```
3511  TACAATACTAATTGTACATACAAGCAAATAGTTAGTTATTGAATTAGCTCATTTTAATATCTGAACTAGCAAATGTCTTAGCTTTCC
3601  TTTACTTTTTCTTTTCCTTTCTTTCCTTCCTTTCCTTTCTTTCCTTTCTTTTTTTTTTAAAGCAATGTCTTTGT
3691  GTTCGCCCAGACTTATCACAAACTCCTGCTTCAGATTCCTGGGTGCTGGACCACAGGCACAGTGGCTCTTTGACTCTCTTAATTGTGTG
3781  TAAGGAATCATACATATACTCACGATTAGAGAAAACTCGTCTGAAGATTTGTTTCTTTCATGGTTGTTTCTTTCTTTCTTTCTTT
3871  CTTTCTTTCGTTATAGTGTAGTGGGATTAGAACAAGTAAGGTTGACTGTGTTTAATGAATTATCTTTGCAGAAGGAAGGAATTAAGG
3961  TTTTATTCCTTTTCTTTGCAAACAGGACTTCATTCTATATCACTCAACACAGTGTTTCAGGCTCACTGCTAAAATAGTGTGCACATCTTAT
4051  ATTTTTAAATGAAGATAGTAATCAACCCTGCTGTCCACTTGTAGCCAAGCTGTTCTAAAAGCACTTCATTTATGTCTGTATGAAATCAAGT
4141  GATTCTCCAATTCCTCTGAAATCTAAATAATATAGAGTCCAACTAAGGTTGCAGAGTTGGCTCTGGCCTCAATGTATCATGTATCAGAGA
4231  ACAAAGCATTTCTATTAACTAATAATATAGAGTCCAACTAAGGTTGCAGAGTTGGCTCTGGCCTCAATGTATCATGTATCAGAGA
4321  ACGTGGTCCGGGCTGAATATTTCAGATCAATTCTGGTGCTGGGCTCATTCGAAGTCTTTTTACCCTCATAATCAAATGACAAGGTGAGAT
4411  GACAAATGAGGAAGCACAGTCCTTGAAAAGTCACTCGTCATCCTCCAAGCATAGCAAGTACCTTACTCAGGCATTGCCTGTCTGGTGTTG
4501  AGCTACCTGAAGGAAAAGTGGGGGGTGGAGCTCTTCAGTTTTCATCAGTGCTGTGGCCCTTATTTATCCATAATCTCATAATCTCCATCAGTAACCA
4591  CAGATTCTAAACGACCAGCAAGTTGTAAGTAGTAAATAAAATTATCCTGAAT (SEQ ID NO:7)
```

FIG. 5E

```
                M  V  D  L  C  N  S  T  K  G  I  C  L  T
  1   GACCATTGTGTATGATTCGTTGTTGACTGCAGCATCACTAGATCCGAGTGATGTTGACCTGTGCAACAGCACCAAGGGCATCTGCCTCACA

15    G  P  S  G  P  P  P  G  A  G  G  L  P  G  H  N  G  L  D  G  Q  P  G  P  P  Q  G  P  P  K
 93   GGACCTTCTGGACCACCACCAGGAGCCGGCGGGGTTGCCAGGACACAACGGATTGGATGGACAGCCTGGTCCTCAGGGCCCAAAA

45    G  E  K  G  A  N  G  K  R  G  K  M  G  I  P  G  A  A  G  N  P  G  E  R  G  E  K  G  D  H
183   GGAGAAAAAGGAGCAAATGGAAAAAGAGGAAAAATGGGGATACCTGGAGCTGCAGGAAATCCAGGGAGAAAGGGAGAAAAAGGGAGACCAT

75    G  E  L  G  L  Q  G  N  E  G  P  P  G  P  P  G  Q  K  G  E  K  G  D  V  S  N  D  V  L  L
273   GGTGAACTGGGCCTGCAGGGAAATGAGGGCCCACCAGGCCCACCCGGTCAAAAGGGTGACAAGGGAGATGTCTCAAACGACGTGCTCCTG

105    A  G  A  K  G  D  Q  G  P  P  G  P  P  G  P  P  G  G  S  R  R  A
363   GCAGGTGCCAAAGGTGACCAAGGCCCACCTGGCCCCCCAGGCCCTCCTGGAAGCAGAAGAGCC

135    K  G  P  R  Q  P  S  M  F  N  G  Q  C  P  G  E  T  C  A  I  P  N  D  D  T  L  V  G  K  A
453   AAAGGCCCCTCGGCAGCCAAGCCATGTTCAACGGCCAAGTGCCCAGGTGAGACTTGTGCCATACCAAATGATGATACCTTGGTTGGAAAAGCT

165    D  E  K  A  S  E  H  H  S  P  Q  A  E  S  M  I  T  S  I  G  N  P  V  Q  V  L  K  V  T  E
543   GATGAGAAAGCCAGTGAACACCATTCCCCACAAGCAGAATCCATGATCACTTCCATTGGAAACCCAGTGCAAGTACTGAAAGTGACAGAG
```

FIG. 6A

```
195  T  F  G  T  W  I  R  E  S  A  N  K  S  D  D  R  I  W  V  T  E  H  F  S  G  I  M  V  K  E
633  ACATTTGGACTTGGATAAGAGAGTCTGCTAACAAGAGTGATGACCGGATTTGGGTGACAGAGCATTTTCAGGCATCATGGTTAAGGAA

225  F  K  D  Q  P  S  L  L  N  G  S  Y  T  F  I  H  L  P  Y  Y  F  H  G  C  G  H  V  A  Y  N
723  TTCAAGGATCAGCCCCTCACTTCTGAATGGCAGTTACACGTTCATCCACTTCCATACTATTTCCATGGCTGTGGGCACGTTGCTTACAAC

255  N  S  L  Y  Y  H  K  G  G  S  N  T  L  V  R  F  E  F  G  Q  E  T  S  Q  T  L  K  L  E  N
813  AACTCTCTCTACTACCACAAAGGGGTTCTAATACCCTAGTGAGATTTGAATTTGGCCAGAGAACATCCCAAACTCTGAAGCTTGAAAAT

285  A  L  Y  F  D  R  K  Y  L  F  A  N  S  K  T  Y  F  N  L  A  V  D  E  K  G  L  W  I  I  Y
903  GCCTTGTATTTTGATCGAAAATACCTTTTTGCAAATTCCAAAACTTACTTCAATCTAGCTGTAGATGAAAAGGGCCTTTGGATTATCTAT

315  A  S  S  V  D  G  S  S  I  L  V  A  Q  L  D  E  R  T  F  S  V  V  Q  H  V  N  T  T  Y  P
993  GCGTCAAGTGTGGACGGCTCGAGCATTCTTGTAGCACAACTGGATGAGAGACATTCTCAGTGTTGTGCAACACGTCAATACCACGTACCCT

345  K  S  K  A  G  N  A  F  I  A  R  G  I  L  Y  V  T  D  T  K  D  M  R  V  T  F  A  F  D  L
1083 AAATCCAAGGCTGGCAACGCCTTCATTGCCCGAGGAATCCTCTATGTCACAGACACCAAAGATATGAGGGTCACATTTGCCTTTGATTTG

375  L  G  G  K  Q  I  N  A  N  F  D  L  R  T  S  Q  S  V  L  A  M  L  A  Y  N  M  R  D  Q  H
1173 TTAGGAGGGAAACAGATCAATGCAAACTTTGATTTAAGAACTTCCCAGTCTGTCTTGCCATGTTAGCATACAACATGAGAGATCAGCAT

405  L  Y  S  W  E  D  G  H  L  M  L  Y  P  V  Q  F  L  S  T  T  L  N  Q   (SEQ ID NO:10)
1263 TTATATTCATGGGAAGATGGCCATTTAATGCTTTATCCTGTGCAGTTTTTGTCAACTACTTTAAATCAGTGATGCTGCATTCGGCTCC
```

FIG. 6B

```
1353  CTTCAGCAAATTTCAGGGGTTTTCTGGGACCAGTTCTCCCCCAACAGGAAACTTGTTTTTTTAACGTCAGCCAGATATTTAGAAAATAAC
1443  CTCAAAAGTGTTTATATGGTCAGTGAGCCCCGCTTAGTGAAATAGCAACAGATTGGAAGTTGAAATGGCTGAGATTGGTGATCTCCCCA
1533  CAGCTGGCTCTGCAAGTTACCTCTCTTTCTCCCTTGGGCCCTTAGTTTCCCCATTGGTAATCTGAATTGGCTAAGATGATTGGGGAGATTTTCT
1623  GTACCTGTAGTAATTTGGTGATTCTTGGTGTGGCTGCTCTCTCACAACTTTTATGTATCTCGCTTCGTGTTTAGCTTTTTAGCCACAT
1713  GCTGACCAAATTTACCTTTGAGTTGATAAGTCCAGTGGCTTGAGTAGTGAATCCCCTCAGTGCTGACTTATATCTGTTCTTTGAAAAAAT
1803  GCATTGACTCTTAAGACATCTAAAGTATCACATTATCCATAATTTATTGCTTTTCTTTGCATCGCACCCTGCCACCACAGAATAACCAT
1893  TACCCTCAGCTGCTGATGGGCAGCTCTGAGATTAGCAAAAGCCAGGACAGCTACATGTTCAGGTTTTTTTTTTTTTTTCAATAG
1983  GCTATTTTTTTCTTTCTTATTTTAAATAGAGAGAGAGAGTCTTGCTATGTTCCCAGGCTGGTCTTGAACTCCTGGGGCTCAAGTGATCC
2073  TCCTGCCTTGGCCTCCCAAATGCTGGATTACAGGCATGTGCCTGGCCCAGGTTTCTTAATAAAACAGAATCATGATCTTCCAGGTTC
2163  CCCCCAGTTCTGATCATGTTGATTGTAGCTGTGTAAGTAGACGTTAAATCTGCTGAACCATGGGAACACTTTGCAGTGTTCAGAGAGAGAGGCTC
2253  TCCACTATCAAAGTACTAAATGCTGTGTAAGTAGACGTTAAATCTGCTGAACCATGGGAACACTTTGCAGTGTTCAGAGAAGAGAGGCTC
2343  CATTTGTGGCTATTATGTAGAACTGGGCCAGAGCCAGTCATTGCCTGTTTTTTAAATAAGGTTTTACTGAGCACAGCCACACTCATTT
2433  GTTTATGCAGTACGGCCTGACATTGCTTTTGCTCCTGCAACAGCAGAGTCGAGTCATTGCAACAAAGAGCATATGGCCCCACAGTGCCTAA
```

FIG. 6C

| | |
|---|---|
| 2523 | AATATTGACCAGCTACCCCTTTATGAAAAAGATTGCTGACTCCTGATAAAGAATATAAGTGAGCCTGATTCTTGAAAAAATCAGAACC |
| 2613 | AGAGCCTGTTTGTTTGTTCTAAACTAAGAAGCCCGCATAGAGGATGTGACTTGGCGTTTGAGTAGAGGGGAAGGCTGATAACGGGCGTAAGA |
| 2703 | TGAAGTGGCCCTCCACAAAGGCTGGTTAGGGACAGTTCTTTCTCTAACATAGTTTTAAAGGATGTGATCTGGTCCCCTTGGATGCCAGG |
| 2793 | AGAGAATCCAGTTGAACTTGCTCCTAAATGCTCTTAAATATTTCTGCCAACTCACTTCTTTAAACATCTTTCAGCCCAGCGCT |
| 2883 | GCCGGCCCCGGGAAGGGCCACTGCGAATAGAGAGGAAGTTCCTGGGGCTCTGCAGCCAGGAAGGGAACCAGGCAAATCTT |
| 2973 | ATGTAAAGATTTTCAGCAACTTGTCCCAATTGTGTGTATTCTGAAACTTTCTCTTTGGGACCAAATTCATTCTCAATGGCCCTGAGTT |
| 3063 | CAATATATTATTAACAGCAGTATTTAAAACTTAGGGTTGAACTGGGCATGTGGCACATAACTGCAATCCCAGCTACTTTGGAGGCAGG |
| 3153 | GATGGGGAGGATCACTTGAGGCCAGGATCTCAGGAGCCAGCAGGAGATCCCATCCTAAAAAATAAAATATAGAAAATAAAACTTAGG |
| 3243 | GGATATACAGATTTAAATATTCAAATCTCCCTGCTCCCCCTGAAAGTCCCCCAGGCAGCTGTTAATGACTGTTGTTTGTGTTCTCAATATG |
| 3333 | ATGGCTATTTGAAACTTCACCTACTTTTCATTAGATTGGTTGTACCATGTCACCTTAGCTTTTAAAGTATTTAAATATATGTTGCTGTTGCTG |
| 3423 | TCTAACAAAGAGTCTCATGTTCAAGATCAATATGTCTAATAAGCGCTGGTGTCCTTTTAAAGTATTTAAATATACATAATGTTATATAAGTAGCAACCAAAAGAGGTTGTT |
| 3513 | AATACAGGAGACCAGGTTAGGAATATAGTTTCATAATAATGTACATACAATAATTGTATATAAGTAGCAACCAAAAGAGGTTGTT |
| 3603 | AATTAGCACATATTCCTTTTAGAAAAATGTTTCAGAAACCTCAGTCTTGATATCTGAGCTATCTGGGCTCCCTACTTGTGAGTAAGGA |

FIG. 6D

```
3693   TCATGCTCACCACTGGAGAAGCTTACACCGGGACTTTTTTTCTTTTTTTTTGCTATGACAGAGTAATGCTAACGTAAGGACA
3783   ACTGAGTTTGATCAGTGTTTAATCGCAGTGGGTAATCTTATCTGATTGTCTTTAAAGTGAAAAGGATTAAGATTTTATTCTTTCTTGTA
3873   AACATTACTTGATTTTTAAAGAAGTTTGGGCTAAAATAGAGTATACAACTGAATGTTTTTAAGTCAAGATACTGTTTTAGG
3963   AGTTTACCCCTCTCATTTATAACCAAAGTTGCTCTAAAACACTTTCCAAATATCTGCACTTCTGATGTCAGAATCAAACCAGATAATTCTC
4053   TAATTCTTCTTTAATCTAAAGTAGATAGCTTCCCACTGGAAAGTAAACAAAACCATCCCTCCCAACCTCAAAGCTAGCCACACTCTATT
4143   TCAAGGCATTTCTTTCAGCTGATAAGGTGTCCCTCCGAAGCCAAGTAGGTGGTTCTGGTCTCCAAGTATCGTTAAGCACAGGTGCTATG
4233   ACAGAAAAGTTCTGGGGTGGAAGTTTAAGATGAGGAGTTCTGATCTTAGGCATCTTAACAGTCACAAGTGAAAAGTCAAATGAAACA
4323   GTACAATTCTTGATGAGTGAGGTGTCATCTTCCAACCACACAGAGGACGTTTGGCTATGATCATCTGATGGCAAGTGAAGGAGAAATGA
4413   GTGATAGGGCTTTGCGTTTCATCAGATGAATGTCTTTTTGGTTGTAATTAACAAGTCAAATAAATAATCATTGCTGAGCACAATCACCAAAAAAAAAA
4503   CAACAAATGAATAACGATGAATGTCTTTTTGGTTGTAATTAACAAGTCAAATAAATAATCATTGCTGAGCACAATCACCAAAAAAAAAA
4593   AAAAAAAAAAAAAAAAAAAAAAAAAAAAAAAAAAAAAAAAAAAAAAAAAAAAAAAAAAAAAAAAAAAACA (SEQ ID NO:9)
```

FIG. 6E

```
  1  M  A  R  G  A  E  G  G  R  G  D  A  G  W  G  L  R  G  A  L  A  A  V  A  L  L  S  A  L  N
  1 ATGGCCCGAGAGGCGCTGAGGGAGGCCGTGGGGACGCGGGTTGGGGCCTGCGTGGCCCTGGCCGTGGCCCTGCTCTCGGCGCTCAAC

31  A  A  G  T  V  F  A  L  C  Q  W  R  G  L  S  S  A  L  R  A  L  E  A  Q  R  G  R  E  Q  R
 91 GCTGCGGGCACGGTGTTCGCGCTGTGCCAGTGGCGCGGGCTGAGCTCGGCGCTGCGGGCTTTGGAGGCCCAGCGCGGGAGAGCAGCGC
```

FIG. 7A

```
 61  E D S A L R S F L A E L S R A P R G A S A P P Q D P A S S A
181  GAGGACAGTGCCCTGCGCTCCTTCCTGGCCGAGTTGAGCCGCGCGCGGGCGTCCGCGACCCCAGCTCAGCT

91  R N K R S H S G E P A P H I R A E S H D M L M M T Y S M V
271  CGCAACAAGCGCAGCCACAGCGGCGAGCCCGCGCCCGAGAGCCATGACATGCTGATGATGACCTACTCCATGGTG

121  P I R V M V D L C N S T K G I C L T G P S G P P P G P A G
361  CCGATCCGAGTGATGGTGGACCTGTGCAACAGCACCAAGGGCATCTGCCTCACAGGACCCTCTGGACCCCCCGGGAGCCGGC

151  G L P G H N G L D G Q P G P Q G P K G E K G A N G K R G K M
451  GGGTTGCCAGGACACAACGGATTGGATGGACAGCCTGGTCCTCAGGGCCCCAAAGGAGAAAAAGGAGCAAATGAAAAGAGGAAAAATG

181  G I P G A A G N P G E R G E K G D H G E L G L Q G N E G P P
541  GGGATACCTGGAGCTGCAGGAAATCCAGGGGAAAGGGAGAAAAGGGGACCATGGCCTGCAGGGAAATGAGGGCCCACCA

211  G Q K G E K G D V S N D V L L A G A K G D Q G P P G P
631  GGGCAGAAGGGAGAAAAGGGTGACAAAGGAGATGTGTCCAATGACGTGCTCCTGGCAGGTGCCAAAGGTGACCAAGGCCCACCCGGTCCA

241  P G P P G P P P G S R R A K G P R Q P P S M F N G Q
721  CCTGGGCCCCCCGGGCCCCCTCCAGGTCCCTCCAGGAGCCGCAGCCAAGCCCTCGGCAGCCAAGCATGTTCAACGGCCAG

271  C P G E T C A I P N D D T L V G K A D E K A S E H H S P Q A
811  TGCCCAGGTGAGACTTGTGCCATACCAAATGATGATACCTTGGTTGGAAAAGCTGATGAGAAAGCCAGTGAACACCATTCCCCACAAGCA
```

FIG. 7B

```
301  E  S  M  I  T  S  I  G  N  P  V  Q  V  L  K  V  T  E  T  F  G  T  W  I  R  E  S  A  N  K
901  GAATCCATGATCACTTCCATTGGAAACCCAGTGCAAGTACTGAAAGTGACAGAGACATTGGGACTTGGATAAGAGAGTCTGCTAACAAG

331  S  D  D  R  I  W  V  T  E  H  F  S  G  I  M  V  K  E  F  K  D  Q  P  S  L  L  N  G  S  Y
991  AGTGATGACCGGATTTGGGTGACAGAGCATTTTTCAGGCATCATGGTTAAGGAATTCAAGGATCAGCCCTCACTTCTGAATGGCAGTTAC

361  T  F  I  H  L  P  Y  Y  F  H  G  C  G  H  V  A  Y  N  N  S  L  Y  Y  H  K  G  G  S  N  T
1081 ACGTTCATCCACCTTCCATACTATTTCCATGGCTGTGGGCACGTTGCTTACAACAACTCTCTACTACCACAAAGGGGTTCTAATACC

391  L  V  R  F  E  F  G  Q  E  T  S  Q  T  L  K  L  E  N  A  L  Y  F  D  R  K  Y  L  F  A  N
1171 CTAGTGAGATTTGAATTTGGCCAGGAAACATCCCAAACTCTGAAGCTTGAAAATGCCTTGTATTTTGATCGAAATACCTTTTTGCAAAT

421  S  K  T  Y  F  N  L  A  V  D  E  K  G  L  W  I  I  Y  A  S  S  V  D  G  S  S  I  L  V  A
1261 TCCAAAACTTACTTCAATCTAGCTGTAGATGAAAAGGGCCTTTGGATTATCTATGCGTCAAGTGTGGACGGCTCGAGCATTCTTGTAGCA

451  Q  L  D  E  R  T  F  S  V  V  Q  H  V  N  T  T  Y  P  K  S  K  A  G  N  A  F  I  A  R  G
1351 CAACTGGATGAGAGGACATTCTCAGTGGTGCAACACGTCAATACCACGTACCCAAATCCAAGGCTGGCAACGCCTTCATTGCCCGAGGA

481  I  L  Y  V  T  D  T  K  D  M  R  V  T  F  A  F  D  L  L  G  G  K  Q  I  N  A  N  F  D  L
1441 ATCCTCTATGTCACAGACACCAAAGATATGAGGGTCACATTTGCCTTTGATTGTTAGGAGGAAACAGATCAATGCAAACTTTGATTTA

511  R  T  S  Q  S  V  L  A  M  L  A  Y  N  M  R  D  Q  H  L  Y  S  W  E  D  G  H  L  M  L  Y
1531 AGAACTTCCCAGTCTGTTCTTGCCATGTTAGCATACAACATGAGAGATCAGCATTTATATTCATGGGAAGATGGCCATTTAATGCTTTAT
```

FIG. 7C

```
541        P  V  Q  F  L  S  T  T  L  N  Q    (SEQ ID NO:12)
1621  CCTGTGCAGTTTTTGTCAACTACCTTAAATCAGTGATGTGCTGGCTCCCTTCAGCAAATTTCAGGGGTTTCTGGGACCAGTTC
1711  TCCCCCAACAGGAAACTTGTTTTTTTTAACGTCAGCCAGATATTTAGAAAATAACCTCAAAGTGTTTATATGGTCAGTGAGCCCCGCTTA
1801  GTGAAATAGCAACAGATTGGAAGTTGAAATCTGAGATTTGGTGATCTCCCCACAGCTGGCTCTGCAAGTTACCTCTTTCTCCTTGGGC
1891  CTTAGTTTCCCCATTGGTCTAAGATGATTGGGGAGATTTTCTGTACCTGTAGGTAATTGGTGTAATTGGTGTTCTTGGTGTGCTGC
1981  TCTTCTCACAACTTTTCTTTCTGCTTCTGTCGTTAGCTTTTTTTAGCCCACATGCTGACCTGACCAAATTTACCTTTGAGTTGATAAGTCCAGT
2071  GGCTTGAGTAGTGAATCCCTCAGTGCTGACTTATATCTGTTCTTTGCATCTGCACCTGCCACCACAGAATAACCATTACCCTCAGCTGCTGATTGGGCAGCTCTGAGATTAG
2161  TCCATAATTTATTGCTTTTTTTTTTTTTTTTTCAATAGGCTATTTTTTTTCTTATTTTAAATAGAGAGA
2251  CAAAAGCCAGGACAGCTACATGTTCAGGTTTTTTTTTTTCCCAGGCTGTCTTGAACTCCTGACCTCAAGTGATCCTCCTGCCTCCCAAAATGCTGGATTACAGGC
2341  GAGTCTTGCTATGTTCCCAGGCTGGTCTTGAACTCCTGACCTCAAGTGATCCTCCTGCCTCCCCAGTTCCCCCCAGTTTCTGATCATGTTGATTGTAGCTGTGG
2431  ATGTGTGCCTGGCCCAGGTTCTTAATAAAACAGAATCATGATCTTCCAGGTTCCCCCAGTTTCTGATCATGTTGATTGTAGCTGTGG
2521  ATCATGAACACTGAATCCCCAGATCACTCTGACTTCTTATGCTTCCTGTGATCCACTACAAAGTACTAAATGCTGTGTAAGTAGAC
2611  GTTAATCTGGCTGGAACCATGGGAAGCACTTTGCAGTGTTCAGAAGAGAGGCTCCATTTGTGGCTATTATGTAGAACTGGGCCAGAGCCA
```

FIG. 7D

```
2701  GTCCATTGCCTGTTTTTTAAATAAGGTTTTACTGAGCACAGCCACACTCATTGTTTATGCAGTACGGCCTGACATTGCTTTGCTCTG
2791  CAACAGCAGAGTCGAGTCATTGCAACAAAGAGCATATGGCCCCACAGTGCCTAAAATATTGACCAGTACCCCTTTATGGAAAAGATTG
2881  CTGACTCCTGATAAAGAATATAAAGTGAGCCTGATTCTTGAAAAAATCAGAACCAGAGCCTGTTTTGTTTGTTCTAAACTAAGAAGCCG
2971  CATAGGATGTGACTTGCGTTTGAGTAGAGGGAAGGCTGATAACGGCGTAAGATGAAGTGCCCTCCACAAAGGCTGGTTAGGGGACAG
3061  TTCTTTCTCTAACATAGTTTTAAAGGATGTGATCTGGTCCCCTTGATGCCAGGAGAGAATCCAGTGAACTTGCTCCTAAATGCTCTTA
3151  AATATGCATATTTCTGCCAACTCACTTCTTTAAACATCTTTCAGCCCAGCGCTGCGCCCCGGGAAGGGGAACCAGGGCAAATCTTATGTAAAGATTTTCAGCAACTTGTCCCAATTGTG
3241  GCTGGAAAAGTTCCCTGGGGCTTCTGCAGCCAGGAAGGGGAACCAGGGCAAATCTTATGTAAAGATTTTCAGCAACTTGTCCCAATTGTG
3331  TGTATTCTGAAACTTTCTCTTTGGGACCAAATTCATTCTCAATGGCCCTGAGTTCAATATATATTATTAACAGCAGTATTTTAAAACTTAGG
3421  GTTGAACTGGGCATGTGGCACATAACTGCAATCCCAGCTACTTTGGAGGCAGGAGGATCACTTGAGGCCAGGAGATCTCAGGACC
3511  AGCCTAGAGATCCCATCTCTAAAAATAAAATATAGAGAAAATAAACTTAGGGGATATACAGATTTAAATATTCAAATCTCCCTGCTC
3601  CCCTGAAAGTCCCCAGGCAGCTGTTAATGACTTGTTTGTTGTGTTCTCAATATGATGGCTATTGAAACTTCACCTACTTTCATTAGAT
3691  TGGTTGTACCCATGTCACCTTAGCTTTTAAAAATACTCTTTCAGATTCACGTTCTCTAACAAAGAGTCTCATGTTCAAGATCAATATGTC
3781  TAATAAGCGCTGGTGTCCTTTTAAAGTATTTAAATATATATATGTGCTGTTGCTGAATACAGGAGACCAGTTAGGAATATAGTTTCATAA
```

FIG. 7E

```
3871  TAATAGTAGTACATACAATACTAATTGTATATAAGGTAGCAACCAAAAGAGGTTGTTAATTAGCACATATTCCTTTTAGAAAAATGTTCAGA
3961  AACCTCAGTCTTGATATCTGGGCTCCCTTACTTGTGAGTAAGGGATCATGCTCACCACTGGAGAAGCTTACACCGGGACTT
4051  TTTTCTCTTTTTCTCTTTTTTTTGCTATGACAGAGTAATGCTAACGTAAGACAACTGAGTTTGATCAGTGTTAATCGCAGTGGGTAAT
4141  CTTATCTGATTGTCTTTAAAAGTGAAAAGGATTAAGATTTTATTCTTTCTGTAAACATTACTTGATTTTTAAAGAAGTTTTGGGCTCA
4231  CTGCTAAAATAGAGTATACAACTGAATGTTTTAAGTCAAGATACTGTTTTAGGAGTTTACCCCTCATTTATAACCAAAGTTGCTCTAA
4321  AACACTTTCCAAATATCTGCACTTCTGATGTCAGAATCAAACCAGATAATTCTCTAATTCTTCTTTAATCTAAAGTAGATAGCTTCCCAC
4411  TGGAAAGTAAACAAAACCATCCCCTCCAAACCTAGGCCACACTCTATTTCAAGGCATTTTCTTTCAGCTGATAAGGTGTCCTCC
4501  TGAAGCCAAGTAGGTGGTTCTGGTCTCCAAGTATCGTTAAGCACAGGTGCTATGACAGAGAAAAAGTTCTGGGGTGGAAGTTTAAGATGAG
4591  GAGTTCTGATCTTAGGCATCTTAACAGTCACAAGGTGAAAAGTCAAATGAAAACAGTACAATTCTTGATGAGTGAGGTGTCATCTTCCAAC
4681  CACCACAGAGGACGTTTGGCTATGATCATCTGATGGCAAGTGAAGGAGAAATGAGTGATAGGGCTTTGCGTTTTCATCCAGATGCTGTGG
4771  CCCTGTGTTTCACAGCATTAAGAGCCATAATTTCCAACCTGCACAGATCCTGAACAACAAATGAATAACGATGAATGTCTTTTTGGTTGT
4861  AATTTAACAAGTCAAATAAATAATCATTGCTGAGCACAATCACCAAAAAAAAAAAAAAAAAAAAAAAAAAAAAAAAAAAAAAAAAAAAAA
4951  AAAAAAGAAAAAAAAAAAAAAAAAAACA (SEQ ID NO:11)
```

FIG. 7F

```
1           15 16                30 31                45 46                60 61                75 76                90
1 rFP-1a     MTRAAERGQGATGWG      LRGALMAVALLSVLN      AVGTVFVLYQWRELS      AALRALEAQHGQEQR      EDSALRAFLAELSRA      PARVPEPPQDPMSAA       90
2 rGliomedin MTRAAERGQGATGWG      LRGALMAVALLSVLN      AVGTVFVLYQWRELS      AALRALEAQHGQEQR      EDSALRAFLAELSRA      PARVPEPPQDPMSAA       90
3 rFP-1b     MTRAAERGQGATGWG      LRGALMAVALLSVLN      AVGTVFVLYQ-----      ---------------      -R-------------      EDSALRAFLAELSRA      PARVPEPPQDPMSAA       72
4 mCRG-L2    MTRAAERGQGATGWG      LRGAIVAIALLSAIN      AAGTVFVLCQWRGLS      AALRALEAQRGREQR      EDSALRAFLAELSRA      PGRVPEPSQDPMSAA       90
5 hCRG-L2    ---------------      ---------------      ---------------      ---------------      ---------------      ---------------        0
6 hFP-1      MARGAEGGRGDAGWG      LRGALAAVALLSAIN      AAGTVPALCQWRGLS      SALRALEAQRGRGEQR     EDSALRSFLAELSRA      PRGASAPPQDPASSA       90

91                105 106              120 121              135 136              150 151              165 166              180
1 rFP-1a     RNKRSHGGEPASHIR      AESQDMMMMTYSMV       PIRVMIDLCNSTQGI      CLTGPGPPGPPGPAG      GLPGHNGSDGQPGLQ      GPKGEKGAVGKRGKM      180
2 rGliomedin RNKRSHGGEPASHIR      AESQDMMMMTYSMV       PIRVMIDLCNSTQGI      CLTGPGPPGPPGPAG      GLPGHNGSDGQPGLQ      GPKGEKGAVGKRGKM      180
3 rFP-1b     RNKRSHGGEPASHIR      AESQDMMMMTYSMV       PIRVMIDLCNSTQGI      CLTGPGPPGPPGPAG      GLPGHNGSDGQPGLQ      GPKGEKGAVGKRGKM      162
4 mCRG-L2    RNKRSHNGEPASHIR      AESQDMMMMTYSMV       PIRVMIDLCNSTQGI      CLTGPGPPGPPGPAG      GLPGHNGSDGQPGLQ      GPKGEKGAIGKRGKM      180
5 hCRG-L2    ---------------      ---MVDLCNSTKGI       CLTGPSGPPGPPGAG      GLPGHNGLDGQPGPQ      GPKGEKGANGKRGKM       56
6 hFP-1      RNKRSHGEPAPHIR       AESHDMLMMTYSMV       PIRVMVDLCNSTKGI      CLTGPSGPPGPPGAG      GLPGHNGLDGQPGPQ      GPKGEKGANGKRGKM      180

181               195 196              210 211              225 226              240 241              255 256              270
1 rFP-1a     GLPGATGNPGEKGEK      GDAGELGLPGNEGPP      GQKGDKGDKGDVSND      VLLTGAKGDQGPPGP      PGPPGPPGPPG---S      RRAKGPRQPNSFTNQ      267
2 rGliomedin GLPGATGNPGEKGEK      GDAGELGLPGNEGPP      GQKGDKGDKGDVSND      VLLTGAKGDQGPPGP      PGPPGPPGPPG---S      RRAKGPRQPNSFTNQ      267
3 rFP-1b     GLPGATGNPGEKGEK      GDAGELGLPGNEGPP      GQKGDKGDKGDVSND      VLLTGAKGDQGPPGP      PGPPGPPGPPG---S      RRAKGPRQPNSFTNQ      249
4 mCRG-L2    GLPGATGNPGEKGEK      GDAGELGLPGNEGPP      GQKGDKGDKGDVSND      VLLTGAKGDQGPPGP      PGPPGPPGPPG---S      RRSKGPRPPNVFNSQ      267
5 hCRG-L2    GIPGAAGNPGERGEK      GDHGELGLQGNEGPP      GQKGEKGDKGDVSND      VLLAGAKGDQGPPGP      PGPPGPPGPPGPPGS      RRAKGPRQPSMFNGQ      146
6 hFP-1      GIPGAAGNPGERGEK      GDHGELGLQGNEGPP      GQKGEKGDKGDVSND      VLLAGAKGDQGPPGP      PGPPGPPGPPGPPGS      RRAKGPRQPSMFNGQ      270
```

FIG. 8A

|   |     | 271        | 285 286    | 300 301    | 315 316    | 330 331    | 345 346    |     |
|---|-----|------------|------------|------------|------------|------------|------------|-----|
| 1 | rFP-1a     | CPGETCVIPNDDTLV | GRADEKVNERHSPQT | EPMITSIGNPAQVLK | VKETFGTWLRESANR | SDDRIWTEHFSGIM | VKEFEDLPALLNSSF | 357 |
| 2 | rGliomedin | CPGETCVIPNDDTLV | GRADEKVNERHSPQT | EPMITSIGNPAQVLK | VKETFGTWLRESANR | SDDRIWTEHFSGIM | VKEFEDLPALLNSSF | 357 |
| 3 | rFP-1b     | CPGETCVIPNDDTLV | GRADEKVNERHSPQT | EPMITSIGNPAQVLK | VKETFGTWLRESANR | SDDRIWTEHFSGIM | VKEFEDLPALLNSSF | 339 |
| 4 | mCRG-L2    | CPGETCVIPNDDTLV | GRADEKANERHSPQT | ESMITSIGNPAQVLK | VRETFGTWMRESANK | SDDRIWTEHFSGIM | VKEFKDLPALLNSSF | 357 |
| 5 | hCRG-L2    | CPGETCAIPNDDTLV | GKADEKASEHHSPQA | ESMITSIGNPVQVLK | VTETFGTWIRESANK | SDDRIWTEHFSGIM | VKEFKDQPSLLNGSY | 236 |
| 6 | hFP-1      | CPGETCAIPNDDTLV | GKADEKASEHHSPQA | ESMITSIGNPVQVLK | VTETFGTWIRESANK | SDDRIWTEHFSGIM | VKEFKDQPSLLNGSY | 360 |

|   |     | 361        | 375 376    | 390 391    | 405 406    | 420 421    | 435 436    |     |
|---|-----|------------|------------|------------|------------|------------|------------|-----|
| 1 | rFP-1a     | TLLHLPHYFHGCGHA | VYNNSLYYHKGGSNT | IVRFEFGKETPQTLK | LEDALYFDRKYLFAN | SKTYFNIAVDEKGIW | IIYASSVDGSSILVA | 447 |
| 2 | rGliomedin | TLLHLPHYFHGCGHA | VYNNSLYYHKGGSNT | IVRFEFGKETPQTLK | LEDALYFDRKYLFAN | SKTYFNIAVDEKGIW | IIYASSVDGSSILVA | 447 |
| 3 | rFP-1b     | TLLHLPHYFHGCGHA | VYNNSLYYHKGGSNT | IVRFEFGKETPQTLK | LEDALYFDRKYLFAN | SKTYFNIAVDEKGIW | IIYASSVDGSSILVA | 429 |
| 4 | mCRG-L2    | TLLHLPHYFHGCCHA | VYNNSLYYHKGGSNT | IVRFEFGKETPQTLK | LERNALYFDRKYLFAN | SKTYFNIAVDEKGIW | IIYASSVDGSSILVA | 447 |
| 5 | hCRG-L2    | TFIHLPYYFHGCGHV | AYNNSLYYHKGGSNT | LVRFEFGQETSQTLK | LERNALYFDRKYLFAN | SKTYFNLAVDEKGIW | IIYASSVDGSSILVA | 326 |
| 6 | hFP-1      | TFIHLPYYFHGCGHV | AYNNSLYYHKGGSNT | LVRFEFGQETSQTLK | LERNALYFDRKYLFAN | SKTYFNLAVDEKGIW | IIYASSVDGSSILVA | 450 |

|   |     | 451        | 465 466    | 480 481    | 495 496    | 510 511    | 525 526    |     |
|---|-----|------------|------------|------------|------------|------------|------------|-----|
| 1 | rFP-1a     | QLDERTFSVLQHINT | TYPKSKAGNAFIAQG | ILYVTDTKDTRVTFA | FDLLRGKQINANFGL | RMSQSVLAMLSYNMR | DQHLYSWEDGHLMLY | 537 |
| 2 | rGliomedin | QLDERTFSVLRHINT | TYPKSKAGNAFIAQG | ILYVTDTKDTRVTFA | FDLLRGKQINANFGL | RMSQSVLAMLSYNMR | DQHLYSWEDGHLMLY | 537 |
| 3 | rFP-1b     | QLDERTFSVLQHINT | TYPKSKAGNAFIAQG | ILYVTDTKDTRVTFA | FDLLRGKQINANFGL | RMSQSVLAMLSYNMR | DQHLYSWEDGHLMLY | 519 |
| 4 | mCRG-L2    | QLDERTFSVLQHINT | TYPKSKAGNAFIARG | ILYVTDTKDTRVTFA | FDLLGGKQINANFDF | RMSQSVLAMLSYNMR | DQHLYSWEDGHLMLY | 537 |
| 5 | hCRG-L2    | QLDERTFSVVQHVNT | TYPKSKAGNAFIARG | ILYVTDTKDMRVTFA | FDLLGGKQINANFDL | RTSQSVLAMLAVNMR | DQHLYSWEDGHLMLY | 416 |
| 6 | hFP-1      | QLDERTFSVVQHVNT | TYPKSKAGNAFIARG | ILYVTDTKDMRVTFA | FDLLGGKQINANFDL | RTSQSVLAMLAVNMR | DQHLYSWEDGHLMLY | 540 |

FIG. 8B

```
                541
1 rFP-1a        PVHFSSTAPSQR    549 - SEQ ID NO: 2
2 rGliomedin   PVHFSSTAPSQR    549 - SEQ ID NO: 4
3 rFP-1b        PVHFSSTAPSQR    531 - SEQ ID NO: 6
4 mCRG-L2       PVQFLSAASSQR    549 - SEQ ID NO: 8
5 hCRG-L2       PVQFLSTTLNQ-    427 - SEQ ID NO: 10
6 hFP-1         PVQFLSTTLNQ-    551 - SEQ ID NO: 12
```

1. rat FP-1a
2. rat gliomedin (AAP22419)
3. rat FP-1b
4. mouse CRG-L2 (NP_796324)
5. human likely ortholog of mouse cancer related gene - liver 2 (CRG-L2): (NP_861454)
6. hypothetical human FP-1 full length

FIG. 8C

|   | 1 | 15 | 16 | 30 | 31 | 45 | 46 | 60 | 61 | 75 | 76 | 90 |   |
|---|---|---|---|---|---|---|---|---|---|---|---|---|---|
| 1 FP-1a | ATGACCCGAGCCGCA | GAGCGAGGCCAAGGG | GCTACAGGCTGGGGA | CTGCGAGGCGCCCTG | ATGGCCGTGGGCGCTG | CTGTCAGTGCTGAAC | 90 |
| 2 rGliomedin | ATGACCCGAGCCGCA | GAGCGAGGCCAAGGG | GCTACAGGCTGGGGA | CTGCGAGGCGCCCTG | ATGGCCGTGGGCGCTG | CTGTCAGTGCTGAAC | 90 |
| 3 hFP-1 | ATGCCCGAGGCGCT | GAGGGAGGCCCGTGGG | GACGCGGGTTGGGGC | CTGCGTGGCGCCCTG | GCGGCCGTGGGCGCTG | CTCTCGGCGCTCAAC | 90 |
| 4 hCrgl2 | --------------- | --------------- | --------------- | --------------- | --------------- | --------------- | 0 |
| 5 FP-1b | ATGACCCGAGCCGCA | GAGCGAGGCCAAGGG | GCTACAGGCTGGGGA | CTGCGAGGCGCCCTG | ATGGCCGTGGGCGCTG | CTGTCAGTGCTGAAC | 90 |
| 6 mCRG-L2 | ATGACCCGAGCCGCA | GAGCGAGGCCAAGGG | GCTACAGGCTGGGGA | CTGCCGGGGCCCCTG | GTGGCCATAGCGCTG | CTGTCCGCACTGAAC | 90 |

```
1 FP-1a       GCCGTGGGCACCGTG TTCGTGCTGCTGTACCAG TGGGGGGAGCTGAGC GCGGGCGCTGCGGGCA CTGGAGGCGCAACAC GGCCAGGAGCAGCGC   180
2 rGliomedin  GCCGTGGGCACCGTG TTCGTGCTGCTGTACCAG TGGGCGCGAGCTGAGC GCGGGCGCTGCGGGCA CTGGAGGCGCAACAC GGCCAGGAGCAGCGC   180
3 hFP-1       GCTGCGGGGCACCGTG TTCGGCGCTGTGCCAG TGGCGCGGGGCTGAGC GCGGGCGCTGCGGGCA TTTGGAGGCGCAGCGG GGCCGGGAGCAGCGC   180
4 hCrgl2      --------------- ------------------ --------------- ---------------- --------------- ---------------     0
5 FP-1b       GCCCGTGGGCACCGTG TTCGTGCTGCTGTACCAG --------------- ---------------- --------------- ----CAGGCGC       126
6 mCRG-L2     GCCGCGGGGCACCGTG TTCGTGCTGCTGTGCCAG TGGCGGGGGGTTAAGC GCGGGCGCTACGGGCG CTGGAGGCTCAACGC GGCCGAGAGCAGCGC   180

181                195 196              210 211              225 226             240 241              255 256              270
1 FP-1a       GAGGACAGCGCCCTA CGGCGCCTTTCTAGCT GAATTAAGTCGTGCG GAACCACCCCAGGAC CCCATGAGTGCAGCG   270
2 rGliomedin  GAGGACAGCGCCCTA CGGCGCCTTTCTAGCT GAATTAAGTCGTGCG CCAGCCCGAGTCCCC GAACCACCCCAGGAC CCCATGAGTGCAGCG   270
3 hFP-1       GAGGACAGTGCCCTG CGTCCTCTTCCTGGCC GAGTTGAGCCGCGCG CCAGCCCGAGTCCCC CCGGGGCGGGGGTCC GCACCACCCCAAGAC CCGGCCAGTCAGCT   270
4 hCrgl2      --------------- ------------------ --------------- ---------------- --------------- ---------------     0
5 FP-1b       GAGGACAGCGCCCTA CGGCGCCTTTCTAGCT GAATTAAGTCGTGCG CCAGCCCGAGTCCCC CCGGCGGCGGGGGTCC GAACCACCCCAGGAC CCCATGAGTGCAGCG   216
6 mCRG-L2     GAGGACAGCGCCCTA CGGCGCCTTTCTGGCC GAATTGAGTCGTGCG CCGGGCCCGGGTCGGG GAACCATCCCAGGAC CCCATGAGCGCAGCG   270

271                285 286              300 301              315 316              330 331              345 346              360
1 FP-1a       CGCAATAAGCGCAGC CACGGCGGGCGAGCC GGGTCACACATCCGC GCGGAGAGCCAGGAC ATGATGATGATGATG ACCTACAGCATGGTG   360
2 rGliomedin  CGCAATAAGCGCAGC CACGGCGGGCGAGCC GGGTCACACATCCGC GCGGAGAGCCAGGAC ATGATGATGATGATG ACCTACAGCATGGTG   360
3 hFP-1       CGCAACAAGGCGCAGC CACAGCGGGCGAGCC GGCCGCCGCATATCCGC GCCGAGAGCCATGAC ATGCTGATGATGATG ACCTACTCCATGGTG   360
4 hCrgl2      --------------- ---------------- --------------- ---------------- --------------- ---------------     0
5 FP-1b       CGCAATAAGCGCAGC CACGGCGGGCGAGCCT GGGTCACACATCCGC GCCGAGAGCCAGGAC --------------- ACCTACAGCATGGTG   306
6 mCRG-L2     CGCAACAAGGCGCAGC CACAACGGCGAGCCGT GGGTCACACATCCGT GCCGAGAGCCAGGAC ATGATGATGATGATG ACCTACTCCATGGTG   360
```

|   | 361 | 375 376 | 390 391 | 405 406 | 420 421 | 435 436 | 450 |   |
|---|---|---|---|---|---|---|---|---|
| 1 FP-1a | CCGATCCGGGTGATG | ATAGACCTGTGCAAC | AGCACCCAGGGCATC | TGCCTTACAGGACCA | CCGGGCCCACCAGGA | CCTCCAGGAGCTGGT | 450 |
| 2 rGliomedin | CCGATCCGGGTGATG | ATAGACCTGTGCAAC | AGCACCCAGGGCATC | TGCCTTACAGGACCA | CCGGGCCCACCAGGA | CCTCCAGGAGCTGGT | 450 |
| 3 hFP-1 | CCGATCCGAGTGATG | GTGGACCTGTGCAAC | AGCACCAAGGGCATC | TCTGGACCACCAGGA | CCTCCGGGAGCCGGC | 450 |
| 4 hCrgl2 | ------ATG | GTGGACCTGTGCAAC | AGCACCAAGGGCATC | TCTCCACAGGACCT | CCTCCGGGAGCCGGC | 78 |
| 5 FP-1b | CCGATCCGGGTGATG | ATAGACCTGTGCAAC | AGCACCCAGGGCATC | TGCCTTACAGGACCA | CCGGGCCCACCAGGA | CCTCCAGGAGCTGGT | 396 |
| 6 mCRG-L2 | CCGATTCGAGTGATG | ATAGACCTGTGCAAC | AGTACCCAGGGCATC | TGCCTTACAGGACCA | CCGGGCCCACCAGGA | CCTCCAGGAGCCGGC | 450 |

|   | 451 | 465 466 | 480 481 | 495 496 | 510 511 | 525 526 | 540 |   |
|---|---|---|---|---|---|---|---|---|
| 1 FP-1a | GGGTTACCAGGCCAC | AATGGATCAGATGGA | CAGCCTGGTCTCCAG | GGCCCAAAAGGAGAA | AAAGGAGCAGTTGGG | AAGAGAGGAAAAATG | 540 |
| 2 rGliomedin | GGGTTACCAGGCCAC | AATGGATCAGATGGA | CAGCCTGGTCTCCAG | GGCCCAAAAGGAGAA | AAAGGAGCAGTTGGG | AAGAGAGGAAAAATG | 540 |
| 3 hFP-1 | GGGTTGCCAGGACAC | AACGGATTGGATGGA | CAGCCTGGTCTTCAG | GGCCCAAAAGGAGAA | AAAGGAGCAAATGGA | AAAAGAGGAAAAATG | 540 |
| 4 hCrgl2 | GGGTTGCCAGGAGCT | GCAGGAAATCCAGGG | CAGCCTGGTCTTCAG | GGCCCAAAAGGAGAA | AAAGGAGCAAATGGA | AAAAGAGGAAAAATG | 168 |
| 5 FP-1b | GGGTTACCAGGCCAC | AATGGATCAGATGGA | CAGCCTGGTCTCCAG | GGCCCAAAAGGAGAA | AAAGGAGCAGTTGGG | AAGAGAGGAAAAATG | 486 |
| 6 mCRG-L2 | GGGTTACCAGGCCAC | AATGGATCAGATGGA | CAGCCTGGTCTCCAG | GGCCCAAAAGGAGAA | AAAGGAGCAATTGGC | AAGAGAGGAAAAATG | 540 |

|   | 541 | 555 556 | 570 571 | 585 586 | 600 601 | 615 616 | 630 |   |
|---|---|---|---|---|---|---|---|---|
| 1 FP-1a | GGGTTACCCTGGAGCC | ACAGGAAATCCAGGG | GAAAAGGGAGAGAAG | GGAGATGCTGGTGAA | CTGGGCCTACCTGGA | AATGAGGACCACCA | 630 |
| 2 rGliomedin | GGGTTACCCTGGAGCC | ACAGGAAATCCAGGG | GAAAAGGGAGAGAAG | GGAGATGCTGGTGAA | CTGGGCCTACCTGGA | AATGAGGACCACCA | 630 |
| 3 hFP-1 | GGGATACCTGGAGCT | GCAGGAAATCCAGGG | GAAAAGGGAGAGAAG | GGAGACCATGGTGAA | CTGGGCCTGCCTGGA | AATGAGGGCCCACCA | 630 |
| 4 hCrgl2 | GGGATACCTGGAGCT | GCAGGAAATCCAGGG | GAAAGGGAGAAAAG | GGAGACCATGGTGAA | CTGGGCCTGCCTGGA | AATGAGGGCCCACCA | 258 |
| 5 FP-1b | GGGTTACCCGGAGCC | ACAGGAAATCCAGGG | GAAAAGGGAGAGAAG | GGAGATGCTGGTGAA | CTGGGCCTACCTGGA | AATGAGGGACCACCA | 576 |
| 6 mCRG-L2 | GGGTTACCTGGAGCC | ACCGGAAATCCAGGG | GAAAAGGGAGAAAAG | GGAGATGCTGGTGAA | CTGGGTCTACCTGGA | AATGAGGGCCCACCA | 630 |

FIG. 9C

```
                  631         645 646                660 661                675 676                690 691                705 706                720
1 FP-1a           GGACAGAAAGGAGAC AAAGGAGAGACAAAGGA GATGTGTCCAATGAC GTGCTTTTGACAGGT GCCAAAGGTGACCAA GGGCCCCCTGGCCCA        720
2 rGliomedin      GGACAGAAAGGAGAA AAAGGAGAGACAAAGGA GATGTGTCCAATGAC GTGCTTTTGACAGGT GCCAAAGGTGACCAA GGGCCCCCTGGCCCA        720
3 hFP-1           GGGCAGAAGGGAGAA AAGGGTGACAAAGGA  GATGTGTCCAACGAC GTGCTCCTGGCAGGT GCCAAAGGTGACCAA GGCCCACCCGGTCCA        720
4 hCrgl2          GGGCAGAAGGGAGAA AAGGGTGACAAAGGA  GATGTGTCCAACGAC GTGCTCCTGGCAGGT GCCAAAGGTGACCAA GGCCCACCCGGTCCA        348
5 FP-1b           GGACAGAAAGGAGAC AAAGGAGAGACAAAGGA GATGTGTCCAATGAC GTGCTTTTGACAGGT GCCAAAGGTGACCAA GGGCCCCCTGGCCCA        666
6 mCRG-L2         GGGCAGAAGGTGAC  AAGGGAGAGACAAAGGA GACGTGTCCAATGAC GTGCTTTGACAGGT  GCCAAAGGTGACCAA GGTCCCCCTGGCCCC        720

721         735 736                750 751                765 766                780 781                795 796                810
1 FP-1a           CCTGGACCCCCAGGG CCTCCAGGCCCTTC-  --------         ---------       AGAAGAGCCAAAGGC CCTCGGCAGCCAAAT TCGTTCACCAACCAG        801
2 rGliomedin      CCTGGACCCCCAGGG CCTCCAGGCCCTCC-  --------         ---------       AGAAGAGCCAAAGGC CCTCGGCAGCCAAAT TCGTTCACCAACCAG        801
3 hFP-1           CCTGGGCCCCCAGGC CCTCCAGGTCCTCCA  ---------        ---------       AGAAGAGCCAAAGGC CCTCGGCAGCCAAGC ATGTTCAACGGCCAG        810
4 hCrgl2          CCTGGGCCCCCAGGC CCTCCAGGTCCTCCA  ---------        ---------       AGAAGAGCCAAAGGC CCTCGGCAGCCAAGC ATGTTCAACGGCCAG        438
5 FP-1b           CCTGGACCCCCAGGG CCTCCAGGCCCTTC-  --------         ---------       AGAAGAGCCAAAGGC CCTCGGCAGCCAAAT TCGTTCACCAACCAG        747
6 mCRG-L2         CCTGGACTTCCAGGG CCTCCAGGCCCTCC-  --------         ---------       AGAAGATCCAAAGGC CCTCCGGCCACCAAAC GTGTTCAACAGCCAG        801

811         825 826                840 841                855 856                870 871                885 886                900
1 FP-1a           TGTCCAGGGGAGACG TGTGTCATACCCAAT  GATGATACCTTGGTG GGGAGAGCTGATGAG AAAGTCAATGAGCGC CATTCTTCCACAAGCA        891
2 rGliomedin      TGCCCAGGTGAGACT TGTGTCATACCCAAAT GATGATACCTTGGTG GGGAGAGCTGATGAG AAAGTCAATGAGCGC CATTCTTCCACAAACA        891
3 hFP-1           TGCCCAGGTGAGACT TGTGTCATACCCAAT  GATGATACCTTGGTT GGAAAAGCTGATGAG AAAGCCAGTGAACAC CATTCCCCACAAGCA        900
4 hCrgl2          TGCCCAGGTGAGACT TGTGTCATACCCAAT  GATGATACCTTGGTT GGAAAAGCTGATGAG AAAGCCAGTGAACAC CATTCCCCACAAGCA        528
5 FP-1b           TGTCCAGGGGAGACT TGTGTCATACCCAAT  GATGATACCTTGGTG GGGAGAGCTGATGAG AAAGTCAATGAGCGC CATTCTTCCACAAGCA        837
6 mCRG-L2         TGTCCAGGGGAGACG TGTGTCATACCCAAT  GATGATACCTTGGTG GGGAGAGCTGATGAG AAAGCAAATGAACGC CATTCACCACAAACA        891
```

FIG. 9D

|   |            | 901        | 915 916    | 930 931    | 945 946    | 960 961    | 975 976    | 990         |      |
|---|------------|------------|------------|------------|------------|------------|------------|-------------|------|
| 1 | FP-1a      | GAACCCATGATCACG | TCCATTGGTAACCCG | GCCCAAGTCCTCAAA | GTGAAAGAGACTTTT | GGGACCTGGCTAAGA | GAGTCTGCTAACAGG |  | 981  |
| 2 | rGliomedin | GAACCCATGATCACG | TCCATTGGTAACCCG | GCCCAAGTCCTCAAG | GTGAAAGAGACTTTT | GGGACCTGGCTAAGA | GAGTCTGCTAACAGG |  | 981  |
| 3 | hFP-1      | GAATCCATGATCACT | TCCATTGGAAACCCA | GTGCAAGTACTGAAA | GTGACAGAGACATTT | GGGACTTGGATAAGA | GAGTCTGCTAACAAG |  | 990  |
| 4 | hCrgl2     | GAATCCATGATCACT | TCCATTGGAAACCCA | GTGCAAGTACTGAAA | GTGACAGAGACATTT | GGGACTTGGATAAGA | GAGTCTGCTAACAAG |  | 618  |
| 5 | FP-1b      | GAACCCATGATCACG | TCCATTGGTAACCCG | GCCCAAGTCCTCAAA | GTGAAAGAGACTTTT | GGGACCTGGCTAAGA | GAGTCTGCTAACAGG |  | 927  |
| 6 | mCRG-L2    | GAATCTATGATCACT | TCCATTGGCAACCCA | GCCCAAGTCCTAAAA | GTGAGAGAGACTTTT | GGGACTTGCATGAGA | GAGTCTGCTAACAAA |  | 981  |

|   |            | 991        | 1005 1006   | 1020 1021   | 1035 1036   | 1050 1051   | 1065 1066   | 1080 |      |
|---|------------|------------|-------------|-------------|-------------|-------------|-------------|------|------|
| 1 | FP-1a      | AGTGATGACCGCATT | TGGGTGACTGAACAT | TTTTCAGGCATGAACAT | GTGAAGGAGTTTGAA | GACCTGCCCGCCCTC | CTGAATAGCAGTTC |  | 1071 |
| 2 | rGliomedin | AGTGACGACCGCATT | TGGGTGACTGAACAT | TTTTCAGGCATGAACAT | GTGAAGGAGTTTGAA | GACCTGCCCGCCCTC | CTGAATAGCAGTTC |  | 1071 |
| 3 | hFP-1      | AGTGATGACCGGATT | TGGGTGACAGAGCAT | TTTTCAGGCATGAACAT | GTTAAGGAATTCAAG | GATCAGCCCTCACTT | CTGAATGGCAGTTAC |  | 1080 |
| 4 | hCrgl2     | AGTGATGACCGGATT | TGGGTGACAGAGAGCAT | TTTTCAGGCATGAACAT | GTTAAGGAATTCAAG | GATCAGCCCTCACTT | CTGAATGGCAGTTAC |  | 708  |
| 5 | FP-1b      | AGTGATGACCGCATT | TGGGTGACTGAACAT | TTTTCAGGCATGAACAT | GTGAAGGAGTTTGAA | GACCTGCCCGCCCTC | CTGAATAGCAGCTTC |  | 1017 |
| 6 | mCRG-L2    | AGTGACGACCGCATT | TGGGTGACTGAACAT | TTTTCAGGCATGAACAT | GTGAAGGAGTTCAA | GACCTGCCGCGGCT | CTCAATAGCAGCTTC |  | 1071 |

|   |            | 1081        | 1095 1096   | 1110 1111   | 1125 1126   | 1140 1141   | 1155 1156   | 1170 |      |
|---|------------|-------------|-------------|-------------|-------------|-------------|-------------|------|------|
| 1 | FP-1a      | ACCCTCCTCCACCTC | CCACATTACTTCCAT | GGCTGCGGGCACGCT | GTTTACAACAACTCT | CTCTACTACCACAAA | GGAGGCTCCAACACC |  | 1161 |
| 2 | rGliomedin | ACCCTCCTCCACCTC | CCACATTACTTCCAT | GGCTGCGGGCACGCT | GTTTACAACAACTCT | CTCTACTACCACAAA | GGAGGCTCCAACACC |  | 1161 |
| 3 | hFP-1      | ACGTTCATCCACCTT | CCATACTATTTCCAT | GGCTGTGGGCACGTT | GCTTACAACAACTCT | CTCTACTACCACAAA | GGGGGTTCTAATACC |  | 1170 |
| 4 | hCrgl2     | AGGTTCATCCACCTT | CCATACTATTTCCAT | GGCTGTGGGCACGTT | GCTTACAACAACTCT | CTCTACTACCACAAA | GGGGGTTCTAATACC |  | 798  |
| 5 | FP-1b      | ACCCTCCTCCACCTC | CCACATTACTTCCAT | GGCTGCGGGCACGCT | GTTTACAACAACTCT | CTCTACTACCACAAA | GGAGGCTCCAACACC |  | 1107 |
| 6 | mCRG-L2    | ACACTCCTCCACCTC | CCACATTATTCCAC | GGCTGTGGGCACGCT | GTTTACAACAACTCT | CTCTACTACCACAAA | GGAGGCTCCAACACC |  | 1161 |

FIG. 9E

```
                 1171       1185 1186       1200 1201       1215 1216       1230 1231       1245 1246       1260
1 FP-1a          ATAGTGAGATTTGAA TTTGGGAAAGAGACA CCTCAAACTCTGAAG CTTGAAGATGCTTTG TATTTTGATCGAAAA TACCTCTTTGCGAAT  1251
2 rGliomedin     ATAGTGAGATTTGAA TTTGGGAAAGAGACA CCTCAAACTCTGAAG CTTGAAGATGCTTTG TATTTTGATCGAAAA TACCTCTTTGCGAAT  1251
3 hFP-1          CTAGTGAGATTTGAA TTTGGCCAGGAAACA TCCCAAACTCTGAAG CTTGAAAATGCCTTG TATTTTGATCGAAAA TACCTTTTTGCAAAT  1260
4 hCrgl2         CTAGTGAGATTTGAA TTTGGCCAGGAAACA TCCCAAACTCTGAAG CTTGAAAATGCCTTG TATTTTGATCGAAAA TACCTTTTTGCAAAT   888
5 FP-1b          ATAGTGAGATTTGAA TTTGGGAAAGAGACA CCTCAAACTCTGAAG CTTGAAGATGCTTTG TATTTTGATCGAAAA TACCTCTTTGCGAAT  1197
6 mCRG-L2        ATAGTGAGATTTGAA TTTGGGAAAGAGACA CCTCAGACTCTGAAG CTGGAAAATGCTTTG TATTTTGATCGAAAA TACCTCTTTGCAAAT  1251

1261       1275 1276       1290 1291       1305 1306       1320 1321       1335 1336       1350
1 FP-1a          TCCAAGACTTACTTC AACATAGCAGTGGAT GAGAAGGGCCCTCTGG ATTATCTACGCCTCG AGTGTGGATGGCTCA AGCATCCTTGTGGCA  1341
2 rGliomedin     TCCAAGACTTACTTC AACATAGCAGTGGAT GAGAAGGGCCCTCTGG ATTATCTACGCCTCG AGTGTGGATGGCTCA AGCATCCTTGTGGCA  1341
3 hFP-1          TCCAAAACTTACTTC AATCTAGCTGTAGAT GAAAAGGGCCCTTTGG ATTATCTATGCGTCA AGTGTGGATGGCTCG AGCATTCTTGTAGCA  1350
4 hCrgl2         TCCAAAACTTACTTC AATCTAGCTGTAGAT GAAAAGGGCCCTTTGG ATTATCTATGCGTCA AGTGTGGATGGCTCG AGCATTCTTGTAGCA   978
5 FP-1b          TCCAAGACTTACTTC AACATAGCAGTGGAT GAGAAGGGCCCTCTGG ATTATCTACGCCTCG AGTGTGGATGGCTCA AGCATCCTTGTGGCA  1287
6 mCRG-L2        TCCAAGACTTACTTC AACATAGCAGTGGAT GAGAAGGGCATCTGG ATTATCTACGCTTCA AGTGTGGATGGCTCA AGCATCCTTGTAGCA  1341

1351       1365 1366       1380 1381       1395 1396       1410 1411       1425 1426       1440
1 FP-1a          CAGCTGGATGAGAGG ACATTCTCTGTGCTG CAGCACATCAATACC ACATACCCCAAGTCC AAGGCTGGCAATGCC TTCATAGCTCAAGGG  1431
2 rGliomedin     CAGCTGGACGAGAGG ACATTCTCTGTGCTG CGGCACATCAATACC ACATACCCCAAGTCC AAGGCTGGCAATGCC TTCATAGCTCAAGGG  1431
3 hFP-1          CAACTGGATGAGAGG ACATTCTCAGTGGTG CAACACGTCAATACC ACGTACCCTAAATCC AAGGCTGGCAACGCC TTCATTGCCCGAGGA  1440
4 hCrgl2         CAACTGGATGAGAGG ACATTCTCAGTGGTG CAACACGTCAATACC ACGTACCCTAAATCC AAGGCTGGCAACGCC TTCATTGCCCGAGGA  1068
5 FP-1b          CAGCTGGACGAGAGG ACATTCTCTGTGCTG CAGCACATCAATACC ACATACCCCAAGTCC AAGGCTGGCAATGCC TTCATAGCCCGAGGG  1377
6 mCRG-L2        CAGCTGGATGAGAGG ACATTCTCCGTGACA CAGCACATCAACACC ACATACCCCAAATCC AAGGCTGGCAATGCC TTCATAGCCCGAGGG  1431
```

FIG. 9F

```
              1441       1455 1456                1470 1471                1485 1486                1500 1501                1515 1516                1530
1 FP-1a       ATCCTCTATGTCACG    GACACCAAAGATACA       AGGGTCACGTTTGCC       TTTGATTTGTTACGA       GGGAAGCAGATCAAT       GCAAACTTCGGTCTC    1521
2 rGliomedin  ATCCTCTATGTCACG    GACACCAAAGATACA       AGGGTCACGTTTGCC       TTTGATTTGTTACGA       GGGAAGCAGATCAAT       GCAAACTTCGGTCTC    1521
3 hFP-1       ATCCTCTATGTCACA    GACACCAAAGATATG       AGGGTCACATTTGCC       TTTGATTTGTTAGGA       GGGAAACAGATCAAT       GCAAACTTTGATTTA    1530
4 hCrgl2      ATCCTCTATGTCACA    GACACCAAAGATATG       AGGGTCACATTTGCC       TTTGATTTGTTAGGA       GGGAAACAGATCAAT       GCAAACTTTGATTTA    1158
5 FP-1b       ATCCTCTATGTCACA    GACACCAAAGATACA       AGGGTCACGTTTGCC       TTTGATTTGTTACGA       GGGAAGCAGATCAAT       GCAAACTTCGGTCTC    1467
6 mCRG-L2     ATCCTCTATGTCACA    GACACCAAAGATACG       AGGGTCACGTTTGCC       TTTGATTTGTTAGGA       GGAAAGCAAATCAAT       GCAAACTTTGATTTC    1521

1531       1545 1546                1560 1561                1575 1576                1590 1591                1605 1606                1620
1 FP-1a       AGAATGTCACAGTCT    GTTCTTGCCATGTTG       TCGTACAATATGAGA       GACCAGCATTTGTAC       TCGTGGGAAGACGGC       CACCTGATGCTCTAT    1611
2 rGliomedin  AGAATGTCACAGTCT    GTTCTTGCCATGTTG       TCGTACAATATGAGA       GACCAGCATTTGTAC       TCGTGGGAAGACGGC       CACCTGATGCTCTAT    1611
3 hFP-1       AGAACTTCCCAGTCT    GTTCTTGCCATGTTA       GCATACAACATGAGA       GATCAGCATTTATAT       TCATGGGAAGATGGC       CATTAATGCTCTAT    1620
4 hCrgl2      AGAACTTCCCAGTCT    GTTCTTGCCATGTTA       GCATACAACATGAGA       GATCAGCATTTATAT       TCATGGGAAGATGGC       CATTAATGCTCTAT    1248
5 FP-1b       AGAATGTCACAGTCT    GTTCTTGCCATGTTG       TCGTACAATATGAGA       GACCAGCATTTGTAC       TCGTGGGAAGATGGC       CATTAATGCTTTAT    1557
6 mCRG-L2     AGAATGTCCCAGTCT    GTTCTTGCCATGTTG       TCATACAACATGAGA       GATCAGCATTTATAC       TCGTGGGAAGATGGC       CATCTGATGCTCTAT    1611

1621       1635 1636                1650 1651
1 FP-1a       CCTGTGCACTTTTCG    TCAACAGCACCCAGC       CAGCGGATAG           1650 - SEQ ID NO: 28
2 rGliomedin  CCTGTGCACTTTTCG    TCAACAGCACCCAGC       CAGCGGATAG           1650 - SEQ ID NO: 29
3 hFP-1       CCTGTGCAGTTTTTG    TCAACTACCTTTAAAT      CAGTGA---            1656 - SEQ ID NO: 30
4 hCrgl2      CCTGTGCAGTTTTTG    TCAACTACCTTTAAAT      CAGTGA---            1284 - SEQ ID NO: 31
5 FP-1b       CCTGTGCACTTTTCG    TCAACAGCACCCAGC       CAGCGGATAG           1596 - SEQ ID NO: 32
6 mCRG-L2     CCTGTGCAGTTTTCT    GTCAGCGGGCATCAAGT     CAGCGGTAG            1650 - SEQ ID NO: 33
```

FIG. 9G

```
1 rFP-1a/b  CLTGPPGPPGPPGAG  GLPGHNGSDGQPGLQ  GPKGEKGAVGKRGKM  GLPGATGNPGEKGEK  195/213
2 hFP-1     CLTGPSGPPGPPGAG  GLPGHNGLDGQPGPQ  GPKGEKGANGKRGKM  GIPGAAGNPGERGEK  195

SEQ ID NO: 34
1 rFP-1a/b  GDAGELGLPGNEGPP  GQKGEDKGDVSND   VLLTGAKGDQGPPGP  PGPPGPPGPPGPPGS---S  252/270
2 hFP-1     GDHGELGLQGNEGPP  GQKGEKGDKGDVSND  VLLAGAKGDQGPPGP  PGPPGPPGPPGPPGS      255

SEQ ID NO: 35
```

```
1 FP-1a/b  RRAKGPRQPNSFTNQ CPGETCVIPNDDTLV GRADEKVNERHSPQT EPMITSIGNPAQVLK   312/320
2 hFP-1    RRAKGPRQPSMFNGQ CPGETCAIPNDDTLV GKADEKASEHHSPQA ESMITSIGNPVQVLK   314
3 OLF      GILAGVGIPVLLAES QYGKS--------- --------------- ---------------   20
                                                  Region 1
1 FP-1a/b  VKETFGTWLRESAN- -RSDDRIWTEHFS- -GIMVKEFEDLPALL NSS-FTLLHLPHYFH   367/385
2 hFP-1    VTETFGTWIRESAN- -KSDDRIWTEHFS- -GIMVKEFKDQPSLL NGS-YTFIHLPYYFH   369
3 OLF      -----GAWMRDPLPN SMKAKRRWMDGFAD VSRVLREYSSMSDFL DGVNKIKYLPHAAS    75
                                                                Region 3
1 FP-1a/b  GCGHAVYNNSLYYHK GGSNTIVRFEFGKET PQTLKLEDALYFDRK YLFAN-SKTYFNIAV   426/444
2 hFP-1    GCGHVAYNNSLYYHK GGSNTLVRFEFGQET SQTLKLENALYFDRK YLFAN-SKTYFNLAV   429
3 OLF      GTGNVVYNGSLYFNK FGSHSIVRYELETGV QVKEELLPEAGYNDC FPYAWGGHSDIDLAV   135
                                                  Region 5
1 FP-1a/b  DEKGLWIIYASSVDG SSILVAQLDERTFSV LQHINTTYPKSKAGN AFIAQGILYVTDTKD   486/504
2 hFP-1    DEKGLWIIYASSVDG SSILVAQLDERTFSV VQHVNTTYPKSKAGN AFIARGILYVTDTKD   489
3 OLF      DENGLWVIYATEQNA GKIVISKLNPATLFV ENTWNTEYNKRSAAN AFMICGVLYVTKSAN   195
                                                  Region 7
1 FP-1a/b  ---TRVTFAFDLLRG KQINANFGLRMSQSV LAMLSYNMRDQHLYS WEDGHLMLYPVHFSS   543/561
2 hFP-1    ---MRVTFAFDLLGG KQINANFDLRTSQSV LAMLAYNMRDQHLYS WEDGHLMLYPVQFLS   546
3 OLF      SLGTKITYAYDTNTG KTIPLDIPFYNPYQY ISMLDYNPLDRKLYA WDNGHLLSYDIRLEE   255
                                                  Region 9
```

SEQ ID NO: 36
                                                                    SEQ ID NO: 37
                                                                    SEQ ID NO: 38

FIG. 10C

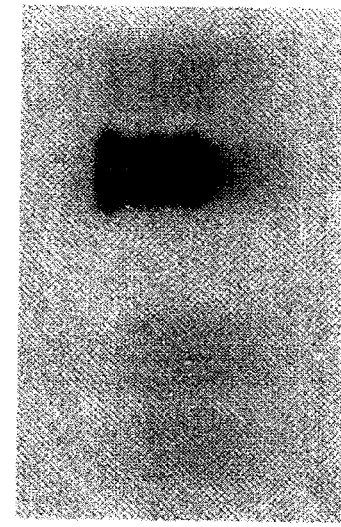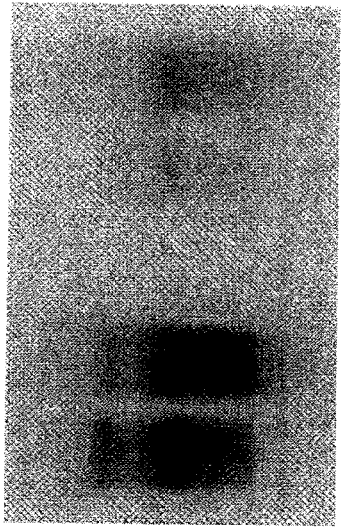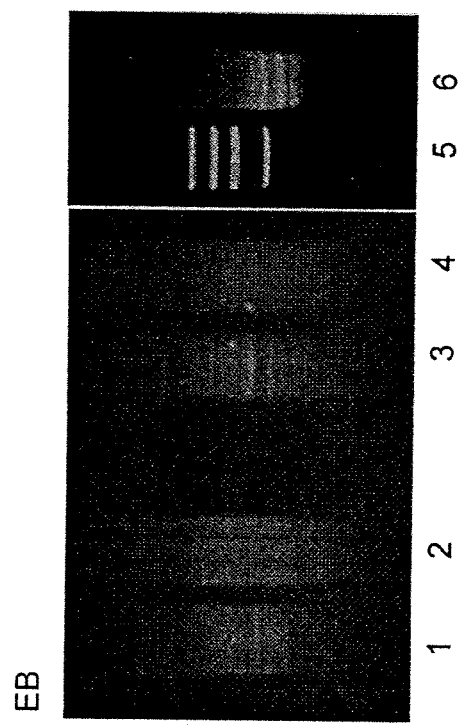
FIG. 11A  FIG. 11B  FIG. 11C  FIG. 11D  FIG. 11E

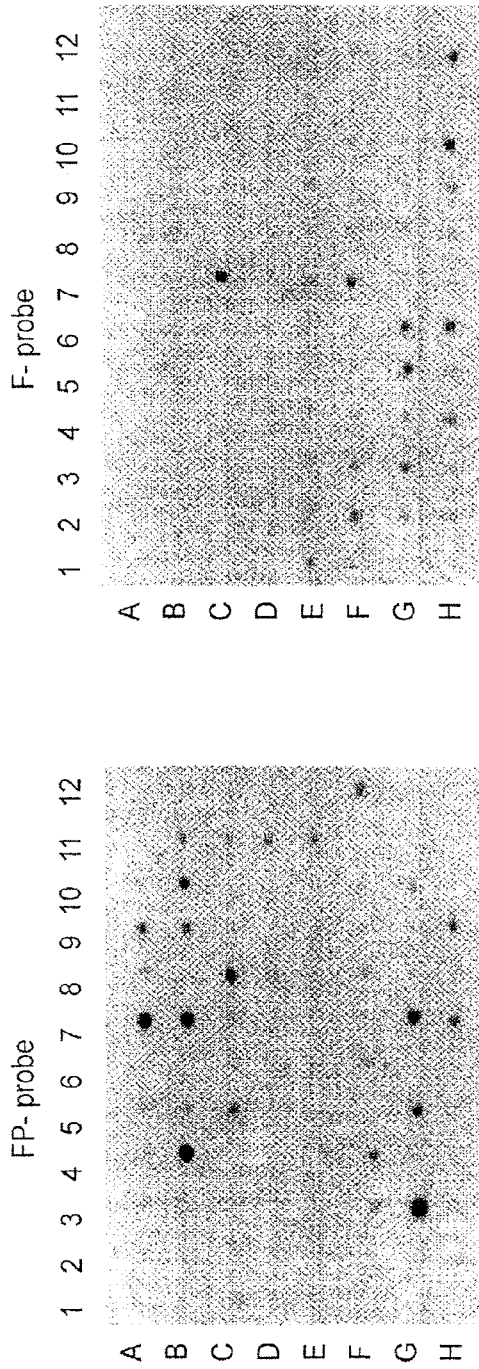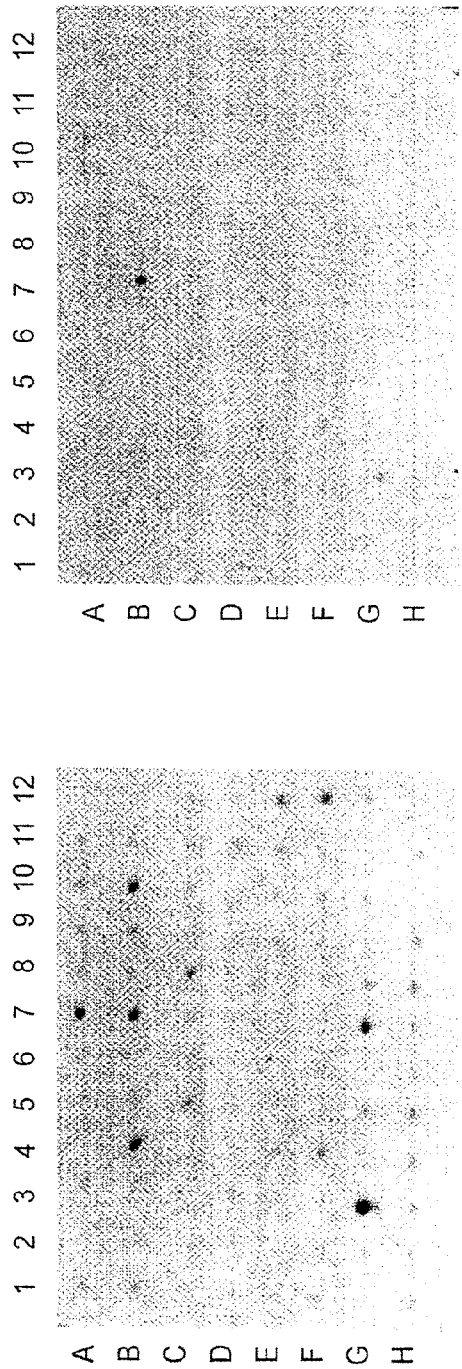
FIG. 12A  FIG. 12B  FIG. 12C  FIG. 12D

```
                          M  T  R  A  A  E  R  G  Q  G  A  T  G  W  G
  1
  1   ACGGGGGAGTGCTGCCCTGAGTCGTTCGGCCTGAGCACAGAGACATGACCCGAGCCGCAGAGCGCCAAGGGGCTACAGGCTGGGA

L  R  G  A  L  M  A  V  A  L  L  S  V  L  N  A  V  G  T  V  F  F  V  L  Y  Q  W  R  E  L  S
 16
 91   CTGCGAGGCGCCCTGATGGCCGTGGCCCTGCTGTCAGTGCTGAATGCCGTGGGCACCGTGTTCGTGTCTACCAGTGGCGAGCTGAGC

A  A  L  R  A  L  E  A  Q  H  G  Q  E  Q  R  E  D  S  A  L  R  A  F  L  A  E  L  S  R  A
 46
181   GCGGCGCTGCGGGCACTGGAGGCGCAACACGGCCAGGAGCAGCGGGAGGACAGCGCCCTTTCTAGCTGAATTAAGTCGTGCG
                                              Epitope 1
     P  A  R  V  P  E  P  P  Q  D  P  M  S  A  A  R  N  K  R  S  H  G  G  E  P  A  S  H  I  R
 76
271   CCAGCCCGAGTCCCCGAACCACCCCAGGACCCCATGAGTGCAGCGCGCAATAAGCGCAGCCATGGCGGCGAGCCTGCTCACACATCCGC A  E  S  Q  D  M  M  M  M  T  Y  S  M  V  P  I  R  V  M  I  D  L  C  N  S  T  Q  G  I
106
361   GCGGAGAGCCAGGACATGATGATGATGACCTACAGCATGGTGCCGATCCGGGTGATGATAGACCTGTGCAACAGCACCCAGGGCATC C  L  T  G  P  P  G  P  P  P  G  P  P  P  G  A  G  G  L  P  G  H  N  G  S  D  G  Q  P  G  L  Q
136
451   TGCCTTACAGGACCACCCGGGCCACCGCCAGGACCTCCAGGACCTGGTGTTACCAGCCACAATGGATCAGATGACAGCCTGGTCTCCAG G  P  K  G  E  K  G  A  V  G  K  R  G  K  M  G  L  P  G  A  T  G  N  P  G  E  K  G  E  K
166
541   GGCCCAAAAAGGAGAAAAAGGCAGTTGGGAAGAGACGGGGAAGATGGGGTTACCCGGAGCAGCACAGGAAATCCAGGGGAAAAAGGAGAGAAG
```

FIG. 15A

```
196  G D A G E L G L P G N E G P P G Q K G D K G D K G D V S N D
631  GGAGATGCTGGTGAACTGGGCCTACCTGGAAATGAGGGACCACCAGGACAAAGGAGACAAAGGAGATGTGTCCAATGAC
                                                          Epitope 2
226  V L L T G A K G D Q G P P P G P P P G P P P G P P S G S R R A
721  GTGCTTTTGACAGGTGCCAAAGGTGACCAAGGCCCCCCTGGCCCCCCAGGCCCCTTCTGGAAGCAGAAGAGCC
                                                          Epitope 3
256  K G P R Q P N S F T N Q C P G E T C V I P N D D T L V G R A
811  AAAGGCCCTCGGCAGCCAAATTCGTTCACCAACCAGTGTCCAGGGAGACGTGTGTCATACCAATGATGATACCTTGGTGGGAGAGCT
         Epitope 4
286  D E K V N E R H S P Q T E P M I T S I G N P A Q V L K V K E
901  GATGAGAAAGTCAATGAGCGCCATTCTCCACAAACAGAACCCATGATCACGTCCATTGGTAACCCGGCCCAAGTCCTCAAAGTGAAAGAG
316  T F G T W L R E S A N R S D D R I W V T E H F S G I M V K E
991  ACTTTTGGGACCTGGCTAAGAGAGTCTGCTAACAGAAGCGATGACCGCATTTGGGTGACTGAACATTTTCAGGCATCATGGTGAAGGAG
346  F E D L P A L L N S S F T L L H L P H Y F H G C G H A V Y N
1081 TTTGAAGACCTGCCCGCCCTCCTGAATAGCAGCTTCACCCTCCACCTCCCACATTACTTCCATGGCTGCGGGCACGCTGTTTACAAC
                                                          Epitope 5
376  N S L Y Y H K G G S N T I V R F E F G K E T P Q T L K L E D
1171 AACTCTCTCTACTACCACAAAGGAGGCTCCAACACCATAGTGAGATTTGAATTTGGGAAAGAGACACCTCAAACTCTGAAGCTTGAAGAT
```

FIG. 15B

```
406   A  L  Y  F  D  R  K  Y  L  F  A  N  S  K  T  Y  F  N  I  A  V  D  E  K  G  L  W  I  I  Y
1261  GCTTTGTATTTGATGAAAATACCTCTTTGCGAATTCCAAGACTTACTTCAACATAGCAGTGGATGAGAAGGGCCTCTGGATTATCTAC

436   A  S  S  V  D  G  S  S  I  L  V  A  Q  L  D  E  R  T  F  S  V  L  Q  H  I  N  T  T  Y  P
1351  GCCTCGAGTGTGGATGGCTCAAGCATCCTTGTGGCACAGCTTGACGAGAGAACATTCTCTGTGCTGCAGCACATCAATACCACATACCCC

466   K  S  K  A  G  N  A  F  I  A  Q  G  I  L  Y  V  T  D  T  K  D  T  R  V  T  F  A  F  D  L
1441  AAGTCCAAGGCTGGCAATGCCTTCATAGCTCAAGGGATCCTCTATGTCACGGACACAAAAGATACAAGGGTCACGTTTGCCTTTGATTTG

496   L  R  G  K  Q  I  N  A  N  F  G  L  R  M  S  Q  S  V  L  A  M  L  S  Y  N  M  R  D  Q  H
1531  TTACGAGGGAAGCAGATCAATGCAAATTCGGTTCTCAGAATGTCACAGTCTGTGTTCTTGCCATGTTGTCGTACAATATGAGAGACCAGCAT

526   L  Y  S  W  E  D  G  H  L  M  L  Y  P  V  H  F  S  S  T  A  P  S  Q  R   (SEQ ID NO:2)
1621  TTGTACTCGTGGGAAGACGGCCACCTGATGCTCTATCCTGTGCACTTTCGTCACAGCCAGCCGATAGCCTCGCAGTCGGCTC

1711  CCTCATTATGCACCACACATTTCTGGGGTTTGACCAAGCCCAACGGAAAGAAGCCTGTAAAGATATCCAGATACTCAGAGCATACGC
1801  CCGTGTTACGGCTTTTGTGCATGTGGCAAGTCCCCTGTAAGCCAGGTAACTAAAGGCTGGAAAGTTGAAATGGATAACATTTGGTGA
1891  CCCTTGGTCCTTCAAACTAGCAAGTTCTGTGAATTCTGTCCCCATCAGTAGTGTCCCCATCAGTAATATGAAACATCTGTGATTGCAG
1981  CATTTCCTATACCTATATGAAGTTCTGCCTGGTTATATATTAGATTGCTTTCAGTTTCTTTTTTCTCCACATGTAA
2071  ATGAGTTACCTGCAGCTTGAGGGGTGCCTATCAGTGATGACGGACATTGTTGTGTTTAGGAAAAAGCATTGTTTCTTATGCT
2161  TTTAAAGTATTATATTCATAATTTGATATTTTTTGAATACGCCCCTGCCACTACGCCAGAATGATTATTTCAGCTCCTAAGTA
2251  CAAATCCAAGATTAATAAAAAAAAAAAAAAAAAAACTGAGAGTATTAGTCGATGTAGGAAAAC  (SEQ ID NO:1)
```

FIG. 15C

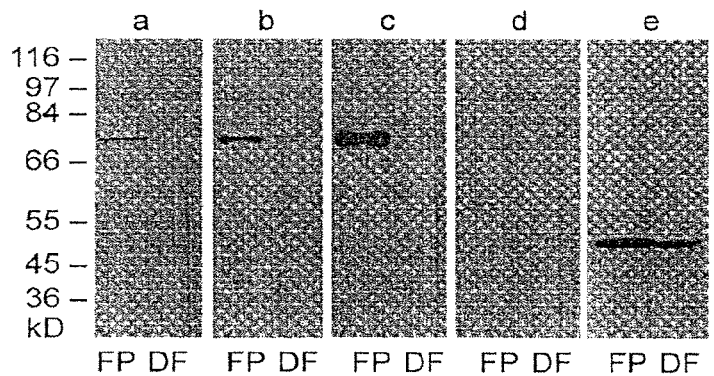
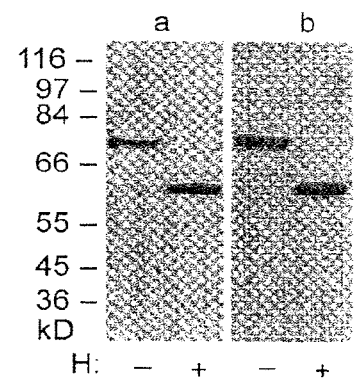
FIG. 16A    FIG. 16B
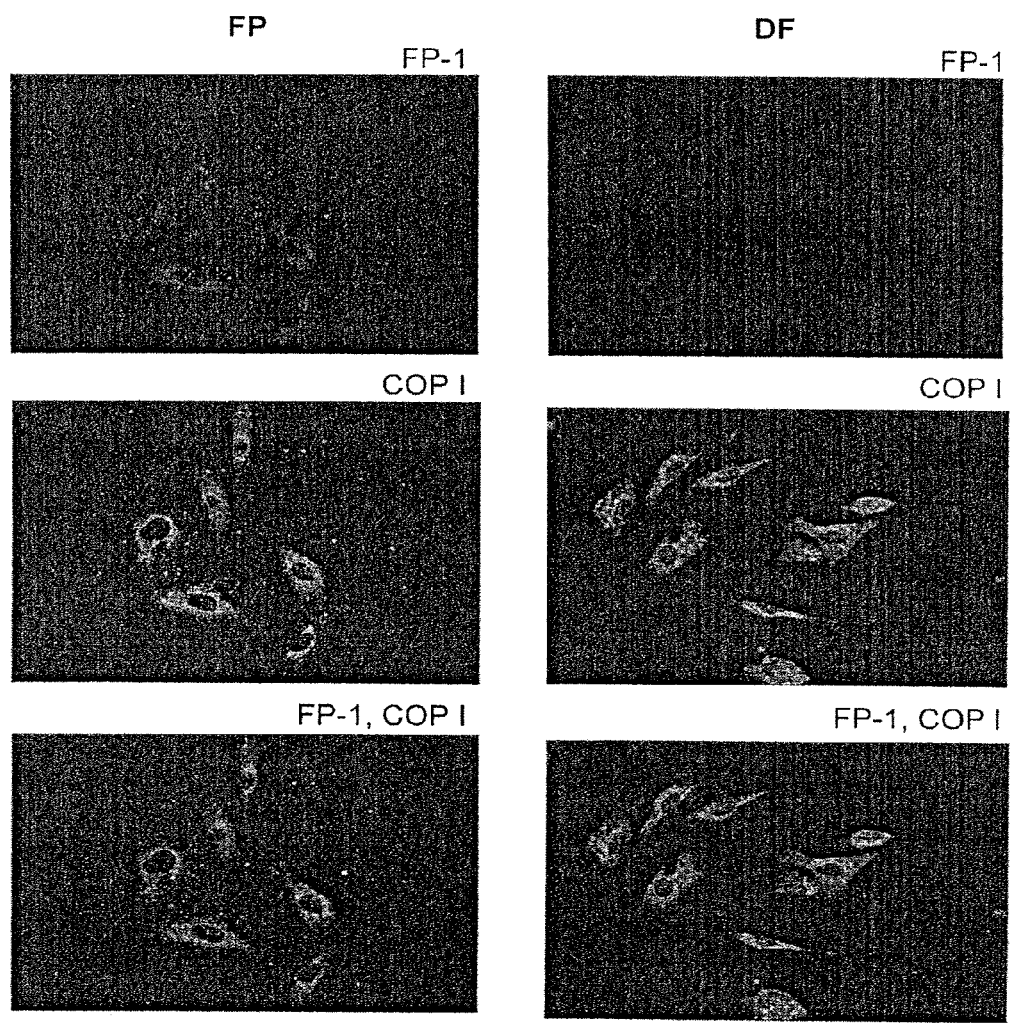
FIG. 16C

COMPOSITIONS FOR CONTROLLING HAIR GROWTH

CROSS REFERENCE TO RELATED APPLICATIONS

This application claims the benefit of U.S. application Ser. No. 11/709,074, entitled "Compositions for Controlling Hair Growth," filed Feb. 21, 2007, now U.S. Pat. No. 7,420,038, which is a divisional of U.S. application Ser. No. 11/096,070 entitled "Compositions for Controlling Hair Growth," filed Mar. 31, 2005, now U.S. Pat. No. 7,223,562, which in turn claims priority to U.S. Provisional Application No. 60/558,341, filed Mar. 31, 2004, the contents of each of which are hereby incorporated by reference in their entirety.

BACKGROUND OF THE INVENTION (a) Field of the Invention

The present invention relates to the field of dermatology. More specifically, the present invention relates to compositions and methods for modulating hair growth.

(b) Background

Although hair growth disorders are not life threatening, their impact on social interactions and on an individual's psychological well being is undeniable. Thus, effective methods of treating hair growth disorders are greatly desired.

One of the most common hair disorders is alopecia, where humans begin losing scalp hair at the temples and on the crown of their head as they age. Although this type of hair loss is predominantly found in males, it is also present in a certain proportion of women. Alopecia can also be induced by chemical agents or physical agents (e.g., during anti-cancer chemotherapy), and the condition also results from specific disease states.

Another type of hair growth disorder results from abnormally accentuated hair growth. For example, hirsutism is manifested as excessive androgen-dependent hair growth in women, whereas hypertrichosis is an increase in androgen-independent hair growth (Bertolino et al., "Disorders of epidermal appendages and related disorders," in *Dermatology in General Medicine,* 4th ed., pp. 671-695, Fitzpatrick et al., eds. (McGraw-Hill, 1993)).

A traditional treatment for alopecia is hair transplantation. This typically involves transplanting plugs of natural hair from areas of the scalp where hair is growing to bald or thinning areas of the scalp. This procedure is costly, time-consuming, painful, and does not provide a sufficient remedy in all cases. Electrical stimulus has been suggested as an alternative way to promote hair growth (see, e.g., U.S. Pat. No. 5,800,477 and references cited therein); however, such methods are of questionable efficacy.

Other methods for stimulating hair growth comprise the use of various chemicals or drugs, mud preparations, and plant extracts (see, e.g., U.S. Pat. Nos. 5,798,341, 5,767,152, 5,753,713, 5,750,107, 5,741,816, 5,739,111, 5,723,149, 5,679,378, 5,674,497, 5,663,160, 5,656,300, 5,643,898, 4,139,619, and references cited therein). There are two compounds currently in clinical use to treat alopecia: finasteride, sold as PROPECIA®, and minoxidil, marketed as ROGAINE®. A drawback of finasteride is that it can only be used by men. Furthermore, its use can result in sexual side effects such as a decreased desire for sex, difficulty in achieving erection, and a decrease in the amount of semen. Minoxidil is a vasodilatory drug which can have side effects in some patients. Similarly, mud preparations and plant extracts can produce unwelcome side effects in various patients and are of questionable efficacy. Moreover such treatments require a normal scalp with no local abrasions, dermatitis, or sunburn, rendering such methods unavailable to many individuals.

In addition to these hair growth disorders, individuals may also desire to increase, decrease, or prevent hair growth purely for cosmetic reasons. As a result, there is immense interest in the development of effective cosmetic and clinical treatments. Yet, most, if not all, of the known methods to control hair growth have several drawbacks.

For example, various procedures have been used to remove unwanted hair from the groin area, legs and face including shaving, electrolysis, use of depilatory creams, waxing, plucking and therapeutic anti-androgens, see, e.g., U.S. Pat. No. 6,093,748. However, these traditional methods have various drawbacks associated with them. For example, shaving can cause nicks, cuts and undesirable stubble. Although electrolysis keeps a treated area free of hair for prolonged periods of time, it can be expensive, painful, and may leave scarring in some cases. Depilatory creams have a high potential to irritate the skin. Waxing and plucking can cause pain, discomfort and poor removal of short hair. Finally, anti-androgens can have undesirable side effects.

Thus, alternative methods for controlling hair growth are needed.

SUMMARY OF THE INVENTION

The follicular papilla, a cluster of mesenchymal cells at the base of the hair follicle, plays an essential role in hair growth. It has been discovered that various genes are selectively expressed in follicular papilla compared to the neighboring dermal fibroblasts cells. For example, it has been discovered that follicular papilla-1 (FP-1) is selectively expressed in follicular papilla compared to dermal fibroblasts cells. This discovery has been exploited to develop the present invention, which relates to nucleic acids and proteins that control hair growth; compositions that control hair growth; compositions for isolating follicular papilla cells; methods for controlling hair growth; methods for repairing hair follicles; methods for screening for, or identifying, agents that control hair growth; methods for diagnosing hair disorders; and methods of diagnosing cancers.

In one aspect, the invention provides an isolated polynucleotide comprising the DNA sequence of rat FP-1. In some embodiments, the sequence of the rat FP-1 comprises SEQ ID NO:1 or SEQ ID NO:3. In additional embodiments, the invention provides an isolated polynucleotide that is the complement of the polynucleotide comprising SEQ ID NO:1 or SEQ ID NO:3.

In another embodiment, the invention provides a recombinant vector comprising any of the polynucleotides of this aspect of the invention. In a further embodiment, the invention provides a host cell comprising a recombinant vector of this aspect.

In a still further embodiment, the invention provides a method of preparing a substantially purified polypeptide encoded by a recombinant vector of this aspect. In this method, host cells transformed or transfected with a recombinant vector according to the invention are cultured under conditions conducive to the synthesis of the polypeptide. The polypeptide, in substantially purified form, is then isolated from the host cells. In another embodiment, the invention provides an isolated polypeptide comprising the amino acid sequence encoded by a polynucleotide having the DNA sequence of rat FP-1 (SEQ ID NO:1 or SEQ ID NO:3). In some embodiments, this polypeptide comprises SEQ ID NO:2 or SEQ ID NO:4.

In a still further embodiment, an antibody that specifically binds rat FP-1 (SEQ ID NO:2 or SEQ ID NO:4), is provided. In yet another embodiment, an antibody that binds both a polypeptide comprising SEQ ID NO: 2 and a polypeptide comprising SEQ ID NO: 12, is provided. In another embodiment, the invention provides an antibody that binds both a polypeptide comprising SEQ ID NO: 4 and a polypeptide comprising SEQ ID NO:12.

In another aspect of the invention, an isolated polynucleotide consisting of SEQ ID NO:1 or SEQ ID NO:3 is provided. In one embodiment, the isolated polynucleotide is the complement of any of the polynucleotides of this aspect. In another embodiment, a recombinant vector comprising any of the polynucleotides of this aspect is provided. In a further embodiment, a host cell comprising a recombinant vector of this aspect is provided.

In another embodiment, the invention provides a method of preparing a substantially purified polypeptide encoded by a recombinant vector comprising the polynucleotide consisting of SEQ ID NO:1 or SEQ ID NO:3. In this method, host cells transformed or transfected with the recombinant vector are cultured under conditions conducive to the synthesis of the polypeptide. The polypeptide is then recovered in substantially purified form from the host cells.

In yet a further embodiment of this aspect of the invention, an isolated polypeptide (SEQ ID NO:2) comprising the amino acid sequence encoded by the polynucleotide consisting of the DNA sequence of rat FP-1 (SEQ ID NO:1) is provided. In a further embodiment of this aspect, the invention provides an isolated polypeptide (SEQ ID NO:4) comprising the amino acid sequence encoded by the polynucleotide consisting of the DNA sequence of rat FP-1 (SEQ ID NO:3).

The invention also provides an isolated polynucleotide comprising the DNA sequence of human FP-1. In one embodiment, the sequence of the human FP-1 comprises SEQ ID NO:11. In an additional embodiment, the invention provides an isolated polynucleotide that is the complement of the polynucleotide comprising SEQ ID NO:11. In another embodiment, the invention provides a recombinant vector comprising any of the polynucleotides of this aspect of the invention. In a further embodiment, the invention provides a host cell comprising the recombinant vector of this aspect.

In a still further embodiment, the invention provides a method of preparing a substantially purified polypeptide encoded by the recombinant vector of this aspect. In this method, host cells transformed or transfected with the recombinant vector according to the invention are cultured under conditions conducive to the synthesis of the polypeptide. The polypeptide, in substantially purified form, is then isolated from the host cells.

In another embodiment, the invention provides an isolated polypeptide comprising the amino acid sequence encoded by the polynucleotide having the DNA sequence of human FP-1 (SEQ ID NO:11). In one embodiment, this polypeptide comprises SEQ ID NO:12. In a still further embodiment, an antibody that specifically binds human FP-1 (SEQ ID NO:12), is provided. In yet another embodiment, an antibody that binds both a polypeptide comprising SEQ ID NO: 2 and a polypeptide comprising SEQ ID NO: 12 is provided.

In still another embodiment, the invention provides an antibody that binds both a polypeptide comprising SEQ ID NO: 4 and a polypeptide comprising SEQ ID NO:12.

The invention also provides an isolated polynucleotide comprising a nucleic acid sequence that encodes a polypeptide comprising the amino acid sequence of rat FP-1 (SEQ ID NO:2 or SEQ ID NO:4). In one embodiment, the polynucleotide comprises a nucleic acid sequence that encodes a polypeptide comprising amino acids 34 to 549 of SEQ ID NO:2 or amino acids 34 to 531 of SEQ ID NO:4. In another embodiment, the isolated polynucleotide is the complement of any of the polynucleotides of this aspect. In another embodiment, a recombinant vector is provided which comprises any of the polynucleotide of this aspect. In a further embodiment, a host cell comprising a recombinant vector comprising any of the polynucleotides of this aspect is provided. In a still further embodiment, the invention provides a method of preparing a substantially purified polypeptide encoded by a recombinant vector comprising any of the polynucleotides of this aspect. In this method, cells transformed or transfected with the recombinant vector according to the invention are cultured under conditions conducive to the synthesis of the polypeptide. The polypeptide is then recovered in substantially purified form from the cells.

The invention also provides an isolated polynucleotide comprising a nucleic acid sequence that encodes a polypeptide comprising the amino acid sequence of human FP-1 (SEQ ID NO:12). In one embodiment, the polynucleotide comprises a nucleic acid sequence that encodes a polypeptide comprising amino acid 34 to 551 of SEQ ID NO:12. In another embodiment, the isolated polynucleotide is the complement of any of the polynucleotides of this aspect. In another embodiment, a recombinant vector is provided which comprises any of the polynucleotide of this aspect. In a further embodiment, a cell comprising a recombinant vector comprising any of the polynucleotides of this aspect is provided.

In a still further embodiment, the invention provides a method of preparing a substantially purified polypeptide encoded by a recombinant vector comprising the polynucleotide of this aspect. In this method, cells transformed or transfected with the recombinant vector according to the invention are cultured under conditions conducive to the synthesis of the polypeptide. The polypeptide is then recovered in substantially purified form from the cells.

In yet another aspect, the invention provides an isolated polynucleotide comprising a nucleic acid sequence that is homologous to SEQ ID NO:1 or SEQ ID NO:3, wherein the isolated polynucleotide molecule encodes a protein that controls hair growth. In some embodiments, the isolated polynucleotide of this aspect has about 80%, about 85%, about 90%, or about 95% identity to SEQ ID NO:1 or SEQ ID NO:3. In another embodiment, the isolated polynucleotide is the complement of any of the polynucleotides of this aspect of the invention. In another embodiment, a recombinant vector comprising a polynucleotide of this aspect is provided. The invention also provides a cell comprising the recombinant vector having any of the polynucleotides of this aspect.

Also provided is a method of preparing a substantially purified polypeptide encoded by a recombinant vector of this aspect of the invention. In this method, cells transformed or transfected with the recombinant vector are cultured under conditions conducive to the synthesis of the polypeptide. The polypeptide is then recovered in substantially purified form from the cells. In yet a further embodiment of this invention, an isolated polypeptide of this aspect, is provided. In a still further embodiment of the invention, an antibody that specifically binds an isolated polypeptide comprising the amino acid sequence encoded by the polynucleotide of the invention is provided.

In yet another aspect, the invention provides an isolated polynucleotide comprising a nucleic acid sequence that is homologous to SEQ ID NO:11, wherein the isolated polynucleotide molecule encodes a protein that controls hair growth. In some embodiments, the isolated polynucleotide of this aspect is about has about 80%, about 85%, about 90%, or about 95% identity to SEQ ID NO:11. In another embodiment, the isolated polynucleotide is the complement of any of the polynucleotides of this aspect of the invention. In another embodiment, a recombinant vector comprising any of the polynucleotides of this aspect is provided. The invention also provides a cell comprising a recombinant vector having any of the polynucleotides of this aspect.

Also provided is a method of preparing a substantially purified polypeptide encoded by a recombinant vector of this aspect of the invention. In this method, cells transformed or transfected with the recombinant vector are cultured under conditions conducive to the synthesis of the polypeptide. The polypeptide is then recovered in substantially purified form from the cells. In yet a further embodiment, the isolated polypeptide of this aspect of the invention is provided. In a still further embodiment of the invention, an antibody that specifically binds an isolated polypeptide comprising the amino acid sequence encoded by the polynucleotide of this aspect is provided.

In another aspect, the invention provides an isolated polynucleotide comprising a nucleic acid sequence that is homologous to a nucleic acid sequence that encodes a polypeptide comprising SEQ ID NO:2 or SEQ ID NO:4, wherein the isolated polynucleotide molecule encodes a protein that controls hair growth. In some embodiments, the isolated polynucleotide of this aspect has about 80%, about 85%, about 90%, or about 95% identity to a nucleic acid sequence that encodes a polypeptide comprising SEQ ID NO:2 or SEQ ID NO:4. In one embodiment of this aspect, the invention provides an isolated polynucleotide that is the complement of any of the polynucleotides of this aspect. In another embodiment, a recombinant vector of this aspect is provided. In a further embodiment, the invention provides a host cell comprising a recombinant vector having any of the polynucleotides of this aspect.

In yet another embodiment, a method of preparing a substantially purified polypeptide encoded by a recombinant vector of this aspect is provided. The method comprises culturing host cells transformed or transfected with a recombinant vector according to the invention under conditions conducive to the synthesis of the polypeptide. The polypeptide is then recovered in substantially purified form from the host cells. In yet a further embodiment of this invention, an isolated polypeptide comprising the amino acid sequence encoded by a polynucleotide of this aspect, is provided.

In a still further embodiment, the invention provides an antibody that specifically binds an isolated polypeptide of this aspect of the invention.

In another aspect, the invention provides an isolated polynucleotide comprising a nucleic acid sequence that is homologous to a nucleic acid sequence that encodes a polypeptide comprising SEQ ID NO:12, wherein the isolated polynucleotide molecule encodes a protein that controls hair growth. In some embodiments, the isolated polynucleotide of this aspect has about 80%, about 85%, about 90%, or about 95% identity to a nucleic acid sequence that encodes a polypeptide comprising SEQ ID NO:12. In one embodiment of this aspect, the invention provides an isolated polynucleotide that is the complement of any of the polynucleotides of this aspect. In another embodiment, a recombinant vector of this aspect is provided. In a further embodiment, the invention provides a host cell comprising a recombinant vector having any of the polynucleotides of this aspect.

In a still further embodiment, a method of preparing a substantially purified polypeptide encoded by a recombinant vector of this aspect is provided. The method comprises culturing host cells transformed or transfected with a recombinant vector according to the invention under conditions conducive to the synthesis of the polypeptide. The polypeptide is then recovered in substantially purified form from the host cells. In yet a further embodiment of this invention, an isolated polypeptide comprising the amino acid sequence encoded by a polynucleotide of this aspect, is provided.

In yet another embodiment, the invention provides an antibody that specifically binds an isolated polypeptide of this aspect of the invention.

In an additional aspect of the invention, an isolated polynucleotide that specifically hybridizes under highly stringent conditions to a complement of a polynucleotide sequence comprising SEQ ID NO:1 or SEQ ID NO:3, wherein the polynucleotide sequence encodes a protein that controls hair growth is provided. In one embodiment, an isolated polynucleotide that is the complement of any of the polynucleotides of this aspect is provided. In another embodiment, the invention provides a recombinant vector comprising a polynucleotide of this aspect. In a further embodiment, a host cell comprising a recombinant vector comprising any of the polynucleotides of this aspect of the invention is provided. In a still further embodiment, the invention provides a method of preparing a substantially purified polypeptide encoded by a recombinant vector according to the invention. The method comprises culturing host cells transformed or transfected with the recombinant vector under conditions conducive to the synthesis of the polypeptide of the invention. The polypeptide is then recovered in substantially purified form from the host cells. In yet a further embodiment of this invention, an isolated polypeptide comprising the amino acid sequence encoded by any of the polynucleotides of this aspect is provided. In a still further embodiment, the invention provides an antibody that specifically binds an isolated polypeptide comprising the amino acid sequence encoded by a polynucleotide according to this aspect.

The invention also provides an isolated polynucleotide that specifically hybridizes under highly stringent conditions to a complement of a polynucleotide sequence comprising SEQ ID NO:11, wherein the polynucleotide sequence encodes a protein that controls hair growth. In one embodiment, an isolated polynucleotide that is the complement of any of the polynucleotides of this aspect is provided. In another embodiment, the invention provides a recombinant vector comprising a polynucleotide of this aspect. In a further embodiment, a host cell comprising a recombinant vector comprising any of the polynucleotides of this aspect of the invention is provided.

In a still further embodiment, the invention provides a method of preparing a substantially purified polypeptide encoded by a recombinant vector according to the invention. The method comprises culturing host cells transformed or transfected with the recombinant vector under conditions conducive to the synthesis of the polypeptide of the invention. The polypeptide is then recovered in substantially purified form from the host cells. In yet a further embodiment of this invention, an isolated polypeptide comprising the amino acid sequence encoded by any of the polynucleotides of this aspect is provided.

In a still further embodiment, the invention provides an antibody that specifically binds an isolated polypeptide comprising the amino acid sequence encoded by a polynucleotide according to this aspect.

The present invention also encompasses an isolated polynucleotide molecule that specifically hybridizes under highly stringent conditions to a complement of a polynucleotide sequence comprising a nucleotide sequence that encodes a polypeptide having SEQ ID NO:2, SEQ ID NO:4 or SEQ ID NO:12, wherein the polynucleotide sequence encodes a protein that controls hair growth. In one embodiment, the present invention provides an isolated polynucleotide that is the complement of any of the polynucleotides of this aspect. In another embodiment, a recombinant vector comprising a polynucleotide molecule of this aspect is provided. In a further embodiment, the invention provides a host cell comprising a recombinant vector comprising any of the polynucleotides of this aspect.

In a still further embodiment, the invention provides a method of preparing a substantially purified polypeptide encoded by a recombinant vector comprising a polynucleotide molecule according to this aspect. In this method, host cells transformed or transfected with the recombinant vector are cultured under conditions conducive to the synthesis of the polypeptide according to the invention. The polypeptide is then recovered in substantially purified form from the host cells. In yet a further embodiment of this invention, an isolated polypeptide comprising the amino acid sequence encoded by the polynucleotide sequence comprising an isolated polynucleotide molecule of this aspect is provided.

In a still further embodiment, the invention provides an antibody that specifically binds an isolated polypeptide comprising the amino acid sequence encoded by any of the polynucleotides of this aspect.

The invention also provides a process for isolating a polynucleotide, comprising hybridizing a polynucleotide selected from the group consisting of polynucleotides having SEQ ID NO:1, SEQ ID NO:3, and SEQ ID NO:11 to genomic DNA under highly stringent conditions and isolating the DNA that hybridizes to the polynucleotide selected from the group consisting of polynucleotides having SEQ ID NO:1, SEQ ID NO:3, and SEQ ID NO:11. In one embodiment of this aspect of the invention, an isolated polynucleotide is prepared according to the process of this aspect of the invention. In another embodiment, an isolated polynucleotide that is the complement of the polynucleotide molecule of this aspect of the invention is provided. In another embodiment, a recombinant vector comprising the polynucleotide molecule of this aspect of the invention is provided. In a further embodiment, a host cell comprising the recombinant vector comprising the polynucleotide molecule of this aspect of the invention is provided.

In a still further embodiment, a method of preparing a substantially purified polypeptide encoded by the recombinant vector of this aspect of the invention, comprising culturing host cells transformed or transfected with the recombinant vector under conditions conducive to the synthesis of the polypeptide, and recovering a substantially purified polypeptide from the host cells, is provided. In yet a further embodiment of this invention, an isolated polypeptide comprising the amino acid sequence encoded by the polynucleotide sequence of this aspect of the invention is provided.

In a still further embodiment, an antibody that specifically binds the isolated polypeptide of this aspect of the invention is provided.

In another aspect, the invention provides a method for increasing or decreasing hair growth, or changing the texture/structure (i.e., rough, smooth, fragile, curly, etc.) of the hair shaft of a subject. In this method, an effective amount of a composition comprising at least any one of the polynucleotides according to the invention is administered to a subject in need thereof. In one embodiment, the method comprises administering a polynucleotide encoding the human homolog of FP-1 (SEQ ID NO:11) to a subject in need thereof. In another embodiment, the method comprises administering to a subject in need thereof a polynucleotide having SEQ ID NO:11; and a second agent. The second agent is any substance that can control hair growth or can assist the polypeptide encoded by a polynucleotide of the invention to control hair growth. In an another embodiment, the method comprises administering a polynucleotide characterized by the nucleic acid sequence of SEQ ID NO:1 with or without a second agent.

In a further aspect, the invention provides another method for increasing or decreasing hair growth, or changing the texture/structure (i.e., rough, smooth, fragile, curly, etc.) of the hair shaft of a subject. In this method, a formulation comprising a polypeptide encoded by any of the polynucleotides according to the invention is administered to the subject in an amount effective to control hair growth. In one embodiment, the method comprises administering to the subject, a polypeptide encoded by a polynucleotide comprising the human homolog of FP-1 (SEQ ID NO:12). In another embodiment, the method comprises administering to a subject, a polypeptide comprising amino acids 34 to 551 of SEQ ID NO:12. In a further embodiment, the subject is administered a polypeptide encoded by any of the nucleic acid molecules according to the invention; and a second agent. The second agent is any substance that can control hair growth or any substance that can assist the polypeptide of the invention to control hair growth.

In yet another aspect, the invention provides a method for controlling hair growth, comprising contacting the skin of a subject with a composition comprising an effective amount of a protein selected from the group consisting of polypeptides having SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, amino acids 34 to 551 of SEQ ID NO:12, and any combination thereof. In one embodiment of this aspect of the invention, the hair follicle of a subject is contacted with the composition of this aspect. In another embodiment of this aspect, the follicular papilla of the subject is contacted with the composition according to the invention. In a further embodiment, the skin of a subject is contacted with a composition comprising an effective amount of a protein selected from the group consisting of polypeptides having SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, amino acids 34 to 551 of SEQ ID NO:12; and a second agent. The second agent is any substance that can control hair growth or any substance that can assist the polypeptides selected from the group consisting of polypeptides having SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, amino acids 34 to 551 of SEQ ID NO:12, to control hair growth.

In a further aspect of the invention, the invention provides a method of treating a subject with a hair growth disorder. In this method, a pharmaceutical composition comprising a pharmaceutically acceptable carrier, and a hair growth-promoting amount of any of the polynucleotides of the invention is administered to the subject. In one embodiment, the method comprises administering a polynucleotide encoding the human homolog of FP-1 (SEQ ID NO:11), and a pharmaceutically acceptable carrier to a subject in need thereof. In a different method, a pharmaceutical composition comprising a pharmaceutically acceptable carrier, and a hair growth-promoting amount of any of the polypeptides of the invention is administered to the subject. In one embodiment the polypeptide comprises an amino acid sequence selected from the group consisting of polypeptides having SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, amino acids 34 to 551 of SEQ ID NO:12.

In yet another aspect of the invention, a method of identifying an agent that modulates hair growth is provided. In one embodiment, skin, isolated follicular papilla cells, or an isolated hair follicle is contacted with a test agent. The expression of FP-1 in follicular papilla is then measured. If the test agent increases the expression of FP-1 in the isolated follicular papilla cells, or the follicular papilla of the isolated hair follicle or of the skin compared to those not contacted with the test agent, the agent is determined to stimulate hair growth. If on the other hand, the test agent decreases the expression of FP-1 in the isolated follicular papilla cells, or the follicular papilla of the isolated hair follicle or of the skin compared to those not contacted with the test agent, the agent is determined to inhibit hair growth.

The invention also provides methods for screening or identifying agents that modulate the ability of FP-1 to control hair growth. The method includes contacting FP-1 with a test agent. In this aspect, a test agent is a substance that is thought to be effective in modulating the activity of FP-1. The method includes determining if the test agent modulates the activity of FP-1. Accordingly, the agent is tested in in vitro hair growth assays to determine its ability to modulate hair growth by FP-1. The test agent is classified as an agent that stimulates hair growth if it increases the ability of FP-1 to promote hair growth, whereas the test agent is determined to be an inhibitor of hair growth if it decreases the activity of FP-1.

The invention also provides a method for stimulating hair growth in a subject, comprising contacting the skin of the subject with an amount of an agent that increases the expression of FP-1 in the follicular papilla. In some embodiments of this aspect, the hair follicle or the follicular papilla of the subject is contacted with the agent. In a further embodiment, the invention provides a method for stimulating hair growth in a subject, comprising contacting the skin of the subject with an amount of an agent that increases the expression of FP-1 in the follicular papilla; and a second agent. The second agent is any substance that controls hair growth or any substance that can assist the polypeptide of the invention to increase hair growth.

The present invention also provides a method for treating alopecia. The method comprises administering to a subject in need thereof an effective amount of FP-1, or an agent that increases the expression of FP-1 in follicular papilla of the subject. In one embodiment, the subject's skin is contacted with FP-1, or an agent that increases the expression of FP-1 in the follicular papilla of the subject. In a particular embodiment, contact with FP-1 or the agent alters the duration of the anagen in the subject. In another specific embodiment, contact with FP-1 or the agent converts telogen follicles into anagen follicles. In yet another embodiment, contact with FP-1 or the agent reverses miniaturization. In a still further embodiment, contact with FP-1 or the agent generates new hair follicles. In an additional embodiment, the method comprises administering to a subject in need thereof an effective amount of FP-1, or an agent that increases the expression of FP-1 in follicular papilla; and a second agent.

In another aspect, the present invention provides methods of diagnosing hair disorders in a subject. The method comprises collecting a blood or tissue sample from the subject and detecting the level of FP-1 expression in the sample. If the FP-1 expression is lower or higher than in blood or tissue samples from a control subject who does not have a hair disorder, the subject is determined to have a hair disorder.

The present invention also provides a method for transplanting hair in a subject. In this method, hair follicles or grafts are contacted with a polynucleotide selected from the group consisting of polynucleotides having SEQ ID NO:1, SEQ ID NO:3, SEQ ID NO:5, SEQ ID NO:7, SEQ ID NO:9, and SEQ ID NO:11, or contacted with a polypeptide selected from the group consisting of polypeptides comprising SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, and amino acids 34 to 551 of SEQ ID NO:12. The contacted hair grafts or follicles are then transplanted to a predetermined bald or thinning area of the subject. The method of this aspect of the invention may further comprise contacting the hair follicles or grafts with additional substance(s) that control hair growth.

In yet another aspect, the invention provides a method for inhibiting hair growth of a subject, comprising contacting a hair follicle with an effective amount of an agent that decreases the expression of FP-1 in follicular papilla or inhibits the activity of FP-1. In some embodiments, the hair follicle is contacted by contacting the skin or the follicular papilla of a subject. In further embodiments, the agent that decreases the expression of FP-1 in follicular papilla or inhibits the activity of FP-1 is an antibody, a mutant form of FP-1, a ribozyme, an siRNA, an antisense molecule, or a small molecule inhibitor. In a further embodiment, the method of this aspect comprises contacting a hair follicle with an effective amount of an agent that decreases the expression of FP-1 in follicular papilla or inhibits the activity of FP-1; and an inhibitor of hair growth.

The invention also provides compositions comprising an antibody that binds FP-1 attached to a surface. In one embodiment, the surface is a solid phase surface. In another embodiment, the surface is a cell surface. In yet another embodiment the solid phase surface is a bead. In a still further embodiment the bead is selected from the group consisting of biodegradable beads, magnetic beads and latex beads.

In a further aspect, the present invention provides a method of identifying and isolating follicular papilla cells. In this method, a mixture of cells from the skin or hair follicles is contacted with an antibody that specifically binds to FP-1. In one embodiment, the antibody that binds FP-1 is coupled to a surface. These FP-1 antibody-bound cells are isolated from the unbound cells. The cells that bind an antibody that specifically binds to FP-1 are determined to be follicular papilla cells.

In another aspect, the invention provides a method for screening or validation of drugs for hair growth disorders. The method comprises contacting isolated follicular papilla cells, isolated hair follicles, or skin, and treating any of these with a test drug (e.g., chemical, compound, peptide, protein, DNA, etc.) and determining whether the test drug changes the expression level of FP-1 (RNA or protein) in the isolated follicular papilla cells, isolated hair follicles, or skin. The change in the expression levels of FP-1 is an indicator of the utility of the test drug for use in increasing or decreasing hair growth, or in regulating the texture/structure of the hair of a subject. If the test drug increases FP-1 expression it indicates that the test drug is effective in promoting hair growth. If, on the other hand, the test drug decreases FP-1 expression, the test agent is effective in inhibiting hair growth.

In an additional aspect, the present invention provides methods of diagnosing cancers. The method comprises isolating blood from a subject and measuring the level of FP-1. If the level of FP-1 is higher than that in the normal population, the subject is determined to be at a risk of developing or having developed a cancer. In another embodiment, the method comprises obtaining a tissue biopsy from a subject. The tissue is then tested for expression of FP-1. If the level of FP-1 is higher than in normal tissues, the subject is determined to be at a risk of developing or having developed a cancer. In one embodiment, the tissue is obtained from the skin. In another embodiment, the tissue is from the hair follicle. In yet another embodiment, the tissue is from the liver. In a further embodiment, the tissue is from the brain. In an even further embodiment, the tissue is from the testes. In an additional embodiment, the tissue is from the muscle (e.g., skeletal muscle). In a further embodiment, the tissue is from the placenta.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 2 is a schematic representation of the nucleic acid (SEQ ID NO:1) and corresponding amino acid sequence of rat FP-1 (SEQ ID NO:2).

FIG. 3 is a schematic representation of the nucleic acid (SEQ ID NO:3) and corresponding amino acid sequence of an alternatively spliced rat FP-1 (SEQ ID NO:4).

FIG. 4 is a schematic representation of the nucleic acid (SEQ ID NO:5) and corresponding amino acid sequence (SEQ ID NO:6) of rat gliomedin.

FIG. 5 is a schematic representation of the nucleic acid (SEQ ID NO:7) and corresponding amino acid sequence (SEQ ID NO:8) of mouse cancer related gene-liver 2 (mCrg-L2).

FIG. 6 is a schematic representation of the nucleic acid (SEQ ID NO:9) and corresponding amino acid sequence (SEQ ID NO:10) of a human homolog of cancer related gene-liver 2 (hCrg-L2).

FIG. 7 is a schematic representation of a nucleic acid encoding human FP-1 (SEQ ID NO:11) and the corresponding amino acid sequence (SEQ ID NO:12).

FIG. 8 is a schematic representation of an alignment of the amino acid sequences of the rat FP-1 sequences of the present invention (SEQ ID NOS: 2 (FP-1a) and 4 (FP-1b)), rat gliomedin (SEQ ID NO: 6), mouse cancer related gene-liver 2 (SEQ ID NO: 8), the human homolog of the mouse cancer related gene-liver 2 (SEQ ID NO: 10), and the human homolog of FP-1 (SEQ ID NO: 12).

FIG. 9 is a schematic representation of an alignment of the coding regions of the nucleic acid sequences of the rat FP-1 sequences of the present invention (SEQ ID NOS: 28 (FP-1a) and 32 (FP-1b)), rat gliomedin (SEQ ID NO: 29), mouse cancer related gene-liver 2 (SEQ ID NO: 33), the human homolog of the mouse cancer related gene-liver 2 (SEQ ID NO: 31), and the human homolog of FP-1 (SEQ ID NO: 30).

FIG. 10C is a schematic representation of an amino acid sequence alignment of the olfactomedin domains of rat FP-1a and b (SEQ ID NOS: 36), human FP-1 (SEQ ID NO: 37) and the olfactomedin-like domain (SEQ ID NO: 38) (OLF: NCBI Conserved Domain Database, gnl/CDD/8214, pfam02191). The seven regions of conservation in olfactomedin-related proteins (Regions 1, 3, and 5-9) as defined by Klein and Green (*Mol. Cell. Prot.,* 1.5:394-403, 2002) are underlined.

FIG. 11A is a photographic representation showing the enrichment of follicular papilla-specific cDNAs in the follicular papilla subtraction library. Specifically, FIG. 11A is a photographic representation of a Southern Blot analysis performed using follicular papilla-specific cDNAs (FP−) as probes. Lane 1: subtracted follicular papilla cDNA; lane 2: nonsubtracted follicular papilla cDNA; lane 3: subtracted fibroblast cDNA; and lane 4: nonsubtracted fibroblast cDNA.

FIG. 11B is a photographic representation of a Southern Blot analysis performed using fibroblasts-specific cDNAs (F−) as probes. Lane 1: subtracted follicular papilla cDNA; lane 2: nonsubtracted follicular papilla cDNA; lane 3: subtracted fibroblast cDNA; and lane 4: nonsubtracted fibroblast cDNA;

FIG. 11C is a photographic representation of a Southern Blot analysis performed using a GAPDH probe. Lane 1: subtracted follicular papilla cDNA; lane 2: nonsubtracted follicular papilla cDNA; lane 3: subtracted fibroblast cDNA; and lane 4: nonsubtracted fibroblast cDNA;

FIG. 11D is a photographic representation of a Southern Blot analysis performed using an FP-1 probe. Lane 1: subtracted follicular papilla cDNA; lane 2: nonsubtracted follicular papilla cDNA; lane 3: subtracted fibroblast cDNA; and lane 4: nonsubtracted fibroblast cDNA;

FIG. 11E is a photographic representation of an ethidium bromide stained gel in which the subtracted and nonsubtracted cDNAs of cultured rat follicular papilla cells, rat fibroblasts and human skeletal muscle control were separated electrophoretically. Lane 1: subtracted follicular papilla cDNA; lane 2: nonsubtracted follicular papilla cDNA; lane 3: subtracted fibroblast cDNA; lane 4: nonsubtracted fibroblast cDNA; lane 5: subtracted control (human skeletal muscle cDNA mixed with φX174/Hae III, and then subtracted with a human skeletal muscle cDNA); and lane 6: nonsubtracted control (human skeletal muscle cDNA).

FIG. 12A is a photographic representation of a nylon membrane dotted with a cDNA array from randomly picked clones of the follicular papilla-specific subtracted library hybridized with the follicular papilla-specific cDNA (FP− probe). The following clones were used as negative controls: H1: a human homolog of a mouse testis-specific gene, and H2: human semenogelin II, which is specific to seminal vesicles.

FIG. 12B is a photographic representation of a duplicate of the cDNA array shown in FIG. 12A, but hybridized with the fibroblast-specific cDNA (F− probe).

FIG. 12C is a photographic representation of a nylon membrane dotted with a bacterial colony array from randomly picked clones of the follicular papilla-specific subtracted library hybridized with the follicular papilla-specific cDNA (FP− probe). The following clones were used as negative controls: H1: a human homolog of a mouse testis-specific gene, and H2: human semenogelin II, which is specific to seminal vesicles.

FIG. 12D is a photographic representation of a duplicate of the bacterial colony array shown in FIG. 12A, but hybridized with the fibroblast-specific cDNA (F— probe).

FIG. 15 is a schematic representation of the cDNA (SEQ ID NO:1) and peptide sequence (SEQ ID NO:2) of the most full-length rat FP-1. The full-length FP-1 cDNA is 2332 bp, with a 1647 bp coding region that encodes a protein having 549 amino acids. Five peptide regions used to generate antisera are underlined and labeled epitopes 1 to 5. The N-terminal 33 amino acid residues of SEQ ID NO:2, which serve as a putative signal peptide, are indicated in bold and underlined. Amino acids 139-222 and 230-251 of SEQ ID NO:2 are homologous to collagen triple helix repeats. A region comprising amino acids 253-543 of SEQ ID NO:2 is homologous to an olfactomedin-related domain. Putative N-glycosylation sites are outlined in bold and underlined.

FIG. 16A is a photographic representation of a Western blot to test the antisera raised to FP-1. Total proteins of cultured rat vibrissa follicular papilla cells (FP) and dermal fibroblasts (DF) were separated electrophoretically on an SDS/polyacrylamide gel. Numbers on the left denote the positions of size markers in kilodalton (kDa). Immunoblots were performed using three separate FP-1 antisera (anti-epitopes 1, 2, and 3, panel a, b, c, respectively), pre-immune serum (panel d), and anti-β-tubulin antibody (panel e).

FIG. 16B is a photographic representation of a Western blot performed to test whether FP-1 was glycosylated. Total proteins of cultured rat vibrissa follicular papilla cells were digested with endoglycosidase-H (+) or left undigested (−) and the proteins were separated electrophoretically on an SDS/polyacrylamide gel. Immunoblotting was performed using two FP-1 antisera (anti-epitopes 2 and 3, panel a and b, respectively).

FIG. 16C is a photographic representation of immunofluorescent staining of FP-1 and COP I in cultured follicular papilla cells. Cultured rat vibrissa follicular papilla cells (FP) and fibroblasts (DF) at passage 4 were double stained with FP-1 rabbit antiserum (anti-epitope 3) and anti-COP I mouse monoclonal antibody.

DETAILED DESCRIPTION OF THE INVENTION

The patents and scientific literature cited herein establishes the knowledge that is available to those with skill in the art. The issued U.S. patents, published and allowed applications, and references cited herein are hereby incorporated by reference in their entirety. Unless otherwise defined, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein.

The present invention relates to compositions and methods for modulating hair growth. Specifically, the present invention is based on the discovery of a protein, follicular papilla-1

(FP-1), which exhibits highly selective expression in the follicular papilla of the hair follicle. Significantly, the mouse FP-1 gene has been localized to a region of the mouse chromosome that has been implicated in a number of hair-related disorders. These discoveries have been exploited to develop the present invention, which relates to proteins and polynucleotides that control hair growth; compositions that control hair growth; compositions and methods for identifying and isolating follicular papilla cells; methods of controlling hair growth; methods for screening for agents that control hair growth; methods of diagnosing hair disorders; and methods of diagnosing cancers.

Figure 1A:
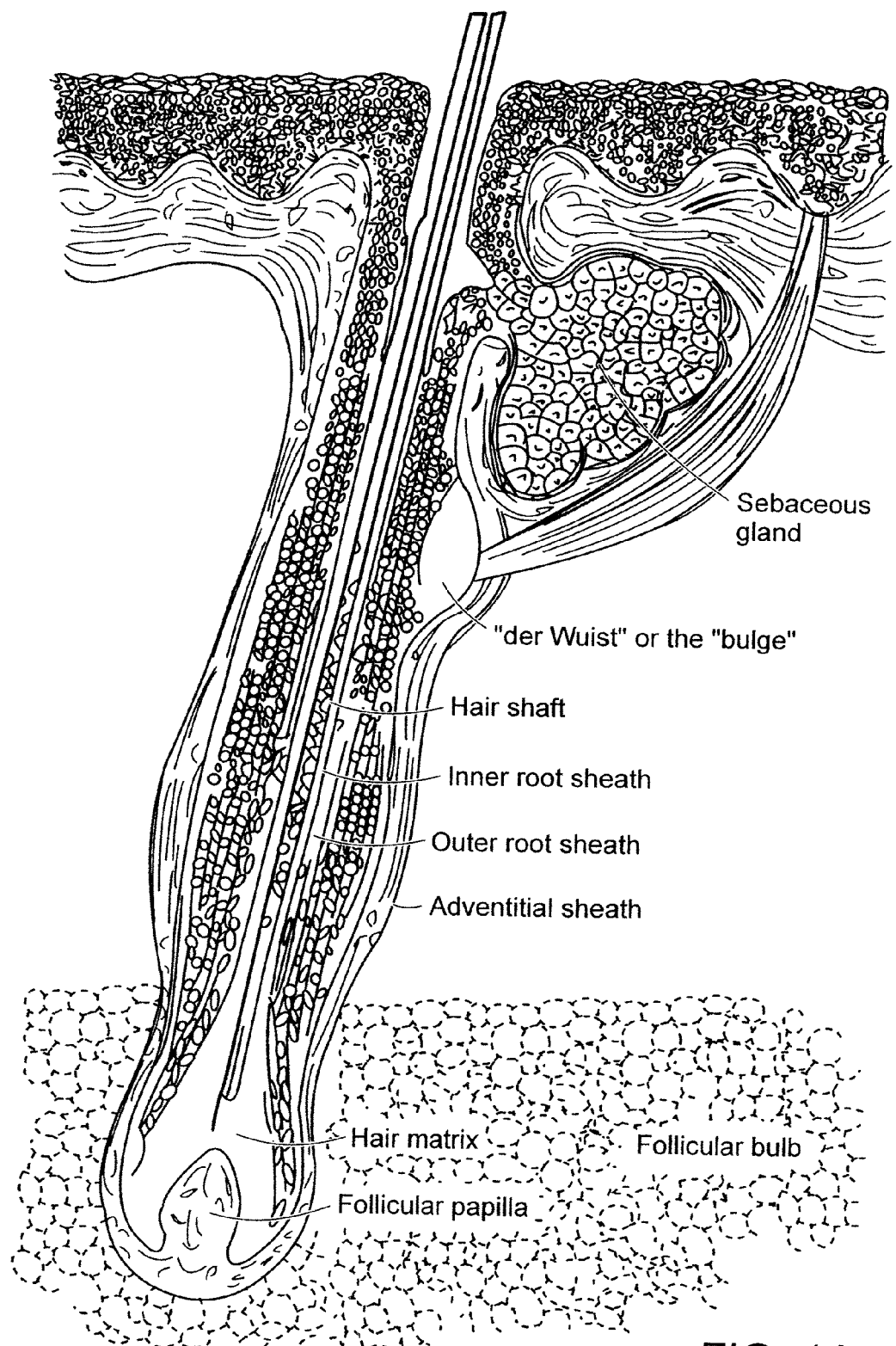
FIG. 1A is a diagrammatic representation of a human hair follicle in anagen.
Figure 1B:
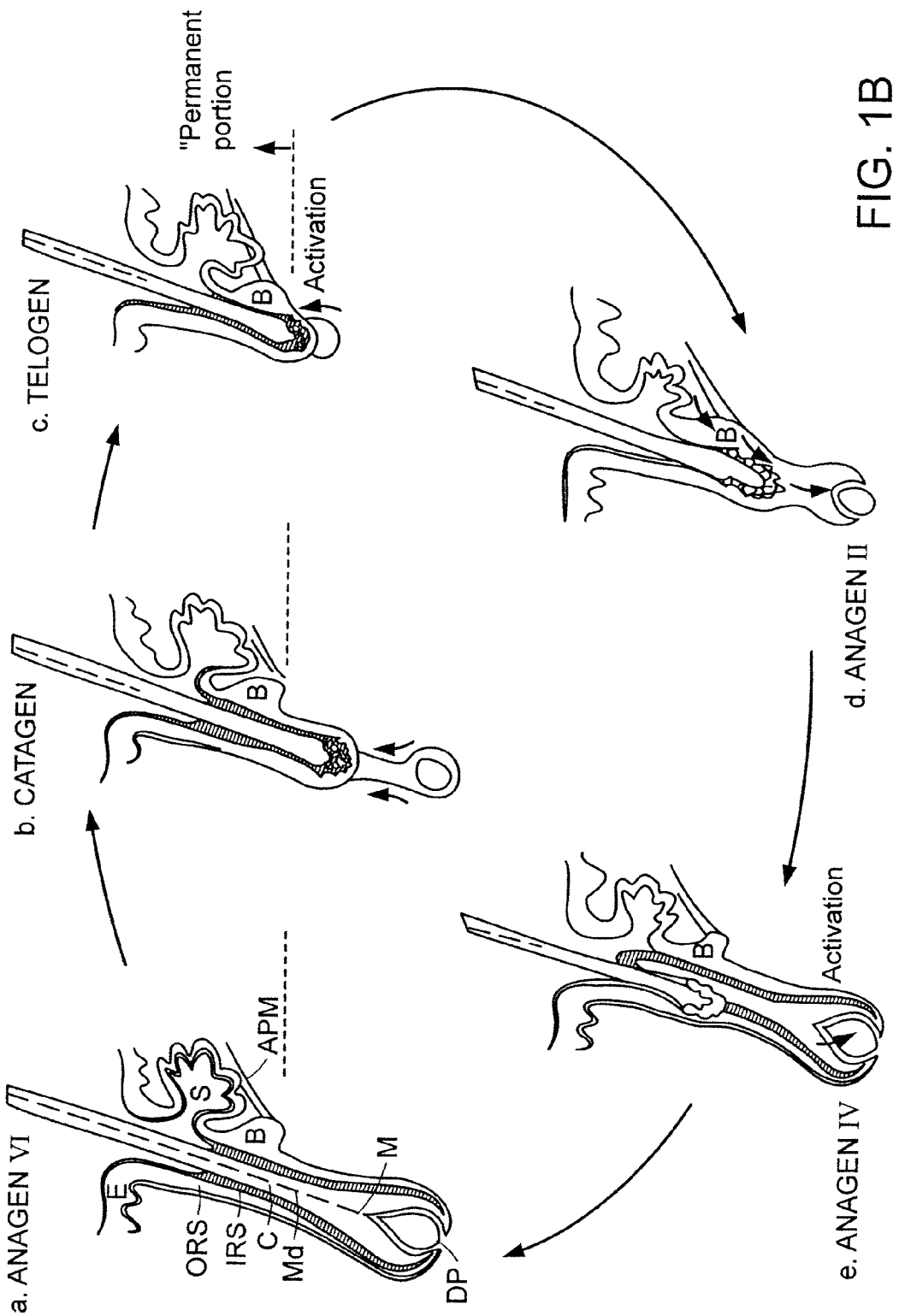
FIG. 1B is a diagrammatic representation of the different stages of a hair follicle cycle.

The outer surface of the hand, limb and body is covered by the epidermis, which is elaborated into a number of specialized appendages. One of the most prominent of these appendages is the hair follicle (FIG. 1A) which produces the hairs that fulfill a number of functions including thermoregulation, collecting sensory information, protection against environmental trauma, social communication, and mimicry (Sterm et al., *Physiol. Rev.* 81:449-494, 2001). Hair follicles have prolific growth characteristics and exhibit a complexity of differentiation (see, FIG. 1B). After initial embryonic morphogenesis, the hair follicle undergoes repeated cycles of regression and regeneration throughout the lifetime of an organism (Porter, *J. Anat.*, 202:125-131, 2003).

Hair follicle morphogenesis is governed by a series of inductive signals between epidermal keratinocytes committed to hair follicle specific differentiation and the mesenchymal cells that form the follicular papilla (Hardy, *Trends Genet.*, 8:55-61, 1992). Hair follicle precursors are first seen as thickenings or placodes in an otherwise uniform surface epithelium. These placodes send signals to the underlying dermis, causing the clustering of a group of cells—the dermal condensate—that will eventually form the follicular papilla. A second dermal signal from the dermal condensate to the follicular epithelium directs the proliferation and downgrowth of follicular epithelial cells into the dermis. These interactions eventually result in the morphogenesis of the hair bulb, in which keratinocytes rapidly proliferate and differentiate into six distinct cell populations, forming the medulla, cortex, and cuticle of the hair shaft, as well as the cuticle, Huxle and Henle layers of the inner root sheath (Bertolino et al., "Differentiation of the hair shaft," in *Differentiation of the Hair Shaft*, pp. 21-37, Olsen E A (ed.), McGraw Hill, Inc. New York, 1994). The inner root sheath separates the hair shaft from the outer root sheath, which forms the external concentric layer of epithelial cells in the hair follicle (Botchkarev et al., *J. Exp. Zool. Mol. Dev. Evol.*, 298 (1):164-180, 2003).

In humans, the formation of hair follicles takes place during embryogenesis, and no new hair follicles form after birth. However, the hair follicle is a highly dynamic structure, which undergoes remodeling throughout the life of a mammal, in a cycle of growth (anagen), regression (catagen), rest (telogen), and shedding (exogen) (Muller-Rover et al., *J. Invest. Dermatol.*, 117:3-15, 2001; Cotsarelis et al., Trends Mol. Med., 7(7):293-301, 2001). During catagen, much of the follicle undergoes programmed cell death. The hair bulb shrinks and pulls away from the mesenchymal cluster of follicular papilla cells, which it previously enveloped. The whole hair follicle then retracts upwards toward the epidermal surface. During this retraction, it undergoes a carefully controlled remodeling to form a shortened structure that significantly, maintains its close association with the follicular papilla. After a period of rest in this shortened form, a signal that is thought to be from the follicular papilla initiates the next anagen phase (Porter, *J. Anat.*, 202:125-131, 2003). Follicular regeneration requires the activation of rarely cycling epithelial stem cells located in the permanent, bulge region of the follicle (Cotsarelis et al., *Cell*, 61:1329-1337, 1990). Stem cell progeny form a new follicle matrix during early anagen, and the hair shaft and inner root sheath are derived from these relatively undifferentiated matrix cells (Oshima et al., *Cell*, 104:233-245, 2001).

It has been well established that follicular papilla cells of the hair follicle play a key role in controlling hair growth. First, the diameter and length of the hair fiber appears to be directly proportional to the size of the follicular papilla (Elliott et al., *J. Invest. Dermatol.*, 1113:873-877, 1999). Second, the surgical removal of the lower half of the rat vibrissa follicle results in follicular degeneration which can be prevented if one implants a follicular papilla, or a pellet of cultured follicular papilla cells, at the bottom of the damaged follicle. Implantation of dermal fibroblasts, which are embryologically closely related to the follicular papilla cells, fail to support hair growth thus establishing the importance of follicular papilla cells in maintaining the viability of the upper follicle (Oliver, *J. Embryol. Exp. Morphol.*, 15:331-347, 1966); Jahoda et al., *Nature*, 311:560-562, 1984). Like the vibrissa, the human follicle has also been shown to regenerate an active hair bulb after follicular amputation (Kim et al., *Dermatol. Surg.*, 21 (4):312-313, 1995). Third, follicular papilla cells implanted under the interfollicular epidermis can induce the formation of new hair follicles; the structure of the induced follicle resembles the original follicle of the follicular papilla (Jahoda, C. A., *Development*, 115:1103-1109, 1992); Reynolds, A. J. et al., *Nature*, 402:33-34, 1999). Fourth, when cultured keratinocytes were combined with follicular papilla cells and grafted onto a nude (athymic) mouse, hair follicles were generated; however, no hair grew when cultured keratinocytes that were mixed with dermal fibroblasts were grafted onto nude mice (Kamimura et al., *J. Invest. Dermatol.*, 109(4):534-40, 1997). Fifth, Jahoda et al. recently showed trans-species hair induction by human scalp follicular papilla cells, but not dermal fibroblasts (Jahoda et al., *Exp. Dermatol.*, 10(4):229-37, 2001). Sixth, minoxidil has been shown to upregulate the synthesis and secretion of VEGF by cultured follicular papilla cells thus providing a possible explanation of the minoxidil stimulation of hair growth (Lachgar et al., *Br. J. Dermatol.*, 138:407-411, 1998). Finally, recent data indicate that hair follicular epithelial stem cells reside in the bulge, and that the interaction between follicular papilla and bulge during telogen may play a role in activating the stem cells allowing the follicle to enter into a new anagen (Cotsarelis et al., *Cell*, 61:1329-1337, 1990; Taylor et al., *Cell*, 102:451-461, 2000). Taken together, these results clearly indicate that follicular papilla cells, unlike their closely related dermal fibroblasts, are endowed with a unique capacity to maintain and to support the growth of the hair follicle.

Given the important role of the follicular papilla in regulating the morphogenesis of the hair follicle, it is of interest to define the molecular basis for why the follicular papilla cells, but not their closely related dermal fibroblasts, support hair growth. Accordingly, a rat follicular papilla-specific subtractive cDNA library was constructed to identify polynucleotides that were selectively expressed in the follicular papilla. The most abundant cDNA that was isolated from this library was named follicular papilla-1 (FP-1). This cDNA was then used to identify the full length rat cDNA.

The rat FP-1 polynucleotide (FIG. 2, SEQ ID NO:1) encodes a protein of 549 amino acids (FIG. 2, SEQ ID NO:2). A second cDNA (FIG. 3, SEQ ID NO:3), which likely corresponds to an alternatively spliced product of the rat FP-1 gene, encodes a protein of 531 amino acids (FIG. 3, SEQ ID NO:4). A search of the GENBANK® database for other FP-1 related proteins led to the discovery of rat gliomedin (FIG. 4, Accession Number AAP22419; SEQ ID NO:6), a mouse protein named cancer related gene-liver 2 (Crg-L2) (FIG. 5, Graveel et al., *Oncogene*, 22:1730-1736, 2003; Accession Number NP_796324; SEQ ID NO: 8), and a human protein named likely ortholog of mouse cancer related gene-liver 2 (FIG. 6, Accession Number NP_861454; SEQ ID NO: 10). An alignment of the rat, mouse, and human sequence (FIG. 8) indicated a high level of homology between these proteins. Interestingly, the human sequence listed in GENBANK® lacks the N-terminal region that is conserved between the mouse and the rat. Thus, it is likely that the human sequence listed in GENBANK® is an incomplete amino acid sequence. Accordingly, the present invention provides the amino acid sequence corresponding to a full-length human FP-1 protein (FIG. 7, SEQ ID NO:12). These rat (SEQ ID NOS: 2, 4, 6), mouse (SEQ ID NO: 8) and human (SEQ ID NOS:10 and 12) proteins, and any portions, derivatives, or variants thereof, are collectively referred to herein as "FP-1 proteins." The rat, mouse, and human FP-1 proteins have an N-terminal signal peptide sequence (FIG. 15) of about 33 amino acids (see for example, amino acids 1 to 33 of SEQ ID NO:2).

Figures 10A, 10B:
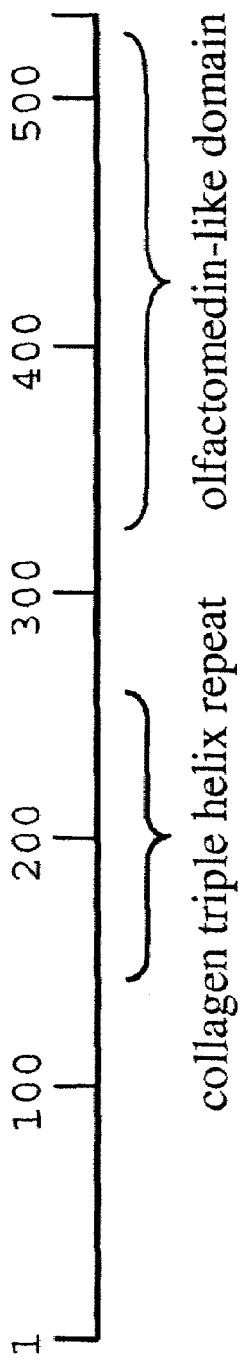
FIG. 10A is a diagrammatic representation of the location of the collagen triple helix repeat and olfactomedin-related domains of FP-1.
FIG. 10B is a schematic representation of an amino acid sequence alignment of the two regions (underlined) of rat FP-1a and b (SEQ ID NO: 34) and human FP-1 (SEQ ID NO: 35) that are homologous to the collagen triple helix repeat.
Figure 13A:
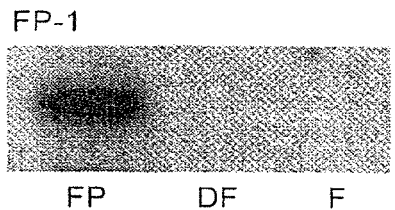
FIG. 13A is a photographic representation of a Southern blot hybridized with an FP-1 probe. FP: PCR-amplified double-stranded cDNAs of follicular papilla cells, F: PCR-amplified double-stranded cDNAs of fibroblasts (1:1:1 mixture of diaphragm, esophagus and stomach fibroblasts), and DF: PCR-amplified double-stranded cDNAs of dermal fibroblasts.
Figure 13B:
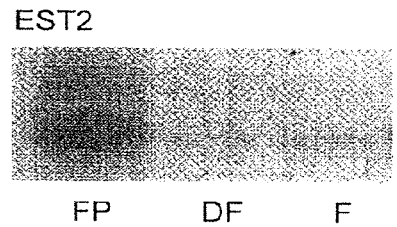
FIG. 13B is a photographic representation of the Southern blot hybridized with an EST2 probe.
Figure 13C:
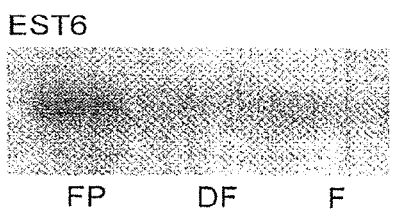
FIG. 13C is a photographic representation of the Southern blot hybridized with an EST6 probe.
Figure 13D:
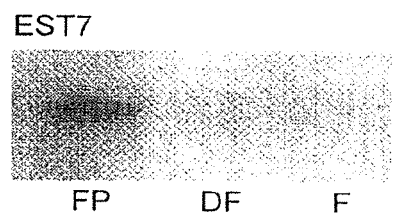
FIG. 13D is a photographic representation of the Southern blot hybridized with an EST7 probe.
Figure 13E:
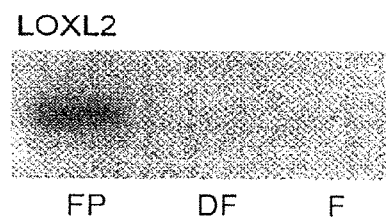
FIG. 13E is a photographic representation of the Southern blot hybridized with a lysyl oxidase-like 2 (LOXL2) probe.
Figure 13F:
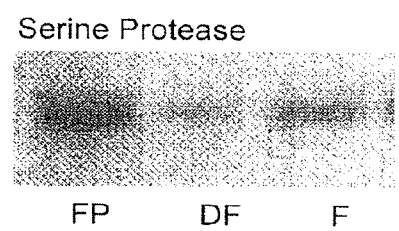
FIG. 13F is a photographic representation of the Southern blot hybridized with a serine protease probe.
Figure 13G:
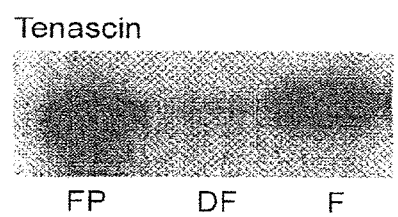
FIG. 13G is a photographic representation of a Southern blot hybridized with a tenascin c probe.
Figure 13H:
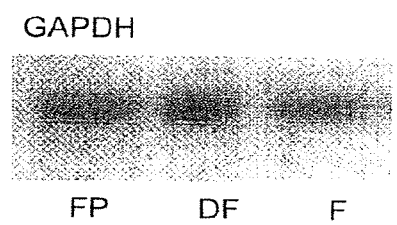
FIG. 13H is a photographic representation of a Southern blot hybridized with a GAPDH probe.

All the FP-1 proteins also possess amino acid sequences (see, e.g., amino acid 139-222 and 230-251 of SEQ ID NO:2) that are homologous to collagen triple helix repeat (20 copies) and several collagen family members such as collagen types IV, XIII and XV (FIG. 10B). Collagens are generally extracellular structural proteins involved in the formation of connective tissue structure. Collagen triple helix repeats contain 20 copies of the G-X-Y repeat (wherein G is glycine; X is any amino acid residue, but is frequently proline; and Y is any amino acid residue, but is frequently hydroxyproline) that forms a triple helix. Collagens are post-translationally modified by proline hydroxylase to form the hydroxyproline residues.

The FP-1 proteins are further characterized by the presence of an olfactomedin-related domain (see, e.g., amino acids 253-543 of SEQ ID NO:2). This domain was first identified in olfactomedin, which is an extracellular matrix glycoprotein specifically expressed in olfactory neuroepithelium (Snyder et al., *Biochem.*, 30(38):9143-153, 1991). Olfactomedin forms homopolymers through disulfide bonds and carbohydrate interactions (Bal et al., *Biochemistry*, 32(4):1047-53, 1993) and has been suggested to influence the growth and differentiation of chemosensory olfactory cilia (Yokoe et al., *Proc. Natl. Acad. Sci. USA* 90:4655-4659, 1993). In addition to olfactomedin, this domain is also found in a wide variety of proteins such as amassin, noelin, myocilin, and tiarin. Interestingly, the olfactomedin domain is primarily found in extracellular proteins. Olfactomedin domain-containing proteins have been reported to possess at least seven amino acid segments of conservation (regions 1, 3, and 5 through 9) (Green et al., *Mol. Cell. Prot.*, 1.5:394-403, 2002). These seven segments are also conserved in FP-1 proteins (see, FIG. 10C).

FP-1 proteins also have six potential glycosylation sites (FIG. 15, amino acids 130, 156, 252, 326, 354 and 461 of SEQ ID NO:2). When cell extracts having FP-1 are treated with endoglycosidase H, the molecular weight of rat FP-1 decreased from 72 kDa to roughly 60 kDa. Thus, FP-1 is a glycoprotein.

A survey of various rat tissues using Northern blot analysis indicated that FP-1 is expressed at an extremely high level in cultured rat vibrissa follicular papilla cells, and can be detected at low levels in the stomach and ovary. However, FP-1 was not detectable in the diaphragm, esophagus, stomach, brain, lung, heart, liver, spleen, kidney, bladder, intestine, colon, uterus, prostate, testis, and skeletal muscle (see, FIG. 14).

FP-1 is an extracellular matrix protein. The extracellular matrix of the follicular papilla undergoes cyclic changes such that it is completely degraded and removed during catagen, and then resynthesized and deposited in early to late anagen. These changes are important for the hair follicle cycle and thus hair growth. Thus, at least in part, FP-1 regulates hair growth by modulating the extracellular matrix of the hair follicle. Cross-species fluorescent in situ hybridization (FISH) on mouse chromosomes using rat FP-1 cDNA indicated that FP-1 is located on mouse chromosome 9 in the B-C region. This was confirmed by a BLAST search performed using rat FP-1 cDNA against the mouse genomic database after the completion of the Mouse Genome Program. Importantly, this region has three hair-related mutants, including rough fur (ruf), rough coat (rc) and fur deficient (fd).

The present invention provides isolated polynucleotides encoding FP-1. The polynucleotides of the invention can be DNA or RNA molecules that are single-stranded or double-stranded. The polynucleotides can include, but are not limited to, RNA, cDNA, genomic DNA, semisynthetic DNA or RNA, and chemically synthesized DNA or RNA sequences.

The polynucleotides comprise the sequences set forth as SEQ ID NO:1, SEQ ID NO:3 or SEQ ID NO:11. The invention also provides a nucleic acid sequence that encodes a polypeptide comprising SEQ ID NO:2, SEQ ID NO:4, or SEQ ID NO:12.

Alternatively, the isolated polynucleotides of the invention comprise a nucleic acid sequence that is homologous to any one of SEQ ID NO:1, SEQ ID NO:3 or SEQ ID NO: 11. By "homologous" is meant a polynucleotide that has at least about 70%, at least about 80%, at least about 90%, at least about 95%, or at least about 98% nucleotide sequence identity to a given nucleotide sequence, which can be determined by any standard nucleotide sequence identity algorithms such as, but not limited to, the GCG program (Devereux et al., *Nucl. Acids Res.*, 12(1): 387, 1984), BLASTN (GENBANK®), and FASTA (Altschul et al., *J. Mol. Biol.*, 215:403, 1990). For example, the invention provides an isolated polynucleotide comprising a nucleic acid sequence that has about 90%, or about 95% nucleic acid sequence identity to SEQ ID NO:1, SEQ ID NO:3, or SEQ ID NO: 11, wherein the isolated polynucleotide molecule encodes a protein that controls hair growth. By "controls hair growth" is meant to increase or decrease hair growth, or change the texture/structure of the hair shaft (e.g., rough, smooth, fragile, curly, etc.), relative to hair growth or hair texture in skin, hair follicles or follicular papilla not contacted with a polynucleotide, polypeptide, agent or composition of the invention. Some useful methods for determining whether FP-1 increases or decreases hair growth are described in the Examples below as well as in Philpott et al., Whole Hair Follicle Culture, in *Dermatologic Clinics* (Whiting D., ed.) 14(4): 595-607 (1966) and the references cited therein; and Wilson et al., Differentiation 55:127-136 (1994). Hair texture and structure can be assessed by direct visual study or by microscopy.

The polynucleotides of the invention alternatively comprise a nucleic acid sequence that is homologous to a nucleic acid sequence that encodes a polypeptide comprising SEQ ID NO:2, SEQ ID NO:4 or SEQ ID NO:12. For example, the polynucleotide may comprise a nucleic acid sequence that has about 90%, or about 95% nucleic acid sequence identity to a nucleic acid sequence that encodes a polypeptide comprising SEQ ID NO:2, SEQ ID NO:4 or SEQ ID NO:12, wherein the isolated polynucleotide molecule encodes a protein that increases or decreases hair growth, or changes hair texture.

The isolated polynucleotide of the invention specifically hybridize under moderately stringent or highly stringent conditions to a complement of a polynucleotide sequence comprising SEQ ID NO:1, SEQ ID NO:3 or SEQ ID NO:11, wherein the polynucleotide sequence encodes a protein that controls hair growth. As used herein, the phrase "specifically hybridizing" means the ability of a nucleic acid molecule to recognize another nucleic acid sequence by forming base pairs with it through hydrogen bonding, under moderately or highly stringent hybridization conditions. By "moderately stringent conditions" is meant hybridization to filter-bound DNA in 0.5 M NaHPO4, 7% sodium dodecyl sulfate (SDS), 1 mM EDTA at 65° C., and washing in 0.2×SSC/0.1% SDS at 42° C. (see, Ausubel et al. (eds.), *Current Protocols in Molecular Biology*, Vol. I, 1989, Green Publishing Associates, Inc., and John Wiley & Sons, Inc., New York at p. 2.10.3). By "highly stringent conditions" is meant hybridization to filter-bound DNA in 0.5 M NaHPO4, 7% sodium dodecyl sulfate (SDS), 1 mM EDTA at 65° C., and washing in 0.1×SSC/0.1% SDS at 68° C. (Ausubel et al., supra). The polynucleotides of the invention specifically hybridize under moderately stringent or highly stringent conditions to a complement of a polynucleotide sequence comprising a nucleotide sequence that encodes a polypeptide having SEQ ID NO:2, SEQ ID NO:4 or SEQ ID NO:12, wherein the polynucleotide sequence encodes a protein that increases or decreases hair growth, or changes hair texture.

Additionally, the invention provides an isolated polynucleotide that is the complement of the polynucleotide comprising any of the polynucleotides of the previous aspects.

The polynucleotides of the invention may be produced by hybridizing the polynucleotide having SEQ ID NO:1, SEQ ID NO:3 or SEQ ID NO:11 to genomic DNA under moderately stringent or highly stringent hybridization conditions and isolating the DNA polynucleotide hybridized to the polynucleotide having SEQ ID NO:1, SEQ ID NO:3 or SEQ ID NO:11. The genomic DNA can be from any eukaryotic organism including mammals, especially humans. Methods of hybridizing a polynucleotide to genomic DNA are well known in the art (Sambrook et al., *Molecular Cloning: A Laboratory Manual*, Third Edition, Cold Spring Harbor Laboratory Press).

The polynucleotides of the invention can be modified by the addition of flanking sequences such as, but not limited to, restriction enzyme recognition sequences, adaptors, nucleic acid sequences encoding epitopes recognized by antibodies (e.g., His, Flag, Myc, HA, MBP, GST) and nucleic acid sequences encoding proteins that permit detection of the fusion protein (e.g., GFP). Methods of adding or ligating desired DNA sequences to a DNA sequence of interest are well known in the art (Sambrook et al., ibid.).

The polynucleotides of the invention can also be mutated to generate polynucleotides that encode mutant FP-1 proteins. A polynucleotide sequence can be mutated by, for example, introducing one or more point mutations (e.g., a missense or nonsense mutation) or by inserting or deleting one or more bases. Any technique for mutagenesis known in the art can be used, including but not limited to, chemical mutagenesis, in vitro site-directed mutagenesis, PCR-based overlap extension, and PCR-based megaprimer mutagenesis. Methods of generating mutations in a DNA sequence are well within the skill of one of ordinary skill in the art (see, Sambrook et al., supra; Hutchinson et al., *J. Biol. Chem.*, 253:6551, 1978; Ho et al., *Gene*, 77:51-59, 1989; Sarkar et al., *Biotechniques*, 8:404-407, 1990; and Stratagene's QuikChange® Kit).

The invention provides oligonucleotides that hybridize to any of the aforementioned polynucleotides of the present invention, or that hybridize to a polynucleotide molecule having a nucleotide sequence that is the complement of any of the aforementioned polynucleotides of the invention. Such oligonucleotide molecules are at least about 10 nucleotides in length, at least about 20 nucleotides in length, at least about 30 nucleotides in length or at least about 40 nucleotides in length, and hybridize to one or more of the aforementioned polynucleotide molecules under moderately or highly stringent hybridization conditions. For shorter oligonucleotide molecules, an example of highly stringent conditions includes washing in 6×SSC/0.5% sodium pyrophosphate at about 37° C. for about 14-base oligonucleotides, at approximately 48° C. for about 17 bp oligonucleotides, at approximately 55° C. for about 20 bp oligonucleotides and at approximately 60° C. for about 23-40 base oligonucleotides. Hybridization conditions can of course be appropriately adjusted as known in the art, depending upon the particular oligonucleotide molecules utilized.

The oligonucleotides of the present invention are useful in a variety of purposes, including as primers in amplifying a FP-1 encoding polynucleotide, or as antisense molecules useful in regulating expression of FP-1 genes and gene products. A "gene product" means a product encoded by a gene, including the transcribed RNA message (including exons and introns), the spliced messenger RNA (mRNA), and the translated protein product encoded by the respective mRNA. Amplification of FP-1 polynucleotides can be carried out using suitably designed oligonucleotide molecules in conjunction with standard techniques, such as the polymerase chain reaction (PCR).

The present invention also provides recombinant cloning and expression vectors comprising any of the polynucleotide molecules of the invention. The choice of the vector and/or expression control sequences to which any of the polynucleotides of the present invention is operably linked depends directly, as well known in the art, on the functional properties desired, e.g., protein expression, and the host cell to be transformed. The regulatory sequences that are used for modulating the expression of an operably linked, protein-encoding sequence are known in the art and include, but are not limited to, inducible promoters, constitutive promoters, enhancers, and other regulatory elements known in the art that serve to drive and/or regulate expression of the polynucleotide coding sequences. The inducible promoter may be readily controlled, such as being responsive to a nutrient in the host cell's medium.

The vectors of the invention containing a polynucleotide according to the invention can include a prokaryotic replicon, i.e., a DNA sequence having the ability to direct autonomous replication and maintenance of the recombinant DNA molecule extra-chromosomally in a prokaryotic host cell, such as a bacterial host cell, transformed therewith. Such replicons are well known in the art. In addition, vectors that include a prokaryotic replicon may also include a gene whose expression confers a detectable marker such as drug resistance. Typical bacterial drug resistance genes are those that confer resistance to ampicillin, chloramphenicol, kanamycin or tetracycline. Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase, and permits transcription to occur. Promoter sequences compatible with bacterial hosts are typically provided in plasmid vectors containing convenient restriction sites for insertion of a polynucleotide or any fragment thereof of the present invention. Typical non-limiting prokaryotic vector plasmids include pUC8, pUC9, pBR322, pBR329 (BioRad Laboratories), pKK223-2 (Clontech), pSE280, pSE380, pSE420, pTrx-Fus, pRSET, pBAD/HisABC, pTrcHis (Invitrogen), pET-3, pET-11, pCAL-n-EK, pCAL-n (Stratagene), pFLAG-1, pFLAG-ATS, pFLAG-CTS, pFLAGShift(12) (Kodak), pET-14b, pET-15b, pET-30LIC, pET-32LIC (Novagen), pMC1871, pRIT2T and pKK223-3 (Pharmacia).

Suitable yeast vectors for use in the present invention are described in U.S. Pat. No. 6,291,212, and include YRp7 (Struhl et al., *Proc. Natl. Acad. Sci. USA,* 76: 1035-1039, 1978), YEp13 (Broach et al., *Gene,* 8:121-133, 1979), pJDB249 and pJDB219 (Beggs, *Nature,* 275:104-108, 1978). Such vectors generally include a selectable marker, which may be one of any number of genes that exhibit a dominant phenotype for which a phenotypic assay exists to enable transformants to be selected. Non-limiting examples of selectable markers include those that complement host cell auxotrophy, provide antibiotic resistance or enable a cell to utilize specific carbon sources, and include LEU2 (Broach et al. ibid.), URA3 (Botstein et al., *Gene,* 8:17, 1979), HIS3 (Struhl et al., ibid.) or POT1 (Kawasaki and Bell, EP 171142). Other suitable selectable markers include the CAT gene, which confers chloramphenicol resistance on yeast cells. Examples of promoters for use in yeast include promoters from yeast glycolytic genes (Hitzeman et al., *J Biol. Chem.,* 225:12073-12080, 1980; Alber and Kawasaki, *J. Mol. Appl. Genet.,* 1:419-434, 1982; Kawasaki, U.S. Pat. No. 4,599,311) or alcohol dehydrogenase genes (Young et al., in *Genetic Engineering of Microorganisms for Chemicals,* Hollander et al., (eds.), p. 355, Plenum, N.Y., 1982; Ammerer, *Meth. Enzymol.* 101: 192-201, 1983). Non-limiting examples of yeast promoters include the TPI1 promoter and the ADH promoter. The yeast expression vector may further comprise a transcriptional terminator such as the TPI1 terminator (Alber and Kawasaki, ibid.).

In addition to yeast, polynucleotides of the present invention can be expressed in filamentous fungi, for example, strains of the fungi Aspergillus. Examples of useful promoters include those derived from *Aspergillus nidulans* glycolytic genes, such as the ADH3 promoter (McKnight et al., *EMBO J.,* 4:2093-2099, 1985) and the tpiA promoter. An example of a suitable terminator is the ADH3 terminator (McKnight et al., ibid.). The expression units utilizing such components may be cloned into vectors that are capable of insertion into the chromosomal DNA of *Aspergillus.*

Expression vectors compatible with mammalian cells can also be used to express the polynucleotides of the present invention. Eukaryotic cell expression vectors are well known in the art and are available from several commercial sources. Typically, such vectors are provided containing convenient restriction sites for insertion of the desired polynucleotide or any fragment thereof. Such vectors may further include a selectable marker that is effective in a eukaryotic cell, preferably a drug resistance selection marker. A useful drug resistance marker is the gene whose expression results in neomycin resistance, i.e., the neomycin phosphotransferase (neo) gene (Southern et al., *J. of Mol. and Appl. Genet.,* 1(4):327-341, 1982). Alternatively, the selectable marker can be present on a separate plasmid, and the two vectors are introduced by co-transfection of the host cell, and selected by culturing in the appropriate drug for the selectable marker.

Mammalian expression vectors for use in carrying out the present invention will include a promoter capable of directing the transcription of a cloned gene or cDNA. Such promoters include viral promoters (e.g., the major late promoter from adenovirus 2 (Kaufman and Sharp, *Mol. Cell. Biol.,* 2: 1304-1319, 1982) and the SV40 promoter (Subramani et al., *Mol. Cell. Biol.,* 1: 854-864, 1981) and cellular promoters (e.g., mouse metallothionein 1 promoter (Palmiter et al., *Science,* 222:809-814, 1983)). These expression vectors may further comprise enhancers. In addition, these expression vectors may also contain a set of RNA splice sites located downstream from the promoter and upstream from the polynucleotide encoding the protein. RNA splice sites may be obtained from adenovirus and/or immunoglobulin genes. Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the adenovirus 5 E1B region and the human growth hormone gene terminator (DeNoto et al., *Nuc. Acids Res.,* 9:3719-3730, 1981). The expression vectors may include a noncoding viral leader sequence, such as the adenovirus 2 tripartite leader, located between the promoter and the RNA splice sites. Non-limiting examples of eukaryotic expression vectors include pACT, pCI, pCI-neo, pCM-VTNT™ (Promega), pTet-On™, pTet-Off™, PMAM neo, IRES Bicistronic, pRetro-Off™, pRetro-On™ (Clontech), pWE1, pWE2, pWE3, pWE4 (ATCC®), pIND(SP1), pCDM8, pcDNA1.1, pcDNA3.1, pZeoSV2, pRcCMV2, pRcRSV, ptracer (Invitrogen Corp.), pSVL, pMSG (Pharmacia), pBPV-1/pML2d (International Biotechnologies, Inc.), pCMVScript™, pBK-CMV, and pBK-RSV (Stratagene).

Methods for constructing recombinant vectors are well known in the art, and any of these can be used to construct the vectors of the present invention. These methods include in vitro recombinant techniques, synthetic techniques, and in vivo genetic recombination (see e.g., Sambrook et al., supra, Ausubel et al., supra).

The present invention further provides host cells comprising a polynucleotide molecule or recombinant vector of the invention. Host cells useful in the practice of the invention include prokaryotic and eukaryotic cells such as mammalian, insect, fungal, plant, bacterial, viral and baculoviral cells. Appropriate host cells can be chosen that modify and process the gene product in the specific fashion desired. Different host cells have characteristic mechanisms for the translational and post-translational processing and modification (e.g., glycosylation, phosphorylation) of proteins. For example, expression in a bacterial system can be used to produce an unglycosylated protein product. Expression in mammalian cells can be used to ensure "native" processing of a protein product. Further, different vector/host expression systems can affect processing reactions to different degrees. Non-limiting examples of prokaryotic host cells include the *E. coli* strains HB101, JM101, DH5α, LE392, RR1, XL1-Blue and KW251. Non-limiting examples of eukaryotic host cells include, COS, 293, 293T, CHO, CV-1, Hela, NIH3T3, BHK, C33A, U20S, and primary follicular papilla cells.

The recombinant vector of the invention is transformed or transfected into one or more host cells of a substantially homogenous culture of cells. Methods of transforming and/or transfecting cells are well known in the art. The expression vector is generally introduced into host cells in accordance with known techniques such as e.g., by protoplast transformation, calcium phosphate precipitation, calcium chloride treatment, microinjection, electroporation, transfection by contact with recombined virus, liposome-mediated transfection, DEAE-dextran transfection, transduction, conjugation, or microprojectile bombardment. Selection of transformants can be conducted by standard procedures, such as by selecting for cells expressing a selectable marker, e.g., antibiotic resistance associated with the recombinant vector, as described above. Once the expression vector is introduced into the host cell, the integration and maintenance of the polynucleotides of the invention, either episomally or in the host cell chromosome can be confirmed by standard techniques, e.g., by Southern hybridization analysis, restriction enzyme analysis, PCR analysis, RT-PCR, or by immunological assays to detect the expected gene product. Host cells containing and/or expressing the recombinant polynucleotide of the invention can be identified by any approach known in the art, including: (i) DNA-DNA, DNA-RNA, or RNA-antisense RNA hybridization; (ii) detecting the presence of "marker" gene functions; (iii) assessing the level of transcription as measured by the expression of the mRNAs produced by the recombinant polynucleotide in the host cell; and (iv) detecting the presence of a mature polypeptide product as measured by, for example, an immunoassay.

Once a polynucleotide of the invention has been introduced into an appropriate host cell, the transformed host cell is cultured under conditions conducive to the maximum production of the polypeptide encoded by the recombinant polynucleotide. Such conditions typically include, e.g., growing cells to high density. Where the expression vector comprises an inducible promoter, appropriate induction conditions such as temperature shift, exhaustion of nutrients, and addition of gratuitous inducers (e.g., zinc chloride, analogs of carbohydrates such as IPTG, etc.) are employed as needed to induce expression. Where the expressed polypeptide is retained inside the host cells, the cells are harvested and lysed, and the polypeptide is isolated and purified from the lysate under extraction conditions known in the art to minimize protein degradation such as, e.g., at 4° C. and/or in the presence of protease inhibitors. Where the expressed polypeptide is secreted from the host cells, the nutrient medium can simply be collected and the polypeptide isolated therefrom.

The polypeptide can be isolated or substantially purified from cell lysates or culture medium, as appropriate, using standard methods including, but not limited to, any combination of the following methods: ammonium sulfate precipitation, gel filtration chromatography, ion exchange chromatography, HPLC, density centrifugation, affinity chromatography and immuno-affinity chromatography. If the polypeptide exhibits any measurable biological activity, increasing purity of the polypeptide preparation can be monitored at each step of the purification procedure by use of an appropriate assay. Whether or not the polypeptide exhibits biological activity, it can be detected at each step of the purification based on size or reactivity with an antibody raised to the polypeptide or by detection with an antibody that binds a fusion tag attached to the protein.

The present invention thus provides a substantially purified or isolated polypeptide encoded by a polynucleotide molecule of the present invention. As used herein, a polypeptide is "substantially purified" where the polypeptide constitutes the majority (i.e., at least about 50%) by weight of the material in a particular preparation.

The polypeptides useful in the method of the invention include rat FP-1 gene products comprising, consisting essentially of, or consisting of, the amino acid sequence of SEQ ID NO:2 or SEQ ID NO:4. In one embodiment, the polypeptide is a rat FP-1 gene product comprising, consisting essentially of, or consisting of amino acids 34 to 549 of SEQ ID NO:2. The polypeptide, alternatively, is a rat FP-1 gene product comprising, consisting essentially of, or consisting of amino acids 34 to 531 of SEQ ID NO:4. Any of the amino acid sequences lacking the signal peptide can further comprise an initiating methionine residue.

The present invention also provides an isolated polypeptide comprising the amino acid sequence encoded by any one of the polynucleotides of the invention. For example, the polypeptide is a human FP-1 gene product comprising, consisting essentially of, or consisting of SEQ ID NO: 12. Alternatively, the polypeptide is a human FP-1 gene product comprising, consisting essentially of, or consisting of amino acid 34 to 551 of SEQ ID NO: 12.

The substantially purified or isolated polypeptides of the present invention are useful for a variety of purposes, such as increasing or decreasing hair growth, changing hair texture, regulating the length of the anagen phase of the hair follicle cycle, screening for proteins or compounds that interact with FP-1 and alter its ability to control hair growth, and for raising antibodies directed to the polypeptide. Such compounds and antibodies can be used in therapeutic methods to treat or prevent hair disorders.

Also within the scope of the present invention are FP-1 proteins or FP-1 fusion proteins comprising one or more amino acid substitutions, insertions or deletions occur in the FP-1 proteins. Such proteins may function as dominant-negative forms of FP-1. The mutant FP-1 proteins or the polynucleotides coding them can be administered to a subject to inhibit or decrease hair growth. Mutant FP-1 encompassed by the invention include, but are not limited to, FP-1 proteins with a deletion or substitution of one or more amino acids in the collagen triple helix repeats, and FP-1 proteins with a deletion or substitution of one or more amino acids in the olfactomedin-related domain.

Non-limiting examples of mutations in the collagen triple helix repeats of FP-1 include, (i) deletion of amino acids 139-222 of SEQ ID NO:2 (or the corresponding region in SEQ ID NOS: 4, 6, 8, 10 and 12); (ii) deletion of amino acids 230-250 of SEQ ID NO:2 (or the corresponding region in SEQ ID NOS: 4, 6, 8, 10 and 12); (iii) deletion of amino acids 139-165 (or the corresponding † region in SEQ ID NOS: 4, 6, 8, 10 and 12); (iv) deletion of amino acids 166-195 (or the corresponding region in SEQ ID NOS: 4, 6, 8, 10 and 12); (v) deletion of amino acids 196-222 (or the corresponding region in SEQ ID NOS: 4, 6, 8, 10 and 12); (vi) mutations of one or more glycines in the region encompassing amino acids 139-222 of SEQ ID NO:2 (or the corresponding region in SEQ ID NOS: 4, 6, 8, 10 and 12) to any other amino acid; and (vii) mutations of one or more glycines in the region encompassing amino acids 230-250 of SEQ ID NO:2 (or the corresponding region in SEQ ID NOS: 4, 6, 8, 10 and 12) to any other amino acid. In one embodiment, the FP-1 proteins with mutations in the collagen triple helix repeat region have decreased or no binding to collagen. Methods of determining binding between mutant FP-1 proteins and collagen can be performed using methods well known in the art. For example, the binding of FP-1 and its mutants to collagen type 1 or other types may be studied using well established methods including gel electrophoresis and affinity chromatography (Keller et al., *Biochim. Biophys. Acta,* 882(1):1-5, 1986). The binding constant can be assessed using affinity co-electrophoresis as described by San Antonio et al. (*J. Cell Biol.,* 125(5):1178-1188). This method can be used to compare the binding of FP-1 to procollagen or collagen fibrils in order to determine whether the binding is collagen assembly-dependent. Finally, the collagen domain that is responsible for the binding of FP-1 can be mapped using synthetic peptides or paryial collagen fragments made as recombinant proteins (Knight et al., *J. Biol. Chem.*, 273(50):33287-33294, 1998).

Non-limiting examples of mutations in the olfactomedin-related domain of FP-1 include, (i) deletion of amino acids 315-325 of SEQ ID NO:2 (or the corresponding region in SEQ ID NOS: 4, 6, 8, 10 and 12); (ii) deletion of amino acids 366-382 of SEQ ID NO:2 (or the corresponding region in SEQ ID NOS: 4, 6, 8, 10 and 12); (iii) deletion of amino acids 408-437 of SEQ ID NO:2 (or the corresponding region in SEQ ID NOS: 4, 6, 8, 10 and 12); (iv) deletion of amino acids 441-466 of SEQ ID NO:2 (or the corresponding region in SEQ ID NOS: 4, 6, 8, 10 and 12); (v) deletion of amino acids 468-484 of SEQ ID NO:2 (or the corresponding region in SEQ ID NOS: 4, 6, 8, 10 and 12); (vi) deletion of amino acids 487-494 of SEQ ID NO:2 (or the corresponding region in SEQ ID NOS: 4, 6, 8, 10 and 12); (vii) deletion of amino acids 519-539 of SEQ ID NO:2 (or the corresponding region in SEQ ID NOS: 4, 6, 8, 10 and 12); (viii) deletion of any combination of the amino acids listed above; (ix) mutation of one or more of G318, W320, R322, E323, G368, G370, A372, V373, Y374, N375, S377, L378, Y379, Y380, K382, F409, Y413, I424, A425, V426, D427, E428, G430, L431, W432, I433, I434, Y435, A436, I444, L445, V446, L449, T453, V456, N461, T462, Y464, K466, A469, N471, A472, F473, A475, G477, I478, L479, Y480, V481, T482, T484, T490, F491, A492, F493, D494, Y519, N520, D523, L526, Y527, W529, E530, D531, G532, H533, L534, Y537 and V539 of SEQ ID NO:2 (or the corresponding amino acid in SEQ ID NOS: 4, 6, 8, 10 and 12) to any other amino acid; (ix) FP-1 comprising a mutation at Y480 of SEQ ID NO:2 (or the corresponding amino acid in SEQ ID NOS: 4, 6, 8, 10 and 12) to any amino acid, for example, but not limited to, histidine and asparagine; (x) FP-1 comprising a mutation at A469 of SEQ ID NO:2 (or the corresponding amino acid in SEQ ID NOS: 4, 6, 8, 10 and 12) to any amino acid, for example, but not limited to, phenylalanine, tyrosine and aspartic acid; (xi) FP-1 comprising a mutation at Y480 of SEQ ID NO:2 (or the corresponding amino acid in SEQ ID NOS: 4, 6, 8, 10 and 12) to any amino acid, for example, but not limited to, histidine and asparagines; and (xii) FP-1 comprising a mutation at N519 of SEQ ID NO:2 (or the corresponding amino acid in SEQ ID NOS: 4, 6, 8, 10 and 12) to any amino acid, for example, but not limited to, lysine and arginine.

In addition, the invention encompasses FP-1 proteins with mutations at one or more of the glycosylation sites of FP-1 that prevent its glycosylation. In one embodiment, N130, N156, S252, N326, N354 and N461 are mutated to a different amino acid residue such as, but not limited to, glycine. Glycosylation of FP-1 and mutant FP-1 proteins can be assessed by comparing SDS-PAGE mobilities of the unmutated and mutated FP-1 proteins. N-glycosylation of each potential glycosylation site will increase the apparent SDS gel molecular weight by approximately 2 kD. Thus, the mutation of one such N-glycosylation site in FP-1 will decrease the molecular weight of FP-1 by 2 kD.

In addition, the invention encompasses FP-1 proteins, or any hair growth-controlling portion thereof, that are fusion proteins. A protein or peptide may be fused either at the N- or C-terminus of FP-1 proteins. In one embodiment, an FP-1 protein is fused to an epitope tag selected from the group consisting of His, Flag, Myc, HA, MBP and GST.

The present invention further provides polyclonal and monoclonal antibodies, or portions thereof, that bind to the polypeptides or peptide fragments of the invention, or to a homologous polypeptide or peptide fragment of the invention. The term "antibody" as used herein refers to immunoglobulin molecules and immunologically active portions of immunoglobulin molecules, i.e., molecules that contain an antigen binding site which specifically binds (immunoreacts with) an antigen, such as FP-1. Antigen-binding fragments are also intended to be designated by the term "antibody." Examples of binding fragments encompassed within the term antibody include Fab, Fd, Fv, dAb, $F(ab')_2$, and single chain Fv (scFv). For example, antibody fragments for use in the present invention are those which are capable of crosslinking their target antigen, e.g., bivalent fragments such as $F(ab')_2$ fragments. In another embodiment, an antibody fragment which does not itself crosslink its target antigen (e.g., a Fab fragment) can be used in conjunction with a secondary antibody which serves to crosslink the antibody fragment, thereby crosslinking the target antigen. An antibody of the invention is further intended to include bispecific and chimeric molecules having a desired binding portion (e.g., FP-1).

An antibody of the present invention is used to detect the polypeptides of the invention; as affinity reagents with which to purify the polypeptides of the invention; as reagents to isolate follicular papilla cells; or to control the activity of the polypeptide of the invention. In this context, "controls hair growth" is meant to increase or decrease hair growth relative to hair growth in skin, hair follicles or follicular papilla not contacted with an antibody of the invention. For example, an antibody that binds FP-1 controls the activity of FP-1 by increasing or decreasing its ability to control hair growth. Methods of determining whether FP-1 increases or decreases hair growth can be assayed using any of the methods described or used in the Examples.

Polyclonal antibodies can be obtained from immunized animals and tested for specificity using standard techniques (Harlow et al., *Antibodies: A Laboratory Manual*, Cold Spring Harbor Laboratory Press, 1988). Alternatively, monoclonal antibodies to any of the polypeptides of the invention can be prepared using any technique that provides for the production of antibody molecules by continuous cell lines in culture. These include, but are not limited to, the hybridoma technique originally described by Kohler and Milstein (*Nature,* 256:495-497, 1975); the human B-cell hybridoma technique (Kosbor et al., *Immunol. Today,* 4:72, 1983; Cote et al., *Proc. Natl. Acad. Sci. USA,* 80:2026-2030, 1983); and the EBV-hybridoma technique (Cole et al., *Monoclonal Antibodies and Cancer Therapy*, Alan R. Liss, Inc., pp. 77-96) and any other methods known in the art (Golding, *Monoclonal Antibodies: Principles and Practice*, Academic Press, 1996). Alternatively, techniques described for the production of single chain antibodies (e.g., U.S. Pat. No. 4,946,778) can be adapted to produce single chain antibodies to the polypeptides of the present invention.

An anti-FP-1 antibody or a fragment thereof may be attached or coupled to a surface (e.g., cell surface, beads etc.). Beads that are used in the invention include, but are not limited to biodegradable beads, magnetic beads, and polymer microbeads. An antibody or fragment thereof can be immobilized directly or indirectly by, for example, by a secondary antibody, to a surface, such as a tissue culture flask or bead (see, for e.g., U.S. Pat. Nos. 6,352,694 and 6,129,916). Alternatively, antibodies can be coupled to a surface, e.g., beads by crosslinking via covalent modification, using tosyl linkage. In one method, an antibody such as anti-FP-1 is in 0.05 M borate buffer, pH 9.5 and added to tosyl activated magnetic immunobeads (Dynal Inc., Great Neck, N.Y.) according to the manufacturer's instructions. After a 24 hr incubation at 22° C., the beads are collected and washed extensively. It is not essential that immunomagnetic beads be used, as other methods are also satisfactory.

In one embodiment of the invention, an FP-1 protein, or a portion of an FP-1 protein, or a modified form of an FP-1 protein, capable of modulating hair growth is localized to the surface of a cell. This can be accomplished by transfecting a cell with a polynucleotide encoding the FP-1 protein in a form suitable for its expression on the cell surface or alternatively by coupling an FP-1 protein to the cell surface.

The FP-1 proteins may be expressed on the surface of a cell by transfection of the cell with a polynucleotide encoding the FP-1 molecule in a form suitable for expression of the molecule on the surface of the cell. The terms "transfection" or "transfected with" refers to the introduction of exogenous nucleic acid into a mammalian cell and encompass a variety of techniques useful for introduction of nucleic acids into mammalian cells including electroporation, calcium-phosphate precipitation, DEAE-dextran treatment, lipofection, microinjection and infection with viral vectors. Suitable methods for transfecting mammalian cells can be found in Sambrook et al., (*Molecular Cloning: A Laboratory Manual*, 2nd Edition, Cold Spring Harbor Laboratory Press, 1989) and other laboratory textbooks. The nucleic acid to be introduced may be any nucleic acid encompassing a polynucleotide encoding FP-1, sense strand RNA encoding FP-1, or a recombinant expression vector containing a cDNA encoding FP-1. Expression of FP-1 on the surface of a cell can be accomplished, for example, by including the transmembrane domain of a protein that localizes to the cell surface in the nucleic acid sequence, or by including signals which lead to modification of the protein, such as a C-terminal inositol-phosphate linkage, that allows for association of the molecule with the outer surface of the cell membrane. Expression of the FP-1 protein on the surface of the cell can be confirmed by immunofluorescence staining of the cells. For example, cells may be stained with a fluorescently labeled monoclonal antibody reactive against the FP-1 molecule.

Alternatively, FP-1 proteins can be coupled to the cell surface by any of a variety of different methods. The terms "coupled" or "coupling" refer to a chemical, enzymatic or other means (e.g., antibody) by which the FP-1 molecule is linked to a cell such that the FP-1 molecule is present on the surface of the cell. For example, the FP-1 molecule can be chemically crosslinked to the cell surface using commercially available crosslinking reagents (Pierce, Rockford Ill.). Another approach to coupling an FP-1 molecule to a cell is to use a bispecific antibody, which binds both the FP-1 molecule and a cell-surface molecule on the cell. Fragments, mutants or variants of a FP-1 molecule can also be used. The level of FP-1 expressed on or coupled to the cell surface can be determined by FACS analysis.

The present invention also encompasses methods of isolating follicular papilla cells. Since FP-1 is a secreted extracellular matrix protein at least some of the protein remains associated with the cell surface of the follicular papilla cells. Thus, antibodies to FP-1 can be used to sort the cells that bind an antibody raised to FP-1 using methods well known in the art. Alternatively, a composition comprising an anti-FP-1 antibody attached to a surface can be used to selectively isolate follicular papilla cells from a mixed population of cells from the skin or hair follicle. In this method, a composition comprising an FP-1 antibody can be used to contact a mixed population of cells from the skin or hair follicle sample from which the follicular papilla cells are to be isolated. The follicular papilla cells that bind to the FP-1 antibody can be separated from the unbound cells by any method known in the art including, but not limited to, fractionation. The isolated follicular papilla cells may be useful for (i) inducing epidermis to form new hair follicles de novo; or (ii) improving the performance of existing hair follicles that may contain defective or fewer numbers of follicular papilla cells than normal hair follicles.

Also within the scope of the present invention are oligonucleotide sequences that include antisense oligonucleotides, ribozymes, and siRNAs that function to bind to, degrade and/or inhibit the translation of the mRNA encoded by the polynucleotides of the invention. Antisense RNAs can be designed based on principles established in the art (e.g., Schiavone et al., *Curr. Pharm. Des.*, 10(7):769-784, 2004; Sczakiel, *Antisense Nucl. Acid Drug Dev.*, 7(4):439-444, 1997; Stein, *Antisense Nucl. Acid Drug Dev.*, 8(2):129-132, 1998; and Summerton et al., *Antisense Nucl. Acid Drug Dev.*, 7(3):187-195, 1997). Methods for designing suitable siRNAs for a target gene are well known in the art (e.g., Elbashir et al., *Nature*, 411:494-498, 2001; Semizarov et al., *Proc. Natl. Acad. Sci. USA*, 100:6347-6352, 2003).

The antisense oligonucleotides, ribozymes and siRNAs of the present invention can be commercially obtained or prepared by known methods. These include techniques for chemical synthesis such as, e.g., by solid phase phosphoramidite chemical synthesis. Alternatively, antisense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters.

Various modifications to any of the polynucleotides and oligonucleotides of the present invention can be introduced to increase intracellular stability and half-life. Possible modifications include, but are not limited to, the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

The present invention also provides pharmaceutical compositions or formulations comprising the polynucleotides, polypeptides, antisense molecules, ribozymes, siRNAs or antibodies of the present invention, as an active component. For example, a pharmaceutical composition may comprise a polynucleotide selected from the group consisting of SEQ ID NO:1, SEQ ID NO:3, SEQ ID NO:5, SEQ ID NO:7, SEQ ID NO:9, SEQ ID NO:11, and any combination thereof. The pharmaceutical composition may instead comprise a polypeptide selected from the group consisting of SEQ ID NO:2, SEQ ID NO:4, SEQ ID NO:6, SEQ ID NO:8, SEQ ID NO:10, SEQ ID NO:12, and any combination thereof. The pharmaceutical composition alternatively may comprise a polypeptide such as one having amino acids 34 to 549 of SEQ ID NO:2, 34 to 531 of SEQ ID NO:4, 34 to 549 of SEQ ID NO:6, 34 to 549 of SEQ ID NO:8, 34 to 427 of SEQ ID NO:10, and/or 34 to 551 of SEQ ID NO:12. The pharmaceutical composition may instead comprise an antibody that binds to FP-1. For example, the antibody may be one that specifically binds to human FP-1, or to both the rat and human FP-1 proteins. The pharmaceutical composition may alternatively comprise an antisense molecule that inhibits or prevents translation of FP-1 mRNA, an siRNA that blocks expression of an FP-1 mRNA, or a ribozyme that cleaves an FP-1 mRNA.

In addition to the FP-1 component of the composition, the therapeutic compositions of the present invention contain suitable pharmaceutically acceptable carriers, and may also comprise excipients and auxiliaries that facilitate processing of the active compounds into preparations, which can be used pharmaceutically for delivery to the site of action. Suitable formulations for parenteral administration include aqueous solutions of the active compounds in water-soluble form, for example, water-soluble salts. In one embodiment, the pharmaceutically acceptable carrier is phosphate buffered saline. In another embodiment, the carrier is water. In addition, suspensions of the active compounds as appropriate oily injection suspensions may be administered. Suitable lipophilic solvents or vehicles include, but are not limited to, fatty oils (e.g., sesame oil), or synthetic fatty acid esters (e.g., ethyl oleate), or triglycerides. Aqueous injection suspensions may contain substances which increase the viscosity of the suspension, for example, sodium carboxymethyl cellulose, sorbitol and dextran. Optionally, the suspension may also contain stabilizers. Liposomes can also be used to encapsulate the composition for delivery into the cell (e.g., U.S. Pat. Nos. 4,828,837 and 6,224,901).

The pharmaceutical formulations of the invention may be administered to a subject in need thereof using standard administration protocols. "A subject in need thereof," is used herein, to mean a mammalian subject who is determined by a health care provider, scientist, veterinarian, animal breeder, or other qualified person to be in need of increasing or decreasing hair growth. In the case of human subjects, the health care provider may determine that the subject is in need of controlling hair growth for health or cosmetic reasons. For non-mammalian subjects, a veterinarian or animal breeder may determine that a particular subject is in need of a pharmaceutical composition of the invention to increase hair growth, e.g., in wool or fur production.

The compositions of the present invention can be administered via topical, parenteral, subcutaneous, intravenous, intramuscular, intraperitoneal, transdermal, or buccal routes. For example, a composition is administered locally to a site via microinfusion, or by topical application in a cream, gel, lotion, ointment, salve, balm, aqueous solution or patch. Alternatively, or concurrently, administration may be by the oral route. Suitable formulations for oral administration include hard or soft gelatin capsules, pills, tablets, including coated tablets, elixirs, suspensions, syrups or inhalations and controlled release forms thereof. Indeed, all types of formulations may be used simultaneously to achieve systematic administration of the active ingredient. The dosage administered is dependent upon the age, health, and weight of the recipient, kind of concurrent treatment, if any, frequency of treatment, and the nature of the desired effect. The present invention further provides compositions containing one or more polypeptides of the invention. While individual needs vary, determination of optimal ranges of effective amounts of each composition of the invention is within the skill of the art. In one non-limiting example, dosages of protein for topical formulations comprise from about 0.1 ng to about 100 ng per ml of the formulation, from about 10 ng to about 50 ng, or about 30 ng.

The pharmaceutical formulations of the present invention can be provided alone, or in combination, or in sequential combination with other agents that modulate hair growth. As used herein, two agents are said to be administered in combination when the two agents are administered simultaneously or are administered independently in a way such that the agents will act at the same or almost the same time.

The use of gene therapy to administer the compositions of the invention is contemplated in one aspect of this invention. More specifically, the polynucleotides of the invention can be applied to the skin or scalp through the delivery of nucleic acid molecules. The delivery of nucleic acid molecules can be accomplished by any means known in the art. Gene delivery vehicles (GDVs) are available for delivery of polynucleotides to cells or tissue for expression. For example, a nucleic acid sequence of the invention can be administered either locally or systematically in a GDV. These constructs can utilize viral or non-viral vector approaches in vivo or ex vivo. Expression of such coding sequence can be induced using endogenous mammalian or heterologous promoters. Expression of the coding sequence in vivo can be either constitutive or regulated. The invention includes gene delivery vehicles capable of expressing the contemplated polynucleotides. The gene delivery vehicle may be a viral vector such as, but not limited to, a retroviral, adenoviral, adeno-associated viral (AAV), herpes viral, or alphavirus vectors. The viral vector can also be an astrovirus, coronavirus, orthomyxovirus, papovavirus, paramyxovirus, parvovirus, picornavirus, poxvirus, togavirus viral vector (see generally, Jolly, *Cancer Gene Therapy*, 1:51-64, 1994; Kimura, *Human Gene Therapy*, 5:845-852, 1994; Connelly, *Human Gene Therapy*, 6:185-193, 1995; and Kaplitt, *Nature Genetics*, 6:148-153, 1994). Delivery of the gene therapy constructs of this invention into cells is not limited to the above-mentioned viral vectors. Other delivery methods and media may be employed such as nucleic acid expression vectors, polycationic condensed DNA linked or unlinked to killed adenovirus alone (Curiel, *Hum. Gene Ther.*, 3:147-154, 1992), ligand linked DNA (Wu, *J. Biol. Chem.*, 264:16985-16987, 1989), eukaryotic cell delivery vehicles cells (U.S. Pat. No. 6,015,686), deposition of photopolymerized hydrogel materials, hand-held gene transfer particle gun (U.S. Pat. No. 5,149,655), ionizing radiation (U.S. Pat. No. 5,206,152 and PCT Patent Publication No. WO 92/11033), nucleic charge neutralization or fusion with cell membranes. Additional approaches are described in Phillip, *Mol. Cell. Biol.*, 14:2411-2418, 1994 and in Woffendin, *Proc. Natl. Acad. Sci. USA*, 91:1581-585, 1994. Briefly, the nucleotide sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands. Naked DNA may also be employed. Exemplary naked DNA introduction methods are described in PCT Patent Publication No. WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes, that can act as gene delivery vehicles are described in U.S. Pat. No. 5,422,120, PCT Patent Publication Nos. WO 95/13796, WO 94/23697, and WO 91/144445, and EP No. 524,968.

The polynucleotide molecules of the invention may be introduced into the skin or scalp using the injectable carrier alone. Liposomal preparations are preferred for methods in which in vitro transfections of cells obtained from the skin or scalp are carried out. The carrier preferably is isotonic, hypotonic, or weakly hypertonic, and has a relatively low ionic strength, such as provided by a sucrose solution. The preparation may further advantageously comprise a source of a cytokine which is incorporated into liposomes in the form of a polypeptide or as a polynucleotide. Alternatively, an even more prolonged effect can be achieved by introducing the DNA sequence into the cell by means of a vector plasmid having the DNA sequence inserted therein. The plasmid may further comprise a replicator.

It is possible to obtain long term administration of a polypeptide to the scalp by introducing a naked DNA sequence operatively coding for the polypeptide interstitially into the skin or scalp, whereby cells of the tissue produce the polypeptide for at least one month or at least 3 months, more preferably at least 6 months. In addition, a method for obtaining transitory expression of a polypeptide in the scalp can be achieved by introducing a naked mRNA sequence operatively coding for the polypeptide interstitially into the skin or scalp, whereby cells of the tissue produce the polypeptide for less than about 20 days, usually less than about 10 days, and often less than 3 or 5 days.

The polypeptides of the invention can also be administered to a patient via depot or transdermal technology. In one embodiment, a pharmaceutical composition comprising FP-1 and a pharmaceutically acceptable carrier are delivered to a subject using one of Alza's D-TRANS® patches, Alza's E-TRANS® systems, and ALZA's Macroflux® transdermal technology. In an alternative embodiment, a pharmaceutical composition comprising FP-1 and a pharmaceutically acceptable carrier are delivered to a subject using one of Alza's DUROS® implant or ALZAMER® Depot technologies.

The pharmaceutical compositions or formulations of the present invention can be used in modulating hair growth in several contexts. By "modulate hair growth" is meant to increase or decrease hair growth. Methods of measuring or assaying hair growth are described in the Examples below, and in Philpott et al., "Whole Hair Follicle Culture" in *Dermatological Clinics* 14(4): 595-607, 1996, and the references cited therein. The compositions comprising polynucleotides encoding FP-1 and FP-1 polypeptides are primarily intended for use in increasing or promoting hair growth, whereas compositions comprising mutant FP-1 polynucleotides or proteins, FP-1 ribozymes, FP-1 antisense molecules, FP-1 siRNAs, and antibodies raised to FP-1, are primarily intended for use in decreasing, or inhibiting hair growth.

Promoting hair growth or attenuating hair loss serves to combat the effects of alopecia in humans and other mammalian species. Conversely, retarding hair growth or promoting hair loss can combat the effects of hirsutism, hypertrichosis, and similar disorders of afflicted individuals. Additionally, the compositions of the invention can be employed to control hair growth in normal skin. Thus, for example, the compositions can be employed in wool or fur production (e.g., applied to alpaca, beaver, calf, chinchilla, coyote, ermine, fisher, fitch, fox, lamb, llama, lynx, marten, mink, muskrat, nutria, opossum, otter, raccoon, Russian squirrel, sable, sheep, and other fur- or wool-producing mammals), to increase hair growth thereby permitting greater net annual wool production or reducing the time needed to produce mature pelts. Alternatively, the compositions of the present invention can be employed to produce custom designs of bare skin or thin, thick, or variegated hair within pelts of treated animals.

The compositions of the present invention are utilized in the methods of the present invention, which include a method of controlling hair growth in a subject comprising administering a pharmaceutical composition of the invention to that subject. The present invention also provides a method for modulating hair growth comprising contacting the skin or hair follicle of a subject with a composition of the invention. Alternatively, the follicular papilla of a subject may be contacted with a pharmaceutical composition of the present invention. Any of these methods can further comprise administering a second agent that controls hair growth. Where it is desired to increase hair growth, the second agent is a substance that either increases hair growth or which assists the composition of the invention to increase hair growth. Where it is desired to decrease or prevent hair growth, the second agent is a substance that decreases hair growth or assists the composition of the invention to decrease hair growth. The compositions of the invention may be administered by any of the methods detailed above. For example, the composition is topically administered to the skin of a subject in an amount sufficient to achieve a dose of at least about 0.01 nmol, at least 0.1 nmol, or at least about 1 nmol per 2 cm by 4.5 cm skin surface area, up to a dose of about 100 nmol, 1,000 nmol, or 10,000 nmol or more per 2 cm×4.5 cm skin surface area.

The present invention also provides a method for transplanting hair in a subject in need thereof including the pretreatment of hair follicles or grafts to be transplanted. In a typical hair transplantation procedure, grafts of skin containing hair are removed from the back or sides of the scalp (donor area) of the individual and are transplanted to other areas, that is, the bald or thinning area (recipient area). To place the grafts onto these areas, a number of incisions are made in the scalp. The incisions are then cleaned and a graft is inserted into each incision. Hair transplantation includes a minigraft for placing only a small number of hairs into the incisions, a micrograft for placing a single hair in the incisions (also, referred to as one-haired minigraft), and a follicular unit hair transplantation.

FP-1 polynucleotides and proteins of the present invention can be used in the pretreatment of hair follicles or grafts before transplantation. Such treatment is contemplated to promote or accelerate hair implantation.

The present invention also relates to diagnostic assays such as quantitative and diagnostic assays for detecting levels of FP-1 protein in cells and tissues. FP-1 levels can be detected at the RNA or protein level. A diagnostic assay in accordance with the invention for detecting under-expression of FP-1 proteins compared to normal control tissue samples, are used to detect whether the subject is likely to develop a hair loss disorder. In one embodiment, the diagnostic assay is used for the prognosis of alopecia. Assay techniques that are used to determine levels of FP-1 proteins of the present invention, in a sample derived from a host, for example blood or scalp tissue, are well known to those of skill in the art. Such assay methods include, but are not limited to, immunoassays, radio-immunoassays, competitive-binding assays, Western Blot analysis, ELISA assays, and immunofluorescence assays. Accordingly, the present invention provides a method for diagnosing alopecia in a subject comprising collecting a blood or tissue sample from said subject and detecting FP-1 proteins in said sample.

Such diagnostic assays can also be used to diagnose cancers. Overexpression of FP-1 correlates with heightened risk for developing or having developed a cancer. In one embodiment, the invention provides a method to diagnose skin cancers (e.g., basal cell carcinoma, pilomatricoma). In other embodiments, the method permits diagnosis of liver cancers, cancers of the nervous system, stomach cancers, testicular cancer and ovarian cancer among others.

The present invention further provides methods of identifying agents that control hair growth. The method comprises contacting skin with a test agent ex vivo. A test agent may be any substance that is contemplated to potentially regulate hair growth. The method further comprises detecting or measuring the expression of FP-1 in the follicular papilla. If the test agent is found to increase expression of FP-1 in the follicular papilla it is determined to be an agent that stimulates hair growth. If, however, the test agent decreases the expression of FP-1 in the follicular papilla it is determined to be an inhibitor of hair growth.

Also contemplated are methods to identify agents that interact with FP-1 and modulate its ability to control hair growth. Methods of identifying other proteins that interact with FP-1 include, but are not limited to, immuno-precipitation and two-hybrid assays (Sambrook et al., cited supra; Fields et al., *Nature*, 340(6230):245-246, 1989; and Fields et al., *Trends Genet.*, 10(8):286-92, 1994).

The present invention also encompasses the production of transgenic non-human animals that express FP-1 protein or FP-1 fusion protein encoding construct of the instant invention. Animals, which contain exogenous DNA sequences in their genome, are referred to as transgenic animals. The successful production of transgenic, non-human animals has been described in a number of patents and publications, such as, for example U.S. Pat. Nos. 6,291,740; 6,281,408; and 6,271,436.

The most widely used method for the production of transgenic animals is the microinjection of DNA into the pronuclei of fertilized embryos (Wall et al., *J. Cell. Biochem.*, 49:113, 1992). Other methods for the production of transgenic animals include the infection of embryos with retroviruses or with retroviral vectors. Infection of both pre- and post-implantation mouse embryos with either wild-type or recombinant retroviruses has been reported (Jaenisch, *Proc. Natl. Acad. Sci. USA*, 73:1260, 1976; Jaenisch et al., *Cell*, 24:519, 1981; Stuhlmann et al., *Proc. Natl. Acad. Sci. USA*, 81:7151, 1984; Jahner et al., *Proc. Natl. Acad. Sci. USA*, 82:6927, 1985; Van der Putten et al., *Proc. Natl. Acad. Sci. USA*, 82:6148-6152, 1985; Stewart et al., *EMBO J.*, 6:383-388, 1987).

An alternative means for infecting embryos with retroviruses is the injection of virus or virus-producing cells into the blastocoele of mouse embryos (Jahner, D. et al., *Nature* 298:623, 1982). The introduction of transgenes into the germline of mice has been reported using intrauterine retroviral infection of the midgestation mouse embryo (Jahner et al., supra, 1982). Infection of bovine and ovine embryos with retroviruses or retroviral vectors to create transgenic animals has been reported. These protocols involve the micro-injection of retroviral particles or growth arrested (i.e., mitomycin C-treated) cells which shed retroviral particles into the perivitelline space of fertilized eggs or early embryos (PCT International Application WO 90/08832; and Haskell and Bowen, *Mol. Reprod. Dev.*, 40:386, 1995). PCT International Application WO 90/08832 describes the injection of wild-type feline leukemia virus B into the perivitelline space of sheep embryos at the 2 to 8 cell stage. Fetuses derived from injected embryos were shown to contain multiple sites of integration.

The ability to alter the genetic make-up of animals, such as domesticated mammals including cows, pigs, goats, horses, cattle, and sheep, allows a number of commercial applications. In the context of the present invention, FP-1 transgenic animals are useful as models to study hair growth, as well as to test drugs, compounds, etc. for use in regulating hair growth.

Without further description, a person of ordinary skill in the art can, using the preceding description and the following illustrative examples, make and utilize the present invention and practice the disclosed methods. The following working examples therefore are not to be construed as limiting in any way the remainder of the disclosure.

EXAMPLES

Example 1

Materials and Methods

I. Cell Culture (a) Follicular Papilla

Vibrissa follicles were isolated individually from the lip region of 4-6 months old male Wistar rats (Charles River). To expose follicular papilla, the lower part of the follicle was opened by a 20 gauge needle. About 35-40 follicular papillae were microdissected from each rat. The isolated follicular papillae were placed in 1 ml Chang's medium (Irvine Scientific) with 100 units/ml penicillin and 100 µg/ml streptomycin in a 35 mm petri plate, and left undisturbed in a 37° C., 5% $CO_2$ incubator for 4 days. Under these conditions most of the papillae formed outgrowths (Jahoda and Oliver, *Br. J. Dermatol.*, 105(6):623-627, 1981; Jahoda and Oliver, *J. Embryol. Exp. Morphol.*, 79:211-24, 1984; Warren et al., *J. Invest. Dermat.*, 98:693-699, 1992). The culture medium was changed every 3 days. Ten to twelve days later, the cells were treated with 0.125% trypsin and 0.01% EDTA in phosphate-buffer saline, and the dissociated single cells were then plated in Dulbecco's Modified Eagle's Medium (DMEM) containing 10% fetal bovine serum (FBS), 100 units/ml penicillin and 100 µg/ml streptomycin. Sub-confluent cells were fed every 3 days by removing old medium and adding fresh medium warmed to 37° C.

(b) Rat Dermal Fibroblasts

Rat dermal fibroblasts were cultured by explant outgrowth from small pieces (<1 $mm^3$) of interfollicular dermis from the same lip skin tissue, from which the vibrissa follicles had been removed. The primary culture and subculture conditions were the same as described above. Rat stomach, esophagus and thoracoabdominal diaphragm tissues were minced thoroughly to <1 $mm^3$ and placed in 1 ml DMEM containing 10% FBS, 100 units/ml penicillin and 100 µg/ml streptomycin in a 30 mm petri plate. After being undisturbed for a few days, fibroblasts grew out from these tissues. The subculture conditions were the same as described above. All experiments were carried out using the fourth passage of the cultured cells. One passage constituted a 1:3 dilution of subculture.

II. Subtractive cDNA Library

Total RNA of cultured cells was isolated by a system using guanidine thiocyanate and CSB (citrate/sarcosine/β-mercaptoethanol) as denaturing buffer followed by phenol extraction (The RNAgents® Total RNA Isolation System, Promega). Poly $A^+$ RNA was separated from the total RNA using a biotinylated oligo (dT) selection with the MagneSphere® mRNA isolation system (Promega).

Cultured rat vibrissa follicular papilla-specific subtractive cDNA library was constructed using the PCR-Select™ cDNA subtraction Kit (Clontech) according to the manufacturer's instructions (Diatchenko et al., *Proc. Natl. Acad. Sci. USA*, 93(12):6025-6030, 1996). For the first strand cDNA synthesis, 2 µg of cultured rat vibrissa follicular papilla cell poly $A^+$ RNA (the "tester") and 2 µg of a mixture (1:1:1) of cultured rat stomach, esophagus and diaphragm fibroblasts poly $A^+$ RNA were reverse-transcribed using MMLV reverse transcriptase (Gibco). The second stranded cDNA was synthesized with a 20× enzyme cocktail containing DNA polymerase I (6 U/µl), RNase H (0.25 U/µl), *E. coli* DNase ligase (1.2 U/µl), and T4 DNA polymerase (1.5 U/µl). The double strand cDNA obtained was phenol extracted and ethanol precipitated. After digesting with Rsa I, the tester (follicular papilla) cDNA was divided into two subpopulations, which were ligated with two different adaptors. The two subpopulations (about 15 ng each) were then hybridized with an excess amount of the driver (3 types of fibroblasts) cDNA (about 470 ng), after which they were combined. Without denaturing the DNA hybrids, the mixture of the two primary hybridization samples was hybridized again with freshly denatured driver cDNA (about 310 ng). To enrich and amplify the differentially expressed sequences, two rounds of selective PCR were performed in both subtracted and unsubtracted cDNA (tester cDNAs ligated with two different adaptors) using primers that anneal to the adaptors sequences. The PCR products were cloned into the pCRII TA cloning vector, which was then transformed into TOP10F' cells (Invitrogen).

In order to perform differential screening later, a reverse subtraction (a rat fibroblast-specific subtractive cDNA library) was also performed by the same PCR-select™ cDNA subtraction technique as described above. In the reverse subtraction, a mixture of the 3 types of fibroblast (cultured rat stomach, esophagus and diaphragm fibroblasts) served as the "tester" and follicular papilla as the "driver."

III. Differential Screening a. cDNA Array

Bacterial colonies were randomly picked from the follicular papilla-specific subtracted library and cultured overnight at 37° C. with shaking. To amplify the cDNA inserts, PCR was performed using adaptor-specific primers (Clontech). After denaturing with 0.6 N NaOH, the PCR products were transferred onto a Hybond™-XL nylon membrane (Amersham Pharmacia Biotech). Two identical blots were prepared for hybridizing with follicular papilla-specific subtracted library (FP probe) and fibroblast-specific subtracted library (F probe). The blots were neutralized with 0.5 M Tris-HCl (pH 7.5) for 2-4 min. and washed with $H_2O$. DNA was crosslinked to the membrane by UV light.

b. Colony Array

The same overnight cultures of the randomly picked bacterial clones were used to perform colony array. Each bacterial culture was transferred onto a Hybond™-XL nylon membrane (Amersham Pharmacia Biotech) placed on the LB/agar plate containing kanamycin. Two identical blots were prepared for hybridizing with the follicular papilla-specific subtracted library (FP probe) and fibroblast-specific subtracted library (F probe). After culturing overnight at 37° C., the blots were denatured with 0.5 M NaOH, 1.5 M NaCl for 4 min, neutralized with 0.5 M Tris-HCl (pH 7.5), 1.5 M NaCl for 4 min, and air dried for 30 min. The DNA was fixed to the membrane by baking at 80° C. for 2 hrs.

c. Preparation of the Subtracted cDNA Probes

The amplified PCR products of the subtracted cDNAs were purified with the NucleoTrap® PCR purification kit (Clontech), and underwent restriction enzyme digestion to remove the adaptor sequences. Three restriction enzymes were used one after another in the following order: Rsa I at 37° C. for 1 hr, Sma I at room temperature for 1 hr, and Eag I at 37° C. for 1 hr. After separation from the adaptor using the NucleoTrap® PCR purification kit (Clontech), the cDNAs were then labeled with [$\alpha$-$^{32}$P] dCTP by the Multiprime™ DNA labeling system (Amersham Pharmacia Biotech). The specific activity of the labeled probe was determined by using a scintillation counter. The total counts per probe was greater than $10^7$ cpm.

d. Hybridization with the Subtracted cDNA Probes

The blots of the cDNA array and colony array were hybridized at 60° C. over night with the labeled subtracted cDNA probes in Church solution (0.25 M $Na_2HPO_4$ (pH 7.2), 1 mM EDTA, 7% SDS, and 1% BSA). Equal amounts (about 3.5× $10^7$ cpm) of the labeled follicular papilla-specific cDNA probe (FP probe) and fibroblast-specific cDNA probe (F probe) were used in an equal amount (7.5 ml) of Church hybridization solution for every two identical colony array or cDNA array blots. Two cDNA fragments were used as hybridization negative controls: (i) a mouse testis-specific gene (GenBank® Accession No. X52128), and (ii) a human semenogelin II (GeneBank® Accession No. ANM81652), which is specific to seminal vesicles.

IV. Virtual Northern

1 μg of total RNA from cultured follicular papilla cells, fibroblasts (diaphragm, esophagus, and stomach fibroblasts in a 1:1:1 mixture), and dermal fibroblasts were separately reverse transcribed to first-strand cDNAs. Double strand cDNA (ds cDNA) was synthesized and then amplified by PCR according to the SMART™ cDNA synthesis technique (Clontech). The optimal number of PCR cycles was titrated to ensure that the ds cDNA synthesis remained in the exponential phase of amplification. The PCR-amplified ds cDNA was electrophoresed on a 1% agarose gel, and then transferred onto a Hybond™-XL nylon membrane (Amersham Pharmacia Biotech). The filter was subjected to hybridization using the procedure used for Northern blot hybridization.

V. 5' RACE (Rapid Amplification of cDNA Ends) of FP-1

5' race of FP-1 was performed according to the manufacturer's instructions (Clontech). 1 μg of poly $A^+$ RNA from the cultured rat vibrissa follicular papilla cells was reverse transcribed into first-strand cDNA. Using the first-strand cDNA as a template, the primary PCR was performed with the Universal Primer (Clontech) and a FP-1 specific primer. The thermal cycling program was as follows: 5 cycles of 94° C., 5 sec; 72° C., 3 min.; 5 cycles of 94° C., 5 sec; 70° C., 10 sec; 72° C., 3 min.; 23 cycles of 94° C., 5 sec; 68° C., 10 sec; 72° C., 3 min. The primary PCR product was diluted to 1:50 and used as a template in the secondary PCR. The second PCR was primed with the Universal Nested Primer (Clontech) and a FP-1 specific nested primer. The thermal cycling program was as follows: 20 cycles of 94° C., 5 sec; 68° C., 10 sec; 72° C., 3 min. The nucleotide sequences of the FP-1 primer and the FP-1 nested primer were: 5' CCCAGTTCACCAG-CATCTCCCTTCTCTC 3' (SEQ ID NO: 13) and 5' GTCTAT-CATCACCCGGATCGGCACCAT 3' (SEQ ID NO:14), respectively. The PCR product from the second PCR reaction was ligated into a TA cloning vector (Invitrogen). Individual clones were sequenced.

VI. Western Blot and Deglycosylation

Cultured cells were dissolved in lysis buffer (1% NP40, 1% deoxycholic acid, 0.1% SDS, 150 mM NaCl, 50 mM Tris-HCl (pH 7.4), 2 mM EDTA and freshly added protease inhibitor). After centrifugation at 14,000 rpm for 20 min at 4° C., the soluble proteins were quantified using a BCA kit (Pierce). 50 μg of the total proteins were resolved on a 12% polyacrylamide gel according to standard procedures (Laemmli, 1970). The separated proteins were transferred electrophoretically to an MSI-nitrocellulose membrane (Towbin et al., *Proc. Natl. Acad. Sci. USA,* 76:4350-4354, 1979; Burnette, *Anal. Biochem.,* 112:195-203, 1981). The membrane was incubated with primary antibodies and HRP-conjugated secondary antibody. Optimal concentration of the primary antibodies was determined by titration: anti-DPI rabbit serum G320 (1:10, 000), anti-β-tubulin mouse monoclonal antibody (Sigma) (1:2,000). The reaction was visualized by an enhanced chemiluminescence detection kit (Pierce) according to the manufacturer's instruction.

VII. Deglycosylation Reaction

For the deglycosylation reaction, about 250 μg total proteins was incubated with the Endo-H reaction buffer (50 mM NaAc (pH 5.5), 0.1% SDS) at room temperature for 20 min, and then digested with 10 mU Endo-H (Roche) in the same reaction buffer in the presence of freshly added 0.05% $NaN_3$ and 10 mM EDTA at 37° C. over night (Kobata, *Anal. Biochem.,* 100(1):1-14, 1979; Trimble and Maley, *Anal. Biochem.,* 141(2):515-22, 1984). Total cell lysate that went through the above procedure, but without the addition of Endo-H was used as the intact glycoprotein control. Samples were stored at −20° C. before being analyzed by Western blotting.

VIII. Endo H Digestion

Half of 100 mm plate cell lysate (about 250 μg total proteins) was incubated with Endo H reaction buffer (20 mM $Na_3PO_4$ (pH 7.5), 0.02% $NaN_3$, 0.1% SDS, 50 mM β-mercaptoethanol) at room temperature for 20 min, and then digested by 30 mU Endo H (Roche) in the same reaction buffer with freshly added 0.75% Nonidet P-40 at 37° C. over night (Tanner et al., *J. Virol.,* 62(12):4452-64, 1988). Total cell lysate that went through the above procedure, but without Endo H was used as the intact glycoprotein control. Samples were stored at −20° C. before being analyzed by Western blot.

IX. FP-1 Antibodies

Five different regions of rat FP-1 (SEQ ID NO:2), which were predicted to be hydrophilic and to be more antigenic than other regions in FP-1 according to several computer algorithms, including one that predicts hydropathy, were selected to produce antibodies to rat FP-1. These five regions of FP-1 included amino acids 87-102, 247-262, 276-297, 321-333, and 392-405 of SEQ ID NO:2.

The synthesized peptides were purified by reverse-phase high performance liquid chromatography (HPLC) and their purity was examined by mass spectrometry. A cysteine residue was placed at either the N- or C-terminus of each peptide to facilitate conjugation to the carrier protein, Keyhole Limpet Hemosyanin (KLH). For each conjugated peptide, two rabbits were immunized by subcutaneous injection of 100 μg of peptide in Freund's complete adjuvant. This primary immunization was followed by booster injections at 2-week intervals. The titer of the antisera was checked by ELISA after 3 booster injections (Genemed Synthesis).

Table I summarizes the information relating to the five polyclonal rabbit anti-rat FP-1 antibodies.

TABLE 1

| Antibody | Epitope | IB dilution | IF dilution | Mismatch/ Total aa Mouse | Mismatch/ Total aa human |
|---|---|---|---|---|---|
| G311 | 1 | 1:1,000 | n.d. | 0/16 | 3/16 |
| G312 | 2 | 1:2,000 | 1:200 | 8/22 | 1/16 |
| G320 | 3 | 1:10,000 | 1:1,000 | 0/22 | 5/22 |
| G324 | 5 | 1:500 | n.d. | 1/14 | 3/14 |
| G325 | 4 | n.d. | n.d. | 2/13 | 1/13 |

Key:
IB = immunoblot
IF = immunofluorescence
n.d. = not determined
Mismatch/Total aa = the number of amino acids that are different between the rat and mouse FP-1, or rat and human FP-1, in the peptide sequences recognized by the rat FP-1 antibodies.

X. Immunofluorescence Staining

Culture cells grown on glass cover slips (12 mm, Fisher) were fixed with cold 1:1 methanol/acetone for 20 min. and then air-dried. Fresh tissues were embedded in OCT medium (Sakura Finetek) in liquid nitrogen and sectioned into 7-8 μm according to standard procedures. The sections were fixed with cold 1:1 methanol/acetone for 10 min and air-dried.

Cover slips with cultured cells or slides with frozen sections were incubated with primary antibodies. Optimal concentration of the primary antibodies was determined by titration: anti-FP1 rabbit serum G320 (1:1,000), anti-β-COP mouse monoclonal antibody (Sigma) (1:80). After washing, the cover slips or slides with PBS for 5 min. three times, the cover slip or slide was incubated with fluorescein FITC or rhodamine conjugated secondary antibody (Molecular Probes, Eugene, Oreg.), mounted with aqueous mounting medium with anti-fading agents (Biomeda, Foster City, Calif.), and examined under a fluorescence microscope (Zeiss, Thornwood, N.Y.).

XI. Fluorescent In Situ Hybridization (FISH)

Lymphocytes were isolated from mouse spleen and cultured at 37° C. in RPMI 1640 medium supplemented with 15% fetal calf serum, 3 μg/ml concanavalin A, 10 μg/ml lipopolysaccharide and $5 \times 10^{-5}$ M mercaptoethanol. After 44 hr, the cultured lymphocytes were treated with 0.18 mg/ml BrdU for an additional 14 hr. The synchronized cells were washed and recultured at 37° C. for 4 hr in α-MEM with thymidine (2.5 μg/ml). Cells were harvested and chromosome slides were made by standard procedures including hypotonic treatment, fixation and air-drying (See DNA Biotech). For probe preparation, a 2.1 kb rat FP-1 cDNA fragment was amplified by PCR using the plasmid of the longest FP-1 positive clone (obtained from screening the follicular papilla cDNA library) as template and primers flanking the cDNA insert on the vector plasmid. The DNA probe was biotinylated with dATP at 15° C. for 1 hr (Gibco BRL BioNick labeling kit, Gaithersburg, Md.) (Heng et al., *Proc. Natl. Acad. Sci. USA,* 89(20):9509-13, 1992). The procedure for FISH was performed according to published methods (Heng et al., ibid; Heng and Tsui, *Chromosoma,* 102(5):325-32, 1993).

Example 2

Identification of Follicular Papilla-Specific Genes by Subtraction cDNA Library

To identify genes that are expressed preferentially in follicular papilla cells, a follicular papilla-specific subtraction cDNA library was constructed. Common messages were eliminated by hybridizing the cDNAs of cultured rat vibrissa follicular papilla cells ("tester") with those of fibroblasts that had been grown under identical culture conditions ("driver"). To examine the subtraction efficiency, a series of Southern blots were performed using the following probes: (1) follicular papilla-specific cDNAs, (2) fibroblast-specific cDNAs, (3) GAPDH, a housekeeping gene, and (4) FP-1, a novel gene identified from the subtraction library. The results showed a greater than 10 fold enrichment of FP-1 in the subtracted follicular papilla library (FIG. 11D), and a greater than 20 fold reduction of GAPDH in both the subtracted follicular papilla-specific library (FIG. 11C). These data indicated that a greater than 200 fold enrichment of the differentially expressed follicular papilla messages had been achieved. Indeed, when the follicular papilla-specific cDNAs were used as the probe (FP− probe), the signals of subtracted follicular papilla cDNAs (FIG. 11A, lane 1) were much stronger than those of subtracted fibroblast cDNAs (FIG. 11A, lane 3). On the contrary, when the fibroblast-specific cDNAs were used as a probe (F− probe), the signals of subtracted fibroblast cDNAs (FIG. 11B, lane 3) were much stronger than those of subtracted follicular papilla cDNAs (FIG. 11B, lane 1). These data indicated that the follicular papilla-specific cDNAs were enriched using the subtraction technique.

To identify the follicular papilla-specific clones in the subtracted library, a differential screening method was used.

Randomly picked clones from the follicular papilla-specific subtracted library were hybridized with the follicular papilla-specific cDNAs (FP– probe) and fibroblast-specific cDNAs (F– probe) (FIG. 12). Clones representing differentially expressed poly A$^+$ species in follicular papilla cells were expected to give strong signals with the FP– probe but weak or no signals with the F– probe (FIG. 12). Clones were considered as "follicular papilla-specific" only when the difference in signal intensity (FP/F) was greater than or equal to 5 fold. By screening 465 randomly picked clones from the follicular papilla-specific subtracted library, about 60 follicular papilla-specific clones representing 9 ESTs and 25 known sequences were obtained.

To minimize the chance of eliminating follicular papilla-specific messages, a mixture of diaphragm, esophagus and stomach fibroblast cDNAs were used as the "driver" to construct the follicular papilla-specific subtraction library. To verify that the clones identified from the subtraction library were really differentially expressed in follicular papilla cells compared to dermal fibroblasts, virtual Northern blots were carried out by hybridizing PCR-amplified cDNAs from cultured cells with some of the identified clones, including EST1 (later named as FP-1), EST2, EST6, EST7, lysyl oxidase-like 2 (LOXL2), serine protease, and tenascin c. The results showed that all the cDNA clones examined by virtual Northern blots were indeed expressed at higher levels in follicular papilla cells than in the (non-dermal) fibroblast mixture (FIG. 13), again indicating the success of the subtraction. When cultured follicular papilla cells were tested against dermal fibroblasts, six out of the seven genes were found to be expressed at higher levels in follicular papilla cells than in dermal fibroblasts; only one, tenascin c, showed about equal intensity in these two cell types (FIG. 13). These data proved the follicular papilla-specificity of the genes identified from the subtraction library. From a gene expression profile point of view, the difference between follicular papilla and various types of fibroblasts was greater than the difference among the different fibroblasts.

Example 3

FP-1, a Novel Follicular Papilla Marker

Figure 14A:
FIG. 14A is a photographic representation of a Northern blot hybridized with an FP-1 probe. Five micrograms of total RNA of cultured rat vibrissa follicular papilla cells (lane 1) and dermal fibroblasts (lane 2) and 10 μg of total RNA of 18 rat tissues (lane 3-20) were separated electrophoretically in a denaturing gel and subjected to Northern blot analysis. Lane 1: cultured follicular papilla cells; Lane 2: cultured dermal fibroblasts; Lane 3: skin; Lane 4: diaphragm; Lane 5: esophagus; Lane 6: stomach; Lane 7: brain; Lane 8: lung; Lane 9: heart; Lane 10: liver; Lane 11: spleen; Lane 12: kidney; Lane 13: bladder; Lane 14: intestine; Lane 15: colon; Lane 16: ovary; Lane 17: uterus; Lane 18: prostate; Lane 19: testis; and Lane 20: skeletal muscle.
Figure 14B:
FIG. 14B is a photographic representation of the Northern blot hybridized with a GAPDH probe.
Figure 14C:
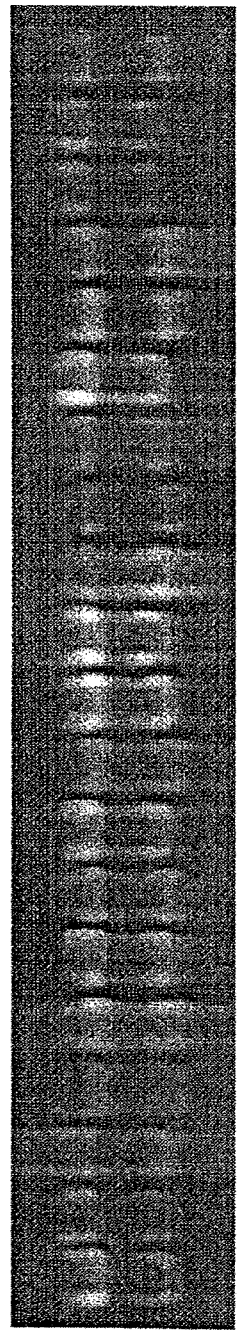
FIG. 14C is a photographic representation of the gel stained with ethidium bromide.
Figure 17A:
FIG. 17A is a photographic representation of an ethidium bromide-stained gel showing the probe used for fluorescent in situ hybridization (FISH). A 2.1 kb rat FP-1 cDNA fragment (lane 2) was amplified by PCR using the plasmid containing the longest FP-1 clone (lane 1) as template.
Figure 17B:
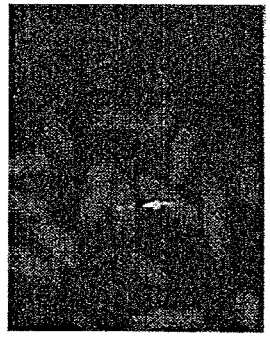
FIG. 17B is a photographic representation of a biotin-labeled rat FP-1 probe localizing specifically to a mouse chromosome (arrow).
Figure 17C:
FIG. 17C is a photographic representation of DAPI staining of mouse chromosomes confirming that mouse FP-1 gene is localized on chromosome 9.
Figure 17D:
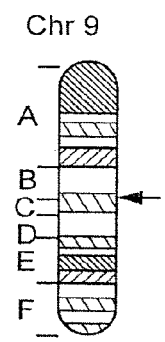
FIG. 17D is a diagrammatic representation of mouse chromosome 9 showing the position of the FP-1 gene as the 9B-C region (arrow).

Among the 25 known genes and 9 EST sequences that had been identified from the follicular papilla-specific subtraction library, EST1 (Genbank®Accession Number A1574756) was most abundant, represented by 8 independent clones. The expression level of this EST in cultured rat vibrissa follicular papilla cells was greater than 30 fold higher than that in cultured rat dermal fibroblasts (FIGS. 13 and 14). To further characterize this cDNA, its tissue distribution was examined in 18 rat tissues including skin, diaphragm, esophagus, stomach, brain, lung, heart, liver, spleen, kidney, bladder, intestine, colon, ovary, uterus, prostate testis, and skeletal muscle. This EST was only detected at relatively low levels in stomach and ovary, while the other 16 tissues were negative (FIG. 14A). Since these data indicated that this clone was preferentially expressed in follicular papilla, it was named "FP-1."

To obtain the full-length cDNA sequence of FP-1, a cDNA phage library of cultured rat vibrissa follicular papilla cells was screened, and a 5' RACE (rapid amplification of cDNA ends) was also performed. The full-length FP-1 cDNA was 2332 bp, which had a 1647 bp coding region encoding 549 amino acids (FIG. 15). FP-1's N- and C-terminus amino acid sequences have domains homologous to collagen triple helix repeat and an olfactomedin-like domain, respectively (FIG. 15). Computer analysis of the FP-1 protein sequence revealed that the N-terminal 31 amino acid residues of FP-1 is a signal peptide (FIG. 15), and that FP-1 has 6 potential glycosylation sites (FIG. 15).

Example 4

Immunoblotting and Immunofluorescence Studies

To examine the protein expression pattern of FP-1, five polyclonal antibodies against FP-1 were generated (the five epitopes are indicated in FIG. 15). Immunoblot analysis showed that three of the FP-1 antisera (anti-epitopes 1, 2, and 3) recognized a single protein band of about 72 kDa in cultured rat follicular papilla cell lysate, with no detectable signals in cultured fibroblast cell lysate (FIG. 16A). Immunofluorescent staining of cultured follicular papilla cells at passage 4 using the FP-1 antisera showed very strong cytoplasmic signals in follicular papilla cells, but negative signals in fibroblasts (FIG. 16C). These data verified that FP-1 was preferentially expressed in cultured follicular papilla cells compared to fibroblasts. Staining of COP I, a Golgi complex marker, overlapped with FP-1 staining, even though FP-1 staining had a broader area (FIG. 16C).

Consistent with the presence of several potential N-glycosylation sites, FP-1 is a glycoprotein. After digestion with endoglycosidase-H, the molecular weight of FP-1 decreased to 60 kDa (FIG. 6B).

Example 5

Temporal Expression of FP-1

To analyze at what time point FP-1 expression was turned on in follicular papilla cells under cultured conditions, immunofluorescent staining was performed using primary cultures 4, 7, and 10 days after microdissection. Starting from day 4, all the cells of the whole colony derived from a follicular papilla were FP-1 positive, whereas cultured fibroblasts were always FP-1 negative (data not shown). Staining was not performed at earlier time points.

Example 6

Survey of Existing FP-1 Mouse Mutants

Since FP-1 is abundantly expressed in follicular papilla cells, which are essential for hair growth, tests were done to determine whether the gene localized to any of the loci corresponding to the 196 mouse mutants that had a hair-related phenotype in the Jackson Laboratory database (Bar Harbor, Me.).

To determine whether FP-1 mapped to any of these existing mouse hair mutants, a cross-species fluorescent in situ hybridization (FISH) on mouse chromosomes using rat FP-1 cDNA as a probe was performed. The FISH analysis indicated that FP-1 was on mouse chromosome 9 B-C region (FIG. 17). Significantly, there are 3 hair-related mutants, including rough fur (ruf), rough coat (rc), and fur deficient (fd) in this region.

To examine whether there were any gross changes in the FP-1 gene in these 3 mouse mutants, a genomic Southern blot was performed. After digestion with 7 different restriction enzymes, the genomic DNA of homozygous and heterozygous mutants and their background strains (considered as wild type to the mutations) were compared. A size change greater than 1 kb due to insertion or deletion, which occurs frequently in the mouse genome, could in theory be detectable by this approach. However, no significant difference in the FP-1 sequence was found in all the 3 mutants suggesting that there was no deletion or insertion of a big DNA fragment (greater than 1 kb) within the genomic region close to FP-1 in these mutants (data not shown). Of course, it must be remembered that this finding does not rule out the possibility that there are other mutations in any of these genes, which cannot be detected by this approach.

Example 7

Immunolocalization of FP-1

To investigate FP-1 localization in hair follicles in vivo, indirect immunofluorescence staining of the depilated mouse back skin using FP-1 antiserum was performed. Back skin of C57BL/6 mice was collected on different days after depilation, snap-frozen, and cryo-sectioned. The sections were fixed with 1:1 methanol/acetone (4° C.), air-dried, and stained by indirect immunofluorescence using the tyramide signal amplification (TSA) system (Perkin Elmer). Polyclonal G320 antibody was used for staining at a dilution of 1:5,000 to 1:20,000. As a control, a preimmune serum at a comparable concentration, and an FP-1 antibody that was blocked by a peptide that bound the FP-1 antibody (the original antigen used to generate the G320 antibody) was used. Specifically, the peptide blocking experiments were performed, using the G320 antibody pre-incubated at 25° C. with the FP-1 peptide having the sequence PNDDTLVGRADEKVNERHSPQT (aa 276-297 of rat FP-1; SEQ ID NO:27). The antibody: peptide ratio for the blocking experiment was 1:4, and the antibody was incubated with the peptide for 45 minutes before the FP-1 antibody was used to stain the sections in the control experiments.

Figure 18:
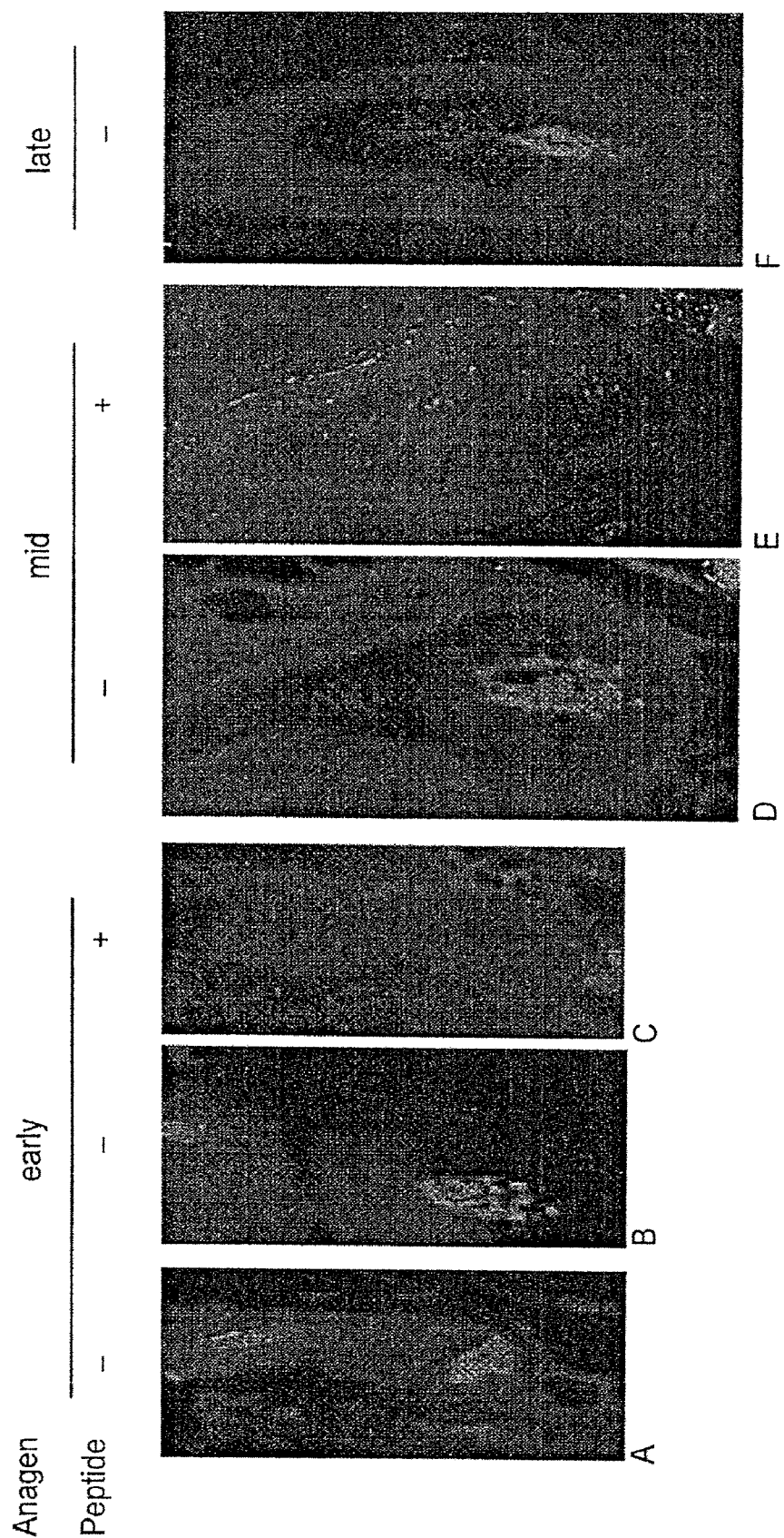
FIG. 18A is a photographic representation of immunofluorescent staining of FP-1 on C57BL/6 mouse back skin at 3 days after hair depilation.
FIG. 18B is a photographic representation of immunofluorescent staining of FP-1 on C57BL/6 mouse back skin at 5 days after hair depilation.
FIG. 18C is a photographic representation of immunofluorescent staining of FP-1 on C57BL/6 mouse back skin at 5 days after hair depilation. In this case, note that the FP-1 antiserum was pre-adsorbed with peptide antigen prior to staining.
FIG. 18D is a photographic representation of immunofluorescent staining of FP-1 on C57BL/6 mouse back skin at 8 days after hair depilation.
FIG. 18E is a photographic representation of immunofluorescent staining of FP-1 on C57BL/6 mouse back skin at 8 days after hair depilation. In this case, note that the FP-1 antiserum was pre-adsorbed with peptide antigen prior to staining.
FIG. 18F is a photographic representation of immunofluorescent staining of FP-1 on C57BL/6 mouse back skin at 12 days after hair depilation.

FP-1 was strongly expressed in the follicular papillae during the anagen phase (FIG. 18), but not in the catagen and telogen phases of the hair cycle (data not shown). This hair-cycle dependent expression pattern strongly suggested that FP-1 is involved in the control of hair growth. No staining was noted in the epidermis and other skin cells.

To analyze FP-1 expression in the follicular papilla cells under the cultured conditions, we performed immunofluorescent staining using primary cultures 4, 7 and 10 days after plating. Starting from day 4, all the cells of the whole colony derived from a follicular papilla were FP-1 positive, whereas FP-1 was barely detectable in cultured fibroblasts (FIG. 16B).

Example 8

Inhibition of FP-1 Function in Mouse Skin by Antibodies

Purified polyclonal or monoclonal antibodies that specifically bind to FP-1 are used to block FP-1 activity in the hair follicle in vivo. As a control, peptide-blocked FP-1 antibody prepared as described in Example 7, is used. For example, antibodies are purified using commercial kits, and used at several concentrations (i.e., 1 µg/ml to 1 mg/ml) and based on titration studies the concentration of antibody to be used in the experiments outlined below is determined.

Mice that are around day 35 of life are in a prolonged telogen phase. In the first experiment, mice around day 38 of life are anesthetized, and each of the mice are implanted intraperitoneally with two Alzet osmotic minipumps (Model 2001; Alza Corp., Palo Alto, Calif.). The minipumps are each loaded with 200 µl of FP-1 antibody, or peptide-blocked FP-1 in phosphate buffered saline (PBS) at the concentration determined by the titration studies. The FP-1 antibody, or preimmune antibody, or peptide-blocked FP-1 antibody, is provided systemically for approximately 14 days. The hair of the mice are plucked on day 42 (Wilson et al., *Differentiation*, 55:127-136, 1994). Mice are then sacrificed every 2 days for 17 days and the length of the hair from the dermal papilla to the skin surface is measured. The FP-1 antibody treated and control mice are compared to check whether there are differences in hair growth. Hair growth can be assessed based on the elongation rate of the hair fibers that is measured by clipping the fibers that are exposed on the skin surface. In addition, the hair cycle is analyzed by using histological methods to determine whether the follicle is in anagen, catagen, or telogen (Wilson et al., *Differentiation*, 55:127-136, 1994).

In the second experiment, 200 µl of FP-1 antibody, or the preimmune antibody, or the peptide-blocked FP-1 antibody, at the concentration identified in the titration experiments are injected subcutaneously every 2 days for 15 days (Cotsarelis et al., *Cell* 61:1329-1337, 1990; Taylor et al., *Cell* 102:451-461, 2000). At the end of the subcutaneous injections, mice are sacrificed every 3 days for 15 days and the length of the hair fibers that are exposed on the skin surface is measured as mentioned above, and the length of the follicule from the dermal papilla to the skin surface is measured by histological examination. The FP-1 antibody-treated and control mice are compared to check whether there are differences in hair growth.

In both experiments described above, the FP-1 antibodies bind and neutralize FP-1 thus blocking its in vivo activity. In contrast, the preimmune antibodies and peptide-blocked FP-1 antibody do not impair the in vivo activity of FP-1.

Blocking FP-1 activity using neutralizing FP-1 antibodies results in inhibition of hair growth. However, the peptide-blocked FP-1 antibody (or pre-immune sera or control antibodies that are raised against intracellular antigens such as keratins, if used in the above experiments) show minimal, if any, effects on hair growth. Immunolocalization studies show that mouse skin of FP-1 antibody-treated mice has antibody staining in the extracellular matrix zone of the follicular papilla.

Example 9

Inhibition of FP-1 in Cultured Rat Vibrissa Follicular Papilla Cells

FP-1 expression is inhibited in cultured rat vibrissa follicular papilla cells using inhibitory agents such as antibodies to FP-1, antisense molecules, ribozymes and/or siRNA molecules directed to rat FP-1.

Prediction of suitable siRNA targets and siRNAs are possible using many different sources, (see, for example "siRNA Selection Program," Whitehead Institute for Biomedical Research, 2003; Ambion's siRNA Target Finder, etc.). Examples of siRNA target sequences and sense and antisense strand siRNAs for use in this experiment include:

```
(i) Target Sequence:
5' AATTAAGTCGTGCGCCAGCCC 3',      (SEQ ID NO: 15)
(corresponding to 257-279 of SEQ ID NO: 1);

Sense Strand siRNA:
5' UUAAGUCGUGCGCCAGCCCtt 3';      (SEQ ID NO: 16)

Antisense strand siRNA:
```

```
                         -continued
5' GGGCUGGCGCACGACUUAAtt 3';      (SEQ ID NO: 17)
and (ii) Target Sequence:
5' AATGATGATACCTTGGTGGGG 3',      (SEQ ID NO: 18)
(corresponding to 874-896 of SEQ ID NO: 1);

Sense Strand siRNA:
5' UGAUGAUACCUUGGUGGGGtt 3';      (SEQ ID NO: 19)

Antisense strand siRNA:
5' CCCCACCAAGGUAUCAUCAtt 3';      (SEQ ID NO: 20)
and (iii) Target Sequence:
5' AATGAGCGCCATTCTCCACAA 3',      (SEQ ID NO: 21)
(corresponding to 913-935 of SEQ ID NO: 1);

Sense Strand siRNA:
5' UGAGCGCCAUUCUCCACAAtt 3';      (SEQ ID NO: 22)

Antisense strand siRNA:
5' UUGUGGAGAAUGGCGCUCAtt 3';      (SEQ ID NO: 23)
and (iv) Target Sequence:
5' AACCCATGATCACGTCCATTG 3',      (SEQ ID NO: 24)
(corresponding to 938-960 of SEQ ID NO: 1);

Sense Strand siRNA:
5' CCCAUGAUCACGUCCAUUGtt 3';      (SEQ ID NO: 25)

Antisense strand siRNA:
5' CAAUGGACGUGAUCAUGGGtt 3'.      (SEQ ID NO: 26)
```

Methods of using siRNA to knock down expression of a target gene are well known in the art (Kittler et al., *Semin. Cancer Biol.*, 13(4):259-65, 2003; Scherr et al., *Curr. Med. Chem.*, 10(3):245-56, 2003; and Hudson et al., *Trends Cell Biol.*, 12(6):281-7, 2002).

After treatment of cells with a FP-1 inhibitory agent that inhibits or prevents expression of FP-1, the expression of FP-1 mRNA is tested by Northern blot analysis using well-established methods (Sambrook et al., cited supra). FP-1 protein levels are tested using Western blot analysis using antibodies to FP-1.

The effect of inhibiting FP-1 on the morphological and proliferative properties of the follicular cells is also tested. Neutralizing antibodies to FP-1, FP-1 antisense molecules, FP-1 ribozymes and FP-1 siRNA molecules are expected to cause the cultured rat vibrissa cells to aggregate and suppress their growth. Immunolocalization of FP-1 antibody is expected to show it binding to both the cell surface and the extracellular matrix that is deposited on the plastic dish surface. It is also expected that preimmune sera from healthy rabbits, control antisense, ribozyme and siRNA molecules show no effects on the morphology and growth properties of the cultured vibrissa cells.

Example 10

Isolation of Follicular Papilla Cells from Skin

Rat vibrissa and mouse pelage follicular papilla are surgically isolated as described in Example 1 and dissociated into single cells by trypsinization. The rat follicular papillae are minced and treated with 0.2% trypsin in PBS at 37° C. with stirring for 30-45 minutes. The loosened tissues will be pipetted several times to suspend the cells. The single cells that are released by this procedure will be counted and mixed with an equal volume of DMEM medium containing 10% calf serum that inhibits trypsin. These cells are then treated with rabbit antibodies to FP-1 (see, Example 1), followed by fluorescein-conjugated goat anti-rabbit-IgG antibody (Jackson Laboratories). The cell-surface fluorescein-labeled, FP-1 positive cells are then isolated by fluorescein-activated cell sorting.

Alternatively, magnetic beads (4.5 µm; DYNABEADS® from DYNAL® or MACSiBead™ from Miltenyi Biotec) that are precoated with sheep anti-rabbit IgG antibody are used to adsorb rabbit anti-FP-1 antibodies, which are then used for isolating follicular papilla cells. A dissociated, single cell suspension (as obtained above) containing a mixture of follicular papilla cells and other non-follicular papilla cells (such as the dermal fibroblasts) are mixed with the FP-1 coupled magnetic beads. The FP-1 antibody-coupled magnetic beads coated with the adherent cells are then separated from the non-adherent cells by applying a magnetic field (e.g., OPTICELL® magnetic separation, or magnetic plate, Dynal, Inc., Lake Success, N.Y.). The magnetic beads are then washed with phosphate buffered saline (PBS). Finally, the cells that have bound to the FP-1 antibodies are dissociated by a brief treatment with low pH buffer or with 0.05% trypsin in PBS, or other suitable conditions. The cells that are bound by FP-1 antibody are follicular papilla cells.

Example 11

Hair Reconstitution Experiments

The nude mouse graft model system originally described by Lichti et al. (*J. Invest. Dermatol.*, 101:124S-129S, 1993) is used for testing the role of FP-1 in regulating hair growth. In this system, a mixture of epidermal and dermal cell preparations from newborn mice are grafted onto the backs of athymic nude mouse hosts, resulting in the in vivo reconstitution of hair follicles (Lichti et al., ibid; Weinberg et al., *J. Invest. Dermatol.*, 100:229-236, 1993). Neutralizing antibodies to FP-1 (monoclonal or polyclonal antibodies), that are either perfused into the athymic nude mice system via injection of the antibody into either the left ventricle or a tail vein, or injected subcutaneously, inhibit the reconstitution of the hair follicle.

In a different approach, cultured follicular papilla cells are transfected with either FP-1 cDNA (a/b). It is expected that such FP-1 over-expressing FP cells are particularly active in supporting hair reconstitution in the athymic nude mouse hosts. In striking contrast, it is expected that follicular papilla cells transfected with antisense FP-1 cDNA, or an FP-1 cDNA encoding a dominant negative FP-1 protein, or siRNA that inhibits or prevents expression of FP-1 have a diminished ability to support hair reconstitution in athymic nude mouse hosts. Hair growth can be measured using methods as described in Chamberlain et al., *Australasian J. Dermat.*, 44:10-18, 2003.

Example 12

Determination of Mitogenic Activity of Recombinant FP-1

Isolated human hair follicles are maintained in individual wells of 24-well multiwell plates containing 1 ml of KBM media (Clonetics) supplemented with 100 U/ml penicillin, 10 ng/ml hydrocortisone, 75 µg/ml bovine pituitary extract in an atmosphere of 5% $CO_2$/95% air.

The cell growth of hair follicles is measured by calorimetric MTS assays (Bunger et al., *Artif. Organs.*, 26(2):111-116, 2002; and Vorauer et al., *J. Biochem. Biophys. Methods*, 32(2):85-96, 1996). Specifically, FP-1 is added to culture media at different concentrations at different concentrations (from about 10 ng/ml, about 30 ng/ml, about 100 ng/ml, and about 1 μg/ml), and the isolated human hair follicles are incubated in these media with human FP-1 for 48 hrs before measuring by MTS assay.

A single hair follicle is then plated in a 96-well microtiter per well (see, Philpott et al., supra; Philpott et al., *J. Dermatol. Sci.* 7 Suppl, S55-72; and Philpott et al., J Invest Dermatol., 102:857-861); , and proliferation is measured 4 hr later using a calorimetric MTS assay according to the manufacturer's suggestions (Promega). In each experiment, observations (n=8 hair follicles per group) are performed and the values are reported as mean+/−standard error (S.E.). In the proliferation assay, the negative control is evaluated using untreated hair follicle cells.

The addition of FP-1 results in dose-dependent stimulation of human hair follicle cells.

Example 13

Liposome-Mediated Delivery of FP-1 to Hair Follicles

To achieve targeted delivery of FP-1 to hair follicles, the following protocol is carried out.

Liposomes are prepared by sonication. About 20 mg of egg phosphatidycholine is rotary evaporated with a vacuum drier from a chloroform solution to form a thin film on the walls of a 5 ml round-bottomed flask for about 1 hr. The dried thin film phospholipid is suspended in about 0.5 ml phosphate buffered saline (pH 7.4) on a vortex mixer and then is sonicated with a Branson probe-type sonicator fitted with a microtip at power level 3 for about 8 min. Then 0.5 ml of a solution of mouse FP-1 protein (10 mg/ml) is entrapped with the above suspension by sonication for about an additional 4 min. Liposomes are separated from the non-entrapped FP-1 by gel-filtration on a Sepharose 4B column equilibrated with phosphate buffered saline.

Pieces of outbred white-haired mouse skin derived from 1 to 2 week-old animals (about 2×5×2 mm each) is harvested under a dissection microscope. The samples are then histocultured on collagen-gel supported sponges as described U.S. Pat. No. 6,224,901. Liposome interaction with the skin is initiated after about 24 hrs of histoculture. Mouse skin histocultures are incubated for about 12 hrs with liposomes. As a control, a solution of "free" FP-1 at the same concentration as is used in the liposome preparation is also incubated for about 12 hrs with pieces of the histocultured skin.

Example 14

Liposome-Mediated Delivery of Nucleic Acid to Hair Follicles

About 50 ng of an expression vector comprising DNA encoding mouse FP-1 is purified for liposomal delivery to cultured mouse cells.

Liposomes are prepared by freezing and thawing. About 20 mg of egg phosphatidylcholine (EPC) is rotary evaporated with a vacuum drier from a chloroform solution to form a thin film on the walls of a 5 ml round-bottomed flask for about 1 hr. The dried film phospholipid is suspended in about 0.5 ml phosphate buffered saline solution at a pH of about 7.4 in a vortex mixer and is then sonicated with a Branson probe-type sonicator fitted with a microtip at power level 3 for about 8 min. The 0.5 ml of FP-1 DNA solution is added to the above suspension by extensive vortexing for about 1 minute and is followed by freezing and thawing. Liposomes are separated from the non-entrapped DNA by gel-filtration on a Sepharose 4B column that is equilibrated with PBS. About 50 μl calcein (about 10 mg/ml) is added into the solution in order to mark the liposomes during the separation.

Pieces of outbred white-haired-mouse skin (about 1×5×2 mm) derived from 1 to 5-week-old animals are harvested under a dissection microscope and then histocultured on collagen-gel-supported sponges as described in U.S. Pat. No. 6,224,901. Liposome interaction with the skin is initiated after about 24 hrs of histoculture. Mouse skin histocultures are then incubated for about 44 hrs with liposomes. As a control, a solution of naked DNA (lacking any inserted cDNA) at the same concentration is used in the liposome preparation and is also incubated with skin histocultures. The effects of the liposome-delivered FP-1 cDNA, or antisense RNA, or siRNA, on hair growth is assessed by measuring the length of the hair fibers exposed on the skin surface, and by measuring the length of the follicle in the skin by histology as mentioned in Example 10.

Example 15

Effect of Expressing FP-1 on Mammalian Hair Growth

An expression cassette is created, placing the entire cDNA for the murine FP-1 gene under the control of the HCMV immediate early promoter/enhancer and linked to the poladenylation sequence from SV40. This cassette is subcloned by standard methods into the deleted E1 region of an E1$^-$/E3$^-$ adenovirus vector. Recombinant viruses are isolated, and correct insertion of the expression cassette is verified by Southern hybridization and DNA sequence analysis. The recombinant vector (termed AdFP1) is thereafter purified and grown to high titer.

Groups of 2 to 4, 7 g, 3-week-old C57 Bl/6 mice are injected intradermally with $1 \times 10^8$ pfu of either AdFP1, a control E1$^-$/E3$^-$ vector lacking the FP-1 cDNA, or a sham injection of saline. After seven days, skin in the area of injection is removed from the injected animals, as well as naive animals, and is analyzed.

Northern hybridization of the excised skin patches reveals the presence of elevated levels of FP-1 mRNA in skin patches injected with AdFP1 but not in sham-injected patches, naive patches, or patches injected with the E1$^-$/E3$^-$ control adenoviral vector. Blots of mRNA from the various skin patches are also probed for the expression of hair-specific gene expression, specifically the hair-specific keratin gene (ghHb-1), that is expressed mainly during anagen, which is the growing phase of the hair follicle. Northern blots reveals the presence of some ghHb-1 mRNA in all excised skin patches; however, the level of ghHb-1 signal is more pronounced in the skin injected with AdFP1 than in sham-injected patches, naive patches, and patches injected with the E1$^-$/E3$^-$ control adenoviral vector. The excised skin patches above are visually examined to assess the effect of each treatment on hair growth in the area. To permit such evaluation, the mice are treated carefully during the protocol so as not to induce hair growth by the manner in which they are handled generally. Hair growth is assessed by measuring the length of the hair fibers exposed on the skin surface, and by measuring the length of the follicle in the skin by histology as mentioned in Example 10

Melanogenesis, a pigment synthesis process that occurs in association with hair growth, is evaluated using digital image analysis. Specifically, light is passed through the excised patches and the intensity of transmitted light is measured by determining the average gray scale of a digitally collected image of the transmitted light. The optical density (relative light absorbance) at the injection site is compared with the optical density of the same skin patch at a site distant from the injection site. This analysis is expected to reveal that the optical density of the excised skin patches that are injected with AdFP1 is consistently greater at the site of injection than distal from the injection or that is observed anywhere in sham-injected patches, naive patches, and patches injected with the E1⁻/E3⁻ control adenoviral vector.

The growth phase of the hair follicle cycle is associated with morphologic changes in follicles including an increase in size of the follicle, which can be recognized as an increase in the area of the follicle relative to total dermal/epidermal area. To evaluate hair follicle size, digital images of cross sections of skin patches are collected and analyzed by integrating the number of pixels occupied by either hair follicles or by total dermis/epidermis. The quotient of the two measurements gives the percentage of area occupied by hair follicles. This analysis is expected to reveal that the percentage of skin represented by mature hair follicles is consistently greater in the excised skin patches that are injected with AdFP1 than that is observed in sham-injected patches; naive patches, and patches injected with the E1⁻/E3⁻ control adenoviral vector.

These results indicate that transfer of a gene encoding an FP-1 protein promotes hair growth in the skin. That follicular area increases suggests the presence of larger hair follicles in anagen phase that were actively producing hair shafts. This result is important given the fact that alopecia is often correlated with increased likelihood of finding hair follicles in telogen phase, and that AdFP1 apparently induces anagen within a population of hair follicles initially in telogen.

Example 16

Identification of the FP-1 Regulatory Elements

The promoter of the mouse FP-1 gene is isolated by screening a mouse genomic library using PCR methods (Auch et al., *Nuc. Acids Res.*, 18: 6743-6744, 1990; and Garces et al., *Methods Mol. Biol.*, 161:3-8, 2001). Several overlapping clones are isolated and characterized by restriction mapping and partial sequencing. Combination of these data and the available mouse genomic sequence database allows the identification of the genomic clones having the longest 5'-upstream sequence. A segment of 3 to 6 kb 5'-upstream sequence is inserted into a suitable restriction site upstream from a lacZ reporter gene (Lin et al, *Proc. Natl. Acad. Sci. USA*, 92:679-683, 1995; Mercer et al., *Neuron* 7:703-716, 1991; Peschon et al., *Proc. Natl. Acad. Sci. USA*, 84:5316-5319, 1987). The fusion gene is excised by using suitable restriciton enzymes, gel-purified and microinjected into fertlized mouse eggs, which are implanted into CD-1 foster mothers. The lacZ transgene is identified by Southern blot analysis of the tail DNA. Positive founder mice are back crossed with C57BL/6J×DBA2 F1 hybrids to generate hemizygous animals that are used for studying transgene expression. The promoter activities of the 5'-upstream sequence of various lengths ranging from 1 kb to 5 or 6 kb is tested to compare their expression pattern to identify the minimal sequence that achieves follicular papilla-specific expression of the lacZ reporter gene.

Example 17

Construction of FP-1 Transgenic Mice

FP-1 transgenic mice, which overexpress FP-1, or derivatives (e.g., any of the coding regions of FP-1 smaller than the full length), mutants, or variants thereof, in a follicular papilla-specific manner are constructed by operably linking a promoter that is follicular papilla-specific (for example, the promoter of the FP-1 gene, or the promoter of versican (Kishimoto, J., R. Ehama, et al., *Proc. Natl. Acad. Sci. USA*, 96 (13): 7336-41, 1999) to a FP-1 cDNA, or any portion thereof. The generation of such transgenic mice is done using standard techniques (Joyner, *Gene Targeting* Oxford University Press, New York, 2000, (*Practical Approach Series;* 212), i-xviii).

For example, an appropriate fusion gene, comprising any follicular papilla-specific promoter operably linked to a mouse or rat FP-1 full-length cDNA, is first constructed. The fusion gene is excised from the construction vector, gel purified, and microinjected into fertilized mouse eggs (from F1 hybrids of c57BL/6J×DBA2), which can then be implanted into CDE-1 foster mothers. The transgene is identified by Southern blot analysis of tail cDNA using the mouse FP-1 cDNA as probe. Positive founder mice can be back crossed with c57BL/6J×DBA2 F1 hybrids to generate hemizygous and later homozygous mice. Over-expression of FP-1, which is normally expressed transiently during the anagen (or growing) phase of the hair cycle, prolongs the anagen phase of the hair cycle leading to longer hair fibers.

Example 18

Construction of FP-1 Knock-Out Mice

The ablation of the FP-1 gene in mice is done using standard techniques. Briefly, genomic clones of mouse FP-1 gene are isolated from a 129/Ola mouse P1 genomic library. A targeting vector can be designed to delete the third and fourth exons of the FP-1 gene; this vector can contain four portions: an approximately 3-5 kb mouse FP-1 fragment upstream of exon 2, a neomycin-resistance gene (neo) driven by the phosphoglycerate kinase (PGK) promoter in the opposite direction of exon 2 of FP-1, a 3 to 5 kb mouse FP-1 genomic fragment of exon 4 to be eliminated, and a thymidine kinase (tk) gene of herpes simplex virus driven by the PGK promoter (Joyner, *Gene Targeting*, Oxford University Press, New York, 2000 (Practical Approach Series; 212), i-xviii; Ramirez-Solis et al., *Methods Enzymol.*, 225:855-878, 1993). The linearized vector is electroporated into 129/SvEv embryonic stem cell line W4, and the neo-positive and tk-negative transformants are selected using G418 (240 mg/ml) and gancyclovir (2 mM). The embryonic stem (ES) cell colonies that harbor the correct homologous recombination events are detected by Southern blotting and by long-range PCR using primers. The confirmed ES cell clones are amplified and aggregated with eight cell stage embryos of Swiss Webster mice, and implanted into pseudopregnant females. Chimeric mice from two ES cell lines that are germline-transmitting are bred with SW mice to yield hybrid homozygotes, or mated with 129/SvEv mice to yield inbred 129/SvEv FP-1-knockout mice.

Example 19

Screening Tissue Sections of Cancer Patients and Cancer Cell Lines for FP-1 Expression Levels Frozen sections and paraffin sections of various normal and various abnormal tissues including tumors are prepared by standard techniques (Hu et al., *J. Cell Biol.*, 151:961-972, 2000; Deng et al., *J. Cell Biol.*, 159:685-694, 2002; and Chen et al., *Proc. Natl. Acad. Sci. USA*, 100:14012-14017, 2003) and are stained immunohistochemically using rabbit antibodies to FP-1 (G320 at 1:10,000; G311 at 1:1,000; and G312 at 1:2,000) followed by visualization using secondary goat-anti-rabbit antibodies that have been conjugated with peroxidase or fluorescein.

Cancer cell lines representing cancers of, for example, skin (e.g., basal cell carcinoma), stomach, ovary, liver, brain, etc. are used to prepare RNA. RNA is separated on a gel and is transferred to a filter for Northern analysis (Sanger et al., *Proc. Natl. Acad. Sci. USA.*, 74:5463-5467, 1977). Filters with mRNAs from these cell lines are hybridized with a probe to FP-1. In those instances where the cell lines are derived from mouse cell lines, a mouse FP-1 probe is used; where rat cell lines are use, rat FP-1 probe is used; and where human cell lines are used, a human FP-1 probe is used.

FP-1 is found to be overexpressed in several cancer cell lines.

Example 20

Monoclonal Antibodies that Specifically Bind FP-1

Balb/c mice are immunized with rat or human FP-1 antigen with weekly injections of 200 to 500 µg of recombinant FP-1 protein over a period of 3 to 4 months. Mice showing high serum titers of anti-FP-1 antibodies as determined by ELISA assay against recombinant FP-1, are identified and the spleens of the mice removed. Spleen cells are fused with the mouse myeloma SP2/0 (ATCC® Accession No. CRL-8006) in accordance with the protocol described in Enfield, D. A. et al. *EMBO J.* 7:711, 1988.

Assays for FP-1 specificity are accomplished by ELISA assays against recombinant FP-1. The cell line producing an FP-1 antibody demonstrating the highest binding for recombinant FP-1 while having the least non-specific binding to an unrelated protein is selected.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated polypeptide comprising an amino acid sequence selected from the group consisting of SEQ ID NO:12, and amino acids 34 to 551 of SEQ ID NO:12.

\* \* \* \* \*

SEQUENCE LISTING

```
<160> NUMBER OF SEQ ID NOS: 38

<210> SEQ ID NO 1
<211> LENGTH: 2332
<212> TYPE: DNA
<213> ORGANISM: Rattus sp.
<220> FEATURE:
<221> NAME/KEY: CDS
<222> LOCATION: (46)..(1692)

<400> SEQUENCE: 1
acgcggggag tgctgccctg agtcgttcgg cctgagcaca gagac atg acc cga gcc      57
                                                    Met Thr Arg Ala
                                                      1 gca gag cga ggc caa ggg gct aca ggc tgg gga ctg cga ggc gcc ctg      105
Ala Glu Arg Gly Gln Gly Ala Thr Gly Trp Gly Leu Arg Gly Ala Leu
  5                  10                  15                  20 atg gcc gtg gcg ctg ctg tca gtg ctg aac gcc gtg ggc acc gtg ttc      153
Met Ala Val Ala Leu Leu Ser Val Leu Asn Ala Val Gly Thr Val Phe
                 25                  30                  35 gtg ctg tac cag tgg cgc gag ctg agc gcg gcg ctg cgg gca ctg gag      201
Val Leu Tyr Gln Trp Arg Glu Leu Ser Ala Ala Leu Arg Ala Leu Glu
             40                  45                  50 gcg caa cac ggc cag gag cag cgc gag gac agc gcc cta cgc gcc ttt      249
Ala Gln His Gly Gln Glu Gln Arg Glu Asp Ser Ala Leu Arg Ala Phe
         55                  60                  65 cta gct gaa tta agt cgt gcg cca gcc cga gtc ccc gaa cca ccc cag      297
Leu Ala Glu Leu Ser Arg Ala Pro Ala Arg Val Pro Glu Pro Pro Gln
     70                  75                  80 gac ccc atg agt gca gcg cgc aat aag cgc agc cac ggc ggc gag cct      345
Asp Pro Met Ser Ala Ala Arg Asn Lys Arg Ser His Gly Gly Glu Pro
 85                  90                  95                 100
```

```
gcg tca cac atc cgc gcg gag agc cag gac atg atg atg atg atg acc     393
Ala Ser His Ile Arg Ala Glu Ser Gln Asp Met Met Met Met Met Thr
            105                 110                 115 tac agc atg gtg ccg atc cgg gtg atg ata gac ctg tgc aac agc acc     441
Tyr Ser Met Val Pro Ile Arg Val Met Ile Asp Leu Cys Asn Ser Thr
        120                 125                 130 cag ggc atc tgc ctt aca gga cca ccg ggc cca cca gga cct cca gga     489
Gln Gly Ile Cys Leu Thr Gly Pro Pro Gly Pro Pro Gly Pro Pro Gly
            135                 140                 145 gct ggt ggg tta cca ggc cac aat gga tca gat gga cag cct ggt ctc     537
Ala Gly Gly Leu Pro Gly His Asn Gly Ser Asp Gly Gln Pro Gly Leu
        150                 155                 160 cag ggc cca aaa gga gaa aaa gga gca gtt ggg aag aga gga aaa atg     585
Gln Gly Pro Lys Gly Glu Lys Gly Ala Val Gly Lys Arg Gly Lys Met
165                 170                 175                 180 ggg tta ccc gga gcc aca gga aat cca ggg gaa aag gga gag aag gga     633
Gly Leu Pro Gly Ala Thr Gly Asn Pro Gly Glu Lys Gly Glu Lys Gly
                185                 190                 195 gat gct ggt gaa ctg ggc cta cct gga aat gag gga cca cca gga cag     681
Asp Ala Gly Glu Leu Gly Leu Pro Gly Asn Glu Gly Pro Pro Gly Gln
            200                 205                 210 aaa gga gac aaa gga gac aaa gga gat gtg tcc aat gac gtg ctt ttg     729
Lys Gly Asp Lys Gly Asp Lys Gly Asp Val Ser Asn Asp Val Leu Leu
        215                 220                 225 aca ggt gcc aaa ggt gac caa ggg ccc cct ggc cca cct gga ccc cca     777
Thr Gly Ala Lys Gly Asp Gln Gly Pro Pro Gly Pro Pro Gly Pro Pro
        230                 235                 240 ggg cct cca ggc cct tct gga agc aga aga gcc aaa ggc cct cgg cag     825
Gly Pro Pro Gly Pro Ser Gly Ser Arg Arg Ala Lys Gly Pro Arg Gln
245                 250                 255                 260 cca aat tcg ttc acc aac cag tgt cca ggg gag acg tgt gtc ata ccc     873
Pro Asn Ser Phe Thr Asn Gln Cys Pro Gly Glu Thr Cys Val Ile Pro
                265                 270                 275 aat gat gat acc ttg gtg ggg aga gct gat gag aaa gtc aat gag cgc     921
Asn Asp Asp Thr Leu Val Gly Arg Ala Asp Glu Lys Val Asn Glu Arg
            280                 285                 290 cat tct cca caa aca gaa ccc atg atc acg tcc att ggt aac ccg gcc     969
His Ser Pro Gln Thr Glu Pro Met Ile Thr Ser Ile Gly Asn Pro Ala
        295                 300                 305 caa gtc ctc aaa gtg aaa gag act ttt ggg acc tgg cta aga gag tct    1017
Gln Val Leu Lys Val Lys Glu Thr Phe Gly Thr Trp Leu Arg Glu Ser
        310                 315                 320 gct aac agg agt gat gac cgc att tgg gtg act gaa cat ttt tca ggc    1065
Ala Asn Arg Ser Asp Asp Arg Ile Trp Val Thr Glu His Phe Ser Gly
325                 330                 335                 340 atc atg gtg aag gag ttt gaa gac ctg ccc gcc ctc ctg aat agc agc    1113
Ile Met Val Lys Glu Phe Glu Asp Leu Pro Ala Leu Leu Asn Ser Ser
                345                 350                 355 ttc acc ctc ctc cac ctc cca cat tac ttc cat ggc tgc ggg cac gct    1161
Phe Thr Leu Leu His Leu Pro His Tyr Phe His Gly Cys Gly His Ala
            360                 365                 370 gtt tac aac aac tct ctc tac tac cac aaa gga ggc tcc aac acc ata    1209
Val Tyr Asn Asn Ser Leu Tyr Tyr His Lys Gly Gly Ser Asn Thr Ile
        375                 380                 385 gtg aga ttt gaa ttt ggg aaa gag aca cct caa act ctg aag ctt gaa    1257
Val Arg Phe Glu Phe Gly Lys Glu Thr Pro Gln Thr Leu Lys Leu Glu
        390                 395                 400 gat gct ttg tat ttt gat cga aaa tac ctc ttt gcg aat tcc aag act    1305
Asp Ala Leu Tyr Phe Asp Arg Lys Tyr Leu Phe Ala Asn Ser Lys Thr
```

-continued

```
                    405                 410                 415                 420
tac ttc aac ata gca gtg gat gag aag ggc ctc tgg att atc tac gcc      1353
Tyr Phe Asn Ile Ala Val Asp Glu Lys Gly Leu Trp Ile Ile Tyr Ala
                425                 430                 435 tcg agt gtg gat ggc tca agc atc ctt gtg gca cag ctg gac gag agg      1401
Ser Ser Val Asp Gly Ser Ser Ile Leu Val Ala Gln Leu Asp Glu Arg
        440                 445                 450 aca ttc tct gtg ctg cag cac atc aat acc aca tac ccc aag tcc aag      1449
Thr Phe Ser Val Leu Gln His Ile Asn Thr Thr Tyr Pro Lys Ser Lys
    455                 460                 465 gct ggc aat gcc ttc ata gct caa ggg atc ctc tat gtc acg gac aca      1497
Ala Gly Asn Ala Phe Ile Ala Gln Gly Ile Leu Tyr Val Thr Asp Thr
470                 475                 480 aaa gat aca agg gtc acg ttt gcc ttt gat ttg tta cga ggg aag cag      1545
Lys Asp Thr Arg Val Thr Phe Ala Phe Asp Leu Leu Arg Gly Lys Gln
485                 490                 495                 500 atc aat gca aac ttc ggt ctc aga atg tca cag tct gtt ctt gcc atg      1593
Ile Asn Ala Asn Phe Gly Leu Arg Met Ser Gln Ser Val Leu Ala Met
                505                 510                 515 ttg tcg tac aat atg aga gac cag cat ttg tac tcg tgg gaa gac ggc      1641
Leu Ser Tyr Asn Met Arg Asp Gln His Leu Tyr Ser Trp Glu Asp Gly
            520                 525                 530 cac ctg atg ctc tat cct gtg cac ttt tcg tca aca gca ccc agc cag      1689
His Leu Met Leu Tyr Pro Val His Phe Ser Ser Thr Ala Pro Ser Gln
        535                 540                 545 cga                                                                   1742
Arg
    taggcctgca gtcggctccc tcattatgca ccacacattt tctggggttt gaccaagccc aacggaaaga aggcctgtaa aggatatcca gatactcaga gcatacgccc    1802
gtgttacggg cttttgtgca tgtggcaagt cccccctgtaa gccaggttaa ctaaaggctg    1862
gaaagttgaa atggataaca tttggtgacc cttggtccct cttcaaactt agcaagttag    1922
tgctcccccc tgaccttagt gtccccatca gtaatatgaa acatctgtgt gattgcagca    1982
tttcctatac ctatatgaag ttctgtgatt cttgcctggt tatatattag attgctttca    2042
ggtttctttt tttttttctcc acatgtaaat gagtttacct gcagcttgag gggtgtgcct    2102
atcagtgatg acggacattt gtttggtgtt tagggaaaaa gcattgtttc ttatggcttt    2162
taaagtatta tattatccat aatttgtat tttttttga atacgcccct gccactacag    2222
aatgattatt gttttcagct cctaagtaca aatccaagat taataaaaaa aaaacatgaa    2282
tagaaaaaaa aaaaaaaaaa actcgagagt attagtcgat gtaggaaaac              2332

<210> SEQ ID NO 2
<211> LENGTH: 549
<212> TYPE: PRT
<213> ORGANISM: Rattus sp.

<400> SEQUENCE: 2

Met Thr Arg Ala Ala Glu Arg Gly Gln Gly Ala Thr Gly Trp Gly Leu
1               5                   10                  15

Arg Gly Ala Leu Met Ala Val Ala Leu Leu Ser Val Leu Asn Ala Val
            20                  25                  30

Gly Thr Val Phe Val Leu Tyr Gln Trp Arg Glu Leu Ser Ala Ala Leu
        35                  40                  45

Arg Ala Leu Glu Ala Gln His Gly Gln Glu Gln Arg Glu Asp Ser Ala
    50                  55                  60

Leu Arg Ala Phe Leu Ala Glu Leu Ser Arg Ala Pro Ala Arg Val Pro
65                  70                  75                  80
```

```
Glu Pro Pro Gln Asp Pro Met Ser Ala Ala Arg Asn Lys Arg Ser His
                    85                  90                  95
Gly Gly Glu Pro Ala Ser His Ile Arg Ala Glu Ser Gln Asp Met Met
            100                 105                 110
Met Met Met Thr Tyr Ser Met Val Pro Ile Arg Val Met Ile Asp Leu
        115                 120                 125
Cys Asn Ser Thr Gln Gly Ile Cys Leu Thr Gly Pro Gly Pro Pro
130                 135                 140
Gly Pro Pro Gly Ala Gly Gly Leu Pro Gly His Asn Gly Ser Asp Gly
145                 150                 155                 160
Gln Pro Gly Leu Gln Gly Pro Lys Gly Glu Lys Gly Ala Val Gly Lys
                    165                 170                 175
Arg Gly Lys Met Gly Leu Pro Gly Ala Thr Gly Asn Pro Gly Glu Lys
            180                 185                 190
Gly Glu Lys Gly Asp Ala Gly Glu Leu Gly Leu Pro Gly Asn Glu Gly
        195                 200                 205
Pro Pro Gly Gln Lys Gly Asp Lys Gly Asp Lys Gly Asp Val Ser Asn
210                 215                 220
Asp Val Leu Leu Thr Gly Ala Lys Gly Asp Gln Gly Pro Pro Gly Pro
225                 230                 235                 240
Pro Gly Pro Pro Gly Pro Pro Gly Pro Ser Gly Arg Arg Ala Lys
                    245                 250                 255
Gly Pro Arg Gln Pro Asn Ser Phe Thr Asn Gln Cys Pro Gly Glu Thr
            260                 265                 270
Cys Val Ile Pro Asn Asp Asp Thr Leu Val Gly Arg Ala Asp Glu Lys
        275                 280                 285
Val Asn Glu Arg His Ser Pro Gln Thr Glu Pro Met Ile Thr Ser Ile
    290                 295                 300
Gly Asn Pro Ala Gln Val Leu Lys Val Lys Glu Thr Phe Gly Thr Trp
305                 310                 315                 320
Leu Arg Glu Ser Ala Asn Arg Ser Asp Asp Arg Ile Trp Val Thr Glu
                    325                 330                 335
His Phe Ser Gly Ile Met Val Lys Glu Phe Glu Asp Leu Pro Ala Leu
            340                 345                 350
Leu Asn Ser Ser Phe Thr Leu Leu His Leu Pro His Tyr Phe His Gly
        355                 360                 365
Cys Gly His Ala Val Tyr Asn Asn Ser Leu Tyr Tyr His Lys Gly Gly
370                 375                 380
Ser Asn Thr Ile Val Arg Phe Glu Phe Gly Lys Glu Thr Pro Gln Thr
385                 390                 395                 400
Leu Lys Leu Glu Asp Ala Leu Tyr Phe Asp Arg Lys Tyr Leu Phe Ala
                    405                 410                 415
Asn Ser Lys Thr Tyr Phe Asn Ile Ala Val Asp Glu Lys Gly Leu Trp
            420                 425                 430
Ile Ile Tyr Ala Ser Ser Val Asp Gly Ser Ser Ile Leu Val Ala Gln
        435                 440                 445
Leu Asp Glu Arg Thr Phe Ser Val Leu Gln His Ile Asn Thr Thr Tyr
    450                 455                 460
Pro Lys Ser Lys Ala Gly Asn Ala Phe Ile Ala Gln Gly Ile Leu Tyr
465                 470                 475                 480
Val Thr Asp Thr Lys Asp Thr Arg Val Thr Phe Ala Phe Asp Leu Leu
                    485                 490                 495
```

-continued

```
Arg Gly Lys Gln Ile Asn Ala Asn Phe Gly Leu Arg Met Ser Gln Ser
            500                 505                 510

Val Leu Ala Met Leu Ser Tyr Asn Met Arg Asp Gln His Leu Tyr Ser
        515                 520                 525

Trp Glu Asp Gly His Leu Met Leu Tyr Pro Val His Phe Ser Ser Thr
    530                 535                 540

Ala Pro Ser Gln Arg
545

<210> SEQ ID NO 3
<211> LENGTH: 2278
<212> TYPE: DNA
<213> ORGANISM: Rattus sp.
<220> FEATURE:
<221> NAME/KEY: CDS
<222> LOCATION: (46)..(1638)

<400> SEQUENCE: 3
acgcggggag tgctgccctg agtcgttcgg cctgagcaca gagac atg acc cga gcc      57
                                                Met Thr Arg Ala
                                                  1 gca gag cga ggc caa ggg gct aca ggc tgg gga ctg cga ggc gcc ctg     105
Ala Glu Arg Gly Gln Gly Ala Thr Gly Trp Gly Leu Arg Gly Ala Leu
  5              10                  15                  20 atg gcc gtg gcg ctg ctg tca gtg ctg aac gcc gtg ggc acc gtg ttc     153
Met Ala Val Ala Leu Leu Ser Val Leu Asn Ala Val Gly Thr Val Phe
                 25                  30                  35 gtg ctg tac cag cag cgc gag gac agc gcc cta cgc gcc ttt cta gct     201
Val Leu Tyr Gln Gln Arg Glu Asp Ser Ala Leu Arg Ala Phe Leu Ala
             40                  45                  50 gaa tta agt cgt gcg cca gcc cga gtc ccc gaa cca ccc cag gac ccc     249
Glu Leu Ser Arg Ala Pro Ala Arg Val Pro Glu Pro Pro Gln Asp Pro
         55                  60                  65 atg agt gca gcg cgc aat aag cgc agc cac ggc ggc gag cct gcg tca     297
Met Ser Ala Ala Arg Asn Lys Arg Ser His Gly Gly Glu Pro Ala Ser
     70                  75                  80 cac atc cgc gcg gag agc cag gac atg atg atg atg atg acc tac agc     345
His Ile Arg Ala Glu Ser Gln Asp Met Met Met Met Met Thr Tyr Ser
 85                  90                  95                 100 atg gtg ccg atc cgg gtg atg ata gac ctg tgc aac agc acc cag ggc     393
Met Val Pro Ile Arg Val Met Ile Asp Leu Cys Asn Ser Thr Gln Gly
                105                 110                 115 atc tgc ctt aca gga cca ccg ggc cca cca gga cct cca gga gct ggt     441
Ile Cys Leu Thr Gly Pro Pro Gly Pro Pro Gly Pro Pro Gly Ala Gly
             120                 125                 130 ggg tta cca ggc cac aat gga tca gat gga cag cct ggt ctc cag ggc     489
Gly Leu Pro Gly His Asn Gly Ser Asp Gly Gln Pro Gly Leu Gln Gly
         135                 140                 145 cca aaa gga gaa aaa gga gca gtt ggg aag aga gga aaa atg ggg tta     537
Pro Lys Gly Glu Lys Gly Ala Val Gly Lys Arg Gly Lys Met Gly Leu
     150                 155                 160 ccc gga gcc aca gga aat cca ggg gaa aag gga gag aag gga gat gct     585
Pro Gly Ala Thr Gly Asn Pro Gly Glu Lys Gly Glu Lys Gly Asp Ala
165                 170                 175                 180 ggt gaa ctg ggc cta cct gga aat gag gga cca cca gga cag aaa gga     633
Gly Glu Leu Gly Leu Pro Gly Asn Glu Gly Pro Pro Gly Gln Lys Gly
                185                 190                 195 gac aaa gga gac aaa gga gat gtg tcc aat gac gtg ctt ttg aca ggt     681
Asp Lys Gly Asp Lys Gly Asp Val Ser Asn Asp Val Leu Leu Thr Gly
             200                 205                 210
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gcc | aaa | ggt | gac | caa | ggg | ccc | cct | ggc | cca | cct | gga | ccc | cca | ggg | cct | 729  |
| Ala | Lys | Gly | Asp | Gln | Gly | Pro | Pro | Gly | Pro | Pro | Gly | Pro | Pro | Gly | Pro |      |
|     |     | 215 |     |     |     | 220 |     |     |     | 225 |     |     |     |     |     |      |

| | | | | | | | | | | | | | | | | |
|---|---|---|---|---|---|---|---|---|---|---|---|---|---|---|---|---|
| cca | ggc | cct | tct | gga | agc | aga | aga | gcc | aaa | ggc | cct | cgg | cag | cca | aat | 777 |
| Pro | Gly | Pro | Ser | Gly | Ser | Arg | Arg | Ala | Lys | Gly | Pro | Arg | Gln | Pro | Asn | |
| | | 230 | | | | | 235 | | | | | 240 | | | | |

| | | | | | | | | | | | | | | | | |
|---|---|---|---|---|---|---|---|---|---|---|---|---|---|---|---|---|
| tcg | ttc | acc | aac | cag | tgt | cca | ggg | gag | acg | tgt | gtc | ata | ccc | aat | gat | 825 |
| Ser | Phe | Thr | Asn | Gln | Cys | Pro | Gly | Glu | Thr | Cys | Val | Ile | Pro | Asn | Asp | |
| 245 | | | | | 250 | | | | | 255 | | | | | 260 | |

| | | | | | | | | | | | | | | | | |
|---|---|---|---|---|---|---|---|---|---|---|---|---|---|---|---|---|
| gat | acc | ttg | gtg | ggg | aga | gct | gat | gag | aaa | gtc | aat | gag | cgc | cat | tct | 873 |
| Asp | Thr | Leu | Val | Gly | Arg | Ala | Asp | Glu | Lys | Val | Asn | Glu | Arg | His | Ser | |
| | | | | 265 | | | | | 270 | | | | | 275 | | |

| | | | | | | | | | | | | | | | | |
|---|---|---|---|---|---|---|---|---|---|---|---|---|---|---|---|---|
| cca | caa | aca | gaa | ccc | atg | atc | acg | tcc | att | ggt | aac | ccg | gcc | caa | gtc | 921 |
| Pro | Gln | Thr | Glu | Pro | Met | Ile | Thr | Ser | Ile | Gly | Asn | Pro | Ala | Gln | Val | |
| | | | 280 | | | | | 285 | | | | | 290 | | | |

| | | | | | | | | | | | | | | | | |
|---|---|---|---|---|---|---|---|---|---|---|---|---|---|---|---|---|
| ctc | aaa | gtg | aaa | gag | act | ttt | ggg | acc | tgg | cta | aga | gag | tct | gct | aac | 969 |
| Leu | Lys | Val | Lys | Glu | Thr | Phe | Gly | Thr | Trp | Leu | Arg | Glu | Ser | Ala | Asn | |
| | | | 295 | | | | | 300 | | | | | 305 | | | |

| | | | | | | | | | | | | | | | | |
|---|---|---|---|---|---|---|---|---|---|---|---|---|---|---|---|---|
| agg | agt | gat | gac | cgc | att | tgg | gtg | act | gaa | cat | ttt | tca | ggc | atc | atg | 1017 |
| Arg | Ser | Asp | Asp | Arg | Ile | Trp | Val | Thr | Glu | His | Phe | Ser | Gly | Ile | Met | |
| 310 | | | | | 315 | | | | | 320 | | | | | | |

| | | | | | | | | | | | | | | | | |
|---|---|---|---|---|---|---|---|---|---|---|---|---|---|---|---|---|
| gtg | aag | gag | ttt | gaa | gac | ctg | ccc | gcc | ctc | ctg | aat | agc | agc | ttc | acc | 1065 |
| Val | Lys | Glu | Phe | Glu | Asp | Leu | Pro | Ala | Leu | Leu | Asn | Ser | Ser | Phe | Thr | |
| 325 | | | | | 330 | | | | | 335 | | | | | 340 | |

| | | | | | | | | | | | | | | | | |
|---|---|---|---|---|---|---|---|---|---|---|---|---|---|---|---|---|
| ctc | ctc | cac | ctc | cca | cat | tac | ttc | cat | ggc | tgc | ggg | cac | gct | gtt | tac | 1113 |
| Leu | Leu | His | Leu | Pro | His | Tyr | Phe | His | Gly | Cys | Gly | His | Ala | Val | Tyr | |
| | | | | 345 | | | | | 350 | | | | | 355 | | |

| | | | | | | | | | | | | | | | | |
|---|---|---|---|---|---|---|---|---|---|---|---|---|---|---|---|---|
| aac | aac | tct | ctc | tac | tac | cac | aaa | gga | ggc | tcc | aac | acc | ata | gtg | aga | 1161 |
| Asn | Asn | Ser | Leu | Tyr | Tyr | His | Lys | Gly | Gly | Ser | Asn | Thr | Ile | Val | Arg | |
| | | | 360 | | | | | 365 | | | | | 370 | | | |

| | | | | | | | | | | | | | | | | |
|---|---|---|---|---|---|---|---|---|---|---|---|---|---|---|---|---|
| ttt | gaa | ttt | ggg | aaa | gag | aca | cct | caa | act | ctg | aag | ctt | gaa | gat | gct | 1209 |
| Phe | Glu | Phe | Gly | Lys | Glu | Thr | Pro | Gln | Thr | Leu | Lys | Leu | Glu | Asp | Ala | |
| | | 375 | | | | | 380 | | | | | 385 | | | | |

| | | | | | | | | | | | | | | | | |
|---|---|---|---|---|---|---|---|---|---|---|---|---|---|---|---|---|
| ttg | tat | ttt | gat | cga | aaa | tac | ctc | ttt | gcg | aat | tcc | aag | act | tac | ttc | 1257 |
| Leu | Tyr | Phe | Asp | Arg | Lys | Tyr | Leu | Phe | Ala | Asn | Ser | Lys | Thr | Tyr | Phe | |
| 390 | | | | | 395 | | | | | 400 | | | | | | |

| | | | | | | | | | | | | | | | | |
|---|---|---|---|---|---|---|---|---|---|---|---|---|---|---|---|---|
| aac | ata | gca | gtg | gat | gag | aag | ggc | ctc | tgg | att | atc | tac | gcc | tcg | agt | 1305 |
| Asn | Ile | Ala | Val | Asp | Glu | Lys | Gly | Leu | Trp | Ile | Ile | Tyr | Ala | Ser | Ser | |
| 405 | | | | | 410 | | | | | 415 | | | | | 420 | |

| | | | | | | | | | | | | | | | | |
|---|---|---|---|---|---|---|---|---|---|---|---|---|---|---|---|---|
| gtg | gat | ggc | tca | agc | atc | ctt | gtg | gca | cag | ctg | gac | gag | agg | aca | ttc | 1353 |
| Val | Asp | Gly | Ser | Ser | Ile | Leu | Val | Ala | Gln | Leu | Asp | Glu | Arg | Thr | Phe | |
| | | | | 425 | | | | | 430 | | | | | 435 | | |

| | | | | | | | | | | | | | | | | |
|---|---|---|---|---|---|---|---|---|---|---|---|---|---|---|---|---|
| tct | gtg | ctg | cag | cac | atc | aat | acc | aca | tac | ccc | aag | tcc | aag | gct | ggc | 1401 |
| Ser | Val | Leu | Gln | His | Ile | Asn | Thr | Thr | Tyr | Pro | Lys | Ser | Lys | Ala | Gly | |
| | | | 440 | | | | | 445 | | | | | 450 | | | |

| | | | | | | | | | | | | | | | | |
|---|---|---|---|---|---|---|---|---|---|---|---|---|---|---|---|---|
| aat | gcc | ttc | ata | gct | caa | ggg | atc | ctc | tat | gtc | acg | gac | aca | aaa | gat | 1449 |
| Asn | Ala | Phe | Ile | Ala | Gln | Gly | Ile | Leu | Tyr | Val | Thr | Asp | Thr | Lys | Asp | |
| | | 455 | | | | | 460 | | | | | 465 | | | | |

| | | | | | | | | | | | | | | | | |
|---|---|---|---|---|---|---|---|---|---|---|---|---|---|---|---|---|
| aca | agg | gtc | acg | ttt | gcc | ttt | gat | ttg | tta | cga | ggg | aag | cag | atc | aat | 1497 |
| Thr | Arg | Val | Thr | Phe | Ala | Phe | Asp | Leu | Leu | Arg | Gly | Lys | Gln | Ile | Asn | |
| 470 | | | | | 475 | | | | | 480 | | | | | | |

| | | | | | | | | | | | | | | | | |
|---|---|---|---|---|---|---|---|---|---|---|---|---|---|---|---|---|
| gca | aac | ttc | ggt | ctc | aga | atg | tca | cag | tct | gtt | ctt | gcc | atg | ttg | tcg | 1545 |
| Ala | Asn | Phe | Gly | Leu | Arg | Met | Ser | Gln | Ser | Val | Leu | Ala | Met | Leu | Ser | |
| 485 | | | | | 490 | | | | | 495 | | | | | 500 | |

| | | | | | | | | | | | | | | | | |
|---|---|---|---|---|---|---|---|---|---|---|---|---|---|---|---|---|
| tac | aat | atg | aga | gac | cag | cat | ttg | tac | tcg | tgg | gaa | gac | ggc | cac | ctg | 1593 |
| Tyr | Asn | Met | Arg | Asp | Gln | His | Leu | Tyr | Ser | Trp | Glu | Asp | Gly | His | Leu | |
| | | | | 505 | | | | | 510 | | | | | 515 | | |

| | | | | | | | | | | | | | | |
|---|---|---|---|---|---|---|---|---|---|---|---|---|---|---|
| atg | ctc | tat | cct | gtg | cac | ttt | tcg | tca | aca | gca | ccc | agc | cag | cga | 1638 |
| Met | Leu | Tyr | Pro | Val | His | Phe | Ser | Ser | Thr | Ala | Pro | Ser | Gln | Arg | |
| | | | 520 | | | | | 525 | | | | | 530 | | |

-continued

```
taggcctgca gtcggctccc tcattatgca ccacacattt tctggggttt gaccaagccc      1698
aacggaaaga aggcctgtaa aggatatcca gatactcaga gcatacgccc gtgttacggg      1758
cttttgtgca tgtggcaagt cccctgtaa gccaggttaa ctaaaggctg gaaagttgaa       1818
atggataaca tttggtgacc cttggtccct cttcaaactt agcaagttag tgctccccccc     1878 tgaccttagt gtccccatca gtaatatgaa acatctgtgt gattgcagca tttcctatac      1938
ctatatgaag ttctgtgatt cttgcctggt tatatattag attgctttca ggtttctttt      1998
ttttttctcc acatgtaaat gagtttacct gcagcttgag gggtgtgcct atcagtgatg      2058
acggacattt gtttggtgtt tagggaaaaa gcattgtttc ttatggcttt taaagtatta      2118
tattatccat aatttgatat tttttttga atacgcccct gccactacag aatgattatt       2178
gttttcagct cctaagtaca aatccaagat taataaaaaa aaacatgaa tagaaaaaaa       2238 aaaaaaaaaa actcgagagt attagtcgat gtaggaaaac                            2278
```

```
<210> SEQ ID NO 4
<211> LENGTH: 531
<212> TYPE: PRT
<213> ORGANISM: Rattus sp.

<400> SEQUENCE: 4

Met Thr Arg Ala Ala Glu Arg Gly Gln Gly Ala Thr Gly Trp Gly Leu
  1               5                  10                  15

Arg Gly Ala Leu Met Ala Val Ala Leu Leu Ser Val Leu Asn Ala Val
             20                  25                  30

Gly Thr Val Phe Val Leu Tyr Gln Gln Arg Glu Asp Ser Ala Leu Arg
         35                  40                  45

Ala Phe Leu Ala Glu Leu Ser Arg Ala Pro Ala Arg Val Pro Glu Pro
     50                  55                  60

Pro Gln Asp Pro Met Ser Ala Ala Arg Asn Lys Arg Ser His Gly Gly
 65                  70                  75                  80

Glu Pro Ala Ser His Ile Arg Ala Glu Ser Gln Asp Met Met Met Met
                 85                  90                  95

Met Thr Tyr Ser Met Val Pro Ile Arg Val Met Ile Asp Leu Cys Asn
            100                 105                 110

Ser Thr Gln Gly Ile Cys Leu Thr Gly Pro Gly Pro Pro Gly Pro
        115                 120                 125

Pro Gly Ala Gly Gly Leu Pro Gly His Asn Gly Ser Asp Gly Gln Pro
    130                 135                 140

Gly Leu Gln Gly Pro Lys Gly Glu Lys Gly Ala Val Gly Lys Arg Gly
145                 150                 155                 160

Lys Met Gly Leu Pro Gly Ala Thr Gly Asn Pro Gly Glu Lys Gly Glu
                165                 170                 175

Lys Gly Asp Ala Gly Glu Leu Gly Leu Pro Gly Asn Glu Gly Pro
            180                 185                 190

Gly Gln Lys Gly Asp Lys Gly Asp Lys Gly Asp Val Ser Asn Asp Val
        195                 200                 205

Leu Leu Thr Gly Ala Lys Gly Asp Gln Gly Pro Pro Gly Pro Pro Gly
    210                 215                 220

Pro Pro Gly Pro Pro Gly Pro Ser Gly Ser Arg Arg Ala Lys Gly Pro
225                 230                 235                 240

Arg Gln Pro Asn Ser Phe Thr Asn Gln Cys Pro Gly Glu Thr Cys Val
                245                 250                 255
```

```
Ile Pro Asn Asp Asp Thr Leu Val Gly Arg Ala Asp Glu Lys Val Asn
                260                 265                 270

Glu Arg His Ser Pro Gln Thr Glu Pro Met Ile Thr Ser Ile Gly Asn
            275                 280                 285

Pro Ala Gln Val Leu Lys Val Lys Glu Thr Phe Gly Thr Trp Leu Arg
        290                 295                 300

Glu Ser Ala Asn Arg Ser Asp Asp Arg Ile Trp Val Thr Glu His Phe
305                 310                 315                 320

Ser Gly Ile Met Val Lys Glu Phe Glu Asp Leu Pro Ala Leu Leu Asn
                325                 330                 335

Ser Ser Phe Thr Leu Leu His Leu Pro His Tyr Phe His Gly Cys Gly
            340                 345                 350

His Ala Val Tyr Asn Asn Ser Leu Tyr Tyr His Lys Gly Gly Ser Asn
        355                 360                 365

Thr Ile Val Arg Phe Glu Phe Gly Lys Glu Thr Pro Gln Thr Leu Lys
    370                 375                 380

Leu Glu Asp Ala Leu Tyr Phe Asp Arg Lys Tyr Leu Phe Ala Asn Ser
385                 390                 395                 400

Lys Thr Tyr Phe Asn Ile Ala Val Asp Glu Lys Gly Leu Trp Ile Ile
                405                 410                 415

Tyr Ala Ser Ser Val Asp Gly Ser Ser Ile Leu Val Ala Gln Leu Asp
            420                 425                 430

Glu Arg Thr Phe Ser Val Leu Gln His Ile Asn Thr Thr Tyr Pro Lys
        435                 440                 445

Ser Lys Ala Gly Asn Ala Phe Ile Ala Gln Gly Ile Leu Tyr Val Thr
    450                 455                 460

Asp Thr Lys Asp Thr Arg Val Thr Phe Ala Phe Asp Leu Leu Arg Gly
465                 470                 475                 480

Lys Gln Ile Asn Ala Asn Phe Gly Leu Arg Met Ser Gln Ser Val Leu
                485                 490                 495

Ala Met Leu Ser Tyr Asn Met Arg Asp Gln His Leu Tyr Ser Trp Glu
            500                 505                 510

Asp Gly His Leu Met Leu Tyr Pro Val His Phe Ser Ser Thr Ala Pro
        515                 520                 525

Ser Gln Arg
    530

<210> SEQ ID NO 5
<211> LENGTH: 2416
<212> TYPE: DNA
<213> ORGANISM: Rattus sp.
<220> FEATURE:
<221> NAME/KEY: CDS
<222> LOCATION: (189)..(1835)

<400> SEQUENCE: 5
gaattcggca cgagggggggc ttctggggcg ccacgattac tgtccccaac ccgcctcgcc      60
agacgggtct aaaggcagct tgactcacga ctctgccacc agcccaccac tcgcgcgagg     120
gtataaaacc tgccactgcg ggaggaggcc cagtgctgcc ctgagtcgtt cggcctgagc     180 acagagac atg acc cga gcc gca gag cga ggc caa ggg gct aca ggc tgg      230
         Met Thr Arg Ala Ala Glu Arg Gly Gln Gly Ala Thr Gly Trp
         1               5                   10 gga ctg cga ggc gcc ctg atg gcc gtg gcg ctg ctg tca gtg ctg aac      278
Gly Leu Arg Gly Ala Leu Met Ala Val Ala Leu Leu Ser Val Leu Asn
 15                  20                  25                  30
```

-continued

| | |
|---|---|
| gcc gtg ggc acc gtg ttc gtg ctg tac cag tgg cgc gag ctg agc gcg<br>Ala Val Gly Thr Val Phe Val Leu Tyr Gln Trp Arg Glu Leu Ser Ala<br>               35                      40                    45 | 326 |
| gcg ctg cgg gca ctg gag gcg caa cac ggc cag gag cag cgc gag gac<br>Ala Leu Arg Ala Leu Glu Ala Gln His Gly Gln Glu Gln Arg Glu Asp<br>     50                      55                      60 | 374 |
| agc gcc cta cgc gcc ttt cta gct gaa tta agt cgt gcg cca gcc cga<br>Ser Ala Leu Arg Ala Phe Leu Ala Glu Leu Ser Arg Ala Pro Ala Arg<br>        65                      70                      75 | 422 |
| gtc ccc gaa cca ccc cag gac ccc atg agt gca gcg cgc aat aag cgc<br>Val Pro Glu Pro Pro Gln Asp Pro Met Ser Ala Ala Arg Asn Lys Arg<br>80                      85                      90 | 470 |
| agc cac ggc ggc gag cct gcg tca cac atc cgc gcg gag agc cag gac<br>Ser His Gly Gly Glu Pro Ala Ser His Ile Arg Ala Glu Ser Gln Asp<br>95                     100                 105               110 | 518 |
| atg atg atg atg atg acc tac agc atg gtg ccg atc cgg gtg atg ata<br>Met Met Met Met Met Thr Tyr Ser Met Val Pro Ile Arg Val Met Ile<br>                  115                 120               125 | 566 |
| gac ctg tgc aac agc acc cag ggc atc tgc ctt aca gga cca ccg ggc<br>Asp Leu Cys Asn Ser Thr Gln Gly Ile Cys Leu Thr Gly Pro Pro Gly<br>          130                 135               140 | 614 |
| cca cca gga cct cca gga gct ggt ggg tta cca ggc cac aat gga tca<br>Pro Pro Gly Pro Pro Gly Ala Gly Gly Leu Pro Gly His Asn Gly Ser<br>             145                 150               155 | 662 |
| gat gga cag cct ggt ctc cag ggc cca aaa gga gaa aaa gga gca gtt<br>Asp Gly Gln Pro Gly Leu Gln Gly Pro Lys Gly Glu Lys Gly Ala Val<br>          160                 165               170 | 710 |
| ggg aag aga gga aaa atg ggg tta ccc gga gcc aca gga aat cca ggg<br>Gly Lys Arg Gly Lys Met Gly Leu Pro Gly Ala Thr Gly Asn Pro Gly<br>175                   180                 185               190 | 758 |
| gaa aag gga gag aag gga gat gct ggt gaa ctg ggc cta cct gga aat<br>Glu Lys Gly Glu Lys Gly Asp Ala Gly Glu Leu Gly Leu Pro Gly Asn<br>                  195                 200               205 | 806 |
| gag gga cca cca gga cag aaa gga gac aaa gga gac aaa gga gat gtg<br>Glu Gly Pro Pro Gly Gln Lys Gly Asp Lys Gly Asp Lys Gly Asp Val<br>             210                 215               220 | 854 |
| tcc aat gac gtg ctt ttg aca ggt gcc aaa ggt gac caa ggg ccc cct<br>Ser Asn Asp Val Leu Leu Thr Gly Ala Lys Gly Asp Gln Gly Pro Pro<br>          225                 230               235 | 902 |
| ggc cca cct gga ccc cca ggg cct cca ggc cct cct gga agc aga aga<br>Gly Pro Pro Gly Pro Pro Gly Pro Pro Gly Pro Pro Gly Ser Arg Arg<br>240                   245                 250 | 950 |
| gcc aaa ggc cct cgg cag cca aat tcg ttc acc aac cag tgt cca ggg<br>Ala Lys Gly Pro Arg Gln Pro Asn Ser Phe Thr Asn Gln Cys Pro Gly<br>255                   260                 265               270 | 998 |
| gag acg tgt gtc ata ccc aat gat gat acc ttg gtg ggg aga gct gat<br>Glu Thr Cys Val Ile Pro Asn Asp Asp Thr Leu Val Gly Arg Ala Asp<br>             275                 280               285 | 1046 |
| gag aaa gtc aat gag cgc cat tct cca caa aca gaa ccc atg atc acg<br>Glu Lys Val Asn Glu Arg His Ser Pro Gln Thr Glu Pro Met Ile Thr<br>          290                 295               300 | 1094 |
| tcc att ggt aac ccg gcc caa gtc ctc aag gtg aaa gag act ttt ggg<br>Ser Ile Gly Asn Pro Ala Gln Val Leu Lys Val Lys Glu Thr Phe Gly<br>                  305                 310               315 | 1142 |
| acc tgg cta aga gag tct gct aac agg agt gac gac cgc att tgg gtg<br>Thr Trp Leu Arg Glu Ser Ala Asn Arg Ser Asp Asp Arg Ile Trp Val<br>          320                 325               330 | 1190 |
| act gaa cat ttt tca ggc atc atg gtg aag gag ttt gaa gac ctg ccc<br>Thr Glu His Phe Ser Gly Ile Met Val Lys Glu Phe Glu Asp Leu Pro<br>335                   340                 345               350 | 1238 |

```
gcc ctc ctg aat agc agc ttc acc ctc ctc cac ctc cca cat tac ttc    1286
Ala Leu Leu Asn Ser Ser Phe Thr Leu Leu His Leu Pro His Tyr Phe
            355                 360                 365 cat ggc tgc ggg cac gct gtt tac aac aac tct ctc tac tac cac aaa    1334
His Gly Cys Gly His Ala Val Tyr Asn Asn Ser Leu Tyr Tyr His Lys
            370                 375                 380 gga ggc tcc aac acc ata gtg aga ttt gaa ttt ggg aaa gag aca cct    1382
Gly Gly Ser Asn Thr Ile Val Arg Phe Glu Phe Gly Lys Glu Thr Pro
            385                 390                 395 caa act ctg aag ctt gaa gat gct ttg tat ttt gat cga aaa tac ctc    1430
Gln Thr Leu Lys Leu Glu Asp Ala Leu Tyr Phe Asp Arg Lys Tyr Leu
400                 405                 410 ttt gcg aat tcc aag act tac ttc aac ata gca gtg gat gag aag ggc    1478
Phe Ala Asn Ser Lys Thr Tyr Phe Asn Ile Ala Val Asp Glu Lys Gly
415                 420                 425                 430 ctc tgg att atc tac gcc tcg agt gtg gat ggc tca agc atc ctt gtg    1526
Leu Trp Ile Ile Tyr Ala Ser Ser Val Asp Gly Ser Ser Ile Leu Val
                435                 440                 445 gca cag ctg gac gag agg aca ttc tct gtg ctg cgg cac atc aat acc    1574
Ala Gln Leu Asp Glu Arg Thr Phe Ser Val Leu Arg His Ile Asn Thr
            450                 455                 460 aca tac ccc aag tcc aag gct ggc aat gcc ttc ata gct caa ggg atc    1622
Thr Tyr Pro Lys Ser Lys Ala Gly Asn Ala Phe Ile Ala Gln Gly Ile
            465                 470                 475 ctc tat gtc acg gac acc aaa gat aca agg gtc acg ttt gcc ttt gat    1670
Leu Tyr Val Thr Asp Thr Lys Asp Thr Arg Val Thr Phe Ala Phe Asp
480                 485                 490 ttg tta cga ggg aag cag atc aat gca aac ttc ggt ctc aga atg tca    1718
Leu Leu Arg Gly Lys Gln Ile Asn Ala Asn Phe Gly Leu Arg Met Ser
495                 500                 505                 510 cag tct gtt ctt gcc atg ttg tcg tac aat atg aga gac cag cat ttg    1766
Gln Ser Val Leu Ala Met Leu Ser Tyr Asn Met Arg Asp Gln His Leu
                515                 520                 525 tac tcg tgg gaa gac ggc cac ctg atg ctc tat cct gtg cac ttt tcg    1814
Tyr Ser Trp Glu Asp Gly His Leu Met Leu Tyr Pro Val His Phe Ser
            530                 535                 540 tca aca gca ccc agc cag cga taggcctgca gtcggctccc tcattatgca       1865
Ser Thr Ala Pro Ser Gln Arg
            545 ccacacattt tctggggttt gaccaagccc aacggaaaga aggcctgtaa aggatatcca  1925 gatactcaga gcatacgccc gtgctacggg ctcttgtgca tgtggcaagt ccccctgtaa  1985 gccaggttag ctagaggctg aagttgaaa tggataacat ctggtgaccc ttggtccctc   2045 ttcaaactta gcaagttagt gctccccct gaccttagtg tccccatcag taatatgaaa   2105 catctgtgtg attgacagca tttcctctac ctatatgaag ttctgtgatt cttgcctggt  2165 tatatattag attgctttct ggtttctttt ttttttctcc acatgtaaat gagtttacct  2225 gcagcttgag gggtgtgcct atcagtgatg acggacattt gtttggtgtt tagggaagat  2285 gcattgtctc ttatggcttc taaagtatta tattatccat aatttgatat ttttctctga  2345 atacgcacct gccactacag aatgattatt gtttcagctc ctaagtacaa atccaaaaaa  2405 aaaaaaaaaa a                                                      2416

<210> SEQ ID NO 6
<211> LENGTH: 549
<212> TYPE: PRT
<213> ORGANISM: Rattus sp.
```

<400> SEQUENCE: 6

```
Met Thr Arg Ala Ala Glu Arg Gly Gln Gly Ala Thr Gly Trp Gly Leu
 1               5                  10                  15

Arg Gly Ala Leu Met Ala Val Ala Leu Leu Ser Val Leu Asn Ala Val
            20                  25                  30

Gly Thr Val Phe Val Leu Tyr Gln Trp Arg Glu Leu Ser Ala Ala Leu
        35                  40                  45

Arg Ala Leu Glu Ala Gln His Gly Gln Glu Gln Arg Glu Asp Ser Ala
    50                  55                  60

Leu Arg Ala Phe Leu Ala Glu Leu Ser Arg Ala Pro Ala Arg Val Pro
65                  70                  75                  80

Glu Pro Pro Gln Asp Pro Met Ser Ala Ala Arg Asn Lys Arg Ser His
                85                  90                  95

Gly Gly Glu Pro Ala Ser His Ile Arg Ala Glu Ser Gln Asp Met Met
            100                 105                 110

Met Met Met Thr Tyr Ser Met Val Pro Ile Arg Val Met Ile Asp Leu
        115                 120                 125

Cys Asn Ser Thr Gln Gly Ile Cys Leu Thr Gly Pro Pro Gly Pro Pro
    130                 135                 140

Gly Pro Pro Gly Ala Gly Gly Leu Pro Gly His Asn Gly Ser Asp Gly
145                 150                 155                 160

Gln Pro Gly Leu Gln Gly Pro Lys Gly Glu Lys Gly Ala Val Gly Lys
                165                 170                 175

Arg Gly Lys Met Gly Leu Pro Gly Ala Thr Gly Asn Pro Gly Glu Lys
            180                 185                 190

Gly Glu Lys Gly Asp Ala Gly Glu Leu Gly Leu Pro Gly Asn Glu Gly
        195                 200                 205

Pro Pro Gly Gln Lys Gly Asp Lys Gly Asp Lys Gly Asp Val Ser Asn
    210                 215                 220

Asp Val Leu Leu Thr Gly Ala Lys Gly Asp Gln Gly Pro Pro Gly Pro
225                 230                 235                 240

Pro Gly Pro Pro Gly Pro Gly Pro Pro Gly Ser Arg Arg Ala Lys
                245                 250                 255

Gly Pro Arg Gln Pro Asn Ser Phe Thr Asn Gln Cys Pro Gly Glu Thr
            260                 265                 270

Cys Val Ile Pro Asn Asp Asp Thr Leu Val Gly Arg Ala Asp Glu Lys
        275                 280                 285

Val Asn Glu Arg His Ser Pro Gln Thr Glu Pro Met Ile Thr Ser Ile
    290                 295                 300

Gly Asn Pro Ala Gln Val Leu Lys Val Lys Glu Thr Phe Gly Thr Trp
305                 310                 315                 320

Leu Arg Glu Ser Ala Asn Arg Ser Asp Asp Arg Ile Trp Val Thr Glu
                325                 330                 335

His Phe Ser Gly Ile Met Val Lys Glu Phe Glu Asp Leu Pro Ala Leu
            340                 345                 350

Leu Asn Ser Ser Phe Thr Leu Leu His Leu Pro His Tyr Phe His Gly
        355                 360                 365

Cys Gly His Ala Val Tyr Asn Asn Ser Leu Tyr Tyr His Lys Gly Gly
    370                 375                 380

Ser Asn Thr Ile Val Arg Phe Glu Phe Gly Lys Glu Thr Pro Gln Thr
385                 390                 395                 400

Leu Lys Leu Glu Asp Ala Leu Tyr Phe Asp Arg Lys Tyr Leu Phe Ala
                405                 410                 415
```

```
Asn Ser Lys Thr Tyr Phe Asn Ile Ala Val Asp Glu Lys Gly Leu Trp
        420                 425                 430

Ile Ile Tyr Ala Ser Ser Val Asp Gly Ser Ser Ile Leu Val Ala Gln
        435                 440                 445

Leu Asp Glu Arg Thr Phe Ser Val Leu Arg His Ile Asn Thr Thr Tyr
        450                 455                 460

Pro Lys Ser Lys Ala Gly Asn Ala Phe Ile Ala Gln Gly Ile Leu Tyr
465                 470                 475                 480

Val Thr Asp Thr Lys Asp Thr Arg Val Thr Phe Ala Phe Asp Leu Leu
                485                 490                 495

Arg Gly Lys Gln Ile Asn Ala Asn Phe Gly Leu Arg Met Ser Gln Ser
            500                 505                 510

Val Leu Ala Met Leu Ser Tyr Asn Met Arg Asp Gln His Leu Tyr Ser
        515                 520                 525

Trp Glu Asp Gly His Leu Met Leu Tyr Pro Val His Phe Ser Ser Thr
530                 535                 540

Ala Pro Ser Gln Arg
545

<210> SEQ ID NO 7
<211> LENGTH: 4649
<212> TYPE: DNA
<213> ORGANISM: Mus sp.
<220> FEATURE:
<221> NAME/KEY: CDS
<222> LOCATION: (40)..(1686)

<400> SEQUENCE: 7
tcagtgctgc cctgagccgc ccggcctgag cacgcagac atg acc cga gcc gca      54
                                            Met Thr Arg Ala Ala
                                              1               5 gag cga ggc caa ggg gct aca ggc tgg ggg ctg cgc ggc gcc ctg gtg    102
Glu Arg Gly Gln Gly Ala Thr Gly Trp Gly Leu Arg Gly Ala Leu Val
                10                  15                  20 gcc ata gcg ctg ctg tcc gca ctg aac gcc gcg ggc acc gtg ttc gtg    150
Ala Ile Ala Leu Leu Ser Ala Leu Asn Ala Ala Gly Thr Val Phe Val
            25                  30                  35 ctg tgc cag tgg cgg ggg tta agc gcg gcg cta cgg gcg ctg gag gct    198
Leu Cys Gln Trp Arg Gly Leu Ser Ala Ala Leu Arg Ala Leu Glu Ala
        40                  45                  50 caa cgc ggc cga gag cag cgc gag gac agc gcc cta cgc gcc ttt ctg    246
Gln Arg Gly Arg Glu Gln Arg Glu Asp Ser Ala Leu Arg Ala Phe Leu
    55                  60                  65 gcc gaa ttg agt cgt gcg ccg ggc cgg gtc ccc gaa cca tcc cag gac    294
Ala Glu Leu Ser Arg Ala Pro Gly Arg Val Pro Glu Pro Ser Gln Asp
70                  75                  80                  85 ccc atg agc gca gcg cgc aac aag cgc agc cac aac ggc gag cct gcg    342
Pro Met Ser Ala Ala Arg Asn Lys Arg Ser His Asn Gly Glu Pro Ala
                90                  95                 100 tca cac atc cgt gcg gag agc cag gac atg atg atg atg acc tac        390
Ser His Ile Arg Ala Glu Ser Gln Asp Met Met Met Met Thr Tyr
            105                 110                 115 tcc atg gtg ccg att cga gtg atg ata gac ctg tgc aac agt acc cag    438
Ser Met Val Pro Ile Arg Val Met Ile Asp Leu Cys Asn Ser Thr Gln
        120                 125                 130 ggc atc tgc ctc aca gga cca ccg ggc cca cca gga cct cca gga gcc    486
Gly Ile Cys Leu Thr Gly Pro Pro Gly Pro Pro Gly Pro Pro Gly Ala
    135                 140                 145
```

```
                                                          -continued ggc ggg tta cca ggc cac aat gga tca gat gga cag cct ggt ctc cag      534
Gly Gly Leu Pro Gly His Asn Gly Ser Asp Gly Gln Pro Gly Leu Gln
150             155                 160                 165 ggc cca aaa gga gaa aaa gga gca att ggc aag aga gga aaa atg ggg      582
Gly Pro Lys Gly Glu Lys Gly Ala Ile Gly Lys Arg Gly Lys Met Gly
            170                 175                 180 tta cct gga gcc acc gga aat cca ggg gaa aag gga gaa aag gga gat      630
Leu Pro Gly Ala Thr Gly Asn Pro Gly Glu Lys Gly Glu Lys Gly Asp
                185                 190                 195 gct ggt gaa ctg ggt cta cct gga aat gag ggc cca cca ggg cag aaa      678
Ala Gly Glu Leu Gly Leu Pro Gly Asn Glu Gly Pro Pro Gly Gln Lys
200                 205                 210 ggt gac aag gga gac aaa gga gac gtg tcc aat gac gtg ctt ttg aca      726
Gly Asp Lys Gly Asp Lys Gly Asp Val Ser Asn Asp Val Leu Leu Thr
        215                 220                 225 ggt gcc aaa ggt gac caa ggt ccc cct ggc ccc cct gga cct cca ggg      774
Gly Ala Lys Gly Asp Gln Gly Pro Pro Gly Pro Pro Gly Pro Pro Gly
230                 235                 240                 245 cct cca ggc cct cct gga agc aga aga tcc aaa ggc cct cgg cca cca      822
Pro Pro Gly Pro Pro Gly Ser Arg Arg Ser Lys Gly Pro Arg Pro Pro
                250                 255                 260 aac gtg ttc aac agc cag tgt cca ggg gag acg tgt gtc ata ccc aat      870
Asn Val Phe Asn Ser Gln Cys Pro Gly Glu Thr Cys Val Ile Pro Asn
            265                 270                 275 gat gat acc ttg gtg gga aga gct gat gag aaa gca aat gaa cgc cat      918
Asp Asp Thr Leu Val Gly Arg Ala Asp Glu Lys Ala Asn Glu Arg His
                280                 285                 290 tca cca caa aca gaa tct atg atc act tcc att ggc aac cca gcc caa      966
Ser Pro Gln Thr Glu Ser Met Ile Thr Ser Ile Gly Asn Pro Ala Gln
295                 300                 305 gtc cta aaa gtg aga gag act ttt ggg act tgg atg aga gag tct gct     1014
Val Leu Lys Val Arg Glu Thr Phe Gly Thr Trp Met Arg Glu Ser Ala
310                 315                 320                 325 aac aaa agt gac gac cgc att tgg gtg act gaa cat ttt tca ggc atc     1062
Asn Lys Ser Asp Asp Arg Ile Trp Val Thr Glu His Phe Ser Gly Ile
                330                 335                 340 atg gtg aag gag ttc aaa gac ctg ccg gcg ctc ctc aat agc agc ttc     1110
Met Val Lys Glu Phe Lys Asp Leu Pro Ala Leu Leu Asn Ser Ser Phe
            345                 350                 355 aca ctc ctc cac ctc cca cat tat ttc cac ggc tgt ggg cac gct gtt     1158
Thr Leu Leu His Leu Pro His Tyr Phe His Gly Cys Gly His Ala Val
                360                 365                 370 tac aac aac tct ctc tac tac cac aaa gga ggc tcc aac acc ata gtg     1206
Tyr Asn Asn Ser Leu Tyr Tyr His Lys Gly Gly Ser Asn Thr Ile Val
375                 380                 385 aga ttt gaa ttt ggg aaa gag aca cct cag act ctg aag ctg gaa aat     1254
Arg Phe Glu Phe Gly Lys Glu Thr Pro Gln Thr Leu Lys Leu Glu Asn
390                 395                 400                 405 gct ttg tat ttt gat cga aaa tac ctc ttt gca aat tcc aag act tac     1302
Ala Leu Tyr Phe Asp Arg Lys Tyr Leu Phe Ala Asn Ser Lys Thr Tyr
                410                 415                 420 ttc aac ata gca gtg gat gag aag ggc atc tgg att atc tac gct tca     1350
Phe Asn Ile Ala Val Asp Glu Lys Gly Ile Trp Ile Ile Tyr Ala Ser
                425                 430                 435 agt gtg gat ggc tca agc atc ctt gta gca cag ctg gat gag agg aca     1398
Ser Val Asp Gly Ser Ser Ile Leu Val Ala Gln Leu Asp Glu Arg Thr
                440                 445                 450 ttc tcc gtg aca cag cac atc aac acc aca tac ccc aaa tcc aag gct     1446
Phe Ser Val Thr Gln His Ile Asn Thr Thr Tyr Pro Lys Ser Lys Ala
455                 460                 465
```

```
                                                                -continued ggc aat gcc ttc ata gcc cga ggg atc ctc tat gtc aca gac acc aaa      1494
Gly Asn Ala Phe Ile Ala Arg Gly Ile Leu Tyr Val Thr Asp Thr Lys
470                 475                 480                 485 gat acg agg gtc acg ttt gcc ttt gat ttg tta gga gga aag caa atc      1542
Asp Thr Arg Val Thr Phe Ala Phe Asp Leu Leu Gly Gly Lys Gln Ile
                490                 495                 500 aat gca aac ttt gat ttc aga atg tcc cag tct gtt ctt gcc atg ctg      1590
Asn Ala Asn Phe Asp Phe Arg Met Ser Gln Ser Val Leu Ala Met Leu
            505                 510                 515 tca tac aac atg aga gat cag cat tta tac tcg tgg gaa gat ggc cat      1638
Ser Tyr Asn Met Arg Asp Gln His Leu Tyr Ser Trp Glu Asp Gly His
        520                 525                 530 ctg atg ctc tat cct gtg cag ttt ctg tca gcg gca tca agt cag cgg      1686
Leu Met Leu Tyr Pro Val Gln Phe Leu Ser Ala Ala Ser Ser Gln Arg
    535                 540                 545 tagggttccc tcggctgtct gctccctctc tatactccac attgtctagg gtttggtcaa    1746
gcccaacaga aagctagccg gtaaaggata cccaggcact cggagcgtaa gcccatgcca    1806
cgggctcttg cacaagcggc gagtccgctc taagccaggt tgttgaaata gctacagatt    1866
agaaatggat gtggaagaga tctggtgacc cagtatccct cctcaaactc agcaagttag    1926
ctctcccccg accgtagcgt ccccataggt aatacgaaac atctgggtat gactgacatt    1986
tcctcttcct agatgaaatt ctgtgattct tgcctgatta tatattagaa tgctttctgg    2046
attctttttt ttttttctcc acatgtaagt gagcttactt gcagcttgag gggtgggcct    2106
ttcagtgatg acttatttgg tatttaggga aggtgcactg gctcttatgg cttctaaggt    2166
tttattttat tcataatttg ttattttctc tgaatattca cctaccacta cagaatgatc    2226
attgttttca gctcctaaac acaaatccaa gattaataaa caaacaaaca aaccatgaat    2286
agatacaggc tcagaactct aaatggagct gcatcaggcc cataggccat ctagatgctg    2346
tcaatttctg atcatattgt ttgctgctgg gaaagtaaac aggatatctt cagttcgtgg    2406 tccctttttgc caaggccatg ggattgttat cagagtgtca acactaagt ggccaataat    2466 ctggttagaa gcatgaaaac atgatggttt tttcagaaaa caggcaccat ttatacttac    2526
tgtttagaat gagggaaggc aattggctca aaggccaaag tcagcttagc tcttttttcct   2586 gtaccatcgc atccctgcac ctaagaatct cgcctcagag tgtgtcagca gtgaagcaga    2646
gccgctctgt aaatcctgaa ccattactgc ctggccttta cagaaagaaa gaaaaaaaaa    2706
tgttgacctt tcatctaagg acagggaacg agccaggttc tcagaagggc tcactccctg    2766
agtctggtta ggcttttttac ggactgacag gcagcatttt atgtggcttg gctttggca    2826 gagggaacag gtaaggacag catcagatgg agtaagagaa cctccagccg tggagatgtt    2886
cactcccacg tggtcctcaa agttgggtct gtcctcttgg atagcaagga tctagtttaa    2946
ttggttccta caagacctta ataaccacg ttctctgtca actcattgag ttccaggcag     3006
gcctgtggag cttcaaagag gaagctgtgg atttcatcgc ccccccccc ccggaatata     3066 gaaaaagaca ctacagaaac tgtccaggaa agactggcca gctgttccaa acccactctc    3126
agtgggcctg tgacctggtt tagtttttttt aatagaagca tcttgaggct tggggtatgc   3186
attttaacta tttaactttc cctgccctct gaaagcaccc aggcagctgt tactggtgaa    3246
cctgttgagt tctcaaggtc atgggtccca agcttcccc acttcttgat tagatggttt     3306
tgcagttggt catcacagct tttaaagata ttctctcaga ttcatttgtt gcaatgtaga    3366
gttctaatgt ttcatcagtg tatctaatga atggtattgt tcttttaaag tattcaaata    3426
```

```
tgagatactg tttctgagtg cggtagacct ggatatacat ataattccat tttttatta    3486 cttagtagca ttgctgagaa tagatacaat actaattgta catacaagca aaatagttta    3546
gttattgaat tagctcattt ttaatatctg aactagcaaa tgtcttagct ttcctttact    3606
tttttctttc ttttcctttc ttttctcttc ttttcctttc tttcctttcc ttttcttttc    3666
ttttttttaa agcaatgtct ttgtgttcgc ccagacttat cacaaactcc tgcttcagat    3726
tcctgggtgc tgggaccaca ggcacagtgg ctctttgact ctcttaattg tgtgtaagga    3786
atcatacata tactcacgat tagagaaact cgtctgaaga ttttgtttct tttcatggtt    3846
gtttctttct ttctttcttt ctttctttct ttcgttatag tgtagtggga ttagaacaag    3906
taaggttgac tggtgtttaa tgaatttatc tttgcagaag gaaaggaatt aaggttttat    3966 tcctttctt gcaaacagga cttcattcta tatcactcaa cacagtgttt caggctcact    4026
gctaaaatag tgtgcacatc ttatattttt aaatgaagat agtaatcaac cctgctgtca    4086
cttgtagcca agctgttcta aaagcacttc atttatgtct gtatgaaatc aagtgattct    4146
ccaattcctc tgaaatctaa agtagatacc attatactag aaaccacacc ttccagcttc    4206
aaaggtaggc cagactcaac atttacaaag catttctatt aactaatata gagtccaact    4266
aaggttgcag agttggctct ggcctcaatg tatcatgtat caatgtatca gagaacgtgg    4326
tccgggctga atatttcaga tcaattctgg tgctgggctc attcgaagtc tttttaccct    4386
cataatcaaa tgacaaggtg agatgacaaa tgaggaagca cagtccttga aaagtcactc    4446
gtcatcctcc aagcatagca agtaccttac tcaggcattg cctgtctggt gttgagctac    4506
ctgaaggaaa agtgggggt ggagctcttc agttttcatc agtgctgtgg ccttatttat    4566
ctcataatct cccatcagta accacagatt ctaaacgacc agcaagtaac agttgtaagt    4626
agtaaaataa aattatcctg aat                                           4649

<210> SEQ ID NO 8
<211> LENGTH: 549
<212> TYPE: PRT
<213> ORGANISM: Mus sp.

<400> SEQUENCE: 8

Met Thr Arg Ala Ala Glu Arg Gly Gln Gly Ala Thr Gly Trp Gly Leu
 1               5                  10                  15

Arg Gly Ala Leu Val Ala Ile Ala Leu Leu Ser Ala Leu Asn Ala Ala
            20                  25                  30

Gly Thr Val Phe Val Leu Cys Gln Trp Arg Gly Leu Ser Ala Ala Leu
        35                  40                  45

Arg Ala Leu Glu Ala Gln Arg Gly Arg Glu Gln Arg Glu Asp Ser Ala
    50                  55                  60

Leu Arg Ala Phe Leu Ala Glu Leu Ser Arg Ala Pro Gly Arg Val Pro
65                  70                  75                  80

Glu Pro Ser Gln Asp Pro Met Ser Ala Ala Arg Asn Lys Arg Ser His
                85                  90                  95

Asn Gly Glu Pro Ala Ser His Ile Arg Ala Glu Ser Gln Asp Met Met
            100                 105                 110

Met Met Met Thr Tyr Ser Met Val Pro Ile Arg Val Met Ile Asp Leu
        115                 120                 125

Cys Asn Ser Thr Gln Gly Ile Cys Leu Thr Gly Pro Pro Gly Pro Pro
    130                 135                 140

Gly Pro Pro Gly Ala Gly Gly Leu Pro Gly His Asn Gly Ser Asp Gly
145                 150                 155                 160
```

```
Gln Pro Gly Leu Gln Gly Pro Lys Gly Glu Lys Gly Ala Ile Gly Lys
                165                 170                 175

Arg Gly Lys Met Gly Leu Pro Gly Ala Thr Gly Asn Pro Gly Glu Lys
            180                 185                 190

Gly Glu Lys Gly Asp Ala Gly Glu Leu Gly Leu Pro Gly Asn Glu Gly
        195                 200                 205

Pro Pro Gly Gln Lys Gly Asp Lys Gly Asp Lys Gly Asp Val Ser Asn
    210                 215                 220

Asp Val Leu Leu Thr Gly Ala Lys Gly Asp Gln Gly Pro Pro Gly Pro
225                 230                 235                 240

Pro Gly Pro Pro Gly Pro Pro Gly Pro Pro Gly Ser Arg Arg Ser Lys
                245                 250                 255

Gly Pro Arg Pro Pro Asn Val Phe Asn Ser Gln Cys Pro Gly Glu Thr
            260                 265                 270

Cys Val Ile Pro Asn Asp Asp Thr Leu Val Gly Arg Ala Asp Glu Lys
        275                 280                 285

Ala Asn Glu Arg His Ser Pro Gln Thr Glu Ser Met Ile Thr Ser Ile
    290                 295                 300

Gly Asn Pro Ala Gln Val Leu Lys Val Arg Glu Thr Phe Gly Thr Trp
305                 310                 315                 320

Met Arg Glu Ser Ala Asn Lys Ser Asp Asp Arg Ile Trp Val Thr Glu
                325                 330                 335

His Phe Ser Gly Ile Met Val Lys Glu Phe Lys Asp Leu Pro Ala Leu
            340                 345                 350

Leu Asn Ser Ser Phe Thr Leu Leu His Leu Pro His Tyr Phe His Gly
        355                 360                 365

Cys Gly His Ala Val Tyr Asn Asn Ser Leu Tyr Tyr His Lys Gly Gly
    370                 375                 380

Ser Asn Thr Ile Val Arg Phe Glu Phe Gly Lys Glu Thr Pro Gln Thr
385                 390                 395                 400

Leu Lys Leu Glu Asn Ala Leu Tyr Phe Asp Arg Lys Tyr Leu Phe Ala
                405                 410                 415

Asn Ser Lys Thr Tyr Phe Asn Ile Ala Val Asp Glu Lys Gly Ile Trp
            420                 425                 430

Ile Ile Tyr Ala Ser Ser Val Asp Gly Ser Ser Ile Leu Val Ala Gln
        435                 440                 445

Leu Asp Glu Arg Thr Phe Ser Val Thr Gln His Ile Asn Thr Thr Tyr
    450                 455                 460

Pro Lys Ser Lys Ala Gly Asn Ala Phe Ile Ala Arg Gly Ile Leu Tyr
465                 470                 475                 480

Val Thr Asp Thr Lys Asp Thr Arg Val Thr Phe Ala Phe Asp Leu Leu
                485                 490                 495

Gly Gly Lys Gln Ile Asn Ala Asn Phe Asp Phe Arg Met Ser Gln Ser
            500                 505                 510

Val Leu Ala Met Leu Ser Tyr Asn Met Arg Asp Gln His Leu Tyr Ser
        515                 520                 525

Trp Glu Asp Gly His Leu Met Leu Tyr Pro Val Gln Phe Leu Ser Ala
    530                 535                 540

Ala Ser Ser Gln Arg
545

<210> SEQ ID NO 9
<211> LENGTH: 4654
```

```
<212> TYPE: DNA
<213> ORGANISM: Homo sapiens
<220> FEATURE:
<221> NAME/KEY: CDS
<222> LOCATION: (51)..(1331)

<400> SEQUENCE: 9
gaccattgtg tatgattcgt tgttgactgc agcatcacta gatccgagtg atg gtg        56
                                                       Met Val
                                                         1 gac ctg tgc aac agc acc aag ggc atc tgc ctc aca gga cct tct gga      104
Asp Leu Cys Asn Ser Thr Lys Gly Ile Cys Leu Thr Gly Pro Ser Gly
          5                  10                  15 cca cca gga cct ccg gga gcc ggc ggg ttg cca gga cac aac gga ttg      152
Pro Pro Gly Pro Pro Gly Ala Gly Gly Leu Pro Gly His Asn Gly Leu
     20                  25                  30 gat gga cag cct ggt cct cag ggc cca aaa gga gaa aaa gga gca aat      200
Asp Gly Gln Pro Gly Pro Gln Gly Pro Lys Gly Glu Lys Gly Ala Asn
 35                  40                  45                  50 gga aaa aga gga aaa atg ggg ata cct gga gct gca gga aat cca ggg      248
Gly Lys Arg Gly Lys Met Gly Ile Pro Gly Ala Ala Gly Asn Pro Gly
                 55                  60                  65 gaa agg gga gaa aag gga gac cat ggt gaa ctg ggc ctg cag gga aat      296
Glu Arg Gly Glu Lys Gly Asp His Gly Glu Leu Gly Leu Gln Gly Asn
             70                  75                  80 gag ggc cca cca ggg cag aag gga gaa aag ggt gac aaa gga gat gtg      344
Glu Gly Pro Pro Gly Gln Lys Gly Glu Lys Gly Asp Lys Gly Asp Val
         85                  90                  95 tcc aac gac gtg ctc ctg gca ggt gcc aaa ggt gac caa ggc cca ccc      392
Ser Asn Asp Val Leu Leu Ala Gly Ala Lys Gly Asp Gln Gly Pro Pro
    100                 105                 110 ggt cca cct ggg ccc cca ggc cct cca ggt cct cca ggg ccc cct gga      440
Gly Pro Pro Gly Pro Pro Gly Pro Pro Gly Pro Pro Gly Pro Pro Gly
115                 120                 125                 130 agc aga aga gcc aaa ggc cct cgg cag cca agc atg ttc aac ggc cag      488
Ser Arg Arg Ala Lys Gly Pro Arg Gln Pro Ser Met Phe Asn Gly Gln
                135                 140                 145 tgc cca ggt gag act tgt gcc ata cca aat gat gat acc ttg gtt gga      536
Cys Pro Gly Glu Thr Cys Ala Ile Pro Asn Asp Asp Thr Leu Val Gly
            150                 155                 160 aaa gct gat gag aaa gcc agt gaa cac cat tcc cca caa gca gaa tcc      584
Lys Ala Asp Glu Lys Ala Ser Glu His His Ser Pro Gln Ala Glu Ser
        165                 170                 175 atg atc act tcc att gga aac cca gtg caa gta ctg aaa gtg aca gag      632
Met Ile Thr Ser Ile Gly Asn Pro Val Gln Val Leu Lys Val Thr Glu
    180                 185                 190 aca ttt ggg act tgg ata aga gag tct gct aac aag agt gat gac cgg      680
Thr Phe Gly Thr Trp Ile Arg Glu Ser Ala Asn Lys Ser Asp Asp Arg
195                 200                 205                 210 att tgg gtg aca gag cat ttt tca ggc atc atg gtt aag gaa ttc aag      728
Ile Trp Val Thr Glu His Phe Ser Gly Ile Met Val Lys Glu Phe Lys
                215                 220                 225 gat cag ccc tca ctt ctg aat ggc agt tac acg ttc atc cac ctt cca      776
Asp Gln Pro Ser Leu Leu Asn Gly Ser Tyr Thr Phe Ile His Leu Pro
            230                 235                 240 tac tat ttc cat ggc tgt ggg cac gtt gct tac aac aac tct ctc tac      824
Tyr Tyr Phe His Gly Cys Gly His Val Ala Tyr Asn Asn Ser Leu Tyr
        245                 250                 255 tac cac aaa ggg ggt tct aat acc cta gtg aga ttt gaa ttt ggc cag      872
Tyr His Lys Gly Gly Ser Asn Thr Leu Val Arg Phe Glu Phe Gly Gln
    260                 265                 270
```

-continued

| | | |
|---|---|---|
| gaa aca tcc caa act ctg aag ctt gaa aat gcc ttg tat ttt gat cga<br>Glu Thr Ser Gln Thr Leu Lys Leu Glu Asn Ala Leu Tyr Phe Asp Arg<br>275                    280                    285                    290 | 920 |

```
gaa aca tcc caa act ctg aag ctt gaa aat gcc ttg tat ttt gat cga       920
Glu Thr Ser Gln Thr Leu Lys Leu Glu Asn Ala Leu Tyr Phe Asp Arg
275                 280                 285                 290 aaa tac ctt ttt gca aat tcc aaa act tac ttc aat cta gct gta gat       968
Lys Tyr Leu Phe Ala Asn Ser Lys Thr Tyr Phe Asn Leu Ala Val Asp
                295                 300                 305 gaa aag ggc ctt tgg att atc tat gcg tca agt gtg gac ggc tcg agc      1016
Glu Lys Gly Leu Trp Ile Ile Tyr Ala Ser Ser Val Asp Gly Ser Ser
            310                 315                 320 att ctt gta gca caa ctg gat gag agg aca ttc tca gtg gtg caa cac      1064
Ile Leu Val Ala Gln Leu Asp Glu Arg Thr Phe Ser Val Val Gln His
        325                 330                 335 gtc aat acc acg tac cct aaa tcc aag gct ggc aac gcc ttc att gcc      1112
Val Asn Thr Thr Tyr Pro Lys Ser Lys Ala Gly Asn Ala Phe Ile Ala
    340                 345                 350 cga gga atc ctc tat gtc aca gac acc aaa gat atg agg gtc aca ttt      1160
Arg Gly Ile Leu Tyr Val Thr Asp Thr Lys Asp Met Arg Val Thr Phe
355                 360                 365                 370 gcc ttt gat ttg tta gga ggg aaa cag atc aat gca aac ttt gat tta      1208
Ala Phe Asp Leu Leu Gly Gly Lys Gln Ile Asn Ala Asn Phe Asp Leu
                375                 380                 385 aga act tcc cag tct gtt ctt gcc atg tta gca tac aac atg aga gat      1256
Arg Thr Ser Gln Ser Val Leu Ala Met Leu Ala Tyr Asn Met Arg Asp
            390                 395                 400 cag cat tta tat tca tgg gaa gat ggc cat tta atg ctt tat cct gtg      1304
Gln His Leu Tyr Ser Trp Glu Asp Gly His Leu Met Leu Tyr Pro Val
        405                 410                 415 cag ttt ttg tca act acc tta aat cag tgatgtgctg cattcggctc            1351
Gln Phe Leu Ser Thr Thr Leu Asn Gln
    420                 425 ccttcagcaa atttcagggg ttttctggga ccagttctcc cccaacagga aacttgtttt    1411
tttaacgtca gccagatatt tagaaaataa cctcaaaagt gtttatatgg tcagtgagcc    1471
ccgcttagtg aaatagcaac agattggaag ttgaaatggc tgagatttgg tgatctcccc    1531
acagctggct ctgcaagtta cctctttctc cttgggcctt agtttcccca ttggtaatct    1591
gaattggcta agatgattgg ggagattttc tgtacctgta ggtaatttgg tgattcttgg    1651
tggctgctct tctcacaact tttatgtatc tgcttctgtc gtttagcttt tttagccaca    1711
tgctgaccaa atttaccttt gagttgataa gtccagtggc ttgagtagtg aatccctcag    1771
tgctgactta tatcttgttc tttgaaaaaa tgcattgact cttttaagaca tctaaagtat    1831 cacattatcc ataatttatt gcttttcttt gcatctgcac ctgccaccac agaataacca    1891
ttaccctcag ctgctgattg ggcagctctg agattagcaa aagccaggga cagctacatg    1951
ttcaggtttt tttttttttt ttttttcaata ggctattttt tttctttttct tattttaaat    2011 agagagagag tcttgctatg tttcccaggc tggtcttgaa ctcctggggc tcaagtgatc    2071
ctcctgcctt ggcctcccaa aatgctggat tacaggcatg tgtgcctggc ccaggtttct    2131
taataaaaca gaatcatgat cttccaggtt cccccccagtt tctgatcatg ttgatttgta    2191
gctgtggatc atgaacactg aatccccaga tcactctgac ttcttatgct tctcctgtgg    2251
atccactatc aaagtactaa atgctgtgta agtagacgtt aatctggctg gaaccatggg    2311
aagcactttg cagtgttcag aagagaggct ccatttgtgg ctattatgta gaactgggcc    2371
agagccagtc cattgcctgt tttttttaaat aaggttttac tgagcacagc cacactcatt    2431
tgtttatgca gtacggcctg acattgcttt tgctctgcaa cagcagagtc gagtcattgc    2491
```

```
aacaaagagc atatggcccc acagtgccta aaatattgac cagctacccc tttatggaaa    2551
aagattgctg actcctgata aagaatataa agtgagcctg attcttgaaa aaatcagaac    2611
cagagcctgt tttgttttgt tctaaactaa gaagccgcat aggatgtgac ttgcgttttg    2671
agtagagggg aaggctgata acggcgtaag atgaagtggc cctccacaaa ggctggttag    2731
gggacagttc tttctctaac atagttttaa aggatgtgat ctggtcccct tggatgccag    2791
gagagaatcc agttgaactt gctcctaaat gctcttaaat atgcatattt tctgccaact    2851
cacttcttta aacatctttc agcccagcgc tgcggcccg ggaagggcca ctgcgaatag     2911
agaggaagct ggaaaagttc ctggggctct gcagccagga aggggaacca gggcaaatct    2971
tatgtaaaga ttttcagca acttgtccca atttgtgtgt attctgaaac tttctctttg     3031
ggaccaaatt cattctcaat ggccctgagt tcaatatatt attaacagca gtattttaaa    3091
acttagggtt gaactgggca tggtggcaca taactgcaat cccagctact ttggaggcag    3151
ggatgggagg atcacttgag gccaggatct caggaccagc ctagagagat cccatctcta    3211
aaaaataaaa tataagaaaa taaaacttag gggatataca gatttaaata ttcaaatctc    3271
cctgctcccc tgaaagtccc caggcagctg ttaatgactt gtttgttgtg ttctcaatat    3331
gatggctatt tgaaacttca cctactttc attagattgg ttgtaccatg tcaccttagc     3391
ttttaaaaat actcttttca gattcacgtt ctctaacaaa gagtctcatg ttcaagatca    3451
atatgtctaa taagcgctgg tgtccttta aagtatttaa atatatatgt tgctgttgct     3511
gaatacagga gaccaggtta ggaatatagt ttcataataa tagtacatac aatactaatt    3571
gtatataagg tagcaaccaa aagaggttgt taattagcac atattccttt tagaaaaatg    3631
tttcagaaac ctcagtcttg atatctgagc tatctgggct cccttacttg tgagtaaggg    3691
atcatgctca ccactggaga agcttacacc gggactttt ttctttttc tttttttttt      3751 gctatgacag agtaatgcta acgtaaggac aactgagttt gatcagtgtt taatcgcagt    3811
gggtaatctt atctgattgt ctttaaaagt gaaaaggatt aagattttat tctttcttgt    3871
aaacattact tgattttta aagaagtttt gggctcactg ctaaaataga gtatacaact     3931 gaatgtttt aagtcaagat actgttttag gagtttaccc tctcatttat aaccaaagtt     3991
gctctaaaac actttccaaa tatctgcact tctgatgtca gaatcaaacc agataattct    4051
ctaattcttc tttaatctaa agtagatagc ttcccactgg aaagtaaaca aaaccatccc    4111
tcccaacctc aaagctaggc cacactctat ttcaaggcat tttctttcag ctgataaggt    4171
gtcctcctga agccaagtag gtggttctgg tctccaagta tcgttaagca caggtgctat    4231
gacagaaaaa gttctggggt ggaagtttta agatgaggag ttctgatctt aggcatctta    4291
acagtcacaa ggtgaaaagt caaatgaaac agtacaattc ttgatgagtg aggtgtcatc    4351
ttccaaccac acagaggacg ttttggctat gatcatctga tggcaagtga aggagaaatg    4411
agtgataggg ctttgcgttt tcatccagat gctgtggccc tgtgtttcac agcattaaga    4471
gccataattt ccaacctgca cagatcctga acaacaaatg aataacgatg aatgtctttt    4531
tggttgtaat ttaacaagtc aaataaataa tcattgctga gcacaatcac caaaaaaaaa    4591
aaaaaaaaaa aaaaaaaaaa aaaaaaaaaa aaaaaaaaa aagaaaaaa aaaaaaaaa       4651 aca                                                                  4654

<210> SEQ ID NO 10
<211> LENGTH: 427
<212> TYPE: PRT
<213> ORGANISM: Homo sapiens
```

<400> SEQUENCE: 10

```
Met Val Asp Leu Cys Asn Ser Thr Lys Gly Ile Cys Leu Thr Gly Pro
1               5                   10                  15

Ser Gly Pro Pro Gly Pro Gly Ala Gly Gly Leu Pro Gly His Asn
            20                  25                  30

Gly Leu Asp Gly Gln Pro Gly Pro Gln Gly Pro Lys Gly Glu Lys Gly
                35                  40                  45

Ala Asn Gly Lys Arg Gly Lys Met Gly Ile Pro Gly Ala Ala Gly Asn
    50                  55                  60

Pro Gly Glu Arg Gly Glu Lys Gly Asp His Gly Glu Leu Gly Leu Gln
65                  70                  75                  80

Gly Asn Glu Gly Pro Pro Gly Gln Lys Gly Glu Lys Gly Asp Lys Gly
                85                  90                  95

Asp Val Ser Asn Asp Val Leu Leu Ala Gly Ala Lys Gly Asp Gln Gly
                100                 105                 110

Pro Pro Gly Pro Pro Gly Pro Pro Gly Pro Pro Gly Pro Pro Gly Pro
        115                 120                 125

Pro Gly Ser Arg Arg Ala Lys Gly Pro Arg Gln Pro Ser Met Phe Asn
        130                 135                 140

Gly Gln Cys Pro Gly Glu Thr Cys Ala Ile Pro Asn Asp Asp Thr Leu
145                 150                 155                 160

Val Gly Lys Ala Asp Glu Lys Ala Ser Glu His His Ser Pro Gln Ala
                165                 170                 175

Glu Ser Met Ile Thr Ser Ile Gly Asn Pro Val Gln Val Leu Lys Val
                180                 185                 190

Thr Glu Thr Phe Gly Thr Trp Ile Arg Glu Ser Ala Asn Lys Ser Asp
                195                 200                 205

Asp Arg Ile Trp Val Thr Glu His Phe Ser Gly Ile Met Val Lys Glu
        210                 215                 220

Phe Lys Asp Gln Pro Ser Leu Leu Asn Gly Ser Tyr Thr Phe Ile His
225                 230                 235                 240

Leu Pro Tyr Tyr Phe His Gly Cys Gly His Val Ala Tyr Asn Asn Ser
                245                 250                 255

Leu Tyr Tyr His Lys Gly Gly Ser Asn Thr Leu Val Arg Phe Glu Phe
                260                 265                 270

Gly Gln Glu Thr Ser Gln Thr Leu Lys Leu Glu Asn Ala Leu Tyr Phe
                275                 280                 285

Asp Arg Lys Tyr Leu Phe Ala Asn Ser Lys Thr Tyr Phe Asn Leu Ala
        290                 295                 300

Val Asp Glu Lys Gly Leu Trp Ile Ile Tyr Ala Ser Ser Val Asp Gly
305                 310                 315                 320

Ser Ser Ile Leu Val Ala Gln Leu Asp Glu Arg Thr Phe Ser Val Val
                325                 330                 335

Gln His Val Asn Thr Thr Tyr Pro Lys Ser Lys Ala Gly Asn Ala Phe
                340                 345                 350

Ile Ala Arg Gly Ile Leu Tyr Val Thr Asp Thr Lys Asp Met Arg Val
        355                 360                 365

Thr Phe Ala Phe Asp Leu Leu Gly Gly Lys Gln Ile Asn Ala Asn Phe
    370                 375                 380

Asp Leu Arg Thr Ser Gln Ser Val Leu Ala Met Leu Ala Tyr Asn Met
385                 390                 395                 400

Arg Asp Gln His Leu Tyr Ser Trp Glu Asp Gly His Leu Met Leu Tyr
```

```
                    405                 410                 415
Pro Val Gln Phe Leu Ser Thr Thr Leu Asn Gln
            420                 425

<210> SEQ ID NO 11
<211> LENGTH: 4976
<212> TYPE: DNA
<213> ORGANISM: Homo sapiens
<220> FEATURE:
<221> NAME/KEY: CDS
<222> LOCATION: (1)..(1653)

<400> SEQUENCE: 11 atg gcc cga ggc gct gag gga ggc cgt ggg gac gcg ggt tgg ggc ctg        48
Met Ala Arg Gly Ala Glu Gly Gly Arg Gly Asp Ala Gly Trp Gly Leu
  1               5                  10                  15 cgt ggc gcc ctg gcg gcc gtg gcg ctg ctc tcg gcg ctc aac gct gcg        96
Arg Gly Ala Leu Ala Ala Val Ala Leu Leu Ser Ala Leu Asn Ala Ala
                 20                  25                  30 ggc acg gtg ttc gcg ctg tgc cag tgg cgc ggg ctg agc tcg gcg ctg       144
Gly Thr Val Phe Ala Leu Cys Gln Trp Arg Gly Leu Ser Ser Ala Leu
             35                  40                  45 cgg gct ttg gag gcg cag cgg ggc cgg gag cag cgc gag gac agt gcc       192
Arg Ala Leu Glu Ala Gln Arg Gly Arg Glu Gln Arg Glu Asp Ser Ala
         50                  55                  60 ctg cgc tcc ttc ctg gcc gag ttg agc cgc gcg ccg cgc ggg gcg tcc       240
Leu Arg Ser Phe Leu Ala Glu Leu Ser Arg Ala Pro Arg Gly Ala Ser
 65                  70                  75                  80 gca cca ccc caa gac ccg gcc agc tca gct cgc aac aag cgc agc cac       288
Ala Pro Pro Gln Asp Pro Ala Ser Ser Ala Arg Asn Lys Arg Ser His
                 85                  90                  95 agc ggc gag ccc gcg ccg cat atc cgc gcc gag agc cat gac atg ctg       336
Ser Gly Glu Pro Ala Pro His Ile Arg Ala Glu Ser His Asp Met Leu
            100                 105                 110 atg atg atg acc tac tcc atg gtg ccg atc cga gtg atg gtg gac ctg       384
Met Met Met Thr Tyr Ser Met Val Pro Ile Arg Val Met Val Asp Leu
        115                 120                 125 tgc aac agc acc aag ggc atc tgc ctc aca gga cct tct gga cca cca       432
Cys Asn Ser Thr Lys Gly Ile Cys Leu Thr Gly Pro Ser Gly Pro Pro
    130                 135                 140 gga cct ccg gga gcc ggc ggg ttg cca gga cac aac gga ttg gat gga       480
Gly Pro Pro Gly Ala Gly Gly Leu Pro Gly His Asn Gly Leu Asp Gly
145                 150                 155                 160 cag cct ggt cct cag ggc cca aaa gga gaa aaa gga gca aat gga aaa       528
Gln Pro Gly Pro Gln Gly Pro Lys Gly Glu Lys Gly Ala Asn Gly Lys
                165                 170                 175 aga gga aaa atg ggg ata cct gga gct gca gga aat cca ggg gaa agg       576
Arg Gly Lys Met Gly Ile Pro Gly Ala Ala Gly Asn Pro Gly Glu Arg
            180                 185                 190 gga gaa aag gga gac cat ggt gaa ctg ggc ctg cag gga aat gag ggc       624
Gly Glu Lys Gly Asp His Gly Glu Leu Gly Leu Gln Gly Asn Glu Gly
        195                 200                 205 cca cca ggg cag aag gga gaa aag ggt gac aaa gga gat gtg tcc aac       672
Pro Pro Gly Gln Lys Gly Glu Lys Gly Asp Lys Gly Asp Val Ser Asn
    210                 215                 220 gac gtg ctc ctg gca ggt gcc aaa ggt gac caa ggc cca ccc ggt cca       720
Asp Val Leu Leu Ala Gly Ala Lys Gly Asp Gln Gly Pro Pro Gly Pro
225                 230                 235                 240 cct ggg ccc cca ggc cct cca ggt cct cca ggg ccc cct gga agc aga       768
Pro Gly Pro Pro Gly Pro Pro Gly Pro Pro Gly Pro Pro Gly Ser Arg
                245                 250                 255
```

```
aga gcc aaa ggc cct cgg cag cca agc atg ttc aac ggc cag tgc cca    816
Arg Ala Lys Gly Pro Arg Gln Pro Ser Met Phe Asn Gly Gln Cys Pro
        260                 265                 270 ggt gag act tgt gcc ata cca aat gat gat acc ttg gtt gga aaa gct    864
Gly Glu Thr Cys Ala Ile Pro Asn Asp Asp Thr Leu Val Gly Lys Ala
            275                 280                 285 gat gag aaa gcc agt gaa cac cat tcc cca caa gca gaa tcc atg atc    912
Asp Glu Lys Ala Ser Glu His His Ser Pro Gln Ala Glu Ser Met Ile
290                 295                 300 act tcc att gga aac cca gtg caa gta ctg aaa gtg aca gag aca ttt    960
Thr Ser Ile Gly Asn Pro Val Gln Val Leu Lys Val Thr Glu Thr Phe
305                 310                 315                 320 ggg act tgg ata aga gag tct gct aac aag agt gat gac cgg att tgg   1008
Gly Thr Trp Ile Arg Glu Ser Ala Asn Lys Ser Asp Asp Arg Ile Trp
                325                 330                 335 gtg aca gag cat ttt tca ggc atc atg gtt aag gaa ttc aag gat cag   1056
Val Thr Glu His Phe Ser Gly Ile Met Val Lys Glu Phe Lys Asp Gln
                    340                 345                 350 ccc tca ctt ctg aat ggc agt tac acg ttc atc cac ctt cca tac tat   1104
Pro Ser Leu Leu Asn Gly Ser Tyr Thr Phe Ile His Leu Pro Tyr Tyr
                355                 360                 365 ttc cat ggc tgt ggg cac gtt gct tac aac aac tct ctc tac tac cac   1152
Phe His Gly Cys Gly His Val Ala Tyr Asn Asn Ser Leu Tyr Tyr His
        370                 375                 380 aaa ggg ggt tct aat acc cta gtg aga ttt gaa ttt ggc cag gaa aca   1200
Lys Gly Gly Ser Asn Thr Leu Val Arg Phe Glu Phe Gly Gln Glu Thr
385                 390                 395                 400 tcc caa act ctg aag ctt gaa aat gcc ttg tat ttt gat cga aaa tac   1248
Ser Gln Thr Leu Lys Leu Glu Asn Ala Leu Tyr Phe Asp Arg Lys Tyr
                405                 410                 415 ctt ttt gca aat tcc aaa act tac ttc aat cta gct gta gat gaa aag   1296
Leu Phe Ala Asn Ser Lys Thr Tyr Phe Asn Leu Ala Val Asp Glu Lys
                420                 425                 430 ggc ctt tgg att atc tat gcg tca agt gtg gac ggc tcg agc att ctt   1344
Gly Leu Trp Ile Ile Tyr Ala Ser Ser Val Asp Gly Ser Ser Ile Leu
            435                 440                 445 gta gca caa ctg gat gag agg aca ttc tca gtg gtg caa cac gtc aat   1392
Val Ala Gln Leu Asp Glu Arg Thr Phe Ser Val Val Gln His Val Asn
450                 455                 460 acc acg tac cct aaa tcc aag gct ggc aac gcc ttc att gcc cga gga   1440
Thr Thr Tyr Pro Lys Ser Lys Ala Gly Asn Ala Phe Ile Ala Arg Gly
465                 470                 475                 480 atc ctc tat gtc aca gac acc aaa gat atg agg gtc aca ttt gcc ttt   1488
Ile Leu Tyr Val Thr Asp Thr Lys Asp Met Arg Val Thr Phe Ala Phe
                485                 490                 495 gat ttg tta gga ggg aaa cag atc aat gca aac ttt gat tta aga act   1536
Asp Leu Leu Gly Gly Lys Gln Ile Asn Ala Asn Phe Asp Leu Arg Thr
                500                 505                 510 tcc cag tct gtt ctt gcc atg tta gca tac aac atg aga gat cag cat   1584
Ser Gln Ser Val Leu Ala Met Leu Ala Tyr Asn Met Arg Asp Gln His
            515                 520                 525 tta tat tca tgg gaa gat ggc cat tta atg ctt tat cct gtg cag ttt   1632
Leu Tyr Ser Trp Glu Asp Gly His Leu Met Leu Tyr Pro Val Gln Phe
530                 535                 540 ttg tca act acc tta aat cag tgatgtgctg cattcggctc ccttcagcaa      1683
Leu Ser Thr Thr Leu Asn Gln
545                 550 atttcagggg ttttctggga ccagttctcc cccaacagga aacttgtttt tttaacgtca 1743
```

```
gccagatatt tagaaaataa cctcaaaagt gtttatatgg tcagtgagcc ccgcttagtg    1803
aaatagcaac agattggaag ttgaaatggc tgagatttgg tgatctcccc acagctggct    1863
ctgcaagtta cctctttctc cttgggcctt agtttcccca ttggtaatct gaattggcta    1923
agatgattgg ggagattttc tgtacctgta ggtaatttgg tgattcttgg tggctgctct    1983
tctcacaact tttatgtatc tgcttctgtc gtttagcttt tttagccaca tgctgaccaa    2043
atttaccttt gagttgataa gtccagtggc ttgagtagtg aatccctcag tgctgactta    2103
tatcttgttc tttgaaaaaa tgcattgact ctttaagaca tctaaagtat cacattatcc    2163
ataatttatt gcttttcttt gcatctgcac ctgccaccac agaataacca ttaccctcag    2223
ctgctgattg ggcagctctg agattagcaa aagccaggga cagctacatg ttcaggtttt    2283
tttttttttt tttttcaata ggctattttt tttcttttct tattttaaat agagagagag    2343
tcttgctatg tttcccaggc tggtcttgaa ctcctggggc tcaagtgatc ctcctgcctt    2403
ggcctcccaa aatgctggat tacaggcatg tgtgcctggc ccaggtttct taataaaaca    2463
gaatcatgat cttccaggtt cccccagtt tctgatcatg ttgatttgta gctgtggatc    2523
atgaacactg aatccccaga tcactctgac ttccttatgct tctcctgtgg atccactatc    2583
aaagtactaa atgctgtgta agtagacgtt aatctggctg gaaccatggg aagcactttg    2643
cagtgttcag aagagaggct ccatttgtgg ctattatgta gaactgggcc agagccagtc    2703
cattgcctgt tttttaaat aaggttttac tgagcacagc cacactcatt tgtttatgca    2763
gtacggcctg acattgcttt tgctctgcaa cagcagagtc gagtcattgc aacaaagagc    2823
atatggcccc acagtgccta aaatattgac cagctacccc tttatggaaa aagattgctg    2883
actcctgata aagaatataa agtgagcctg attcttgaaa aaatcagaac cagagcctgt    2943
tttgttttgt tctaaactaa gaagccgcat aggatgtgac ttgcgttttg agtagagggg    3003
aaggctgata acggcgtaag atgaagtggc cctccacaaa ggctggttag gggacagttc    3063
tttctctaac atagttttaa aggatgtgat ctggtcccct tggatgccag gagagaatcc    3123
agttgaactt gctcctaaat gctcttaaat atgcatattt tctgccaact cacttcttta    3183
aacatctttc agcccagcgc tgcggccccg ggaagggcca ctgcgaatag agaggaagct    3243
ggaaaagttc ctggggctct gcagccagga aggggaacca gggcaaatct tatgtaaaga    3303
tttttcagca acttgtccca atttgtgtgt attctgaaac tttctctttg ggaccaaatt    3363
cattctcaat ggccctgagt tcaatatatt attaacagca gtattttaaa acttagggtt    3423
gaactgggca tggtggcaca taactgcaat cccagctact tggaggcag ggatgggagg    3483 atcacttgag gccaggatct caggaccagc ctagagagat cccatctcta aaaataaaa    3543 tataagaaaa taaaacttag gggatataca gatttaaata ttcaaatctc cctgctcccc    3603
tgaaagtccc caggcagctg ttaatgactt gtttgttgtg ttctcaatat gatggctatt    3663
tgaaacttca cctactttc attagattgg ttgtaccatg tcaccttagc ttttaaaaat    3723
actcttttca gattcacgtt ctctaacaaa gagtctcatg ttcaagatca atatgtctaa    3783
taagcgctgg tgtcctttta aagtatttaa atatatatgt tgctgttgct gaatacagga    3843
gaccaggtta ggaatatagt ttcataataa tagtacatac aatactaatt gtatataagg    3903
tagcaaccaa aagaggttgt taattagcac atattccttt tagaaaaatg tttcagaaac    3963
ctcagtcttg atatctgagc tatctgggct cccttacttg tgagtaaggg atcatgctca    4023
ccactggaga agcttacacc gggacttttt ttcttttttc tttttttttt gctatgacag    4083
agtaatgcta acgtaaggac aactgagttt gatcagtgtt taatcgcagt gggtaatctt    4143
```

-continued

```
atctgattgt ctttaaaagt gaaaaggatt aagattttat tctttcttgt aaacattact    4203 tgattttta aagaagtttt gggctcactg ctaaaataga gtatacaact gaatgttttt    4263
aagtcaagat actgttttag gagtttaccc tctcatttat aaccaaagtt gctctaaaac    4323
actttccaaa tatctgcact tctgatgtca gaatcaaacc agataattct ctaattcttc    4383
tttaatctaa agtagatagc ttcccactgg aaagtaaaca aaaccatccc tcccaacctc    4443
aaagctaggc cacactctat ttcaaggcat tttctttcag ctgataaggt gtcctcctga    4503
agccaagtag gtggttctgg tctccaagta tcgttaagca caggtgctat gacagaaaaa    4563
gttctggggt ggaagtttta agatgaggag ttctgatctt aggcatctta acagtcacaa    4623
ggtgaaaagt caaatgaaac agtacaattc ttgatgagtg aggtgtcatc ttccaaccac    4683
acagaggacg ttttggctat gatcatctga tggcaagtga aggagaaatg agtgataggg    4743
ctttgcgttt tcatccagat gctgtggccc tgtgtttcac agcattaaga gccataattt    4803
ccaacctgca cagatcctga acaacaaatg aataacgatg aatgtctttt tggttgtaat    4863
ttaacaagtc aaataaataa tcattgctga gcacaatcac caaaaaaaaa aaaaaaaaaa    4923
aaaaaaaaaa aaaaaaaaaa aaaaaaaaaa aaagaaaaaa aaaaaaaaaa aca           4976
```

<210> SEQ ID NO 12
<211> LENGTH: 551
<212> TYPE: PRT
<213> ORGANISM: Homo sapiens

<400> SEQUENCE: 12

```
Met Ala Arg Gly Ala Glu Gly Gly Arg Gly Asp Ala Gly Trp Gly Leu
 1               5                  10                  15

Arg Gly Ala Leu Ala Ala Val Ala Leu Leu Ser Ala Leu Asn Ala Ala
                20                  25                  30

Gly Thr Val Phe Ala Leu Cys Gln Trp Arg Gly Leu Ser Ser Ala Leu
            35                  40                  45

Arg Ala Leu Glu Ala Gln Arg Gly Arg Glu Gln Arg Glu Asp Ser Ala
        50                  55                  60

Leu Arg Ser Phe Leu Ala Glu Leu Ser Arg Ala Pro Arg Gly Ala Ser
 65                  70                  75                  80

Ala Pro Pro Gln Asp Pro Ala Ser Ala Arg Asn Lys Arg Ser His
                85                  90                  95

Ser Gly Glu Pro Ala Pro His Ile Arg Ala Glu Ser Asp Met Leu
            100                 105                 110

Met Met Met Thr Tyr Ser Met Val Pro Ile Arg Val Met Val Asp Leu
        115                 120                 125

Cys Asn Ser Thr Lys Gly Ile Cys Leu Thr Gly Pro Ser Gly Pro Pro
    130                 135                 140

Gly Pro Pro Gly Ala Gly Gly Leu Pro Gly His Asn Gly Leu Asp Gly
145                 150                 155                 160

Gln Pro Gly Pro Gln Gly Pro Lys Gly Glu Lys Gly Ala Asn Gly Lys
                165                 170                 175

Arg Gly Lys Met Gly Ile Pro Gly Ala Ala Gly Asn Pro Gly Glu Arg
            180                 185                 190

Gly Glu Lys Gly Asp His Gly Glu Leu Gly Leu Gln Gly Asn Glu Gly
        195                 200                 205

Pro Pro Gly Gln Lys Gly Glu Lys Gly Asp Lys Gly Asp Val Ser Asn
    210                 215                 220
```

Asp Val Leu Leu Ala Gly Ala Lys Gly Asp Gln Gly Pro Pro Gly Pro
225                 230                 235                 240

Pro Gly Pro Gly Pro Pro Gly Pro Pro Gly Pro Pro Gly Ser Arg
            245                 250                 255

Arg Ala Lys Gly Pro Arg Gln Pro Ser Met Phe Asn Gly Gln Cys Pro
            260                 265                 270

Gly Glu Thr Cys Ala Ile Pro Asn Asp Asp Thr Leu Val Gly Lys Ala
        275                 280                 285

Asp Glu Lys Ala Ser Glu His His Ser Pro Gln Ala Glu Ser Met Ile
        290                 295                 300

Thr Ser Ile Gly Asn Pro Val Gln Val Leu Lys Val Thr Glu Thr Phe
305                 310                 315                 320

Gly Thr Trp Ile Arg Glu Ser Ala Asn Lys Ser Asp Asp Arg Ile Trp
                325                 330                 335

Val Thr Glu His Phe Ser Gly Ile Met Val Lys Glu Phe Lys Asp Gln
            340                 345                 350

Pro Ser Leu Leu Asn Gly Ser Tyr Thr Phe Ile His Leu Pro Tyr Tyr
            355                 360                 365

Phe His Gly Cys Gly His Val Ala Tyr Asn Asn Ser Leu Tyr Tyr His
        370                 375                 380

Lys Gly Gly Ser Asn Thr Leu Val Arg Phe Glu Phe Gly Gln Glu Thr
385                 390                 395                 400

Ser Gln Thr Leu Lys Leu Glu Asn Ala Leu Tyr Phe Asp Arg Lys Tyr
                405                 410                 415

Leu Phe Ala Asn Ser Lys Thr Tyr Phe Asn Leu Ala Val Asp Glu Lys
            420                 425                 430

Gly Leu Trp Ile Ile Tyr Ala Ser Ser Val Asp Gly Ser Ser Ile Leu
        435                 440                 445

Val Ala Gln Leu Asp Glu Arg Thr Phe Ser Val Val Gln His Val Asn
450                 455                 460

Thr Thr Tyr Pro Lys Ser Lys Ala Gly Asn Ala Phe Ile Ala Arg Gly
465                 470                 475                 480

Ile Leu Tyr Val Thr Asp Thr Lys Asp Met Arg Val Thr Phe Ala Phe
                485                 490                 495

Asp Leu Leu Gly Gly Lys Gln Ile Asn Ala Asn Phe Asp Leu Arg Thr
            500                 505                 510

Ser Gln Ser Val Leu Ala Met Leu Ala Tyr Asn Met Arg Asp Gln His
        515                 520                 525

Leu Tyr Ser Trp Glu Asp Gly His Leu Met Leu Tyr Pro Val Gln Phe
        530                 535                 540

Leu Ser Thr Thr Leu Asn Gln
545                 550

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cccagttcac cagcatctcc cttctctc                                          28

<210> SEQ ID NO 14
<211> LENGTH: 27

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtctatcatc acccggatcg gcaccat                                              27

<210> SEQ ID NO 15
<211> LENGTH: 21
<212> TYPE: DNA
<213> ORGANISM: Rattus sp.

<400> SEQUENCE: 15
aattaagtcg tgcgccagcc c                                                    21

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 16
uuaagucgug cgccagccct t                                                    21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
gggcuggcgc acgacuuaat t                                                    21

<210> SEQ ID NO 18
<211> LENGTH: 21
<212> TYPE: DNA
<213> ORGANISM: Rattus sp.

<400> SEQUENCE: 18
aatgatgata ccttggtggg g                                                    21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
ugaugauacc uuggugggt t                                                     21
```

```
<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 20
ccccaccaag guaucaucat t                                             21

<210> SEQ ID NO 21
<211> LENGTH: 21
<212> TYPE: DNA
<213> ORGANISM: Rattus sp.

<400> SEQUENCE: 21
aatgagcgcc attctccaca a                                             21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 22
ugagcgccau ucuccacaat t                                             21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 23
uuguggagaa uggcgcucat t                                             21

<210> SEQ ID NO 24
<211> LENGTH: 21
<212> TYPE: DNA
<213> ORGANISM: Rattus sp.

<400> SEQUENCE: 24
aacccatgat cacgtccatt g                                             21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

-continued

```
<400> SEQUENCE: 25
cccaugauca cguccauugt t                                               21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 26
caauggacgu gaucaugggt t                                               21

<210> SEQ ID NO 27
<211> LENGTH: 22
<212> TYPE: PRT
<213> ORGANISM: Rattus sp.

<400> SEQUENCE: 27

Pro Asn Asp Asp Thr Leu Val Gly Arg Ala Asp Glu Lys Val Asn Glu
 1               5                  10                  15

Arg His Ser Pro Gln Thr
             20

<210> SEQ ID NO 28
<211> LENGTH: 1650
<212> TYPE: DNA
<213> ORGANISM: Rattus sp.

<400> SEQUENCE: 28
atgacccgag ccgcagagcg aggccaaggg gctacaggct ggggactgcg aggcgccctg      60
atggccgtgg cgctgctgtc agtgctgaac gccgtgggca ccgtgttcgt gctgtaccag    120
tggcgcgagc tgagcgcggc gctgcgggca ctggaggcgc aacacggcca ggagcagcgc    180
gaggacagcg ccctacgcgc ctttctagct gaattaagtc gtgcgccagc ccgagtcccc    240
gaaccacccc aggaccccat gagtgcagcg cgcaataagc gcagccacgg cggcgagcct    300
gcgtcacaca tccgcgcgga gagccaggac atgatgatga tgatgaccta cagcatggtg    360
ccgatccggg tgatgataga cctgtgcaac agcacccagg gcatctgcct tacaggacca    420
ccgggcccac caggacctcc aggagctggt gggttaccag gccacaatgg atcagatgga    480
cagcctggtc tccagggccc aaaaggagaa aaggagcag ttgggaagag aggaaaaatg    540
gggttacccg gagccacagg aaatccaggg gaaaagggaga agaagggaga tgctggtgaa    600
ctgggcctac ctggaaatga gggaccacca ggacagaaag gagacaaagg agacaaagga    660
gatgtgtcca atgacgtgct tttgacaggt gccaaaggtg accaagggcc cctggcccca    720
cctggacccc cagggcctcc aggcccttct ggaagcagaa gagccaaagg ccctcggcag    780
ccaaattcgt tcaccaacca gtgtccaggg gagacgtgtg tcatacccaa tgatgatacc    840
ttggtgggga gagctgatga gaaagtcaat gagcgccatt ctccacaaac agaacccatg    900
atcacgtcca ttggtaaccc ggcccaagtc ctcaaagtga agagacttt tgggacctgg    960 ctaagagagt ctgctaacag gagtgatgac cgcatttggg tgactgaaca ttttttcaggc   1020 atcatggtga aggagtttga agacctgccc gcctcctga atagcagctt caccctcctc   1080
cacctcccac attacttcca tggctgcggg cacgctgttt acaacaactc tctctactac   1140
```

```
cacaaaggag gctccaacac catagtgaga tttgaatttg ggaaagagac acctcaaact   1200
ctgaagcttg aagatgcttt gtattttgat cgaaaatacc tctttgcgaa ttccaagact   1260
tacttcaaca tagcagtgga tgagaagggc ctctggatta tctacgcctc gagtgtggat   1320
ggctcaagca tccttgtggc acagctggac gagaggacat tctctgtgct gcagcacatc   1380
aataccacat accccaagtc caaggctggc aatgccttca tagctcaagg gatcctctat   1440
gtcacggaca caaaagatac aagggtcacg tttgcctttg atttgttacg agggaagcag   1500
atcaatgcaa acttcggtct cagaatgtca cagtctgttc ttgccatgtt gtcgtacaat   1560
atgagagacc agcatttgta ctcgtgggaa gacggccacc tgatgctcta tcctgtgcac   1620
ttttcgtcaa cagcacccag ccagcgatag                                    1650
```

<210> SEQ ID NO 29
<211> LENGTH: 1650
<212> TYPE: DNA
<213> ORGANISM: Rattus sp.

<400> SEQUENCE: 29

```
atgacccgag ccgcagagcg aggccaaggg gctacaggct ggggactgcg aggcgccctg     60
atggccgtgg cgctgctgtc agtgctgaac gccgtgggca ccgtgttcgt gctgtaccag    120
tggcgcgagc tgagcgcggc gctgcgggca ctggaggcgc aacacggcca ggagcagcgc    180
gaggacagcg ccctacgcgc ctttctagct gaattaagtc gtgcgccagc ccgagtcccc    240
gaaccacccc aggaccccat gagtgcagcg cgcaataagc gcagccacgg cggcgagcct    300
gcgtcacaca tccgcgcgga gagccaggac atgatgatga tgatgaccta cagcatggtg    360
ccgatccggg tgatgataga cctgtgcaac agcacccagg gcatctgcct tacaggacca    420
ccgggcccac caggacctcc aggagctggt gggttaccag ccacaatgga atcagatgga    480
cagcctggtc tccagggccc aaaaggagaa aaggagcagt tgggaagag aggaaaaatg    540 gggttacccg gagccacagg aaatccaggg gaaaagggag agaagggaga tgctggtgaa    600
ctgggcctac ctggaaatga gggaccacca ggacagaaag gagacaaagg agacaaagga    660
gatgtgtcca atgacgtgct tttgacaggt gccaaaggtg accaagggcc cctggcccca    720
cctgaccccc agggcctcc aggccctcct ggaagcagaa gagccaaagg ccctcggcag    780
ccaaattcgt tcaccaacca gtgtccaggg gagacgtgtg tcatacccaa tgatgatacc    840
ttggtgggga gagctgatga gaaagtcaat gagcgccatt ctccacaaac agaacccatg    900
atcacgtcca ttggtaaccc ggcccaagtc ctcaaggtga agagactttt tgggacctgg    960
ctaagagagt ctgctaacag gagtgacgac cgcatttggg tgactgaaca ttttttcaggc   1020 atcatggtga aggagtttga agacctgccc gccctcctga atagcagctt caccctcctc   1080
cacctcccac attacttcca tggctgcggg cacgctgttt acaacaactc tctctactac   1140
cacaaaggag gctccaacac catagtgaga tttgaatttg ggaaagagac acctcaaact   1200
ctgaagcttg aagatgcttt gtattttgat cgaaaatacc tctttgcgaa ttccaagact   1260
tacttcaaca tagcagtgga tgagaagggc ctctggatta tctacgcctc gagtgtggat   1320
ggctcaagca tccttgtggc acagctggac gagaggacat tctctgtgct gcggcacatc   1380
aataccacat accccaagtc caaggctggc aatgccttca tagctcaagg gatcctctat   1440
gtcacggaca ccaaagatac aagggtcacg tttgcctttg atttgttacg agggaagcag   1500
atcaatgcaa acttcggtct cagaatgtca cagtctgttc ttgccatgtt gtcgtacaat   1560
```

```
atgagagacc agcatttgta ctcgtgggaa gacggccacc tgatgctcta tcctgtgcac    1620
ttttcgtcaa cagcacccag ccagcgatag                                     1650

<210> SEQ ID NO 30
<211> LENGTH: 1656
<212> TYPE: DNA
<213> ORGANISM: Homo sapiens

<400> SEQUENCE: 30
atggcccgag cgctgaggg aggccgtggg gacgcgggtt ggggcctgcg tggcgccctg      60
gcggccgtgg cgctgctctc ggcgctcaac gctgcgggca cggtgttcgc gctgtgccag   120
tggcgcgggc tgagctcggc gctgcgggct ttggaggcgc agcggggccg ggagcagcgc   180
gaggacagtg ccctgcgctc cttcctggcc gagttgagcc gcgcgccgcg cggggcgtcc   240
gcaccacccc aagacccggc cagctcagct cgcaacaagc gcagccacag cggcgagccc   300
gcgccgcata tccgcgccga gagccatgac atgctgatga tgatgaccta ctccatggtg   360
ccgatccgag tgatggtgga cctgtgcaac agcaccaagg gcatctgcct cacaggacct   420
tctggaccac caggacctcc gggagccggc gggttgccag acacaacgg attggatgga     480 cagcctggtc ctcagggccc aaaaggagaa aaggagcaa atggaaaaag aggaaaaatg   540
gggatacctg gagctgcagg aaatccaggg gaaaggggga aaagggaga ccatggtgaa    600 ctgggcctgc agggaaatga gggcccacca gggcagaagg gagaaaaggg tgacaaagga   660
gatgtgtcca cgacgtgct cctgcaggt gccaaggtg accaaggccc acccggtcca      720
cctgggcccc caggccctcc aggtcctcca gggcccctg gaagcagaag agccaaaggc    780
cctcggcagc caagcatgtt caacggccag tgcccaggtg agacttgtgc cataccaaat   840
gatgatacct tggttggaaa agctgatgag aaagccagtg aacaccattc cccacaagca   900
gaatccatga tcacttccat tggaaaccca gtgcaagtac tgaaagtgac agagacattt   960
gggacttgga taagagagtc tgctaacaag agtgatgacc ggatttgggt gacagagcat  1020
ttttcaggca tcatggttaa ggaattcaag gatcagccct cacttctgaa tggcagttac  1080
acgttcatcc accttccata ctatttccat ggctgtgggc acgttgctta caacaactct  1140
ctctactacc acaaaggggg ttctaatacc ctagtgagat ttgaatttgg ccaggaaaca  1200
tcccaaactc tgaagcttga aaatgccttg tattttgatc gaaaatacct ttttgcaaat  1260
tccaaaactt acttcaatct agctgtagat gaaaagggcc tttggattat ctatgcgtca  1320
agtgtggacg gctcgagcat tcttgtagca caactggatg agaggacatt ctcagtggtg  1380
caacacgtca ataccacgta ccctaaatcc aaggctggca acgccttcat gcccgagga   1440 atcctctatg tcacagacac caaagatatg agggtcacat ttgcctttga tttgttagga  1500
gggaaacaga tcaatgcaaa cttttgattta agaacttccc agtctgttct tgccatgtta  1560
gcatacaaca tgagagatca gcatttatat tcatgggaag atggccattt aatgctttat  1620
cctgtgcagt ttttgtcaac taccttaaat cagtga                            1656

<210> SEQ ID NO 31
<211> LENGTH: 1284
<212> TYPE: DNA
<213> ORGANISM: Homo sapiens

<400> SEQUENCE: 31
atggtggacc tgtgcaacag caccaagggc atctgcctca caggaccttc tggaccacca     60
ggacctccgg gagccggcgg gttgccagga cacaacggat tggatggaca gcctggtcct   120
```

```
cagggcccaa aaggagaaaa aggagcaaat ggaaaagag gaaaatggg gataccgga      180 gctgcaggaa atccagggga aaggggagaa aagggagacc atggtgaact gggcctgcag   240
ggaaatgagg ccccaccagg gcagaaggga gaaaagggtg acaaaggaga tgtgtccaac   300
gacgtgctcc tggcaggtgc caaaggtgac caaggcccac ccggtccacc tgggccccca   360
ggccctccag gtcctccagg gccccctgga agcagaagag ccaaaggccc tcggcagcca   420
agcatgttca acggccagtg cccaggtgag acttgtgcca taccaaatga tgataccttg   480
gttggaaaag ctgatgagaa agccagtgaa caccattccc cacaagcaga atccatgatc   540
acttccattg gaaacccagt gcaagtactg aaagtgacag agacatttgg gacttggata   600
agagagtctg ctaacaagag tgatgaccgg atttgggtga cagagcattt ttcaggcatc   660
atggttaagg aattcaagga tcagccctca cttctgaatg gcagttacac gttcatccac   720
cttccatact atttccatgg ctgtgggcac gttgcttaca caactctct ctactaccac    780 aaagggggtt ctaataccct agtgagattt gaatttggcc aggaaacatc ccaaactctg   840
aagcttgaaa atgccttgta ttttgatcga aaatacctt ttgcaaattc caaaacttac    900
ttcaatctag ctgtagatga aaagggcctt tggattatct atgcgtcaag tgtggacggc   960
tcgagcattc ttgtagcaca actggatgag aggacattct cagtggtgca acacgtcaat  1020
accacgtacc ctaaatccaa ggctggcaac gccttcattg cccgaggaat cctctatgtc  1080
acagacacca agatatgag gtcacattt gcctttgatt tgttaggagg gaaacagatc    1140
aatgcaaact ttgatttaag aacttcccag tctgttcttg ccatgttagc atacaacatg  1200
agagatcagc atttatattc atgggaagat ggccatttaa tgctttatcc tgtgcagttt  1260
ttgtcaacta ccttaaatca gtga                                         1284

<210> SEQ ID NO 32
<211> LENGTH: 1596
<212> TYPE: DNA
<213> ORGANISM: Rattus sp.

<400> SEQUENCE: 32
atgacccgag ccgcagagcg aggccaaggg gctacaggct ggggactgcg aggcgccctg    60
atggccgtgg cgctgctgtc agtgctgaac gccgtgggca ccgtgttcgt gctgtaccag   120
cagcgcgagg acagcgccct acgcgccttt ctagctgaat taagtcgtgc gccagcccga   180
gtccccgaac caccccagga ccccatgagt gcagcgcgca ataagcgcag ccacggcggc   240
gagcctgcgt cacacatccg cgcggagagc caggacatga tgatgatgat gacctacagc   300
atggtgccga tccgggtgat gatagacctg tgcaacagca cccagggcat ctgccttaca   360
ggaccaccgg gccaccagg acctccagga gctggtgggt taccaggcca caatggatca   420 gatgacagc tggtctcca gggcccaaaa ggagaaaag gagcagttgg aagagagga      480 aaaatgggt tacccggagc acaggaaat ccaggggaaa agggagagaa gggagatgct    540
ggtgaactgg gcctacctgg aaatgaggga ccaccaggac agaaaggaga caaaggagac   600
aaaggagatg tgtccaatga cgtgcttttg acaggtgcca aaggtgacca agggccccct   660
ggcccacctg accccccagg gcctccaggc ccttctggaa gcagaagagc caaaggccct   720
cggcagccaa attcgttcac caaccagtgt ccaggggaga cgtgtgtcat acccaatgat   780
gataccttgg tggggagagc tgatgagaaa gtcaatgagc ccattctcc acaaacagaa   840 cccatgatca cgtccattgg taacccggcc caagtcctca agtgaaaga gacttttggg   900
```

| | |
|---|---:|
| acctggctaa gagagtctgc taacaggagt gatgaccgca tttgggtgac tgaacatttt | 960 |
| tcaggcatca tggtgaagga gtttgaagac ctgcccgccc tcctgaatag cagcttcacc | 1020 |
| ctcctccacc tcccacatta cttccatggc tgcgggcacg ctgtttacaa caactctctc | 1080 |
| tactaccaca aaggaggctc aacaccata gtgagatttg aatttgggaa agagacacct | 1140 |
| caaactctga agcttgaaga tgctttgtat tttgatcgaa aatacctctt tgcgaattcc | 1200 |
| aagacttact tcaacatagc agtggatgag aagggcctct ggattatcta cgcctcgagt | 1260 |
| gtggatggct caagcatcct tgtggcacag ctggacgaga ggacattctc tgtgctgcag | 1320 |
| cacatcaata ccacataccc caagtccaag gctggcaatg ccttcatagc tcaagggatc | 1380 |
| ctctatgtca cggacacaaa agatacaagg gtcacgtttg cctttgattt gttacgaggg | 1440 |
| aagcagatca atgcaaactt cggtctcaga atgtcacagt ctgttcttgc catgttgtcg | 1500 |
| tacaatatga gagaccagca tttgtactcg tgggaagacg gccacctgat gctctatcct | 1560 |
| gtgcactttt cgtcaacagc acccagccag cgatag | 1596 |

<210> SEQ ID NO 33
<211> LENGTH: 1650
<212> TYPE: DNA
<213> ORGANISM: Mus sp.

<400> SEQUENCE: 33

| | |
|---|---:|
| atgacccgag ccgcagagcg aggccaaggg gctacaggct gggggctgcg cggcgccctg | 60 |
| gtggccatag cgctgctgtc cgcactgaac gccgcgggca ccgtgttcgt gctgtgccag | 120 |
| tggcgggggt taagcgcggc gctacgggcg ctggaggctc aacgcggccg agagcagcgc | 180 |
| gaggacagcg ccctacgcgc cttcctggcc gaattgagtc gtgcgccggg ccgggtcccc | 240 |
| gaaccatccc aggaccccat gagcgcagcg cgcaacaagc gcagccacaa cggcgagcct | 300 |
| gcgtcacaca tccgtgcgga gagccaggac atgatgatga tgatgaccta ctccatggtg | 360 |
| ccgattcgag tgatgataga cctgtgcaac agtacccagg gcatctgcct cacaggacca | 420 |
| ccgggcccac caggacctcc aggagccggc gggttaccag gccacaatgg atcagatgga | 480 |
| cagcctggtc tccagggccc aaaaggagaa aaggagcaa ttggcaagag aggaaaaatg | 540 |
| gggttacctg gagccaccgg aaatccaggg gaaaagggag aaaagggaga tgctggtgaa | 600 |
| ctgggtctac ctggaaatga gggcccacca gggcagaaag gtgacaaggg agacaaagga | 660 |
| gacgtgtcca atgacgtgct tttgacaggt gccaaggtg accaaggtcc ccctggcccc | 720 |
| cctggacctc cagggcctcc aggccctcct ggaagcagaa gatccaaagg ccctcggcca | 780 |
| ccaaacgtgt tcaacagcca gtgtccaggg gagacgtgtg tcatacccaa tgatgatacc | 840 |
| ttggtgggaa gagctgatga gaaagcaaat gaacgccatt caccacaaac agaatctatg | 900 |
| atcacttcca ttggcaaccc agcccaagtc ctaaaagtga gagagacttt tgggacttgg | 960 |
| atgagagagt ctgctaacaa aagtgacgac cgcatttggg tgactgaaca ttttttcaggc | 1020 |
| atcatggtga aggagttcaa agacctgccg gcgctcctca atagcagctt cacactcctc | 1080 |
| cacctcccac attatttcca cggctgtggg cacgctgttt acaacaactc tctctactac | 1140 |
| cacaaaggag gctccaacac catagtgaga tttgaatttg gaaagagac acctcagact | 1200 |
| ctgaagctga aaaatgcttt gtattttgat cgaaaatacc tctttgcaaa ttccaagact | 1260 |
| tacttcaaca tagcagtgga tgagaagggc atctggatta tctacgcttc aagtgtggat | 1320 |
| ggctcaagca tccttgtagc acagctggat gagaggacat tctccgtgac acagcacatc | 1380 |
| aacaccacat accccaaatc caaggctggc aatgccttca tagcccgagg gatcctctat | 1440 |

-continued

```
gtcacagaca ccaaagatac gagggtcacg tttgcctttg atttgttagg aggaaagcaa      1500
atcaatgcaa actttgattt cagaatgtcc cagtctgttc ttgccatgct gtcatacaac      1560
atgagagatc agcatttata ctcgtgggaa gatggccatc tgatgctcta tcctgtgcag      1620
tttctgtcag cggcatcaag tcagcggtag                                       1650
```

<210> SEQ ID NO 34
<211> LENGTH: 117
<212> TYPE: PRT
<213> ORGANISM: Rattus sp.

<400> SEQUENCE: 34

Cys Leu Thr Gly Pro Pro Gly Pro Pro Gly Ala Gly Gly
 1               5                  10                  15

Leu Pro Gly His Asn Gly Ser Asp Gly Gln Pro Gly Leu Gln Gly Pro
                20                  25                  30

Lys Gly Glu Lys Gly Ala Val Gly Lys Arg Gly Lys Met Gly Leu Pro
            35                  40                  45

Gly Ala Thr Gly Asn Pro Gly Glu Lys Gly Glu Lys Gly Asp Ala Gly
        50                  55                  60

Glu Leu Gly Leu Pro Gly Asn Glu Gly Pro Pro Gly Gln Lys Gly Asp
    65                  70                  75                  80

Lys Gly Asp Lys Gly Asp Val Ser Asn Asp Val Leu Leu Thr Gly Ala
                85                  90                  95

Lys Gly Asp Gln Gly Pro Pro Gly Pro Pro Gly Pro Pro Gly Pro Pro
                100                 105                 110

Gly Pro Pro Gly Ser
        115

<210> SEQ ID NO 35
<211> LENGTH: 120
<212> TYPE: PRT
<213> ORGANISM: Homo sapiens

<400> SEQUENCE: 35

Cys Leu Thr Gly Pro Ser Gly Pro Pro Gly Pro Gly Ala Gly Gly
 1               5                  10                  15

Leu Pro Gly His Asn Gly Leu Asp Gly Gln Pro Gly Pro Gln Gly Pro
                20                  25                  30

Lys Gly Glu Lys Gly Ala Asn Gly Lys Arg Gly Lys Met Gly Ile Pro
            35                  40                  45

Gly Ala Ala Gly Asn Pro Gly Glu Arg Gly Glu Lys Gly Asp His Gly
        50                  55                  60

Glu Leu Gly Leu Gln Gly Asn Glu Gly Pro Pro Gly Gln Lys Gly Glu
    65                  70                  75                  80

Lys Gly Asp Lys Gly Asp Val Ser Asn Asp Val Leu Leu Ala Gly Ala
                85                  90                  95

Lys Gly Asp Gln Gly Pro Pro Gly Pro Pro Gly Pro Pro Gly Pro Pro
                100                 105                 110

Gly Pro Pro Gly Pro Pro Gly Ser
        115                 120

<210> SEQ ID NO 36
<211> LENGTH: 291
<212> TYPE: PRT
<213> ORGANISM: Rattus sp.

```
<400> SEQUENCE: 36

Arg Arg Ala Lys Gly Pro Arg Gln Pro Asn Ser Phe Thr Asn Gln Cys
  1               5                  10                  15

Pro Gly Glu Thr Cys Val Ile Pro Asn Asp Asp Thr Leu Val Gly Arg
             20                  25                  30

Ala Asp Glu Lys Val Asn Glu Arg His Ser Pro Gln Thr Glu Pro Met
         35                  40                  45

Ile Thr Ser Ile Gly Asn Pro Ala Gln Val Leu Lys Val Lys Glu Thr
     50                  55                  60

Phe Gly Thr Trp Leu Arg Glu Ser Ala Asn Arg Ser Asp Asp Arg Ile
 65                  70                  75                  80

Trp Val Thr Glu His Phe Ser Gly Ile Met Val Lys Glu Phe Glu Asp
                 85                  90                  95

Leu Pro Ala Leu Leu Asn Ser Ser Phe Thr Leu Leu His Leu Pro His
            100                 105                 110

Tyr Phe His Gly Cys Gly His Ala Val Tyr Asn Asn Ser Leu Tyr Tyr
        115                 120                 125

His Lys Gly Gly Ser Asn Thr Ile Val Arg Phe Glu Phe Gly Lys Glu
    130                 135                 140

Thr Pro Gln Thr Leu Lys Leu Glu Asp Ala Leu Tyr Phe Asp Arg Lys
145                 150                 155                 160

Tyr Leu Phe Ala Asn Ser Lys Thr Tyr Phe Asn Ile Ala Val Asp Glu
                165                 170                 175

Lys Gly Leu Trp Ile Ile Tyr Ala Ser Ser Val Asp Gly Ser Ser Ile
            180                 185                 190

Leu Val Ala Gln Leu Asp Glu Arg Thr Phe Ser Val Leu Gln His Ile
        195                 200                 205

Asn Thr Thr Tyr Pro Lys Ser Lys Ala Gly Asn Ala Phe Ile Ala Gln
    210                 215                 220

Gly Ile Leu Tyr Val Thr Asp Thr Lys Asp Thr Arg Val Thr Phe Ala
225                 230                 235                 240

Phe Asp Leu Leu Arg Gly Lys Gln Ile Asn Ala Asn Phe Gly Leu Arg
                245                 250                 255

Met Ser Gln Ser Val Leu Ala Met Leu Ser Tyr Asn Met Arg Asp Gln
            260                 265                 270

His Leu Tyr Ser Trp Glu Asp Gly His Leu Met Leu Tyr Pro Val His
        275                 280                 285

Phe Ser Ser
    290

<210> SEQ ID NO 37
<211> LENGTH: 291
<212> TYPE: PRT
<213> ORGANISM: Homo sapiens

<400> SEQUENCE: 37

Arg Arg Ala Lys Gly Pro Arg Gln Pro Ser Met Phe Asn Gly Gln Cys
  1               5                  10                  15

Pro Gly Glu Thr Cys Ala Ile Pro Asn Asp Asp Thr Leu Val Gly Lys
             20                  25                  30

Ala Asp Glu Lys Ala Ser Glu His His Ser Pro Gln Ala Glu Ser Met
         35                  40                  45

Ile Thr Ser Ile Gly Asn Pro Val Gln Val Leu Lys Val Thr Glu Thr
     50                  55                  60
```

```
Phe Gly Thr Trp Ile Arg Glu Ser Ala Asn Lys Ser Asp Asp Arg Ile
 65                  70                  75                  80

Trp Val Thr Glu His Phe Ser Gly Ile Met Val Lys Glu Phe Lys Asp
                 85                  90                  95

Gln Pro Ser Leu Leu Asn Gly Ser Tyr Thr Phe Ile His Leu Pro Tyr
            100                 105                 110

Tyr Phe His Gly Cys Gly His Val Ala Tyr Asn Asn Ser Leu Tyr Tyr
        115                 120                 125

His Lys Gly Gly Ser Asn Thr Leu Val Arg Phe Glu Phe Gly Gln Glu
    130                 135                 140

Thr Ser Gln Thr Leu Lys Leu Glu Asn Ala Leu Tyr Phe Asp Arg Lys
145                 150                 155                 160

Tyr Leu Phe Ala Asn Ser Lys Thr Tyr Phe Asn Leu Ala Val Asp Glu
                165                 170                 175

Lys Gly Leu Trp Ile Ile Tyr Ala Ser Ser Val Asp Gly Ser Ser Ile
            180                 185                 190

Leu Val Ala Gln Leu Asp Glu Arg Thr Phe Ser Val Val Gln His Val
        195                 200                 205

Asn Thr Thr Tyr Pro Lys Ser Lys Ala Gly Asn Ala Phe Ile Ala Arg
    210                 215                 220

Gly Ile Leu Tyr Val Thr Asp Thr Lys Asp Met Arg Val Thr Phe Ala
225                 230                 235                 240

Phe Asp Leu Leu Gly Gly Lys Gln Ile Asn Ala Asn Phe Asp Leu Arg
                245                 250                 255

Thr Ser Gln Ser Val Leu Ala Met Leu Ala Tyr Asn Met Arg Asp Gln
                260                 265                 270

His Leu Tyr Ser Trp Glu Asp Gly His Leu Met Leu Tyr Pro Val Gln
            275                 280                 285

Phe Leu Ser
    290

<210> SEQ ID NO 38
<211> LENGTH: 255
<212> TYPE: PRT
<213> ORGANISM: Unknown Organism
<220> FEATURE:
<223> OTHER INFORMATION: Description of Unknown Organism: Amino acid
      sequence of the olfactomedin-like domain

<400> SEQUENCE: 38

Gly Ile Leu Ala Gly Val Gly Ile Pro Val Leu Leu Ala Glu Ser Gln
  1               5                  10                  15

Tyr Gly Lys Ser Gly Ala Trp Met Arg Asp Pro Leu Pro Asn Ser Met
             20                  25                  30

Lys Ala Lys Arg Arg Trp Val Met Asp Gly Phe Ala Asp Val Ser Arg
         35                  40                  45

Val Leu Arg Glu Tyr Ser Ser Met Ser Asp Phe Leu Asp Gly Val Asn
     50                  55                  60

Lys Ile Lys Tyr Tyr Leu Pro His Ala Ala Ser Gly Thr Gly Asn Val
 65                  70                  75                  80

Val Tyr Asn Gly Ser Leu Tyr Phe Asn Lys Phe Gly Ser His Ser Ile
                 85                  90                  95

Val Arg Tyr Glu Leu Glu Thr Gly Val Gln Val Lys Glu Glu Leu Leu
            100                 105                 110

Pro Glu Ala Gly Tyr Asn Asp Cys Phe Pro Tyr Ala Trp Gly Gly His
        115                 120                 125
```

```
Ser Asp Ile Asp Leu Ala Val Asp Glu Asn Gly Leu Trp Val Ile Tyr
    130                 135                 140

Ala Thr Glu Gln Asn Ala Gly Lys Ile Val Ile Ser Lys Leu Asn Pro
145                 150                 155                 160

Ala Thr Leu Phe Val Glu Asn Thr Trp Asn Thr Glu Tyr Asn Lys Arg
                165                 170                 175

Ser Ala Ala Asn Ala Phe Met Ile Cys Gly Val Leu Tyr Val Thr Lys
            180                 185                 190

Ser Ala Asn Ser Leu Gly Thr Lys Ile Thr Tyr Ala Tyr Asp Thr Asn
        195                 200                 205

Thr Gly Lys Thr Ile Pro Leu Asp Ile Pro Phe Tyr Asn Pro Tyr Gln
    210                 215                 220

Tyr Ile Ser Met Leu Asp Tyr Asn Pro Leu Asp Arg Lys Leu Tyr Ala
225                 230                 235                 240

Trp Asp Asn Gly His Leu Leu Ser Tyr Asp Ile Arg Leu Glu Glu
                245                 250                 255
```